（12） United States Patent
Lebreton et al.

(10) Patent No.: US 7,465,811 B2
(45) Date of Patent: Dec. 16, 2008

(54) INDOLINE COMPOUNDS

(75) Inventors: Luc Lebreton, Dijon (FR); Christine Dumas, Talant (FR); Christine Massardier, Dijon (FR); Michel Bondoux, Fontaine les Dijon (FR)

(73) Assignee: Laboratoires Fournier S.A., Dijon Cedex (FR)

( * ) Notice: Subject to any disclaimer, the term of this patent is extended or adjusted under 35 U.S.C. 154(b) by 0 days.

(21) Appl. No.: 11/947,998

(22) Filed: Nov. 30, 2007

(65) Prior Publication Data

US 2008/0119465 A1 May 22, 2008

Related U.S. Application Data

(63) Continuation of application No. PCT/FR2006/050487, filed on May 29, 2006.

(30) Foreign Application Priority Data

May 30, 2005 (FR) .................................. 05 05432

(51) Int. Cl.
C07D 209/00 (2006.01)
C07D 233/00 (2006.01)
C07D 239/00 (2006.01)
C07D 401/00 (2006.01)
C07D 413/00 (2006.01)
C07D 405/00 (2006.01)
A01N 43/58 (2006.01)
A01N 43/40 (2006.01)
A01N 43/64 (2006.01)
A01N 43/50 (2006.01)
A61K 31/535 (2006.01)
A61K 31/497 (2006.01)
A61K 31/40 (2006.01)

(52) U.S. Cl. .................... 548/452; 548/400; 548/416; 548/300.1; 514/228.8; 514/231.2; 514/252.06; 514/252.12; 514/315; 514/336; 514/359; 514/385; 514/408; 514/412; 544/106; 544/111; 544/141; 544/144; 544/336; 544/358; 544/376; 544/224; 544/238; 546/184; 546/196; 546/200; 546/201; 546/255

(58) Field of Classification Search .................. 514/183, 514/228.8, 231.2, 247, 252.01, 252.05, 252.06, 514/252.1, 252.12, 315, 336, 359, 385, 408, 514/410, 412; 544/98, 106, 111, 141, 142, 544/143, 144, 224, 238, 336, 358, 359, 372, 544/373, 376; 546/184, 192, 195, 196, 200, 546/201, 250, 255; 548/400, 416, 452, 300.1
See application file for complete search history.

(56) References Cited

U.S. PATENT DOCUMENTS

2003/0008861 A1 1/2003 Lin et al.
2006/0100230 A1 5/2006 Bischoff et al.

FOREIGN PATENT DOCUMENTS

FR WO 2005/121093 * 12/2005 ................. 549/200
WO WO 00/54759 A2 9/2000
WO WO 03/43985 A1 5/2003
WO WO 2004/005253 A1 1/2004

OTHER PUBLICATIONS

International Search Report dated May 30, 2005 with English translation of relevant portion (Four (4) pages).

* cited by examiner

*Primary Examiner*—Kamal Saeed
*Assistant Examiner*—Samantha L Shterengarts
(74) *Attorney, Agent, or Firm*—Crowell & Moring LLP

(57) ABSTRACT

Sulfonylindoline compounds of formula I,

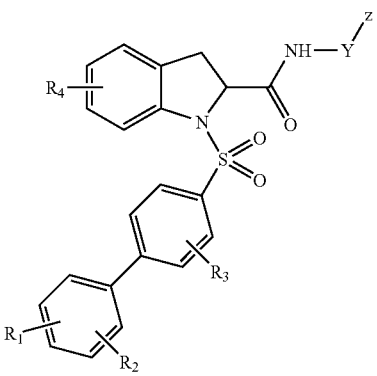

wherein R1 through R4, Y and Z have defined meanings, a process for preparation of such compounds, and the use as pharmaceutically active substances, particularly for the treatment or inhibition of neurodegeneration, cardiovascular disease, inflammatory disease, hypercholesterolemia, dyslipidemia, obesity or diabetes.

9 Claims, No Drawings

INDOLINE COMPOUNDS

CROSS REFERENCE TO RELATED APPLICATIONS

This application is a continuation of international patent application no. PCT/FR2006/050487, filed May 29, 2006, designating the United States of America, and published in French on Jan. 4, 2007 as WO 2007/000550, the entire disclosure of which is incorporated herein by reference. Priority is claimed based on French patent application no. FR 0505432, filed May 30, 2005.

BACKGROUND OF THE INVENTION

The present invention relates to novel compounds capable of modulating the activity of LXRs, to the process for their manufacture and to pharmaceutical compositions containing them.

Liver X receptors (LXRs) are transcription factors belonging to the superfamily of the nuclear receptors, which also include retinoic acid receptors (RXRs), farnesoid X receptors (FXRs) and peroxisome proliferator-activated receptors (PPARs). On binding to RXRs, LXRs form a heterodimer which attaches itself specifically to the DNA response elements (LXREs), leading to the transactivation of target genes (*Genes Dev.* 1995; 9: 1033-45).

These receptors are involved in many metabolic pathways and participate particularly in the homeostasis of cholesterol, bile acids, triglycerides and glucose.

Modulation of the activity of these nuclear receptors influences the progression of metabolic disorders such as type II diabetes, dyslipidemia and the development of atherosclerosis.

The LXR/RXR heterodimer can be activated by LXR and/or RXR ligands. Transactivation of the target genes requires the recruitment of co-activators such as Grip-1 (*Nature* 1996; 383: 728-31).

The two types of LXRs identified hitherto, namely LXRα and LXRβ, have a high degree of similarity in their amino acid sequence, but differ in their tissue distribution. LXRα is strongly expressed in the liver and to a lesser extent in the kidneys, the intestine, the adipose tissue and the spleen. LXRβ is distributed ubiquitously (*Gene* 2000; 243: 93-103; *N.Y. Acad. Sci.* 1995; 761: 38-49).

Although LXRs are not activated directly by cholesterol, they are activated by mono-oxidized derivatives of cholesterol (oxysterols), more particularly 22 (R)-hydroxycholesterol, 24 (S)-hydroxycholesterol and 24 (S), 25-epoxycholesterol. These oxysterols are considered to be the physiological ligands of LXRs (*Nature* 1996; 383: 728-31; *J. Biol. Chem.* 1997; 272: 3137-40). Also, it has been shown that the oxysterol 5,6,24 (S), 25-diepoxycholesterol is a specific ligand of LXRα, which suggests that it is possible to develop specific ligands of LXRα and/or LXRβ (*Proc. Natl. Acad. Sci. USA* 1999; 96: 26-71; *Endocrinology* 2000; 141: 4180-4).

Elsewhere, it has been possible to demonstrate that human plasma contains natural antagonists of LXRα and β (*Steroids* 2001, 66. 473-479).

Using rat hepatocytes, it has been possible to show that unsaturated fatty acids substantially increase the expression of LXRα without affecting LXRβ (*Mol. Endocrinol.* 2000; 14: 161-171). Furthermore, activators of PPARα and γ also induce the expression of LXRα in human primary macrophages.

The high concentrations of LXRα in the liver and the identification of endogenous ligands of LXR have suggested that these receptors play an essential role in the metabolism of cholesterol. Under physiological conditions, the homeostasis of cholesterol is maintained via regulation of the pathways of de novo synthesis and catabolism. Via a feedback mechanism involving transcription factors such as SREBP-1 and SREBP-2, the accumulation of sterols in the liver leads to inhibition of the biosynthesis of cholesterol (*Cell* 1997; 89: 331-40). The excess cholesterol also activates another metabolic pathway, which leads to conversion of the cholesterol to bile acids. Cholesterol is converted to 7α-hydroxycholesterol by an enzyme located in the liver (CYP7A: 7α-hydroxylase) (*J. Biol. Chem.* 1997; 272: 313-40).

The involvement of LXR in the synthesis of bile acids, and hence in the regulation of cholesterol homeostasis, has been demonstrated by means of LXRα-deficient mice, which, when subjected to a fatty diet, accumulate large amounts of cholesterol esters in the liver (*Cell* 1998; 93: 693-704). LXRβ-deficient mice have the same physiological resistance as normal mice to a fat-enriched diet. The expression of unchanged LXRβ in LXR-deficient mice tends to demonstrate that LXRβ on its own is incapable of substantially increasing cholesterol metabolism (*J. Clin. Invest.* 2001; 107: 565-573).

LXRs expressed in macrophages also play an important role in the regulation of certain macrophage functions. More particularly, they are involved in the control of reverse cholesterol transport, which enables the excess cholesterol to be exported from the peripheral tissues to the liver. The cholesterol is taken in charge by pre-bHDLs via apoA1 and ABCA1 for transportation to the liver, where it is catabolized to bile acids and then eliminated.

ABCA1 is a member of the superfamily of transport proteins (ATP-binding cassette), whose importance is illustrated by the fact that a mutation in the ABCA1 gene is responsible for Tangier disease (*Nat. Genet.* 1999; 22: 336-45).

The expression of ABCA1 and the efflux of cholesterol are induced by loading of the human macrophages with cholesterol and activation of the LXRs (*Biochem. Biophys. Res. Comm.* 1999; 257: 29-33). It has subsequently also been demonstrated that the expression of ABCG1, ABCG5 and ABCG8, other members of the family of ABC-type transporters, in the intestine is also regulated by the RXR/LXR heterodimer (*J. Biol. Chem.* 2000; 275: 14700-14707; *Proc. Natl. Acad. Sci. USA* 2000; 97: 817-22; *J. Biol. Chem.* 2002; 277: 18793-18800; *Proc. Natl. Acad. Sci. USA* 2002; 99: 16237-16242).

It has also been shown that agonistic ligands of LXR reduce atheromatous lesions in two different mouse models (ApoE−/− mice and LDLR−/− mice) (*Proc. Natl. Acad. Sci. USA* 2002; 99: 7604-7609; *FEBS Letters* 2003; 536: 6-11). These results suggest that LXR ligands can constitute therapeutic agents for the treatment of atherosclerosis.

Finally, it is known that macrophages play an important role in inflammation, particularly in the pathogenesis of atherosclerosis. It has been shown that the activation of LXRs inhibits the expression of the genes involved in inflammation in macrophages (*Nature Medicine* 2003; 9: 213-219). In vitro the expression of mediators such as nitric oxide synthase, cyclooxygenase-2 (COX-2) and interleukin-6 (IL-6) is inhibited. In vivo LXR agonists reduce inflammation in a dermatitis model and inhibit the expression of the genes involved in the inflammation of atheromatous mouse aortas.

Because the homeostasis of cholesterol also seems to play an essential role in the function of the central nervous system and the mechanisms of neurodegeneration, the expression of ABCA1 has also been studied in cultures of primary neurons, astrocytes and microglia isolated from rat embryo brains. The results of these studies show that activation of the LXRs leads to a decrease in the secretion of amyloid β and consequently to a reduction in amyloid deposits in the brain. These studies suggest that activation of the LXRs may constitute a novel approach to the treatment of Alzheimer's disease (*J. Biol. Chem.* 2003; 275 (15): 13244-13256, *J. Biol. Chem.* 2003; 278 (30): 27688-27694).

LXRs are also involved in regulating the expression of apolipoprotein E (ApoE). This protein is greatly involved in the hepatic clearance of lipoproteins and favors the efflux of cholesterol from lipid-rich macrophages. It has been demonstrated that the activation of LXRs leads to an increase in the expression of ApoE via an LXR response element (LXRE) situated in the sequence of the ApoE promoter (*Proc. Natl. Acad. Sci. USA* 2001; 98: 507-512).

The activation of LXRs would also favor cholesterol reverse transport via modulation of the expression of CETP (cholesterol ester transfer protein), which is involved in the transfer of esterified cholesterol from the HDLs to the triglyceride-rich lipoproteins eliminated by the liver (*J. Clin. Invest.* 2000; 105: 513-520).

In summary, the activation of LXRs leads to an increase in the expression of numerous genes that favor the elimination of excess cholesterol from the peripheral tissues. In macrophages loaded with cholesterol, the activation of LXRs increases the expression of ABCA1, ABCG1, ABCG5, ABCG8 and ApoE, causing an increase in the efflux of cholesterol from the macrophages to the liver, where it is excreted in the form of bile acids. Induction of the expression of CETP and CYP7A in the liver leads respectively to an increase in the hepatic clearance of cholesterol esters from the HDLs and to the catabolism of cholesterol.

Elsewhere, it has also been demonstrated that LXRs play an important role in the metabolism of glucose. The treatment of diabetic rodents with an LXR agonist leads to a drastic decrease in the plasma glucose levels. Particularly in the insulin-resistant Zucker (fa/fa) rat, the activation of LXRs inhibits the expression of the genes involved in gluconeogenesis, including more particularly phosphoenolpyruvate carboxykinase (PEPCK) (*J. Biol. Chem.* 2003, 278 (2): 1131-1136).

Also, it has been shown that an LXR agonist increases glucose tolerance in a mouse model of insulin resistance and obesity (*Proc. Natl. Acad. Sci. USA* 2003; 100: 5419-5424). Gene expression analysis demonstrates regulation of the genes involved in glucose metabolism in the liver:

decrease in the expression of peroxisome proliferator-activated receptor coactivator-1α (PGC-1), phosphoenolpyruvate carboxykinase (PEPCK) and glucose-6-phosphatase;

induction of the expression of glucokinase, which favors the utilization of hepatic glucose.

A transcriptional induction of insulin-sensitive glucose transporter (GLUT4) in the adipose tissue has also been demonstrated.

These results emphasize the importance of LXRs in the coordination of glucose metabolism.

It is also known that LXRs participate in inflammation regulation processes (*Nature Medicine* 2003, 9: 213-219).

Compounds that modulate LXR activity are known in the state of the art, especially from the documents WO 03/090869, WO 03/90746, WO 03/082192 or WO 03/082802, or the documents WO 03/043985 and WO 04/005253, which describe compounds of the benzenesulfonamide type which are PPAR agonists.

In this context there is a significant interest in finding novel compounds which modulate LXR activity and which would be useful in the treatment of certain pathological conditions such as cardiovascular disease, hypercholesterolemia, dyslipidemia, myocardial infarction, atherosclerosis, diabetes, obesity, inflammation and neurodegenerative disease.

The present invention is based precisely on the discovery of novel compounds that modulate LXR activity.

Thus, according to a first feature, the aim of the present invention is to protect, as a novel industrial product, a sulfonylindoline compound, wherein it is selected from:

i) the compounds of the formula

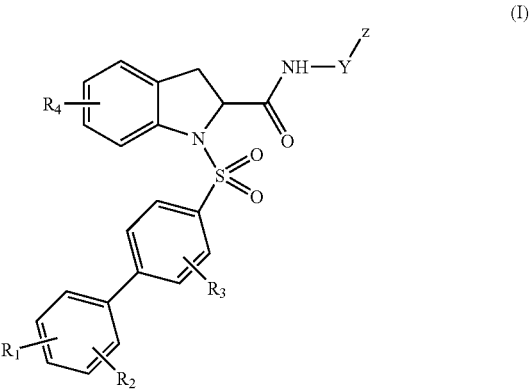

(I)

in which:

$R_1$ is a hydrogen atom, a halogen, a $C_1$-$C_4$ alkyl group, a $C_1$-$C_4$ alkoxy group, a trifluoromethyl group or a totally or partially halogenated methoxy group, $R_2$ is a hydrogen atom, a halogen, a $C_1$-$C_4$ alkyl group or a trifluoromethyl group, $R_3$ is a hydrogen atom, a halogen, a $C_1$-$C_4$ alkyl group or a trifluoromethyl group, with the proviso that $R_1$, $R_2$ and $R_3$ are not simultaneously a hydrogen atom, $R_4$ is a hydrogen atom or a $C_1$-$C_4$ alkoxy group, Y is a linear or branched $C_1$-$C_8$ alkylene group optionally substituted by a trifluoromethyl group or by a phenyl ring, or containing a cyclized part having 3 to 6 carbon atoms, or is a group —$(CH_2)_n$—W—, W is an oxygen atom, a group —NH— or a sulfur atom, n is 2, 3 or 4, Z is an optionally partially halogenated $C_1$-$C_4$ alkyl group, trifluoromethyl, —$COR_a$, —$CH_2$—$N(R)_2$, or an aromatic, heteroaromatic or heterocyclic ring selected from phenyl, pyrrolidinyl, pyrrolidinylone, imidazolyl, pyridinyl, pyridinyl oxide, piperidinyl, piperazinyl, pyridazinyl, morpholinyl and indolinylone groups, and optionally substituted by one, two or three identical or different substituents selected from a halogen, a $C_1$-$C_4$ alkyl group, $C_1$-$C_4$ alkoxy, trifluoromethyl, nitro, $N(R)_2$, —$CH_2$—$N(R)_2$, —O—$(CH_2)_n$—$N(R)_2$, hydroxyl, cyano, $C_2$-$C_3$ cyanoalkyl, 5-oxo-1,2,4-oxadiazolidinyl and a group of the formula —X—$[C(R)_2]_p$—$COR_a$, X is a single bond, an oxygen atom, —O—$CH_2$—, a sulfur atom, a group —NR— or a 1,1-cyclopropylene group, $R_a$ is OR or $N(R)_2$, R is a hydrogen atom or a $C_1$-$C_4$ alkyl group, and p is equal to 0, 1, 2, 3 or 4; and ii) the pharmaceutically acceptable salts of said compounds of formula (I).

According to a second feature, the invention relates to the above-mentioned compounds for their use as pharmacologically active substances.

In particular, the invention relates to the use of at least one compound of formula (I) or one of its pharmaceutically acceptable salts as active principles for the preparation of a drug to be used in therapeutics, especially for combating hypercholesterolemia, dyslipidemia, hypertriglyceridemia, obesity and the cardiovascular diseases which are the consequence of a serum lipoprotein imbalance. The compounds according to the invention are also useful as active principles of drugs for the prevention or treatment of atherosclerosis, myocardial infarction, certain inflammatory diseases, e.g. dermatitis, and neurodegeneration, e.g. Alzheimer's disease. The compounds according to the invention are also useful as active principles of drugs for the treatment of diabetes and hyperglycemia.

DETAILED DESCRIPTION

Within the framework of the present patent application:
- $C_1$-$C_4$ alkyl group is understood as meaning a saturated hydrocarbon chain having from 1 to 4 carbon atoms which is linear or branched or comprises a ring having 3 or 4 carbon atoms, e.g. a methyl, ethyl, propyl, butyl, 1-methylethyl, 1-methylpropyl, 2-methylpropyl, 1,1-dimethylethyl, cyclopropyl, methylcyclopropyl or cyclopropylmethyl group;
- partially halogenated $C_1$-$C_4$ alkyl group is understood as meaning a $C_1$-$C_4$ alkyl group as defined above in which one (or more) hydrogen atoms has (have) been replaced by a corresponding number of halogen atoms;
- $C_1$-$C_4$ alkoxy group is understood as meaning a $C_1$-$C_4$ O-alkyl group in which the $C_1$-$C_4$ alkyl group is as defined above, e.g. a methoxy, ethoxy, propoxy, butoxy, 1-methylethoxy, 1-ethylethoxy or 1- or 2-methylpropoxy group;
- totally or partially hydrogenated methoxy group is understood as meaning a methoxy group in which 1 to 3 hydrogen atoms has (have) been replaced by a corresponding number of halogen atoms, e.g. a group —O—$CH_2F$, —O—$CHF_2$ or —O—$CF_3$;
- halogen is understood as meaning a fluorine, chlorine, bromine or iodine atom, fluorine and chlorine atoms being preferred; and
- alkylene is understood as meaning a saturated hydrocarbon chain.

The compounds in which $R_a$ is OH are carboxylic acids which can be used in the form of free acids or in the form of salts, said salts being obtained by combining the acid with a pharmaceutically acceptable, non-toxic mineral or organic base. Examples of mineral bases used are sodium, potassium, magnesium and calcium hydroxides. Examples of organic bases used are amines, amino alcohols, basic amino acids such as lysine or arginine, or compounds carrying a quaternary ammonium group, such as betaine or choline.

In the group of the formula —X—[C(R)$_2$]$_p$—COR$_a$, the substituents R carried by the carbon can be identical or different. For example, one can be a hydrogen atom and the other an alkyl group, in which case the group comprises an asymmetric carbon and the compound can be either a racemic mixture of one of the two enantiomers, R or S.

The compounds according to the invention comprise an asymmetric carbon (carrying the carboxamide group bonded to the indoline group) which can be either racemic, or of R configuration or of S configuration (Fig. Ia). Of these different configurations, the preferred compounds of formula (Ia) are those in which the asymmetric carbon of the indoline group is of S configuration.

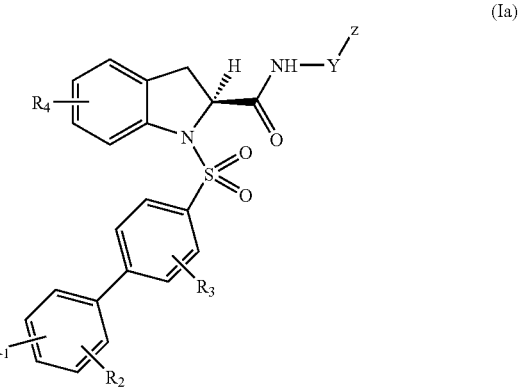

(Ia)

Other preferred compounds of formula (I) are those in which the asymmetric carbon is of S configuration and/or $R_1$ is a fluorine atom or a trifluoromethyl group.

Other preferred compounds are those in which Y is a group —$CH_2$— or a group —$(CH_2)_2$—O— and Z is an aromatic ring substituted by a group containing a carboxylic acid group, said aromatic ring optionally containing one or two other substituents selected from a halogen, a $C_1$-$C_4$ alkyl group, preferably methyl, a $C_1$-$C_4$ alkoxy group, preferably methoxy, and a trifluoromethyl group.

The compounds according to the invention can be prepared by a process that involves the steps consisting in:
a) reacting an acid of the formula

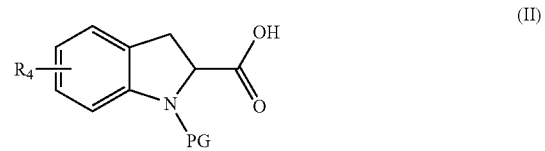

(II)

in which PG is an amino-protecting group, e.g. a Boc group (1,1-dimethylethoxycarbonyl), and $R_4$ is a hydrogen atom or a $C_1$-$C_4$ alkoxy group, with an amine of the formula

$H_2N$—Y-Z (III)

in which:
Y is a linear or branched $C_1$-$C_8$ alkylene group optionally substituted by a trifluoromethyl group or by a phenyl ring, or containing a cyclized part having 3 to 6 carbon atoms, or is a group —$(CH_2)_n$—W—,
W is an oxygen atom, a group —NH— or a sulfur atom,
n is 2, 3 or 4,
Z is an optionally partially halogenated $C_1$-$C_4$ alkyl group, trifluoromethyl, COR$_a$, $CH_2$—N(R)$_2$, or an, aromatic, heteroaromatic or heterocyclic ring selected from phenyl, pyridinyl, 1-imidazolyl, 1-piperidinyl, 4-alkyl-1-piperazinyl, 4-morpholinyl, 1-pyrrolidinyl, indolinylone and pyrrolidinylone groups, and optionally substituted by one, two or three identical or different substituents selected from a halogen, a $C_1$-$C_4$ alkyl group, $C_1$-$C_4$ alkoxy, trifluoromethyl, nitro, N(R)$_2$, —O—(CH$_2$)$_n$—N(R)$_2$, hydroxyl, cyano, C$_2$-C$_3$ cyanoalkyl, 5-oxo-1,2,4-oxadiazolidinyl and a group of the formula —X—[C(R)$_2$]$_p$—COR$_a$, X is a single bond, —O—CH$_2$—, an oxygen atom, a sulfur atom or a 1,1-cyclopropylene group, R$_a$ is OR or N(R)$_2$, R is a C$_1$-C$_4$ alkyl group, and p is equal to 0, 1, 2, 3 or 4, in an anhydrous solvent such as dichloromethane, and in the presence of a coupling agent such as EDCI (1-(3-dimethylaminopropyl)-3-ethylcarbodiimide hydrochloride), DCC (dicyclohexylcarbodiimide), either free or grafted onto a resin, or HOAT (1-hydroxy-7-azabenzotriazole), at a temperature close to room temperature, for 2 to 20 hours, to give the amide of formula (IV):

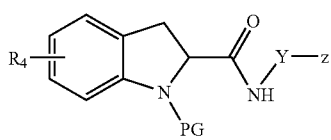

(IV)

in which Y, Z, R$_4$ and PG are as defined in the starting compounds, b) reacting the compound of formula (IV) obtained above with trifluoroacetic acid in a solvent such as dichloromethane, at room temperature, for 2 to 20 hours, to give the compound of formula (V):

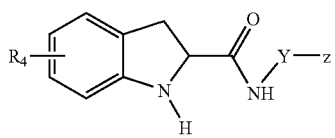

(V)

in which Y, R$_4$ and Z are as defined in the compound (IV), c) reacting the compound of formula (V) with a benzenesulfonyl chloride of formula (VI):

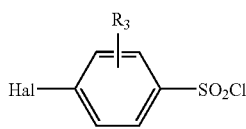

(VI)

in which:

R$_3$ is a hydrogen atom, a fluorine atom, a chlorine atom, a C$_1$-C$_4$ alkyl group or a trifluoromethyl group, and Hal is an iodine or bromine atom, in a solvent such as dichloromethane, at room temperature, for 2 to 20 hours, to give the compound of formula (VII):

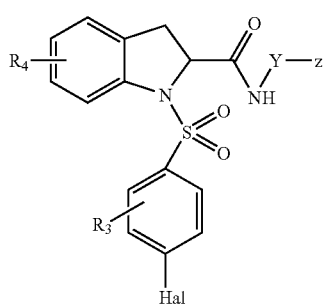

(VII)

in which Y, Z, R$_3$, R$_4$ and Hal are as defined in the starting compounds, d) reacting the compound of formula (VII) obtained above with a phenylboronic acid of the formula

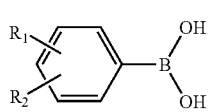

(VIII)

in which:

R$_1$ is a hydrogen atom, a fluorine or chlorine atom, a C$_1$-C$_4$ alkyl group, a C$_1$-C$_4$ alkoxy group, a trifluoromethyl group or a totally or partially halogenated methoxy group, and R$_2$ is a hydrogen atom, a fluorine atom, a chlorine atom, a C$_1$-C$_4$ alkyl group or a trifluoromethyl group, in a so-called SUZUKI reaction (cf., for example, *Chem. Rev.* 1995, 95, 2457), in the presence of an organometallic catalyst such as tetrakis(triphenylphosphine)palladium, and of a base such as sodium carbonate, in a solvent such as a mixture of glycol ether and water, at a temperature between 30° C. and the reflux temperature of the solvent, for 5 to 24 hours, to give the compound of formula I:

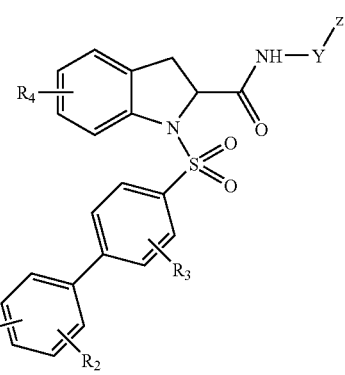

(I)

in which R$_1$, R$_2$, R$_3$, R$_4$, Y and Z are as defined in the starting compounds, e) if necessary, if the substituent Z comprises an ester group, hydrolyzing the ester group, e.g. by reaction with lithium hydroxide or sodium hydroxide if the hydrolysis can be carried out in an alkaline medium, or by reaction with trifluoroacetic acid if the ester is a t-butyl ester, to give the corresponding carboxylic acid derivative, and f) if necessary, preparing a salt of the acid obtained above with a mineral or organic base by methods well known to those skilled in the art.

As a variant of the process described above, the compounds of formula I according to the invention can be obtained by a process consisting in:

reacting a benzenesulfonyl chloride of the formula

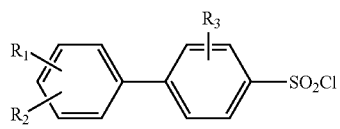
(IX)

in which:
- $R_1$ is a hydrogen atom, a halogen, a $C_1$-$C_4$ alkyl group, a $C_1$-$C_4$ alkoxy group, a trifluoromethyl group or a totally or partially halogenated methoxy group,
- $R_2$ is a hydrogen atom, a halogen, a $C_1$-$C_4$ alkyl group or a trifluoromethyl group, and
- $R_3$ is a hydrogen atom, a halogen, a $C_1$-$C_4$ alkyl group or a trifluoromethyl group, with the proviso that $R_1$, $R_2$ and $R_3$ are not simultaneously a hydrogen atom, with an indoline derivative of the formula

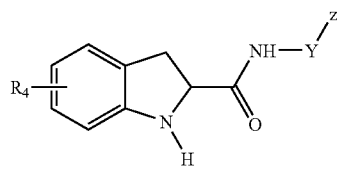
(V)

in which:
- $R_4$ is a hydrogen atom or a $C_1$-$C_4$ alkoxy group,
- Y is a linear or branched $C_1$-$C_8$ alkylene group optionally substituted by a trifluoromethyl group or by a phenyl ring, or containing a cyclized part having 3 to 6 carbon atoms, or is a group —$(CH_2)_n$—W—,
- W is an oxygen atom, a group —NH— or a sulfur atom,
- n is 2, 3 or 4,
- Z is an optionally partially halogenated $C_1$-$C_4$ alkyl group, trifluoromethyl, $COR_a$, $CH_2$—$N(R)_2$, or an aromatic, heteroaromatic or heterocyclic ring selected from phenyl, 1-pyrrolidinyl, pyrrolidinylone, 1-imidazolyl, pyridinyl, 1-piperidinyl, 4-alkyl-1-piperazinyl, pyridazinyl, 4-morpholinyl and indolinylone groups, and optionally substituted by one, two or three identical or different substituents selected from a halogen, a $C_1$-$C_4$ alkyl group, $C_1$-$C_4$ alkoxy, trifluoromethyl, nitro, $N(R)_2$, —$CH_2$—$N(R)_2$, —O—$(CH_2)_n$—$N(R)_2$, hydroxyl, cyano, $C_2$-$C_3$ cyanoalkyl and a group of the formula —X—$[C(R)_2]_p$—$COR_a$,
- X is a single bond, —O—$CH_2$—, an oxygen atom, a sulfur atom, a group —NR— or a 1,1-cyclopropylene group,
- $R_a$ is OR or $N(R)_2$,
- R is a $C_1$-$C_4$ alkyl group, and
- p is equal to 0, 1, 2, 3 or 4, in an anhydrous solvent such as dichloromethane, at room temperature, for 2 to 10 hours, to give the compound of the formula

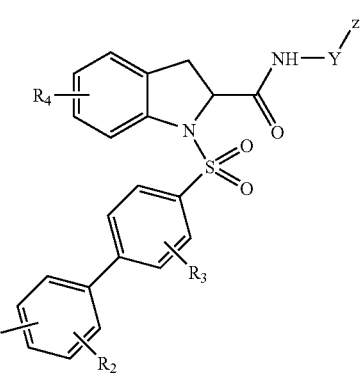
(I)

in which $R_1$, $R_2$, $R_3$, $R_4$, Y and Z are as defined in the starting compounds.

Another variant of the process for the preparation of the compounds of formula (I) involves carrying out the steps consisting in:

a) reacting a benzenesulfonyl chloride of the formula

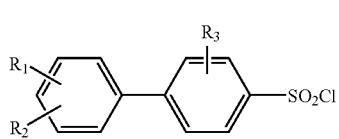
(IX)

in which:
- $R_1$ is a hydrogen atom, a halogen, a $C_1$-$C_4$ alkyl group, a $C_1$-$C_3$ alkoxy group, a trifluoromethyl group or a totally or partially halogenated methoxy group,
- $R_2$ is a hydrogen atom, a halogen, a $C_1$-$C_4$ alkyl group or a trifluoromethyl group, and
- $R_3$ is a hydrogen atom, a halogen, a $C_1$-$C_4$ alkyl group or a trifluoromethyl group, with the proviso that $R_1$, $R_2$ and $R_3$ are not simultaneously a hydrogen atom, with an indoline ester of the formula

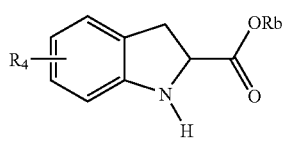
(X)

in which Rb is a $C_1$-$C_4$ alkyl group, preferably a methyl group, and $R_4$ is a hydrogen atom or a $C_1$-$C_4$ alkoxy group, under conditions analogous to those of the above process, to give the compound of the formula

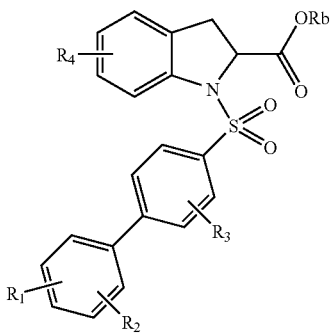

(XI)

in which $R_1$, $R_2$, $R_3$, $R_4$ and Rb are as defined in the starting compounds, b) converting the ester (XI) to the acid by reaction with a base in an aqueous-alcoholic medium, by techniques well known to those skilled in the art, to give the acid of formula (XII):

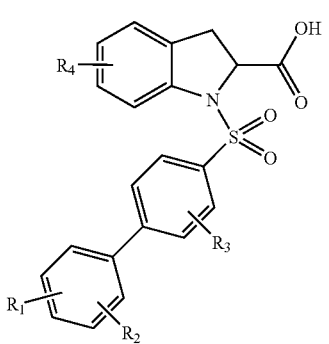

(XII)

in which $R_1$, $R_2$, $R_3$ and $R_4$ remain unchanged, and c) reacting the acid compound (XII) with a primary amine of formula (III):

NH$_2$—Y-Z    (III)

in which:

Y is a linear or branched $C_1$-$C_8$ alkylene group optionally substituted by a trifluoromethyl group or by a phenyl ring, or containing a cyclized part having 3 to 6 carbon atoms, or is a group —(CH$_2$)$_n$—W—, W is an oxygen atom, —NH— or a sulfur atom, n is 2, 3 or 4, Z is an optionally partially halogenated $C_1$-$C_4$ alkyl group, trifluoromethyl, COR$_a$, CH$_2$—N(R)$_2$, or an aromatic, heteroaromatic or heterocyclic ring selected from phenyl, pyridinyl, 1-imidazolyl, 1-piperidinyl, 4-alkyl-1-piperazinyl, pyridazinyl, 4-morpholinyl, 1-pyrrolidinyl, pyrrolidinone and indolinylone, and optionally substituted by one, two or three identical or different substituents selected from a halogen, a $C_1$-$C_4$ alkyl group, $C_1$-$C_4$ alkoxy, trifluoromethyl, nitro, N(R)$_2$, —CH$_2$—N(R)$_2$, —O—(CH$_2$)$_n$—N(R)$_2$, hydroxyl, cyano, $C_2$-$C_3$ cyanoalkyl and a group of the formula —X—[C(R)$_2$]$_p$—COR$_a$, X is a single bond, an oxygen atom, a group —O—CH$_2$—, a sulfur atom or a group —NR—, R$_a$ is OR or N(R)$_2$, R is a $C_1$-$C_3$ alkyl group, and p is equal to 0, 1, 2, 3 or 4, by a procedure analogous to that described in step (a) of the first process described above, to give the compound of formula (I):

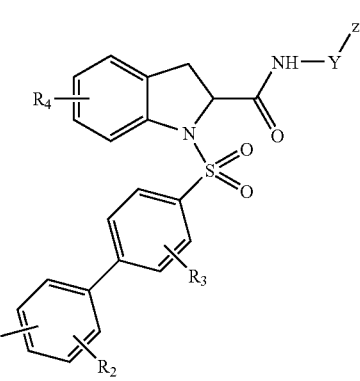

(I)

in which $R_1$, $R_2$, $R_3$, $R_4$, Y and Z are as defined in the starting compounds.

The compounds of formula (I) in which Z comprises an amino group can be obtained from their nitro homologs by means of a chemical reduction reaction or catalytic hydrogenation reaction by conventional processes well known to those skilled in the art. These compounds are also accessible from the compounds of formula I comprising a cyano group, which is reduced by processes known to those skilled in the art, especially by catalytic hydrogenation.

The compounds in which Z comprises a free NH$_2$ or NH group can also be obtained from amines or nitrogen-containing heterocycles in which the NH$_2$ or NH group has first been protected by an amino-protecting group, e.g. a Boc group (1,1-dimethylethoxycarbonyl), this amino-protecting group then being removed after the coupling reaction has been carried out to form the amide linkage —CONH— or sulfonamide linkage —SO$_2$N= of the compound of formula I.

The compounds of formula I in which the asymmetric carbon is of a given configuration, R or S, are preferably obtained from indoline-2-carboxylic acids of R or S configuration. They can also be obtained by separation from the racemic compound in a manner known per se, although this second method is generally less advantageous.

The following Examples of the preparation of compounds of formula (I) will afford a better understanding of the invention.

In these Examples, "Preparation" denotes the Examples that describe the synthesis of intermediates, and "Example" denotes those that describe the synthesis of compounds of formula (I) according to the invention. Among the abbreviations, "mmol" denotes millimol. The melting points are measured on a Koffler bench or in a capillary and the nuclear magnetic resonance spectral values are characterized by the chemical shift calculated relative to TMS, by the number of protons associated with the signal and by the shape of the signal (s for singlet, d for doublet, dd for doublet of doublets, t for triplet, q for quadruplet, m for multiplet). The operating frequency and the solvent used are indicated for each compound. Room temperature is 20° C.±2° C.

The following abbreviations are used in the description of these Examples and Preparations:

HOAT: 1-hydroxy-7-azabenzotriazole
HOBT: 1-hydroxybenzotriazole
EDCI: 1-(3-dimethylaminopropyl)-3-ethylcarbodiimide hydrochloride
DBAD: di-t-butyl azodicarboxylate
DCC: dicyclohexylcarbodiimide
DCM: dichloromethane
DIAD: diisopropyl azodicarboxylate
DME: dimethoxyethane
DMF: dimethylformamide
DMSO: dimethyl sulfoxide
MTBE: methyl t-butyl ether
TFA: trifluoroacetic acid
THF: tetrahydrofuran
$PdCl_2dppf$: dichloro-1,1'-bis(diphenylphosphino)ferrocene-palladium(II)

Preparation I

2-[[[2-(2-Fluorophenyl)ethyl]amino]carbonyl]-2,3-dihydro-(2S)-1H-indole-1-carboxylic acid 1,1-dimethylethyl ester A solution of 2 g (7.6 mmol) of 2,3-dihydro-(2S)-1H-indole-1,2-dicarboxylic acid 1-(1,1-dimethylethyl) ester in 15 ml of dichloromethane is prepared and 1.74 g (9.11 mmol) of EDCI (1-(3-dimethylaminopropyl)-3-ethylcarbodiimide hydrochloride) and 206 mg (1.52 mmol) of HOAT (1-hydroxy-7-azabenzotriazole) are then added. After stirring for 10 minutes at room temperature, 1.20 ml (9.11 mmol) of 2-fluorobenzeneethanamine are added. The reaction medium is then stirred at room temperature for 20 hours. The medium is then treated by adding dichloromethane and the organic phase is washed with water. The organic phase is dried over magnesium sulfate and then concentrated under reduced pressure. The crude product obtained is then purified by chromatography on silica gel using a dichloromethane/ethyl acetate mixture (90/10; v/v) as the eluent to give the expected product in the form of a white solid (yield=84%).
M.p.=133° C.

Preparation II

N-[2-(fluorophenyl)ethyl]-2,3-dihydro-(2S)-1H-indole-2-carboxamide

A solution of 2.38 g (6.19 mmol) of the compound obtained according to Preparation I in 25 ml of dichloromethane is prepared and 9.3 ml of trifluoroacetic acid are added. The reaction mixture is stirred at room temperature for 4 hours and the solvent is then driven off under reduced pressure. The evaporation residue is then taken up with water and the mixture is neutralized by adding saturated sodium bicarbonate solution. The white precipitate formed is filtered off and washed with water. The solid obtained is dried over phosphorus pentoxide under vacuum to give the expected compound in the form of a white solid (yield=98%).
M.p.=135° C.

Preparation III

N-[2-(2-fluorophenyl)ethyl]-2,3-dihydro-1-[(4-iodophenyl)sulfonyl]-(2S)-1H-indole-2-carboxamide A solution of 100 mg (0.351 mmol) of the compound obtained according to Preparation II in 2 ml of dichloromethane is prepared and 74 µl of triethylamine and 117 mg (0.386 mmol) of 4-iodobenzenesulfonyl chloride are added. The reaction mixture is stirred at room temperature for 4 hours. The medium is then treated by adding dichloromethane and the organic phase is washed with water, dried over magnesium sulfate and then concentrated under reduced pressure. The crude product obtained is then purified by chromatography on silica gel using a toluene/ethyl acetate mixture (90/10; v/v) as the eluent to give the expected product in the form of a colorless oil (yield=57%).
$^1$H NMR (DMSO, 300 MHz) δ: 8.26 (t, NH); 7.92 (d, 2H); 7.50 (d, 2H); 7.25 (d, 1H); 7.3-7 (m, 7H); 4.71 (dd, 1H); 3.5-3.2 (m, 2H); 3.1 (dd, 1H); 2.9-2.70 (dd and m, 3H).

EXAMPLE 1

N-[2-(2-fluorophenyl)ethyl]-2,3-dihydro-1-[[4'-(trifluoromethyl)[1,1'-biphenyl]-4-yl]sulfonyl]-(2S)-1H-indole-2-carboxamide 102 mg (0.185 mmol) of the compound obtained according to Preparation III are mixed with 2 ml of DME in a microwave reaction tube and 0.66 ml of water is added, followed by 30 mg (0.278 mmol) of sodium carbonate, 15 mg (0.0185 mmol) of $PdCl_2dppf$ {dichloro-1,1'-bis(diphenylphosphino)ferrocenepalladium(II)} and 71 mg (0.37 mmol) of 4-(trifluoromethyl)phenylboronic acid. The reaction medium is heated for 10 min at 110° C. in a microwave oven. A further 15 mg (0.0185 mmol) of dichloro-1,1'-bis(diphenylphosphino)ferrocenepalladium(II) are added and the reaction medium is heated again for 30 min at 110° C. in the microwave oven. After cooling, dichloromethane is added to the reaction medium and the organic phase is washed with sodium carbonate solution and then with water, dried over magnesium sulfate and concentrated under reduced pressure. The crude product is purified by chromatography on silica gel using a toluene/ethyl acetate mixture (9/1; v/v) as the eluent to give the product in the form of a colorless foam (yield=66%).
$^1$H NMR (DMSO, 300 MHz) δ: 8.30 (t, NH); 8.0-7.8 (m, 8H); 7.50 (d, 1H); 7.4-7.15 (m, 3H); 7.12-6.95 (m, 4H); 4.78 (dd, 1H); 3.5-3.2 (m, 2H); 3.1 (dd, 1H); 2.9-2.70 (dd and m, 3H).

EXAMPLE 2

N-[2-(2-fluorophenyl)ethyl]-2,3-dihydro-1-[[3'-(trifluoromethyl)[1,1'-biphenyl]-4-yl]sulfonyl]-(2S)-1H-indole-2-carboxamide 100 mg (0.181 mmol) of the compound obtained according to Preparation III are mixed with 2 ml of DME in a microwave reaction tube and 0.66 ml of water is added, followed by 29 mg (0.272 mmol) of sodium carbonate, 15 mg (0.0185 mmol) of $PdCl_2dppf$ and 69 mg (0.363 mmol) of 3-(trifluoromethyl)phenylboronic acid. The reaction medium is heated for 10 min at 110° C. in a microwave oven. After cooling, dichloromethane is added to the reaction medium and the organic phase is washed with sodium carbonate solution and then with water, dried over magnesium sulfate and concentrated under reduced pressure.
The crude product is purified by chromatography on silica gel using a toluene/ethyl acetate mixture (9/1; v/v) as the eluent to give the product in the form of a white foam (yield=70%).
$^1$H NMR (DMSO, 300 MHz) δ: 8.28 (t, NH); 8.1-8.0 (m, 2H); 7.93 (d, 2H); 7.86 (d, 2H); 7.85-7.60 (m, 2H); 7.50 (d, 1H); 7.30-7 (m, 7H); 4.78 (dd, 1H); 3.5-3.2 (m, 2H); 3.08 (dd, 1H); 2.9-2.70 (dd and m, 3H).

EXAMPLE 3

N-[2-(2-fluorophenyl)ethyl]-2,3-dihydro-1-[[2'-(trifluoromethyl)[1,1'-biphenyl]-4-yl]sulfonyl]-(2S)-1H-indole-2-carboxamide By following a procedure analogous to Example 2 starting from 2-(trifluoromethyl)phenylboronic acid, the expected product is obtained in the form of a pink foam (yield=67%).

$^1$H NMR (DMSO, 250 MHz) δ: 8.29 (t, NH); 7.9-7.6 (m, 5H); 7.55-7.35 (m, 4H); 7.3-7.0 (m, 7H); 4.77 (dd, 1H); 3.5-3.2 (m, 2H); 3.05-2.07 (m, 4H).

Preparation IV (2S)-2,3-dihydro-1-[[3'-(trifluoromethyl)[1,1'-biphenyl]-4-yl]sulfonyl]-1H-indole-2-carboxylic acid a) (2S)-2,3-dihydro-1-[(4-iodophenyl)sulfonyl]indole-2-carboxylic acid A mixture of 16.18 g (99.2 mmol) of (2S)-2,3-dihydroindole-2-carboxylic acid, 1700 ml of acetonitrile, 400 ml of water and 2.37 g (99.2 mmol) of lithium hydroxide is prepared. This mixture is stirred until the solids have dissolved, and 30 g (99.2 mmol) of 4-iodobenzenesulfonyl chloride are added at room temperature. The reaction medium is stirred for 15 hours at room temperature and then concentrated under reduced pressure. The evaporation residue is taken up in sodium carbonate solution and the aqueous phase obtained is washed with 200 ml of ethyl acetate and then acidified to pH 2 with hydrochloric acid. The precipitate obtained is filtered off and recrystallized from 500 ml of acetic acid to give 32 g of the expected acid in the form of beige crystals (yield=76%).

M.p.=194-198° C.

b) (2S)-2,3-dihydro-1-[[3'-(trifluoromethyl)[1,1'-biphenyl]-4-yl]sulfonyl]-1H-indole-2-carboxylic acid A mixture of 20 g (46.6 mmol) of the acid obtained above, 1700 ml of acetonitrile, 9.73 g (51.2 mmol) of 3-(trifluoromethyl)phenylboronic acid, 190 ml of water, 14.81 g (139.8 mmol) of sodium carbonate and 1.04 g (4.6 mmol) of palladium acetate is prepared. This mixture is stirred for 3 hours at room temperature. 400 ml of ethyl acetate are then added and the medium is acidified to pH 3 with N hydrochloric acid solution. The organic phase is separated off, washed with water and then dried over magnesium sulfate and concentrated under reduced pressure. The crude product is taken up in 200 ml of a hot acetic acid/water mixture. After cooling, the crystals formed are filtered off and dried to give 19.2 g of the expected acid in the form of beige crystals (yield=92%).

M.p.=108-112° C.

EXAMPLE 4

3-[2-[[[(2S)-2,3-dihydro-1-[[3'-(trifluoromethyl)[1,1'-biphenyl]-4-yl]sulfonyl]-1H-indol-2-yl]carbonyl]amino]ethyl]benzoic acid methyl ester By following a procedure analogous to Preparation I starting from the acid obtained according to Preparation IV and the methyl ester of 3-(2-aminoethyl)benzoic acid, the expected product is obtained in the form of a white foam (yield=48%).

$^1$H NMR (DMSO, 300 MHz) δ: 8.23 (t, NH); 8.1-7.6 (m, 10H); 7.55-7.35 (m, 3H); 7.3-7.0 (m, 3H); 4.78 (dd, 1H); 3.5-3.2 (m, 2H); 3.07 (dd, 1H); 2.95-2.75 (m, 3H).

EXAMPLE 5

3-[2-[[[(2S)-2,3-dihydro-1-[[3'-(trifluoromethyl)[1,1'-biphenyl]-4-yl]sulfonyl]-1H-indol-2-yl]carbonyl]amino]ethyl]benzoic acid 663 mg (1.08 mmol) of the ester obtained according to Example 4 are mixed with 5 ml of tetrahydrofuran and 5 ml of water, and 104 mg (4.35 mmol) of lithium hydroxide are added at room temperature, with stirring. This reaction mixture is stirred at room temperature for 24 hours and then acidified to pH 3 with N acetic acid solution, diluted with water and then extracted with ethyl acetate. The combined organic phases are dried over magnesium sulfate and concentrated under reduced pressure to give the expected product in the form of a white foam (yield=75%).

$^1$H NMR (DMSO, 250 MHz) δ: 13 (bs, CO$_2$H); 8.25 (t, NH); 8.1-7.65 (m, 10H); 7.55-7.30 (m, 3H); 7.3-6.95 (m, 3H); 4.78 (dd, 1H); 3.5-3.2 (m, 2H); 3.08 (dd, 1H); 2.95-2.70 (m, 3H).

EXAMPLE 6

2,3-Dihydro-N-[(1-phenylcyclohexyl)methyl]-1-[[3'-(trifluoromethyl)[1,1'-biphenyl]-4-yl]sulfonyl]-(2S)-1H-indole-2-carboxamide By following a procedure analogous to Example 4 starting from 1-phenylcyclohexanemethanamine, the expected product is obtained in the form of a white foam (yield=33%).

$^1$H NMR (DMSO, 250 MHz) δ: 8.05-8.0 (m, 2H); 7.93 (d, 2H); 7.86 (d, 2H); 7.82-7.67 (m, 2H); 7.47-7.38 (m, 1H and NH); 7.37-7.30 (m, 4H); 7.28-7.17 (m, 2H); 7.11 (d, 1H); 7.02 (td, 1H); 4.87 (dd, 1H); 3.5-3.1 (m, 2H); 3.02 (dd, 1H); 2.73 (dd, 1H); 2.15-2.0 (m, 2H); 1.7-1.1 (m, 8H).

Preparation V 2,3-Dihydro-1-[[2'-(trifluoromethyl)[1,1'-biphenyl]-4-yl]sulfonyl]-(2S)-1H-indole-2-carboxylic acid A solution of 2.15 g (4.66 mmol) of the 2,3-dihydro-1-[(4-iodophenyl)sulfonyl]-(2S)-1H-indole-2-carboxylic acid obtained according to Preparation IV(a) in 40 ml of DME is prepared and 13 ml of water are added, followed by 1.24 g (11.6 mmol) of sodium carbonate, 380 mg (0.46 mmol) of PdCl$_2$dppf and 1.77 g (9.3 mmol) of 2-(trifluoromethyl)phenylboronic acid. The reaction medium is stirred at room temperature for 30 min and then at 90° C. for 30 min. After cooling, water is added and the medium is acidified with N hydrochloric acid. The mixture is then extracted with ethyl acetate. The organic phase obtained is washed with water, dried over magnesium sulfate and concentrated under reduced pressure. The crude product is purified by reversed phase chromatography on RP18-grafted silica gel using an acetonitrile/water/trifluoroacetic acid mixture (8/2/0.02; v/v/v) as the eluent to give the product in the form of an orange oil (yield=80%).

$^1$H NMR (CDCl$_3$, 250 MHz) δ: 7.8-7.7 (m, 3H); 7.65 (d, 1H); 7.65-7.45 (m, 2H); 7.38 (d, 2H); 7.3-7.2 (m, 2H); 7.15-7.0 (m, 2H); 4.84 (dd, 1H); 3.23 (dd, 1H); 3.09 (dd, 1H).

Preparation VI 2,3-Dihydro-1-[[2'-(trifluoromethyl)[1,1'-biphenyl]-4-yl]sulfonyl]-(2S)-1H-indole-2-carboxylic acid chloride 1.57 g (3.5 mmol) of the acid obtained according to Preparation V are dissolved in 10 ml of toluene. 1 drop of DMF is added at room temperature and a solution of 0.603 ml (7.02 mmol) of oxalyl chloride in 5 ml of toluene is then added dropwise. The reaction medium is stirred for 30 min at room temperature. Toluene is added and the reaction medium is concentrated under reduced pressure to drive off the excess oxalyl chloride. The expected product is thus obtained in the form of a brown oil (yield=92%).

$^1$H NMR (CDCl$_3$, 250 MHz) δ: 7.85-7.65 (m, 3H); 7.60-7.45 (m, 3H); 7.45-7.35 (d, 2H); 7.3-7 (m, 4H); 5.11 (dd, 1H); 3.35-3.2 (m, 2H).

EXAMPLE 7

2,3-Dihydro-N-[2-(1-piperidinyl)ethyl]-1-[[2'-(trifluoromethyl)[1,1'-biphenyl]-4-yl]sulfonyl]-(2S)-1H-indole-2-carboxamide 168 mg (0.644 mmol) of DIEA resin (polystyrene resin grafted with a 4-(diisopropylaminomethyl)phenyl group) are mixed with 2 ml of dichloromethane in a syringe and the resin is left to swell. The resin is filtered off and then rinsed with dichloromethane. 1 ml of dichloromethane is then added to this resin, followed by 27.5 mg (0.214 mmol) of 1-piperidinethanamine and 100 mg (0.214 mmol) of the acid chloride obtained according to Preparation VI in 2 ml of dichloromethane. The reaction medium is stirred for 1 h at room temperature and then filtered and the resin is washed with dichloromethane. The filtrates are combined and concentrated under reduced pressure. The crude product is purified by chromatography on silica gel using a dichloromethane/ethanol mixture (95/5; v/v) as the eluent to give the product in the form of a colorless oil (yield=49%).

$^1$H NMR (DMSO, 300 MHz) δ: 8.04 (t, NH); 7.95-7.60 (m, 5H); 7.55-7.45 (m, 3H); 7.39 (d, 1H); 7.24 (t, 1H); 7.14 (d, 1H); 7.05 (t, 1H); 4.84 (dd, 1H); 3.4-3.05 (m, 2H); 2.98 (d, 2H); 2.45-2.2 (m, 6H); 1.6-1.25 (m, 6H).

The compounds below are obtained by following a procedure analogous to Example 7 starting from known amines:

EXAMPLE 8

2,3-Dihydro-N-[3-(1-pyrrolidinyl)propyl]-1-[[2'-(trifluoromethyl)[1,1'-biphenyl]-4-yl]sulfonyl]-(2S)-1H-indole-2-carboxamide Yield=68%; colorless foam.

$^1$H NMR (DMSO, 300 MHz) δ: 8.45 (t, NH); 7.95-7.8 (m, 3H); 7.8-7.6 (m, 2H); 7.5-7.45 (m, 3H); 7.40 (d, 1H); 7.25 (t, 1H); 7.15 (d, 1H); 7.05 (t, 1H); 4.79 (dd, 1H); 3.5-2.8 (m, 10H); 2-1.7 (m, 6H).

EXAMPLE 9

2,3-Dihydro-N-[3-(2-methyl-1-piperidinyl)propyl]-1-[[2'-(trifluoromethyl)[1,1'-biphenyl]-4-yl]sulfonyl]-(2S)-1H-indole-2-carboxamide Yield=75%; colorless foam.

$^1$H NMR (DMSO, 300 MHz) δ: 8.0 (bs, NH); 7.95-7.8 (m, 3H); 7.8-7.6 (m, 2H); 7.5-7.45 (m, 3H); 7.36 (d, 1H); 7.24 (t, 1H); 7.15 (d, 1H); 7.05 (t, 1H); 4.82 (dd, 1H); 3.4-2.6 (m, 9H); 2-1.35 (m, 8H); 1.22 (d, CH$_3$).

EXAMPLE 10

2,3-Dihydro-N-[4-(1-pyrrolidinyl)butyl]-1-[[2'-(trifluoromethyl)[1,1'-biphenyl]-4-yl]sulfonyl]-(2S)-1H-indole-2-carboxamide Yield=72%; colorless foam.

$^1$H NMR (DMSO, 300 MHz) δ: 8.31 (t, NH); 7.9-7.8 (m, 3H); 7.8-7.6 (m, 2H); 7.55-7.45 (m, 3H); 7.40 (d, 1H); 7.25 (t, 1H); 7.15 (d, 1H); 7.06 (t, 1H); 4.81 (dd, 1H); 3.4-2.8 (m, 10H); 2-1.8 (m, 4H); 1.75-1.4 (m, 4H).

EXAMPLE 11

2,3-Dihydro-N-[2-(4-morpholinyl)ethyl]-1-[[2'-(trifluoromethyl)[1,1'-biphenyl]-4-yl]sulfonyl]-(2S)-1H-indole-2-carboxamide Yield=81%; colorless foam.

$^1$H NMR (DMSO, 300 MHz) δ: 8.08 (t, NH); 7.9-7.8 (m, 3H); 7.8-7.6 (m, 2H); 7.55-7.45 (m, 3H); 7.39 (d, 1H); 7.25 (t, 1H); 7.15 (d, 1H); 7.05 (t, 1H); 4.85 (t, 1H); 3.54 (t, 4H); 3.4-3.1 (m, 2H); 2.98 (d, 2H); 2.45-2.25 (m, 6H).

EXAMPLE 12

2,3-Dihydro-N-[3-(4-methyl-1-piperazinyl)propyl]-1-[[2'-(trifluoromethyl)[1,1'-biphenyl]-4-yl]sulfonyl]-(2S)-1H-indole-2-carboxamide Yield=70%; colorless foam.

$^1$H NMR (DMSO, 300 MHz) δ: 8.17 (t, NH); 7.9-7.8 (m, 3H); 7.8-7.6 (m, 2H); 7.55-7.45 (m, 3H); 7.39 (d, 1H); 7.24 (t, 1H); 7.14 (d, 1H); 7.04 (t, 1H); 4.79 (dd, 1H); 3.2-2.85 (m, 4H); 2.5-2.1 (m, 10H); 2.20 (s, CH$_3$); 1.65-1.50 (m, 2H).

EXAMPLE 13

2,3-Dihydro-N-[3-(methoxy)propyl]-1-[[2'-(trifluoromethyl)[1,1'-biphenyl]-4-yl]sulfonyl]-(2S)-1H-indole-2-carboxamide Yield=30%; colorless oil.

$^1$H NMR (DMSO, 300 MHz) δ: 8.19 (t, NH); 7.9-7.8 (m, 3H); 7.8-7.6 (m, 2H); 7.55-7.45 (m, 3H); 7.40 (d, 1H); 7.24 (t, 1H); 7.14 (d, 1H); 7.04 (t, 1H); 4.79 (dd, 1H); 3.4-3.25 (m, 2H); 3.22 (s, 3H); 3.25-3.10 (m, 2H); 3.10-2.90 (m, 2H); 1.75-1.60 (m, 2H).

EXAMPLE 14

2,3-Dihydro-N-[3-(2-oxo-1-pyrrolidinyl)propyl]-1-[[2'-(trifluoromethyl)[1,1'-biphenyl]-4-yl]sulfonyl]-(2S)-1H-indole-2-carboxamide Yield=36%; colorless oil.

$^1$H NMR (DMSO, 300 MHz) δ: 8.24 (t, NH); 7.9-7.8 (m, 3H); 7.8-7.6 (m, 2H); 7.55-7.45 (m, 3H); 7.40 (d, 1H); 7.24 (t, 1H); 7.14 (d, 1H); 7.04 (t, 1H); 4.79 (dd, 1H); 3.4-3.25 (m, 2H); 3.25-2.9 (m, 6H); 2.20 (t, 2H); 1.91 (quint, 2H); 1.61 (quint, 2H).

EXAMPLE 15

2,3-Dihydro-N-[2,2,2-trifluoroethyl]-1-[[2'-(trifluoromethyl)[1,1'-biphenyl]-4-yl]sulfonyl]-(2S)-1H-indole-2-carboxamide Yield=30%; colorless oil.
$^1$H NMR (DMSO, 300 MHz) δ: 8.88 (t, NH); 7.9-7.8 (m, 3H); 7.8-7.6 (m, 2H); 7.55-7.45 (m, 3H); 7.40 (d, 1H); 7.25 (t, 1H); 7.14 (d, 1H); 7.06 (t, 1H); 4.95 (dd, 1H); 4.15-3.8 (m, 2H); 3.13 (dd, 1H); 2.91 (dd, 1H).

EXAMPLE 16

2,3-Dihydro-N-[3-(1H-imidazol-1-yl)propyl]-1-[[2'-(trifluoromethyl)[1,1'-biphenyl]-4-yl]sulfonyl]-(2S)-1H-indole-2-carboxamide Yield=36%; colorless oil.
$^1$H NMR (DMSO, 300 MHz) δ: 8.33 (t, NH); 7.9-7.8 (m, 3H); 7.8-7.6 (m, 2H); 7.58 (s, 1H); 7.55-7.45 (m, 3H); 7.40 (d, 1H); 7.25 (t, 1H); 7.2-7.1 (m, 2H); 7.06 (t, 1H); 6.88 (s, 1H); 4.79 (dd, 1H); 3.97 (t, 2H); 3.2-2.9 (m, 4H); 1.88 (quint, 2H).

EXAMPLE 17

4-[[[[(2S)-2,3-dihydro-1-[[2'-(trifluoromethyl)[1,1'-biphenyl]-4-yl]sulfonyl]-1H-indol-2-yl]carbonyl]amino]methyl]benzoic acid 304 mg (2.01 mmol) of 4-(aminomethyl)benzoic acid are mixed with 25 ml of acetonitrile, 7.3 ml of water and 4.8 ml of triethylamine. The reaction medium is clear. 624 mg (1.34 mmol) of the acid chloride obtained according to Preparation VI, dissolved in 4.8 ml of dichloromethane, are then added. The reaction mixture is stirred at room temperature for 1 hour and the solvents are then evaporated off under reduced pressure. The residual crude product is then taken up with ethyl acetate and the organic phase is washed with water. Animal charcoal is then added and the organic phase is filtered on a silica plug. The filtrate is then concentrated under reduced pressure to give the expected product in the form of a white foam (yield=66%).
$^1$H NMR (DMSO, 250 MHz) δ: 8.85 (t, NH); 7.9-7.8 (m, 5H); 7.8-7.6 (m, 2H); 7.55-7.45 (m, 3H); 7.45-7.35 (m, 3H); 7.26 (t, 1H); 7.15 (d, 1H); 7.07 (t, 1H); 4.91 (dd, 1H); 4.40 (t, 2H); 3.2-2.9 (m, 2H).

The compounds below are obtained by following a procedure analogous to Example 17 starting from known amines:

EXAMPLE 18

4-[2-[[[(2S)-2,3-dihydro-1-[[2'-(trifluoromethyl)[1,1'-biphenyl]-4-yl]sulfonyl]-1H-indol-2-yl]carbonyl]amino]ethoxy]benzoic acid Yield=56%; white foam.
M.p.=cakes at 94° C.

EXAMPLE 19

5-[[[(2S)-2,3-dihydro-1-[[2'-(trifluoromethyl)[1,1'-biphenyl]-4-yl]sulfonyl]-1H-indol-2-yl]carbonyl]amino]pentanoic acid Yield=23%; colorless oil.
$^1$H NMR (DMSO, 250 MHz) δ: 12.1-11.9 (bs, COOH); 8.18 (t, NH); 7.9-7.8 (m, 3H); 7.8-7.6 (m, 2H); 7.55-7.45 (m, 3H); 7.40 (d, 1H); 7.24 (t, 1H); 7.13 (d, 1H); 7.05 (t, 1H); 4.79 (dd, 1H); 3.25-2.85 (m, 4H); 2.22 (t, 2H); 1.6-1.3 (m, 4H).

EXAMPLE 20

2,3-Dihydro-N-[4,4,4-trifluorobutyl]-1-[[2'-(trifluoromethyl)[1,1'-biphenyl]-4-yl]sulfonyl]-(2S)-1H-indole-2-carboxamide Yield=29%; colorless oil.
$^1$H NMR (DMSO, 250 MHz) δ: 8.34 (t, NH); 7.9-7.8 (m, 3H); 7.8-7.6 (m, 2H); 7.55-7.45 (m, 3H); 7.40 (d, 1H); 7.24 (t, 1H); 7.14 (d, 1H); 7.04 (td, 1H); 4.78 (dd, 1H); 3.20 (q, 2H); 3.07 (dd, 1H); 2.94 (dd, 1H); 2.4-2.1 (m, 2H); 1.75-1.60 (m, 2H).

EXAMPLE 21

4-[[[[(2S)-2,3-dihydro-1-[[2'-(trifluoromethyl)[1,1'-biphenyl]-4-yl]sulfonyl]-1H-indol-2-yl]carbonyl]amino]methyl]benzeneacetic acid methyl ester A solution of 500 mg (1.11 mmol) of the acid obtained according to Preparation V in 6 ml of dichloromethane is prepared and 235 mg (1.23 mmol) of EDCI, 167 mg (1.23 mmol) of HOAT and 0.343 ml (2.46 mmol) of triethylamine are then added. After stirring for 10 minutes at room temperature, 265 mg (1.23 mmol) of the methyl ester of 4-(aminomethyl)benzeneacetic acid are added. The reaction medium is then stirred at room temperature for 2 hours 30 minutes. The medium is then treated by adding dichloromethane and the organic phase is washed with water and then dried over magnesium sulfate and concentrated under reduced pressure. The crude product obtained is then purified by chromatography on silica gel using a dichloromethane/ethyl acetate mixture (98/2; v/v) as the eluent to give the expected product in the form of a colorless oil (yield=59%).
$^1$H NMR (DMSO, 300 MHz) δ: 8.74 (t, NH); 7.9-7.8 (m, 3H); 7.8-7.6 (m, 2H); 7.55-7.45 (m, 3H); 7.40 (d, 1H); 7.3-7.1 (m, 6H); 7.05 (t, 1H); 4.89 (dd, 1H); 4.31 (t, 2H); 3.64 (s, CH$_2$); 3.60 (s, CH$_3$); 3.15-2.9 (m, 2H).

EXAMPLE 22

4-[[[[(2S)-2,3-dihydro-1-[[2'-(trifluoromethyl)[1,1'-biphenyl]-4-yl]sulfonyl]-1H-indol-2-yl]carbonyl]amino]methyl]benzeneacetic acid 379 mg (0.622 mmol) of the ester obtained according to Example 21 are mixed with 5 ml of tetrahydrofuran and 2 ml of water, and 60 mg (2.49 mmol) of lithium hydroxide are added at room temperature, with stirring. This reaction mixture is stirred at room temperature for 4 hours, then acidified to pH 3-4 with hydrochloric acid solution, diluted with water and then extracted with ethyl acetate. The combined organic phases are dried over magnesium sulfate and concentrated under reduced pressure to give the expected product in the form of a colorless oil (yield=93%).
$^1$H NMR (DMSO, 250 MHz) δ: 8.72 (t, NH); 7.9-7.8 (m, 3H); 7.8-7.6 (m, 2H); 7.55-7.45 (m, 3H); 7.40 (d, 1H); 7.3-7.1 (m, 6H); 7.05 (t, 1H); 4.89 (dd, 1H); 4.31 (t, 2H); 3.53 (s, CH$_2$); 3.15-2.9 (m, 2H).

EXAMPLE 23

2,3-Dihydro-1-[[2'-(trifluoromethyl)[1,1'-biphenyl]-4-yl]sulfonyl]-N-[3,3,3-trifluoropropyl]-(2S)-1H-indole-2-carboxamide By following a procedure analogous to Example 21 starting from 3,3,3-trifluoropropanamine, the expected compound is obtained in the form of a colorless oil (yield=84%).

$^1$H NMR (DMSO, 250 MHz) δ: 8.42 (t, NH); 7.9-7.6 (m, 5H); 7.55-7.45 (m, 3H); 7.40 (d, 1H); 7.25 (t, 1H); 7.14 (d, 1H); 7.6 (t, 1H); 4.81 (dd, 1H); 3.5-3.25 (m, 2H); 3.15-2.85 (m, 2H); 2.55-2.3 (m, 2H).

EXAMPLE 24

4-[2-[[[(2S)-2,3-dihydro-1-[[2'-(trifluoromethyl)[1,1'-biphenyl]-4-yl]sulfonyl]-1H-indol-2-yl]carbonyl]amino]ethyl]benzeneacetic acid 1,1-dimethylethyl ester By following a procedure analogous to Example 21 starting from the t-butyl ester of 4-(2-aminoethyl)benzeneacetic acid, the expected compound is obtained in the form of a white foam (yield=60%).

$^1$H NMR (DMSO, 250 MHz) δ: 8.22 (t, NH); 7.9-7.6 (m, 5H); 7.55-7.45 (m, 3H); 7.39 (d, 1H); 7.25 (t, 1H); 7.2-7.0 (m, 6H); 4.78 (dd, 1H); 3.49 (s, 2H); 3.4-3.2 (m, 2H); 3.05-2.8 (m, 2H); 2.71 (t, 2H); 1.39 (s, 9H).

EXAMPLE 25

4-[2-[[[(2S)-2,3-dihydro-1-[[2'-(trifluoromethyl)[1,1'-biphenyl]-4-yl]sulfonyl]-1H-indol-2-yl]carbonyl]amino]ethyl]benzeneacetic acid A solution of 541 mg (0.813 mmol) of the ester obtained according to Example 24 in 5 ml of dichloromethane is prepared. 1.2 ml of trifluoroacetic acid are added at room temperature. The reaction medium is stirred for 4 hours at room temperature and then concentrated under reduced pressure and taken up with ethyl acetate. The organic phase is washed with 10% sodium carbonate solution and then with water. The aqueous phases are extracted 3 times with dichloromethane. The combined organic phases are dried over magnesium sulfate and concentrated under reduced pressure to give the expected product in the form of a white solid (yield=89%).

M.p.=152° C.

EXAMPLE 26

3-[2-[[[(2S)-2,3-dihydro-1-[[2'-(trifluoromethyl)[1,1'-biphenyl]-4-yl]sulfonyl]-1H-indol-2-yl]carbonyl]amino]ethyl]benzeneacetic acid 1,1-dimethylethyl ester By following a procedure identical to Example 21 starting from the t-butyl ester of 3-(2-aminoethyl)benzeneacetic acid, the expected compound is obtained in the form of a white foam (yield=80%).

$^1$H NMR (DMSO, 300 MHz) δ: 8.25 (t, NH); 7.9-7.8 (m, 3H); 7.8-7.6 (m, 2H); 7.55-7.45 (m, 3H); 7.40 (d, 1H); 7.3-7.15 (m, 2H); 7.15-7 (m, 5H); 4.80 (dd, 1H); 3.51 (s, 2H); 3.45-3.20 (m, 2H); 2.98 (dd, 1H); 2.88 (dd, 1H); 2.72 (t, 2H); 1.39 (s, 9H).

EXAMPLE 27

3-[2-[[[(2S)-2,3-dihydro-1-[[2'-(trifluoromethyl)[1,1'-biphenyl]-4-yl]sulfonyl]-1H-indol-2-yl]carbonyl]amino]ethyl]benzeneacetic acid By following a procedure identical to Example 25 starting from the ester obtained according to Example 26, the expected compound is obtained in the form of a white solid (yield=95%).

M.p.=78° C.

EXAMPLE 28

6-[[[(2S)-2,3-dihydro-1-[[2'-(trifluoromethyl)[1,1'-biphenyl]-4-yl]sulfonyl]-1H-indol-2-yl]carbonyl]amino]hexanoic acid methyl ester By following a procedure analogous to Preparation I starting from the acid obtained according to Preparation V and the methyl ester of 6-aminohexanoic acid, the expected compound is obtained in the form of a colorless oil (yield=83%).

$^1$H NMR (DMSO, 250 MHz) δ: 8.15 (t, NH); 7.9-7.8 (m, 3H); 7.8-7.6 (m, 2H); 755-7.45 (m, 3H); 7.40 (d, 1H); 7.24 (t, 1H); 7.14 (d, 1H); 7.05 (t, 1H); 4.79 (dd, 1H); 3.57 (s, CH$_3$); 3.2-2.85 (m, 4H); 2.27 (t, 2H); 1.6-1.35 (m, 4H); 1.35-1.15 (m, 2H).

EXAMPLE 29

6-[[[(2S)-2,3-dihydro-1-[[2'-(trifluoromethyl)[1,1'-biphenyl]-4-yl]sulfonyl]-1H-indol-2-yl]carbonyl]amino]hexanoic acid By following a procedure analogous to Example 22 starting from the ester obtained according to Example 28, the expected compound is obtained in the form of a colorless oil (yield=83%).

$^1$H NMR (DMSO, 250 MHz) δ: 8.15 (t, NH); 7.9-7.8 (m, 3H); 7.8-7.6 (m, 2H); 7.55-7.45 (m, 3H); 7.40 (d, 1H); 7.24 (t, 1H); 7.14 (d, 1H); 7.05 (t, 1H); 4.79 (dd, 1H); 3.2-2.85 (m, 4H); 2.17 (t, 2H); 1.6-1.1 (m, 6H).

EXAMPLE 30

2,3-Dihydro-N-[4-(dimethylamino)butyl]-1-[[2'-(trifluoromethyl)[1,1'-biphenyl]-4-yl]sulfonyl]-(2S)-1H-indole-2-carboxamide By following a procedure analogous to Example 28 starting from N,N-dimethylbutanediamine, the expected compound is obtained in the form of a colorless oil (yield=27%).

$^1$H NMR (DMSO, 300 MHz) δ: 8.18 (t, NH); 7.9-7.8 (m, 3H); 7.8-7.6 (m, 2H); 7.55-7.45 (m, 3H); 7.40 (d, 1H); 7.24 (t, 1H); 7.14 (d, 1H); 7.05 (t, 1H); 4.79 (dd, 1H); 3.2-2.85 (m, 4H); 2.16 (t, 2H); 2.08 (s, 6H); 1.5-1.3 (m, 4H).

EXAMPLE 31

4-[[[(2S)-2,3-dihydro-1-[[2'-(trifluoromethyl)[1,1'-biphenyl]-4-yl]sulfonyl]-1H-indol-2-yl]carbonyl]amino]butanoic acid methyl ester By following a procedure analogous to Example 28 starting from the methyl ester of 4-aminobutanoic acid, the expected compound is obtained in the form of a colorless oil (yield=33%).

¹H NMR (DMSO, 300 MHz) δ: 8.26 (t, NH); 7.9-7.8 (m, 3H); 7.8-7.6 (m, 2H); 7.55-7.45 (m, 3H); 7.40 (d, 1H); 7.24 (t, 1H); 7.14 (d, 1H); 7.05 (t, 1H); 4.77 (dd, 1H); 3.58 (s, CH₃); 3.2-2.85 (m, 4H); 2.33 (t, 2H); 1.70 (quint, 2H).

EXAMPLE 32

4-[[[(2S)-2,3-dihydro-1-[[2'-(trifluoromethyl)[1,1'-biphenyl]-4-yl]sulfonyl]-1H-indol-2-yl]carbonyl]amino]butanoic acid By following a procedure analogous to Example 22 starting from the ester obtained according to Example 31, the expected compound is obtained in the form of a colorless oil (yield=57%).

¹H NMR (DMSO, 250 MHz) δ: 8.24 (t, NH); 7.9-7.8 (m, 3H); 7.8-7.6 (m, 2H); 7.55-7.45 (m, 3H); 7.40 (d, 1H); 7.24 (td, 1H); 7.14 (d, 1H); 7.04 (td, 1H); 4.78 (dd, 1H); 3.2-3 (m, 3H); 2.93 (dd, 1H); 2.23 (t, 2H); 1.67 (quint, 2H).

Preparation VIIa

4-[2-[[[(2S)-2,3-dihydro-1-[(4-iodophenyl)sulfonyl]-1H-indol-2-yl]carbonyl]-amino]ethoxy]benzeneacetic acid methyl ester By following a procedure analogous to Preparation I starting from the acid obtained according to Preparation IV(a) and the methyl ester of 4-(2-aminoethoxy)benzeneacetic acid, the expected compound is obtained in the form of a white oil (yield=65%).

¹H NMR (DMSO, 250 MHz) δ: 8.38 (t, NH); 7.93 (dd, 2H); 7.54 (dd, 2H); 7.41 (d, 1H); 7.25-7.10 (m, 4H); 7.02 (td, 1H); 6.89 (dd, 2H); 4.82 (dd, 1H); 4.1-3.9 (m, 2H); 3.60 (s, 5H); 3.6-3.3 (m, 2H); 3.13 (dd, 1H); 2.91 (dd, 1H).

Preparation VIIb

4-[2-[[[(2S)-2,3-dihydro-1-[(4-iodophenyl)sulfonyl]-1H-indol-2-yl]carbonyl]-amino]ethoxy]benzeneacetic acid By following a procedure analogous to Example 22 starting from the ester obtained according to Preparation VIIa, the expected compound is obtained in the form of a white foam (yield=96%).

¹H NMR (DMSO, 250 MHz) δ: 12.2 (bs, COOH); 8.41 (t, NH); 7.93 (dd, 2H); 7.54 (dd, 2H); 7.41 (d, 1H); 7.25-7.10 (m, 4H); 7.02 (td, 1H); 6.88 (dd, 2H); 4.82 (dd, 1H); 4.1-3.9 (m, 2H); 3.48 (s, 2H); 3.6-3.2 (m, 2H); 3.13 (dd, 1H); 2.91 (dd, 1H).

EXAMPLE 33

4-[2-[[[(2S)-2,3-dihydro-1-[[2'-(trifluoromethyl)[1,1'-biphenyl]-4-yl]sulfonyl]-1H-indol-2-yl]carbonyl]amino]ethoxy]benzeneacetic acid By following a procedure analogous to Example 1 starting from the acid obtained according to Preparation VIIb and 2-(trifluoromethyl)phenylboronic acid, the expected compound is obtained in the form of a beige foam (yield=78%).

¹H NMR (DMSO, 300 MHz) δ: 8.42 (t, NH); 7.9-7.8 (m, 3H); 7.8-7.6 (m, 2H); 7.55-7.45 (m, 3H); 7.39 (d, 1H); 7.24 (t, 1H); 7.2-7.1 (m, 3H); 7.05 (t, 1H); 6.87 (d, 2H); 4.88 (dd, 1H); 4.1-3.9 (m, 2H); 3.6-3.15 (m, 2H); 3.45 (s, 2H); 3.2-2.85 (m, 2H).

EXAMPLE 34

4-[2-[[[(2S)-1-[[4'-chloro-3'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 33 starting from 4-chloro-3-(trifluoromethyl)phenylboronic acid, the expected compound is obtained in the form of a beige foam (yield=54%).

¹H NMR (DMSO, 300 MHz) δ: 8.43 (t, NH); 8.10 (d, 1H); 8.02 (dd, 1H); 8.00-7.8 (m, 5H); 7.48 (d, 1H); 7.24 (t, 1H); 7.2-7.1 (m, 3H); 7.03 (t, 1H); 6.89 (d, 2H); 4.89 (dd, 1H); 4.01 (t, 2H); 3.65-3.3 (m, 2H); 3.48 (s, 2H); 3.15 (dd, 1H); 2.93 (dd, 1H).

EXAMPLE 35

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 33 starting from 2-chloro-5-(trifluoromethyl)phenylboronic acid, the expected compound is obtained in the form of a beige foam (yield=37%).

¹H NMR (DMSO, 300 MHz) δ: 8.43 (t, NH); 7.91 (d, 1H); 7.85-7.75 (m, 3H); 7.68 (d, 2H); 7.48 (d, 1H); 7.24 (t, 1H); 7.2-7.1 (m, 3H); 7.04 (t, 1H); 6.88 (d, 2H); 4.89 (dd, 1H); 4.01 (t, 2H); 3.65-3.3 (m, 2H); 3.48 (s, 2H); 3.16 (dd, 1H); 2.94 (dd, 1H).

EXAMPLE 36

4-[2-[[[(2S)-1-[[3'-chloro-4'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 33 starting from 3-chloro-4-(trifluoromethyl)phenylboronic acid, the expected compound is obtained in the form of a beige foam (yield=60%).

¹H NMR (DMSO, 300 MHz) δ: 8.42 (t, NH); 8.10 (d, 1H); 8.02 (dd, 1H); 7.95 (d, 2H); 7.89 (d, 2H); 7.83 (d, 1H); 7.48 (d, 1H); 7.24 (t, 1H); 7.2-7.1 (m, 3H); 7.02 (t, 1H); 6.89 (d, 2H); 4.89 (dd, 1H); 4.01 (t, 2H); 3.65-3.3 (m, 2H); 3.48 (s, 2H); 3.15 (dd, 1H); 2.94 (dd, 1H).

EXAMPLE 37

4-[2-[[[(2S)-2,3-dihydro-1-[[2'-(trifluoromethoxy)[1,1'-biphenyl]-4-yl]sulfonyl]-1H-indol-2-yl]carbonyl]amino]ethoxy]benzeneacetic acid By following a procedure analogous to Example 33 starting from 2-(trifluoromethoxy)phenylboronic acid, the expected compound is obtained in the form of a beige foam (yield=74%).

¹H NMR (DMSO, 300 MHz) δ: 8.42 (t, NH); 7.86 (d, 2H); 7.65-7.45 (m, 7H); 7.24 (t, 1H); 7.2-7.1 (m, 3H); 7.03 (t, 1H); 6.88 (d, 2H); 4.89 (dd, 1H); 4.01 (t, 2H); 3.65-3.3 (m, 4H); 3.1-2.9 (m, 2H).

EXAMPLE 38

4-[2-[[[(2S)-2,3-dihydro-1-[[3'-(trifluoromethoxy)[1,1'-biphenyl]-4-yl]sulfonyl]-1H-indol-2-yl]carbonyl]amino]ethoxy]benzeneacetic acid By following a procedure analogous to Example 33 starting from 3-(trifluoromethoxy)phenylboronic acid, the expected compound is obtained in the form of a beige foam (yield=71%).

$^1$H NMR (DMSO, 300 MHz) δ: 12.2 (bs, COOH); 8.43 (t, NH); 7.90 (s, 4H), 7.76 (d, 1H); 7.70 (s, 1H); 7.63 (t, 1H); 7.48 (d, 1H); 7.44 (d, 1H); 7.24 (t, 1H); 7.2-7.1 (m, 3H); 7.02 (t, 1H); 6.89 (d, 2H); 4.89 (dd, 1H); 4.02 (t, 2H); 3.65-3.35 (m, 2H); 3.48 (s, 2H); 3.16 (dd, 1H); 2.93 (dd, 1H).

EXAMPLE 39

4-[2-[[[(2S)-2,3-dihydro-1-[[3'-(methoxy)[1,1'-biphenyl]-4-yl]sulfonyl]-1H-indol-2-yl]carbonyl]amino]ethoxy]benzeneacetic acid By following a procedure analogous to Example 33 starting from 3-(methoxy)phenylboronic acid, the expected compound is obtained in the form of a brown foam (yield=69%).

$^1$H NMR (DMSO, 300 MHz) δ: 12.2 (bs, COOH); 8.42 (t, NH); 7.85 (s, 4H); 7.48 (d, 1H); 7.40 (t, 1H); 7.3-7.1 (m, 6H); 7.1-6.95 (m, 2H); 6.89 (d, 2H); 4.87 (dd, 1H); 4.02 (t, 2H); 3.81 (s, OCH$_3$); 3.65-3.35 (m, 2H); 3.48 (s, 2H); 3.16 (dd, 1H); 2.92 (dd, 1H).

EXAMPLE 40

4-[2-[[[(2S)-2,3-dihydro-1-[[2'-fluoro[1,1'-biphenyl]-4-yl]sulfonyl]-1H-indol-2-yl]carbonyl]amino]ethoxy]benzeneacetic acid By following a procedure analogous to Example 33 starting from 2--fluoro-phenylboronic acid, the expected compound is obtained in the form of a white foam (yield=71%).

$^1$H NMR (DMSO, 250 MHz) δ: 12.2 (bs, COOH); 8.42 (t, NH); 7.90 (d, 2H); 7.72 (d, 2H); 7.60-7.45 (m, 3H); 7.40-7.10 (m, 6H); 7.02 (t, 1H); 6.89 (d, 2H); 4.89 (dd, 1H); 4.01 (t, 2H); 3.65-3.35 (m, 2H); 3.48 (s, 2H); 3.17 (dd, 1H); 2.93 (dd, 1H).

EXAMPLE 41

4-[2-[[[(2S)-2,3-dihydro-1-[[2'-methyl[1,1'-biphenyl]-4-yl]sulfonyl]-1H-indol-2-yl]carbonyl]amino]ethoxy]benzeneacetic acid By following a procedure analogous to Example 33 starting from 2-methylphenylboronic acid, the expected compound is obtained in the form of a white foam (yield=78%).

$^1$H NMR (DMSO, 250 MHz) δ: 8.40 (t, NH); 7.83 (d, 2H); 7.55-7.4 (m, 3H); 7.35-7.10 (m, 8H); 7.03 (td, 1H); 6.90 (dd, 2H); 4.88 (dd, 1H); 4.0 (t, 2H); 3.48 (s, 2H); 3.65-3.25 (m, 2H); 3.13 (dd, 1H); 2.93 (dd, 1H); 2.16 (s, CH$_3$).

EXAMPLE 42

4-[2-[[[(2S)-2,3-dihydro-1-[[3'-(1-methylethyl)[1,1'-biphenyl]-4-yl]sulfonyl]-1H-indol-2-yl]carbonyl]amino]ethoxy]benzeneacetic acid By following a procedure analogous to Example 33 starting from 3-(1-methylethyl)phenylboronic acid, the expected compound is obtained in the form of a beige foam (yield=79%).

$^1$H NMR (DMSO, 250 MHz) δ: 12.2 (bs, COOH); 8.40 (t, NH); 7.84 (s, 4H); 7.60-7.45 (m, 3H); 7.40 (t, 1H); 7.35-7.10 (m, 5H); 7.02 (t, 1H); 6.89 (d, 2H); 4.87 (dd, 1H); 4.01 (t, 2H); 3.65-3.35 (m, 2H); 3.48 (s, 2H); 3.14 (dd, 1H); 3.05-2.85 (m, 2H); 1.23 (d, 6H).

EXAMPLE 43

4-[2-[[[(2S)-2,3-dihydro-1-[[2'-(methoxy)[1,1'-biphenyl]-4-yl]sulfonyl]-1H-indol-2-yl]carbonyl]amino]ethoxy]benzeneacetic acid By following a procedure analogous to Example 33 starting from 2-(methoxy)phenylboronic acid, the expected compound is obtained in the form of a white foam (yield=63%).

$^1$H NMR (DMSO, 250 MHz) δ: 12.2 (bs, COOH); 8.41 (t, NH); 7.83 (d, 2H); 7.64 (d, 2H); 7.48 (d, 1H); 7.45-7.1 (m, 7H); 7.1-7.0 (m, 2H); 6.88 (d, 2H); 4.88 (dd, 1H); 4.01 (t, 2H); 3.75 (s, OCH$_3$); 3.65-3.35 (m, 2H); 3.48 (s, 2H); 3.18 (dd, 1H); 2.93 (dd, 1H).

EXAMPLE 44

4-[2-[[[(2S)-2,3-dihydro-1-[[3'-chloro[1,1'-biphenyl]-4-yl]sulfonyl]-1H-indol-2-yl]carbonyl]amino]ethoxy]benzeneacetic acid By following a procedure analogous to Example 33 starting from 3-chlorophenylboronic acid, the expected compound is obtained in the form of a beige foam (yield=79%).

$^1$H NMR (DMSO, 300 MHz) δ: 8.42 (t, NH); 7.88 (s, 4H); 7.78 (dd, 1H); 7.75-7.65 (m, 1H); 7.55-7.45 (m, 3H); 7.24 (t, 1H); 7.2-7.1 (m, 3H); 7.02 (t, 1H); 6.88 (d, 2H); 4.88 (dd, 1H); 4.01 (t, 2H); 3.65-3.35 (m, 2H); 3.48 (s, 2H); 3.15 (dd, 1H); 2.93 (dd, 1H).

EXAMPLE 45

4-[2-[[[(2S)-2,3-dihydro-1-[[4'-chloro[1,1'-biphenyl]-4-yl]sulfonyl]-1H-indol-2-yl]carbonyl]amino]ethoxy]benzeneacetic acid By following a procedure analogous to Example 33 starting from 4--chloro-phenylboronic acid, the expected compound is obtained in the form of a beige foam (yield=74%).

$^1$H NMR (DMSO, 250 MHz) δ: 8.41 (t, NH); 7.86 (s, 4H); 7.74 (dd, 2H); 7.52 (dd, 2H); 7.48 (d, 1H); 7.3-7.1 (m, 4H); 7.01 (t, 1H); 6.89 (dd, 2H); 4.88 (dd, 1H); 4.01 (t, 2H); 3.65-3.35 (m, 2H); 3.48 (s, 2H); 3.15 (dd, 1H); 2.93 (dd, 1H).

EXAMPLE 46

4-[2-[[[(2S)-2,3-dihydro-1-[[2'-chloro[1,1'-biphenyl]-4-yl]sulfonyl]-1H-indol-2-yl]carbonyl]amino]ethoxy]benzeneacetic acid By following a procedure analogous to Example 33 starting from 2--chloro-phenylboronic acid, the expected compound is obtained in the form of a beige foam (yield=75%).

$^1$H NMR (DMSO, 300 MHz) δ: 12.2 (bs, COOH); 8.43 (t, NH); 7.88 (d, 2H); 7.65-7.55 (m, 3H); 7.51-7.49 (m, 4H); 7.25 (t, 1H); 7.2-7.1 (m, 3H); 7.03 (t, 1H); 6.89 (d, 2H); 4.89 (dd, 1H); 4.01 (t, 2H); 3.65-3.25 (m, 2H); 3.48 (s, 2H); 3.15 (dd, 1H); 2.95 (dd, 1H).

EXAMPLE 47

4-[2-[[[(2S)-2,3-dihydro-1-[[3'-fluoro[1,1'-biphenyl]-4-yl]sulfonyl]-1H-indol-2-yl]carbonyl]amino]ethoxy]benzeneacetic acid By following a procedure analogous to Example 33 starting from 3--fluoro-phenylboronic acid, the expected compound is obtained in the form of a beige foam (yield=39%).
$^1$H NMR (DMSO, 300 MHz) δ: 12.2 (bs, COOH); 8.42 (t, NH); 7.88 (s, 4H); 7.65-7.45 (m, 4H); 7.31-7.09 (m, 5H); 7.02 (t, 1H); 6.89 (d, 2H); 4.89 (dd, 1H); 4.01 (t, 2H); 3.65-3.25 (m, 2H); 3.48 (s, 2H); 3.15 (dd, 1H); 2.93 (dd, 1H).

EXAMPLE 48

4-[2-[[[(2S)-2,3-dihydro-1-[[2'-(trifluoromethyl)[1,1'-biphenyl]-4-yl]sulfonyl]-1H-indol-2-yl]carbonyl]amino]ethoxy]benzeneacetic acid By following a procedure analogous to Example 33 starting from 2-(trifluoromethyl)phenylboronic acid, the expected compound is obtained in the form of a beige foam (yield=78%).
$^1$H NMR (DMSO, 300 MHz) δ: 8.42 (t, NH); 7.9-7.8 (m, 3H), 7.8-7.6 (m, 2H), 7.55-7.45 (m, 3H); 7.39 (d, 1H); 7.24 (t, 1H); 7.2-7.1 (m, 3H); 7.04 (td, 1H); 6.87 (dd, 2H); 4.88 (dd, 1H); 4.1-3.9 (m, 2H); 3.45 (s, 2H); 3.6-3.15 (m, 2H); 3.04 (dd, 1H); 2.95 (dd, 1H).

EXAMPLE 49

4-[2-[[[(2S)-2,3-dihydro-1-[[3'-methyl[1,1'-biphenyl]-4-yl]sulfonyl]-1H-indol-2-yl]carbonyl]amino]ethoxy]benzeneacetic acid By following a procedure analogous to Example 33 starting from 3--methyl-phenylboronic acid, the expected compound is obtained in the form of a white foam (yield=85%).
$^1$H NMR (DMSO, 300 MHz) δ: 12.2 (bs, COOH); 8.41 (t, NH); 7.84 (d, 2H), 7.82 (d, 2H); 7.55-7.4 (m, 3H); 7.36 (t, 1H); 7.3-7.1 (m, 5H); 7.02 (td, 1H); 6.89 (dd, 2H); 4.88 (dd, 1H); 4.01 (t, 2H); 3.60 (s, 2H); 3.6-3.4 (m, 2H); 3.13 (dd, 1H); 2.92 (dd, 1H); 2.36 (s, CH$_3$).

Preparation VIII

1-[[2'-(Trifluoromethyl)[1,1'-biphenyl]-4-yl]sulfonyl]-(2S)-1H-indole-2-carboxylic acid tetrabutylammonium salt 2.4 g (5.59 mmol) of the acid obtained according to Preparation V are mixed with 48 ml of water in a microwave tube and 1.802 g (5.59 mmol) of tetrabutylammonium bromide, 1.062 g (5.59 mmol) of 2-(trifluoromethyl)phenyl-boronic acid, 50 mg (0.224 mmol) of palladium acetate and 1.778 g (16.77 mmol) of sodium carbonate are added. The reaction medium is heated for 5 min at 150° C. in a microwave oven. After cooling, dichloromethane and then water are added to the reaction medium and the organic phase is separated from the aqueous phase. The organic phase is then washed twice with water, dried over magnesium sulfate and concentrated under reduced pressure. The crude product is purified by crystallization from toluene to give the product in the form of a white solid (yield=100%).
M.p.=128° C.

EXAMPLE 50

2,3-Dihydro-N-[2-(4-pyridinyl)ethyl]-1-[[3'-(trifluoromethyl)[1,1'-biphenyl]-4-yl]sulfonyl]-(2S)-1H-indole-2-carboxamide By following a procedure analogous to Example 4 starting from 4-(2-aminoethyl)pyridine, the expected compound is obtained in the form of a colorless oil (yield=76%).
$^1$H NMR (DMSO, 300 MHz) δ: 8.41 (dd, 2H); 8.29 (t, NH); 8.05-8.0 (m, 2H); 7.95 (d, 2H); 7.86 (d, 2H); 7.83-7.68 (m, 2H); 7.50 (d, 1H); 7.26 (t, 1H); 7.19 (dd, 2H); 7.13 (d, 1H); 7.04 (td, 1H); 4.79 (dd, 1H); 3.40 (dd, 2H); 3.06 (dd, 1H); 2.9-2.7 (m, 3H).

EXAMPLE 51

2,3-Dihydro-N-[2-(3-pyridinyl)ethyl]-1-[[3'-(trifluoromethyl)[1,1'-biphenyl]-4-yl]sulfonyl]-(2S)-1H-indole-2-carboxamide By following a procedure analogous to Example 50 starting from 3-(2-aminoethyl)pyridine, the expected compound is obtained in the form of a yellow foam (yield=93%).
$^1$H NMR (DMSO, 300 MHz) δ: 8.5-8.4 (m, 2H); 8.3 (t, NH); 8.05-8.0 (m, 2H); 7.94 (d, 2H); 7.87 (d, 2H); 7.85-7.68 (m, 2H); 7.65-7.55 (m, 1H); 7.50 (d, 1H); 7.3-7.2 (m, 2H); 7.12 (d, 1H); 7.06 (t, 1H); 4.79 (dd, 1H); 3.5-3.3 (m, 2H); 3.2-3 (m, 1H); 2.9-2.7 (m, 3H).

EXAMPLE 52

2,3-Dihydro-N-[(4-pyridinyl)methyl]-1-[[3'-(trifluoromethyl)[1,1'-biphenyl]-4-yl]sulfonyl]-(2S)-1H-indole-2-carboxamide By following a procedure analogous to Example 50 starting from 4-(aminomethyl)pyridine, the expected compound is obtained in the form of a white foam (yield=78%).
$^1$H NMR (DMSO, 250 MHz) δ: 8.9 (t, NH); 8.49 (dd, 2H); 8.05-8.0 (m, 2H); 7.95 (d, 2H); 7.91 (d, 2H); 7.85-7.68 (m, 2H); 7.53 (d, 1H); 7.28 (dd, 2H); 7.35-7.20 (m, 1H); 7.15 (d, 1H); 7.05 (t, 1H); 4.92 (dd, 1H); 4.38 (d, 2H); 3.21 (dd, 1H); 2.99 (dd, 1H).

EXAMPLE 53

2,3-Dihydro-N-[(3-pyridinyl)methyl]-1-[[3'-(trifluoromethyl)[1,1'-biphenyl]-4-yl]sulfonyl]-(2S)-1H-indole-2-carboxamide By following a procedure analogous to Example 50 starting from 3-(aminomethyl)pyridine, the expected compound is obtained in the form of a white foam (yield=74%).
$^1$H NMR (DMSO, 250 MHz) δ: 8.86 (t, NH); 8.51 (d, 1H); 8.46 (dd, 1H); 8.05-8.0 (m, 2H); 7.94 (d, 2H); 7.90 (d, 2H); 7.85-7.65 (m, 3H); 7.52 (d, 1H); 7.36 (dd, 1H); 7.25 (t, 1H); 7.15 (d, 1H); 7.07 (td, 1H); 4.89 (dd, 1H); 4.38 (d, 2H); 3.19 (dd, 1H); 2.97 (dd, 1H).

EXAMPLE 54

3-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzoic acid methyl ester By following a procedure analogous to Example 4 starting from the methyl ester of 3-(2-aminoethoxy)benzoic acid, the expected compound is obtained in the form of a pink solid (yield=28%).

¹H NMR (DMSO, 250 MHz) δ: 8.43 (t, NH); 8.1-8.0 (m, 2H); 7.94 (d, 2H); 7.89 (d, 2H); 7.85-7.65 (m, 2H); 7.6-7.4 (m, 4H); 7.3-7.15 (m, 2H); 7.12 (d, 1H); 7.02 (td, 1H); 4.89 (dd, 1H); 4.10 (t, 2H); 3.85 (s, 3H); 3.7-3.4 (m, 2H); 3.15 (dd, 1H); 2.93 (dd, 1H).

EXAMPLE 55

3-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzoic acid By following a procedure analogous to Example 22 starting from the ester obtained according to Example 54, the expected compound is obtained in the form of a white solid (yield=60%).
M.p.=85-92° C.

Preparation IX 2,3-Dihydro-2-[[[2-[4-(2-methoxy-2-oxoethyl)phenoxy]ethyl]amino]carbonyl]-(2S)-1H-indole-1-carboxylic acid 1,1-dimethylethyl ester By following a procedure analogous to Preparation I starting from the methyl ester of 4-(2-aminoethoxy)benzeneacetic acid, the expected compound is obtained in the form of a white foam (yield=48%).

Preparation X

4-[2-[[[(2S)-2,3-dihydro-1H-indol-2-yl]carbonyl]amino]ethoxy]benzeneacetic acid methyl ester By following a procedure analogous to Preparation II starting from the ester obtained according to Preparation IX, the expected compound is obtained in the form of a beige solid (yield=89%).
¹H NMR (DMSO, 250 MHz) δ: 8.03 (t, NH); 7.16 (dd, 2H); 7.05-6.80 (m, 4H); 6.65-6.5 (m, 2H); 5.93 (d, NH); 4.22 (ddd, 1H); 3.99 (t, 2H); 3.59 and 3.58 (2d, 5H); 3.55-3.4 (m, 2H); 3.31 (dd, 1H); 2.90 (dd, 1H).

Preparation XI

4-[2-[[[(2S)-1-[[4-bromo-3-(trifluoromethyl)phenyl]sulfonyl]-2,3-dihydro-1H-indol-2-yl]carbonyl]amino]ethoxy]benzeneacetic acid methyl ester A solution of 750 mg (2.12 mmol) of the compound obtained according to Preparation X in 60 ml of acetonitrile is prepared and 512 μl (4.65 mmol) of N-methylmorpholine and 0.486 ml (2.75 mmol) of 4-bromo-3-(trifluoromethyl)benzenesulfonyl chloride are added. The reaction mixture is stirred at room temperature for 4 hours. The medium is then treated by adding ethyl acetate and the organic phase is washed with water and then dried over magnesium sulfate and concentrated under reduced pressure. The crude product obtained is then purified by chromatography on silica gel using a dichloromethane/ethyl acetate mixture (99/1, then 90/10; v/v) as the eluent to give the expected product in the form of a white foam (yield=93%).
¹H NMR (DMSO, 300 MHz) δ: 8.46 (t, NH); 8.11 (d, 1H); 8.05-7.95 (m, 2H); 7.43 (d, 1H); 7.25 (td, 1H); 7.2-7.1 (m, 3H); 7.06 (td, 1H); 6.89 (dd, 2H); 4.93 (dd, 1H); 4.0 (t, 2H); 3.60 (s, 5H); 3.6-3.35 (m, 2H); 3.17 (dd, 1H); 2.92 (dd, 1H).

EXAMPLE 56

4-[2-[[[(2S)-2,3-dihydro-1-[[2-(trifluoromethyl)[1,1'-biphenyl]-4-yl]sulfonyl]-1H-indol-2-yl]carbonyl]amino]ethoxy]benzeneacetic acid methyl ester By following a procedure analogous to Example 2 starting from the compound obtained according to Preparation XI and phenylboronic acid, the expected compound is obtained in the form of a translucent oil (yield=79%).

EXAMPLE 57

4-[2-[[[(2S)-2,3-dihydro-1-[[2-(trifluoromethyl)[1,1'-biphenyl]-4-yl]sulfonyl]-1H-indol-2-yl]carbonyl]amino]ethoxy]benzeneacetic acid By following a procedure analogous to Example 5 starting from the compound obtained according to Example 56, the expected compound is obtained in the form of a white foam (yield 36%).
¹H NMR (DMSO, 250 MHz) δ: 12.2 (bs, COOH); 8.48 (t, NH); 8.13 (dd, 1H); 8.08 (s, 1H); 7.62 (d, 1H); 7.55-7.4 (m, 4H); 7.48-7.1 (m, 6H); 7.06 (td, 1H); 6.89 (d, 2H); 4.97 (dd, 1H); 4.01 (t, 2H); 3.6-3.3 (m, 2H); 3.48 (s, 2H); 3.20 (dd, 1H); 2.95 (dd, 1H).

EXAMPLE 58

3-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzeneacetic acid methyl ester By following a procedure analogous to Example 4 starting from the methyl ester of 3-(2-aminoethoxy)benzeneacetic acid, the expected compound is obtained in the form of a colorless oil (yield=33%).
¹H NMR (DMSO, 300 MHz) δ: 8.43 (t, NH); 8.08-8 (m, 2H); 7.94 (d, 2H); 7.89 (d, 2H); 7.85-7.65 (m, 2H); 7.49 (d, 1H); 7.3-7.2 (m, 2H); 7.13 (d, 1H); 7.02 (td, 1H); 6.9-6.8 (m, 3H); 4.90 (dd, 1H); 4.02 (t, 2H); 3.64 (s, 2H); 3.61 (s, 3H); 3.6-3.4 (m, 2H); 3.16 (dd, 1H); 2.94 (dd, 1H).

EXAMPLE 59

3-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzeneacetic acid By following a procedure analogous to Example 5 starting from the ester obtained according to Example 58, the expected compound is obtained in the form of a white foam (yield=85%).
¹H NMR (DMSO, 250 MHz) δ: 8.42 (t, NH); 8.08-8 (m, 2H); 7.94 (d, 2H); 7.89 (d, 2H); 7.85-7.65 (m, 2H); 7.49 (d, 1H); 7.3-7.2 (m, 2H); 7.13 (d, 1H); 7.02 (td, 1H); 6.9-6.8 (m, 3H); 4.90 (dd, 1H); 4.02 (t, 2H); 3.52 (s, 2H); 3.65-3.3 (m, 2H); 3.15 (dd, 1H); 2.94 (dd, 1H).

EXAMPLE 60

2,3-Dihydro-N-[(2-nitrophenyl)methyl]-1-[[3'-(trifluoromethyl)[1,1'-biphenyl]-4-yl]sulfonyl]-(2S)-1H-indole-2-carboxamide By following a procedure analogous to Example 21 starting from 2-(aminomethyl)nitrobenzene, the expected compound is obtained in the form of a white foam (yield=71%).

¹H NMR (DMSO, 250 MHz) δ: 8.89 (t, NH); 8.1-8.0 (m, 3H); 8.0-7.85 (m, 4H), 7.85-7.65 (m, 3H); 7.65-7.45 (m, 3H); 7.3-7.1 (m, 2H); 7.04 (dd, 1H); 4.97 (dd, 1H); 4.68 (dd, 1H); 4.60 (dd, 1H); 3.21 (dd, 1H); 2.98 (dd, 1H).

EXAMPLE 61

N-[(2-aminophenyl)methyl]-2,3-dihydro-1-[[3'-(trifluoromethyl)[1,1'-biphenyl]-4-yl]sulfonyl]-(2S)-1H-indole-2-carboxamide 683 mg (1.17 mmol) of the compound obtained according to Example 60 are dissolved in 10 ml of methanol. 68 mg of 10% palladium-on-charcoal are added. The reaction medium is stirred at room temperature under hydrogen atmospheric pressure for 2 h. It is then filtered and the filtrate is concentrated under reduced pressure. The crude product obtained is then purified by chromatography on silica gel using a dichloromethane/ethyl acetate mixture (98/2; v/v) as the eluent to give the expected product in the form of a white foam (yield=80%).
¹H NMR (DMSO, 300 MHz) δ: 8.64 (t, NH); 8.08-8 (m, 2H), 7.94 (d, 2H); 7.89 (d, 2H); 7.85-7.65 (m, 2H), 7.50 (d, 1H); 7.25 (t, 1H); 7.13 (d, 1H); 7.1-6.9 (m, 3H); 6.63 (dd, 1H); 6.51 (td, 1H); 5.03 (bs, NH₂); 4.91 (dd, 1H); 4.24 (dd, 1H); 4.14 (dd, 1H); 3.17 (dd, 1H); 2.96 (dd, 1H).

Preparation XII

2-Cyanobenzenebutanoic acid methyl ester

A solution of 369 mg (3.02 mmol) of 9-BBN (9-borabicyclo[3.3.1]nonane) in 6 ml of anhydrous THF is prepared under an argon atmosphere. 0.32 ml (3.02 mmol) of the methyl ester of 3-butenoic acid is added to this solution. The medium is stirred for 3 h at room temperature. A solution of 500 mg (2.75 mmol) of 2-bromobenzonitrile in 8 ml of anhydrous THF is prepared in a second round-bottomed flask. 445 mg (8.24 mmol) of sodium methylate, 68 mg (0.08 mmol) of PdCl₂dppf and the previous solution are successively added dropwise to this solution under argon. The reaction medium is subsequently refluxed for 2 h and then stirred at room temperature for 16 h and finally under reflux for 3 h. Water and ethyl acetate are added to the reaction medium and the two phases are separated. The organic phase is washed with water, dried over magnesium sulfate, filtered and concentrated under reduced pressure. The crude product obtained is then purified by chromatography on silica gel using a methylcyclohexane/ethyl acetate mixture (90/10; v/v) as the eluent to give the expected product in the form of a colorless oil (yield=36%).
¹H NMR (DMSO, 300 MHz) δ: 7.78 (dd, 1H); 7.62 (td, 1H); 7.47 (dd, 1H), 7.41 (td, 1H); 3.58 (s, CH₃); 2.81 (t, 2H); 2.36 (t, 2H); 1.88 (quint, 2H).

Preparation XIII 2-(Aminomethyl)benzenebutanoic acid methyl ester

A solution of 176 mg (0.866 mmol) of the ester obtained according to Preparation XII in 15 ml of methanol and 0.1 ml of 10 N hydrochloric acid is prepared. 20 mg of 10% palladium-on-charcoal are added and the mixture is stirred for 6 h at room temperature under hydrogen atmospheric pressure. The reaction medium is then filtered and the filtrate is concentrated under reduced pressure. The crude product obtained is then purified by chromatography on silica gel using a dichloromethane/methanol mixture (95/5; v/v) as the eluent to give the expected product in the form of a colorless oil (yield=50%).
¹H NMR (DMSO, 250 MHz) δ: 7.5-7.35 (m, 1H); 7.35-7.1 (m, 3H); 3.97 (s, 2H); 3.60 (s, CH₃); 2.64 (t, 2H); 2.39 (t, 2H); 1.76 (quint, 2H).

EXAMPLE 62

2-[[[[(2S)-2,3-dihydro-1-[[3'-(trifluoromethyl)[1,1'-biphenyl]-4-yl]sulfonyl]-1H-indol-2-yl]carbonyl]amino]methyl]benzenebutanoic acid methyl ester By following a procedure analogous to Example 21 starting from the ester obtained according to Preparation XIII, the expected compound is obtained in the form of a colorless oil (yield=48%).
¹H NMR (DMSO, 500 MHz) δ: 8.65 (t, NH); 8.08-8 (m, 2H); 7.93 (d, 2H), 7.91 (d, 2H); 7.77 (d, 1H); 7.73 (t, 1H); 7.51 (d, 1H); 7.3-7.1 (m, 6H); 7.05 (t, 1H); 4.93 (dd, 1H); 4.41 (dd, 1H); 4.33 (dd, 1H); 3.60 (s, CH₃); 3.17 (dd, 1H); 2.97 (dd, 1H). 2.64 (t, 2H); 2.38 (t, 2H); 1.80 (quint, 2H).

EXAMPLE 63

2-[[[[(2S)-2,3-dihydro-1-[[3'-(trifluoromethyl)[1,1'-biphenyl]-4-yl]sulfonyl]-1H-indol-2-yl]carbonyl]amino]methyl]benzenebutanoic acid By following a procedure analogous to Example 5 starting from the methyl ester obtained according to Example 62, the expected compound is obtained in the form of a white solid (yield=81%).
¹H NMR (DMSO, 300 MHz) δ: 12.1 (bs, COOH); 8.67 (t, NH); 8.08-8 (m, 2H); 7.94 (d, 2H); 7.90 (d, 2H); 7.85-7.65 (m, 2H); 7.50 (d, 1H); 7.3-7.1 (m, 6H); 7.03 (td, 1H); 4.92 (dd, 1H); 4.41 (dd, 1H); 4.32 (dd, 1H); 3.17 (dd, 1H); 2.96 (dd, 1H); 2.63 (t, 2H); 2.28 (t, 2H); 1.76 (quint, 2H).

EXAMPLE 64

2,3-Dihydro-N-[(2-hydroxyphenyl)methyl]-1-[[3'-(trifluoromethyl)[1,1'-biphenyl]-4-yl]sulfonyl]-(2S)-1H-indole-2-carboxamide A solution of 100 mg (0.224 mmol) of the acid obtained according to Preparation IV in 2 ml of dichloromethane is prepared and 47 mg (0.246 mmol) of EDCI and 33 mg (0.246 mmol) of HOBT are then added. After stirring for 10 minutes at room temperature, 28 mg (0.224 mmol) of 2-(aminomethyl)phenol are added. The reaction medium is then stirred at room temperature for 1 hour 50 min. It is then treated by adding dichloromethane and the organic phase is washed with water and then dried over magnesium sulfate and concentrated under reduced pressure to give the expected product in the form of a white foam (yield=99%).
¹H NMR (DMSO, 300 MHz) δ: 9.55 (s, OH); 8.54 (t, NH); 8.1-8 (m, 2H); 7.94 (d, 2H); 7.90 (d, 2H); 7.85-7.65 (m, 2H); 7.51 (d, 1H); 7.25 (t, 1H); 7.2-7.00 (m, 4H); 6.81 (dd, 1H); 6.73 (td, 1H); 4.97 (dd, 1H); 4.33 (dd, 1H); 4.23 (dd, 1H); 3.15 (dd, 1H); 2.98 (dd, 1H).

EXAMPLE 65

2,3-Dihydro-N-[(2-cyanophenyl)methyl]-1-[[3'-(trifluoromethyl)[1,1'-biphenyl]-4-yl]sulfonyl]-(2S)-1H-indole-2-carboxamide By following a procedure analogous to Example 21 starting from 2-(aminomethyl)benzonitrile, the expected compound is obtained in the form of a pink solid (yield=23%).
M.p.=70° C.

Preparation XIV (3-Cyanophenoxy)acetic acid methyl ester

A solution of 5.95 g (50 mmol) of 3-hydroxybenzonitrile in 60 ml of acetone is prepared and 9.2 g (60 mmol) of methyl bromoacetate, 6.9 g of potassium carbonate and 0.15 g of sodium iodide are added. The mixture is stirred at the reflux temperature of the solvent for 3 hours and then concentrated under reduced pressure. The residue is taken up with water and extracted with ethyl acetate. The organic phase is dried over sodium sulfate and then concentrated under reduced pressure. The crude product is recrystallized first from isopropyl ether and then from 30 ml of an ethanol/water mixture (1/1) to give 6 g of the expected ester in the form of white crystals (yield=62%).
M.p.=66° C.

Preparation XV 3-(Aminomethyl)phenoxyacetic acid methyl ester hydrochloride

A solution of 1.9 g (10 mmol) of the methyl ester of (3-cyanophenoxy)acetic acid in 60 ml of methanol and 1 ml of 10 N hydrochloric acid is prepared. 0.2 g of 10% palladium-on-charcoal is added and the mixture is stirred under hydrogen atmospheric pressure at room temperature for 2 hours. The catalyst is filtered off and the filtrate is concentrated under reduced pressure. The crude product is taken up in 10 ml of methanol and the solution is diluted with 50 ml of ethyl ether. The product which crystallizes in this way is filtered off and dried under reduced pressure to give 2 g of the expected ester in the form of white crystals (yield=86%).
M.p.=118° C.

EXAMPLE 66

[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]acetic acid methyl ester By following a procedure analogous to Preparation I starting from the acid obtained in Preparation IV and the amine obtained according to Preparation XV, the expected product is obtained in the form of a white solid (yield=47%).
M.p.=50° C.

EXAMPLE 67

[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]acetic acid methyl ester By following a procedure analogous to Example 66 starting from the methyl ester of (4-aminomethyl)phenoxyacetic acid, the expected product is obtained in the form of a white powder (yield=27%).

$^1$H NMR (DMSO, 300 MHz) δ: 8.70 (t, NH); 8.03 (m, 2H); 7.96-7.90 (m, 4H); 7.88-7.80 (m, 2H); 7.49 (d, 1H); 7.25-7.10 (m, 4H); 7.24 (t, 1H); 6.90 (d, 2H); 4.91 (dd, 1H); 4.77 (s, 2H); 4.27 (m, 2H); 3.69 (s. 3H); 3.3-3.1 (m, 1H); 3.00-2.93 (m, 1H).

Preparation XVI

N-(4-cyanophenyl)-β-alanine

A solution of 3.54 g (30 mmol) of 4-aminobenzonitrile in 10 ml of acetonitrile is prepared and 2.16 g (30 mmol) of propiolactone are added at the reflux temperature of the solvent. The mixture is stirred at the reflux temperature of the solvent for 18 hours and then cooled. The residue is taken up with water and extracted with ethyl acetate. The white precipitate formed is filtered off and washed with 5 ml of ethyl ether and then dried to give 3.4 g of the expected acid in the form of a white solid (yield=59%).
M.p.=150° C.

Preparation XVII

N-(4-cyanophenyl)-β-alanine methyl ester hydrochloride

A solution of 2 g (10.5 mmol) of the acid obtained according to Preparation XVI in 50 ml of methanol is prepared and 2.5 g (21 mmol) of thionyl chloride are added at 0° C. The mixture is subsequently stirred for 2 hours at the reflux temperature of the solvent and then concentrated under reduced pressure. The residue is taken up with toluene and concentrated again under reduced pressure to give 2.72 g of the expected ester salt in the form of a white solid (yield=76%).
M.p.=121° C.

Preparation XVIII

N-[4-(aminomethyl)phenyl]-β-alanine methyl ester dihydrochloride

By following a procedure analogous to Preparation XV starting from the compound obtained according to Preparation XVII, the expected product is obtained in the form of a white solid (yield=99%).
M.p.=201° C.

EXAMPLE 68

N-[4-[[[[(2S)-2,3-dihydro-1-[[3'-(trifluoromethyl)[1,1'-biphenyl]-4-yl]-sulfonyl]-1H-indol-2-yl]carbonyl]amino]methyl]phenyl]-β-alanine methyl ester By following a procedure analogous to Example 66 starting from the compound obtained according to Preparation XVIII, the expected product is obtained in the form of a white solid (yield=57%).
M.p.=61° C.

EXAMPLE 69

N-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]-β-alanine By following a procedure analogous to Example 5 starting from the compound obtained according to Example 68, the expected product is obtained in the form of a white solid (yield=62%).
M.p.=82° C.

Preparation XIX

N-(3-cyanophenyl)-β-alanine

By following a procedure analogous to Preparation XVI starting from 3-aminobenzonitrile, the expected product is obtained in the form of an ecru solid (yield=14%).
M.p.=119° C.

Preparation XX

N-(3-cyanophenyl)-β-alanine methyl ester hydrochloride

By following a procedure analogous to Preparation XVII starting from the compound obtained according to Preparation XIX, the expected product is obtained in the form of an ecru solid (yield=99%).
M.p.=102° C.

Preparation XXI

N-[3-(aminomethyl)phenyl]-β-alanine methyl ester dihydrochloride

By following a procedure analogous to Preparation XVIII starting from the compound obtained according to Preparation XX, the expected product is obtained in the form of a yellow oil (yield=84%).
$^1$H NMR (DMSO, 300 MHz) δ: 8.40 (broad s, 3H); 7.14 (t, 1H); 6.77-6.67 (m, 3H); 3.89 (m, 2H); 3.64 (s, 3H); 3.39 (t, 2H); 2.71 (t, 2H).

EXAMPLE 70

N-[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]-β-alanine methyl ester By following a procedure analogous to Example 66 starting from the compound obtained according to Preparation XXI, the expected product is obtained in the form of a white solid (yield=25%).
M.p.=57° C.

EXAMPLE 71

N-[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]-β-alanine By following a procedure analogous to Example 5 starting from the compound obtained according to Example 70, the expected product is obtained in the form of a white solid (yield=94%).
M.p.=85° C.

Preparation XXII

N-(2-cyanophenyl)-β-alanine methyl ester

By following a procedure analogous to Preparation XVII starting from N-(2-cyanophenyl)-β-alanine, the expected product is obtained in the form of a yellow oil (yield=70%).
$^1$H NMR (DMSO, 250 MHz) δ: 7.47-7.39 (m, 2H); 6.80 (d, 1H); 6.66 (t, 1H); 6.05 (t, 1H); 3.66 (s, 3H); 3.44 (q, 2H); 2.63 (t, 2H).

Preparation XXIII

N-[2-(aminomethyl)phenyl]-β-alanine methyl ester hydrochloride

By following a procedure analogous to Preparation XV starting from the compound obtained according to Preparation XXII, the expected product is obtained in the form of a pale yellow solid (yield=44%).
$^1$H NMR (DMSO, 250 MHz) δ: 8.16 (broad s, 3H); 7.23-7.17 (m, 2H); 6.67 (d, 1H); 6.62 (m, 1H); 5.59 (broad s, 1H); 3.90 (s, 2H); 3.62 (s, 3H); 3.31 (t, 2H); 2.67 (t, 2H).

EXAMPLE 72

N-[2-[[[[(2S)-2,3-dihydro-1-[[3'-(trifluoromethyl)[1,1'-biphenyl]-4-yl]-sulfonyl]-1H-indol-2-yl]carbonyl]amino]methyl]phenyl]-β-alanine methyl ester By following a procedure analogous to Example 66 starting from the compound obtained according to Preparation XXIII, the expected product is obtained in the form of a white solid (yield=73%).
M.p.=60° C.

EXAMPLE 73

N-[2-[[[[(2S)-2,3-dihydro-1-[[3'-(trifluoromethyl)[1,1'-biphenyl]-4-yl]-sulfonyl]-1H-indol-2-yl]carbonyl]amino]methyl]phenyl]-β-alanine By following a procedure analogous to Example 5 starting from the compound obtained according to Example 72, the expected product is obtained in the form of a white solid (yield=79%).
M.p.=94° C.

Preparation XXIV

3-(2-Cyanophenoxy)propanoic acid

By following a procedure analogous to Preparation XVI starting from 2-hydroxybenzonitrile, the expected product is obtained in the form of a brown solid (yield=90%).
$^1$H NMR (DMSO, 300 MHz) δ: 12.42 (broad s, 1H); 7.73-7.66 (m, 2H); 7.29 (d, 1H); 7.10 (t, 1H); 4.36 (t, 2H); 2.77 (t, 2H).

Preparation XXV

3-(2-Cyanophenoxy)propanoic acid methyl ester

By following a procedure analogous to Preparation XVII starting from the compound obtained according to Preparation XXIV, the expected product is obtained in the form of a yellow oil (yield=50%).
$^1$H NMR (DMSO, 250 MHz) δ: 7.73-7.63 (m, 2H); 7.29 (d, 1H); 7.10 (t, 1H); 4.36 (t, 2H); 3.64 (s, 3H); 2.86 (t, 2H).

Preparation XXVI

3-[2-(Aminomethyl)phenoxy]propanoic acid methyl ester hydrochloride

By following a procedure analogous to Preparation XV starting from the compound obtained according to Preparation XXV, the expected product is obtained in the form of an ecru solid (yield=54%).

¹H NMR (DMSO, 300 MHz) δ: 8.2 (broad s, 3H); 7.41-7.34 (m, 2H); 7.3 (d, 1H); 7.02 (t, 1H); 4.26 (t, 2H); 3.91 (s, 2H); 3.65 (s, 3H); 2.88 (t, 2H).

EXAMPLE 74

3-[2-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]propanoic acid methyl ester By following a procedure analogous to Example 66 starting from the compound obtained according to Preparation XXVI, the expected product is obtained in the form of a white solid (yield=25%).
M.p.=131° C.

EXAMPLE 75

3-[2-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]propanoic acid A mixture of 22 mg (0.52 mmol) of lithium hydroxide and 53 mg (1.57 mmol) of 30% hydrogen peroxide in 2 ml of THF (tetrahydrofuran) is prepared and a solution of 278 mg (0.43 mmol) of the compound obtained according to Example 74 in 2 ml of THF is added. The reaction mixture is stirred at room temperature for 20 hours and then acidified with dilute hydrochloric acid solution and extracted with 25 ml of dichloromethane. The organic phase is washed with water, dried over sodium sulfate and concentrated under reduced pressure. The crude product obtained is purified by chromatography on silica gel using a dichloromethane/methanol mixture (9/1; v/v) as the eluent to give 141 mg of the expected acid in the form of a white powder (yield=52%).
M.p.=100° C.

Preparation XXVII

[[3-[[Bis[(1,1-dimethylethoxy)carbonyl]amino]methyl]phenyl]thio]acetic acid methyl ester 44 mg (1.1 mmol) of a 60% dispersion of sodium hydride in oil are suspended in 8 ml of dimethylformamide (DMF), and 238 mg (1.1 mmol) of di-t-butyl iminodicarboxylate are added. The reaction mixture is stirred at 60° C. for 30 min and then cooled to room temperature. A solution of 230 mg (1 mmol) of the methyl ester of [3-(chloromethyl)phenylthio]acetic acid in 3 ml of DMF is then added. The reaction medium is stirred at 50° C. for 90 min and then cooled and poured into 30 ml of water. The aqueous phase obtained is extracted with ethyl acetate (twice) and the combined organic phases are dried over sodium sulfate and concentrated under reduced pressure. The crude product is purified by chromatography on silica gel using a toluene/ethyl acetate mixture (95/5; v/v) as the eluent to give 300 mg of the expected compound in the form of a colorless oil (yield=73%).
¹H NMR (DMSO, 250 MHz) δ: 7.34-7.25 (m, 1H); 7.18 (s, 1H); 7.07 (d, 1H); 4.64 (s, 2H); 3.86 (s, 2H); 3.61 (s, 3H); 1.39 (s, 18).

Preparation XXVIII

[[3-(Aminomethyl)phenyl]thio]acetic acid methyl ester

A solution of 290 mg (0.7 mmol) of the compound obtained according to Preparation XXVII in 4 ml of dioxane saturated with hydrogen chloride is prepared. The reaction mixture is stirred for 2 hours at room temperature and then concentrated under reduced pressure. The crude product is crystallized by trituration in ethyl ether to give 150 mg of the expected compound in the form of a white solid (yield=88%).
M.p.=72° C.

EXAMPLE 76

[[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]acetic acid methyl ester By following a procedure analogous to Example 66 starting from the compound obtained according to Preparation XXVIII, the expected product is obtained in the form of a white solid (yield=63%).
M.p.=51° C.

EXAMPLE 77

[[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]acetic acid By following a procedure analogous to Example 5 starting from the compound obtained according to Example 76, the expected product is obtained in the form of a white solid (yield=98%).
M.p.=75° C.

EXAMPLE 78

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzoic acid methyl ester By following a procedure analogous to Example 66 starting from the hydrochloride of the methyl ester of 4-(aminomethyl)benzoic acid, the expected product is obtained in the form of a white solid (yield 51%).
M.p.=70° C.

EXAMPLE 79

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzoic acid By following a procedure analogous to Example 5 starting from the compound obtained according to Example 78, the expected product is obtained in the form of a white solid (yield=50%).
M.p.=120° C.

EXAMPLE 80

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzoic acid methyl ester By following a procedure analogous to Example 66 starting from the hydrochloride of the methyl ester of 3-(aminomethyl)benzoic acid, the expected product is obtained in the form of a white solid (yield=56%).
M.p.=50° C.
¹H NMR (DMSO, 300 MHz) δ: 8.84 (t, NH); 8.03 (m, 2H); 7.96-7.75 (m, 8H); 7.56-7.48 (m, 3H); 7.25 (t, 1H); 7.14 (d, 1H); 7.05 (t, 1H); 4.921 (dd, 1H); 4.41 (m, 2H); 3.84 (s, 3H); 3.2-3.1 (m, 1H); 3.0-2.93 (m, 1H).

EXAMPLE 81

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzoic acid By following a procedure analogous to Example 5 starting from the compound obtained according to Example 80, the expected product is obtained in the form of a white solid (yield=82%).

M.p.=96° C.

Preparation XXIX 2-(Aminomethyl)benzoic acid 1,1-dimethylethyl ester hydrochloride By following a procedure analogous to Preparation XV starting from the t-butyl ester of 2-cyanobenzoic acid, the expected product is obtained in the form of a white solid (yield=87%).

M.p.=177° C.

EXAMPLE 82

2-[[[[(2S)-2,3-dihydro-1-[[3'-(trifluoromethyl)[1,1'-biphenyl]-4-yl]sulfonyl]-1H-indol-2-yl]carbonyl]amino]methyl]benzoic acid 1,1-dimethylethyl ester By following a procedure analogous to Example 66 starting from the compound obtained according to Preparation XXIX, the expected product is obtained in the form of a white solid (yield=69%).

M.p.=68° C.

EXAMPLE 83

2-[[[[(2S)-2,3-dihydro-1-[[3'-(trifluoromethyl)[1,1'-biphenyl]-4-yl]sulfonyl]-1H-indol-2-yl]carbonyl]amino]methyl]benzoic acid By following a procedure analogous to Example 25 starting from the compound obtained according to Example 82, the expected product is obtained in the form of a white solid (yield=90%).

M.p.=118° C.

EXAMPLE 84

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzeneacetic acid methyl ester By following a procedure analogous to Example 66 starting from the hydrochloride of the methyl ester of 4-(aminomethyl)benzeneacetic acid, the expected product is obtained in the form of a white solid (yield=83%).

M.p.=120° C.

EXAMPLE 85

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzeneacetic acid By following a procedure analogous to Example 5 starting from the compound obtained according to Example 84, the expected product is obtained in the form of a white solid (yield=56%).

M.p.=90° C.

EXAMPLE 85a

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzeneacetic acid potassium salt A solution of 250 mg (0.42 mmol) of the acid obtained according to Example 85 in 1 ml of acetonitrile is prepared and 0.84 ml of 0.5 N aqueous potassium hydroxide solution is added. The mixture is stirred for 1 hour at room temperature and then diluted with 10 ml of pure water and lyophilized to give the expected salt in the form of a white powder.

M.p.=150-160° C.

EXAMPLE 85b

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzeneacetic acid diethanolamine salt By following a procedure analogous to Example 85a with diethanolamine, the expected salt is obtained in the form of a white powder.

M.p.=55-60° C.

EXAMPLE 85c

4-[[[[(2S)-2,3-dihydro-]-[[3'-(trifluoromethyl)[1,1'-biphenyl]-4-yl]sulfonyl]-1H-indol-2-yl]carbonyl]amino]methyl]benzeneacetic acid choline salt By following a procedure analogous to Example 85a with a solution of choline hydroxide in methanol, the expected salt is obtained in the form of a white powder.

M.p.=75-80° C.

EXAMPLE 85d

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzeneacetic acid TRIS salt By following a procedure analogous to Example 85a with 2-amino-2-(hydroxymethyl)-1,3-propanediol, the expected salt is obtained in the form of a white powder.

M.p.=66-70° C.

EXAMPLE 86

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzeneacetic acid methyl ester By following a procedure analogous to Example 66 starting from the hydrochloride of the methyl ester of 3-(aminomethyl)benzeneacetic acid, the expected product is obtained in the form of a white solid (yield=66%).
M.p.=60° C.

EXAMPLE 87

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzeneacetic acid By following a procedure analogous to Example 5 starting from the compound obtained according to Example 86, the expected product is obtained in the form of a white solid (yield=62%).
M.p.=80° C.

Preparation XXX 4-(Aminomethyl)benzenepropanoic acid methyl ester hydrochloride By following a procedure analogous to Preparation XV starting from the methyl ester of (2E)-3-(4-cyanophenyl)-2-propenoic acid, the expected product is obtained in the form of a white solid (yield=72%).
M.p.=215° C.

EXAMPLE 88

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid methyl ester By following a procedure analogous to Example 66 starting from the compound obtained according to Preparation XXX, the expected product is obtained in the form of a white solid (yield=91%).
M.p.=61° C.

EXAMPLE 89

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid By following a procedure analogous to Example 5 starting from the compound obtained according to Example 88, the expected product is obtained in the form of a white solid (yield=53%).
M.p.=85° C.

EXAMPLE 90

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid ethyl ester By following a procedure analogous to Example 66 starting from the hydrochloride of the ethyl ester of 3-[3-(aminomethyl)benzene]propanoic acid, the expected product is obtained in the form of a colorless oil (yield=51%).
$^1$H NMR (DMSO, 250 MHz) δ: 8.73 (t, NH); 8.02 (m, 2H); 7.93 (m, 4H); 7.77-7.72 (m, 2H); 7.50 (d, 1H); 7.25-7.03 (m, 7H); 4.91 (dd, 1H); 4.31 (d, 2H); 4.02 (q, 2H); 3.2-2.9 (m, 2H); 2.81 (t, 2H); 2.58 (t, 2H); 1.14 (t, 3H).

EXAMPLE 91

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid By following a procedure analogous to Example 5 starting from the compound obtained according to Example 90, the expected product is obtained in the form of a white solid (yield=81%).
M.p.=135° C.

Preparation XXXI 2-(Aminomethyl)benzenepropanoic acid ethyl ester hydrochloride By following a procedure analogous to Preparation XXX starting from the ethyl ester of (2E)-3-(2-cyanophenyl)-2-propenoic acid, the expected product is obtained in the form of a white solid (yield=40%).
M.p.=107-110° C.

EXAMPLE 92

2-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid ethyl ester By following a procedure analogous to Example 66 starting from the compound obtained according to Preparation XXXI, the expected product is obtained in the form of a white solid (yield=60%).
M.p.=48° C.

EXAMPLE 93

2-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid By following a procedure analogous to Example 5 starting from the compound obtained according to Example 92, the expected product is obtained in the form of a white solid (yield=77%).
M.p.=94° C.

Preparation XXXII

4-[4-[[Bis[(1,1-dimethylethoxy)carbonyl]amino]methyl]phenyl]butanoic acid methyl ester By following a procedure analogous to Preparation XXVII starting from the methyl ester of 4-(chloromethyl)benzenebutanoic acid, the expected product is obtained in the form of a colorless oil (yield=36%).

¹H NMR (DMSO, 250 MHz) δ: 7.14 (s, 4H); 4.66 (s, 2H); 3.56 (s, 3H); 2.56 (t, 2H); 2.27 (t, 2H); 1.79 (q, 2H); 1.39 (s, 18H).

Preparation XXXIII 4-(Aminomethyl)benzenebutanoic acid methyl ester hydrochloride By following a procedure analogous to Preparation XXVIII starting from the compound obtained according to Preparation XXXII, the expected product is obtained in the form of a white solid (yield=80%).
M.p.=205° C.

EXAMPLE 94

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzenebutanoic acid methyl ester By following a procedure analogous to Example 66 starting from the compound obtained according to Preparation XXXIII, the expected product is obtained in the form of a white solid (yield=71%).
M.p.=55° C.

EXAMPLE 95

4-[[[[(2S)-2,3-dihydro-1-[[3'-(trifluoromethyl)[1,1'-biphenyl]-4-yl]sulfonyl]-1H-indol-2-yl]carbonyl]amino]methyl]benzenebutanoic acid By following a procedure analogous to Example 5 starting from the compound obtained according to Example 94, the expected product is obtained in the form of a white solid (yield=91%).
M.p.=75° C.

Preparation XXXIV 3-(Aminomethyl)benzenebutanoic acid methyl ester hydrochloride By following a procedure analogous to Preparation XV starting from the methyl ester of 3-cyanobenzenebutanoic acid, the expected product is obtained in the form of a white solid (yield=84%).
M.p.=90° C.

EXAMPLE 96

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzenebutanoic acid methyl ester By following a procedure analogous to Example 66 starting from the compound obtained according to Preparation XXXIV, the expected product is obtained in the form of a colorless oil (yield=81%).
¹H NMR (DMSO, 300 MHz) δ: 8.72 (t, NH); 8.02 (m, 2H); 7.93 (m, 4H); 7.78-7.72 (m, 2H); 7.50 (d, 1H); 7.25-7.03 (m, 7H); 4.91 (dd, 1H); 4.31 (d, 2H); 3.57 (s, 3H); 3.2-3.1 (m, 1H); 3.0-2.94 (m, 1H); 2.55 (t, 2H); 2.32 (t, 2H); 1.80 (m, 2H).

EXAMPLE 97

3-[[[[(2S)-2,3-dihydro-1-[[3'-(trifluoromethyl)[1,1'-biphenyl]-4-yl]sulfonyl]-1H-indol-2-yl]carbonyl]amino]methyl]benzenebutanoic acid By following a procedure analogous to Example 5 starting from the compound obtained according to Example 96, the expected product is obtained in the form of a white solid (yield=92%).
M.p.=76° C.

Preparation XXXV (2S)-2,3-dihydro-1-[[3'-(trifluoromethyl)[1,1'-biphenyl]-4-yl]sulfonyl]-1H-indol-2-carboxylic acid chloride By following a procedure analogous to Preparation VI starting from the acid obtained according to Preparation IV, the expected product is obtained in the form of a colorless oil (yield=98%).

Preparation XXXVI

4-[2-[[(Phenylmethoxy)carbonyl]amino]ethoxy]benzeneacetic acid 1,1-dimethylethyl ester A solution of 3 g (9.1 mmol) of 4-[2-[[(phenylmethoxy)carbonyl]amino]-ethoxy]benzeneacetic acid in 60 ml of chloroform is cooled to −30° C. and 1.18 g (10.9 mmol) of ethyl chloroformate and 1.52 ml (10.9 mmol) of triethylamine are added. The mixture is stirred for 1 hour at −30° C. and 1.63 g (22 mmol) of t-butanol and 1.52 ml (10.9 mmol) of triethylamine are then added. The mixture is stirred for 16 hours at room temperature and then concentrated under reduced pressure. The evaporation residue is taken up in 100 ml of ethyl acetate and the organic phase obtained is washed with water and then dried over magnesium sulfate and concentrated under reduced pressure. The crude product is purified by chromatography on silica gel using a dichloromethane/methylcyclohexane mixture (1/1; v/v) as the eluent to give 930 mg of the expected compound (yield=26%).
¹H NMR (DMSO, 300 MHz) δ: 7.46 (t, 1H); 7.38-7.28 (m, 5H); 7.13 (d, 2H); 6.86 (d, 2H); 5.03 (s, 2H); 3.96 (t, 2H); 3.45 (s, 2H); 3.36 (q, 2H); 1.38 (s, 9H).

Preparation XXXVII

4-[2-(Amino)ethoxy]benzeneacetic acid 1,1-dimethylethyl ester 91 mg of 10% palladium-on-charcoal are added to a solution of 910 mg (2.36 mmol) of the compound obtained according to Preparation XXXVI in 15 ml of THF and 1 ml of water and this mixture is stirred under hydrogen atmospheric pressure at room temperature for 1 hour. The catalyst is then filtered off and the filtrate is concentrated under reduced pressure to give 575 mg of the expected product in the form of a colorless oil (yield=97%).
¹H NMR (DMSO, 300 MHz) δ: 7.15 (d, 2H); 6.93 (d, 2H); 3.91 (t, 2H); 6.89 (d, 2H); 2.85 (t, 2H); 3.45 (s, 2H); 1.38 (s, 9H); (NH₂ protons not visible).

EXAMPLE 98

4-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzeneacetic acid 1,1-dimethylethyl ester A solution of 1.1 g (2.35 mmol) of the acid chloride obtained according to Preparation XXXV in 15 ml of dichloromethane is prepared and 575 mg (4.72 mmol) of the amine obtained according to Preparation XXXVII and 0.658 ml of triethylamine are added. The reaction mixture is stirred for 3 hours at room temperature and then concentrated under reduced pressure. The evaporation residue is purified by chromatography on silica gel using a toluene/ethyl acetate mixture (9/1; v/v) as the eluent to give 1.2 g of the expected compound in the form of a beige amorphous solid (yield=77%).

$^1$H NMR (DMSO, 250 MHz) δ: 8.42 (t, 1H); 8.02 (m, 2H); 7.95-7.72 (m, 6H); 7.48 (d, 1H); 7.16-7.11 (m, 5H); 7.03 (t, 1H); 6.89 (d, 2H); 4.89 (dd, 1H); 4.01 (t, 2H); 3.57-3.42 (m, 4H); 3.20-2.89 (m, 2H); 1.38 (s, 9H).

EXAMPLE 99

4-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzeneacetic acid By following a procedure analogous to Example 25 starting from the compound obtained according to Example 98, the expected product is obtained in the form of a white solid (yield=97%).

M.p.=112-113° C.

EXAMPLE 100

4-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzoic acid A solution of 233 mg (1.288 mmol) of 4-(2-aminoethoxy)benzoic acid in 3.73 ml of water and 2.13 ml of triethylamine is prepared. 12.8 ml of acetonitrile are then added at room temperature, followed by a solution of 300 mg (0.644 mmol) of the acid chloride obtained according to Preparation XXXV in 2.13 ml of dichloromethane. The reaction mixture is stirred for 3 hours at room temperature and then concentrated under reduced pressure. The evaporation residue is taken up in dichloromethane and washed with 3% acetic acid solution. The organic phase is concentrated under reduced pressure and the crude product obtained is purified by reversed phase chromatography on RP18-grafted silica using an acetonitrile/water mixture (55/45; v/v) as the eluent to give 350 mg of the expected product in the form of a white solid (yield=89%).

M.p.=95-100° C.

EXAMPLE 101

4-[2-[[[(2S)-2,3-dihydro-1-[[3'-(trifluoromethyl)[1,1'-biphenyl]-4-yl]sulfonyl]-1H-indol-2-yl]carbonyl]amino]ethyl]benzeneacetic acid 1,1-dimethylethyl ester A solution of 177 mg (0.75 mmol) of the t-butyl ester of 4-(2-aminoethyl)-benzeneacetic acid in 3 ml of dichloromethane is prepared. 385 mg (equivalent to 1 mmol) of morpholine supported on a styrene/divinylbenzene copolymer are then added at room temperature, followed by a solution of 350 mg (0.75 mmol) of the acid chloride obtained according to Preparation XXXV in 2.13 ml of dichloromethane. The reaction mixture is stirred for 3 hours at room temperature and then filtered and concentrated under reduced pressure. The crude product obtained is purified by chromatography on silica gel using a toluene/ethyl acetate mixture (8/2; v/v) as the eluent to give 430 mg of the expected product in the form of an oil (yield=95%).

$^1$H NMR (DMSO, 300 MHz) δ: 8.23 (t, 1H); 8.02-7.72 (m, 8H); 7.49 (d, 1H); 7.25 (t, 1H); 7.13-7.11 (m, 5H); 7.03 (t, 1H); 4.80 (dd, 1H); 3.50 (s, 2H); 3.38-3.29 (m, 2H); 3.07 (dd, 1H); 2.84 (dd, 1H); 2.72 (t, 2H); 1.39 (s, 9H).

EXAMPLE 102

4-[2-[[[(2S)-2,3-dihydro-1-[[3'-(trifluoromethyl)[1,1'-biphenyl]-4-yl]sulfonyl]-1H-indol-2-yl]carbonyl]amino]ethyl]benzeneacetic acid By following a procedure analogous to Example 25 starting from the compound obtained according to Example 101, the expected product is obtained in the form of a white solid (yield=69%).

M.p.=110° C.

EXAMPLE 103

3-[2-[[[(2S)-2,3-dihydro-1-[[3'-(trifluoromethyl)[1,1'-biphenyl]-4-yl]sulfonyl]-1H-indol-2-yl]carbonyl]amino]ethyl]benzeneacetic acid 1,1-dimethylethyl ester By following a procedure analogous to Example 98 starting from the t-butyl ester of 3-(2-aminoethyl)benzeneacetic acid, the expected product is obtained in the form of a white paste (yield=95%).

$^1$H NMR (DMSO, 300 MHz) δ: 8.26 (t, 1H); 8.03-7.72 (m, 8H); 7.49 (d, 1H); 7.25-7.03 (m, 7H); 4.81 (dd, 1H); 3.51 (s, 2H); 3.36-3.30 (m, 2H); 3.21 (dd, 1H); 2.90 (dd, 1H); 2.73 (t, 2H); 1.38 (s, 9H).

EXAMPLE 104

3-[2-[[[(2S)-2,3-dihydro-1-[[3'-(trifluoromethyl)[1,1'-biphenyl]-4-yl]sulfonyl]-1H-indol-2-yl]carbonyl]amino]ethyl]benzeneacetic acid By following a procedure analogous to Example 25 starting from the compound obtained according to Example 103, the expected product is obtained in the form of a white solid (yield=84%).

M.p.=90° C.

EXAMPLE 105

(2S)-2,3-dihydro-N-[2-(4-pyridinyloxy)ethyl]-1-[[3'-(trifluoromethyl)[1,1'-biphenyl]-4-yl]sulfonyl]-1H-indole-2-carboxamide By following a procedure analogous to Example 98 starting from 2-(4-pyridinyloxy)ethanamine, the expected product is obtained in the form of a white paste (yield=37%).

$^1$H NMR (DMSO, 300 MHz) δ: 8.45 (t, 1H); 8.39-8.36 (m, 2H); 8.03-7.72 (m, 8H); 7.48 (d, 1H); 7.27 (t, 1H); 7.13 (d,

1H); 7.03 (d, 1H); 6.98-6.95 (m, 2H); 4.87 (dd, 1H); 4.13 (t, 2H); 3.61-3.44 (m, 2H); 3.15 (dd, 1H); 2.93 (dd, 1H).

EXAMPLE 106

(2S)-2,3-dihydro-N-[2-(3-pyridinyloxy)ethyl]-1-[[3'-(trifluoromethyl)[1,1'-biphenyl]-4-yl]sulfonyl]-1H-indole-2-carboxamide By following a procedure analogous to Example 98 starting from 2-(3-pyridinyloxy)ethanamine, the expected product is obtained in the form of a white foam (yield=63%).

$^1$H NMR (DMSO, 300 MHz) δ: 8.48 (t, 1H); 8.30 (dd, 1H); 8.17 (m, 1H); 8.03-7.65 (m, 8H); 7.50-7.02 (m, 6H); 4.89 (dd, 1H); 4.12 (t, 2H); 3.58-3.50 (m, 2H); 3.15 (dd, 1H); 2.93 (dd, 1H).

EXAMPLE 107

γ-[[[(2S)-2,3-dihydro-1-[[3'-(trifluoromethyl)[1,1'-biphenyl]-4-yl sulfonyl]-1H-indol-2-yl]carbonyl]amino]-(γR)-benzenepentanoic acid By following a procedure analogous to Example 100 starting from (γR)-aminobenzenepentanoic acid, the expected product is obtained in the form of a white solid (yield=50%).
M.p.=82-84° C.

EXAMPLE 108

α-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid By following a procedure analogous to Example 100 starting from α-(aminomethyl)benzenepropanoic acid, the expected product is obtained in the form of a white solid (yield=48%).
M.p.=85-90° C.

EXAMPLE 109

7-[[[(2S)-2,3-dihydro-1-[[3'-(trifluoromethyl)[1,1'-biphenyl]-4-yl]sulfonyl]-1H-indol-2-yl]carbonyl]amino]heptanoic acid By following a procedure analogous to Example 100 starting from 7-aminoheptanoic acid, the expected product is obtained in the form of a white solid (yield=14%).
M.p.=65-70° C.

EXAMPLE 110

9-[[[(2S)-2,3-dihydro-1-[[3'-(trifluoromethyl)[1,1'-biphenyl]-4-yl]sulfonyl]-1H-indol-2-yl]carbonyl]amino]nonanoic acid By following a procedure analogous to Example 100 starting from 9-amino-nonanoic acid, the expected product is obtained in the form of a white solid (yield=23%).
M.p.=60° C.

EXAMPLE 111

β-[[[[(2S)-2,3-dihydro-1-[[3'-(trifluoromethyl)[1,1'-biphenyl]-4-yl]sulfonyl]-1H-indol-2-yl]carbonyl]amino]methyl]benzenepropanoic acid A mixture of 38.5 mg (0.215 mmol) of β-(aminomethyl)benzenepropanoic acid, 2 ml of THF, 23 mg (0.217 mmol) of sodium carbonate and 0.7 mg (0.02 mmol) of dodecyltrimethylammonium bromide is prepared. The mixture is stirred for 5 min at room temperature and 100 mg (0.215 mmol) of the acid chloride obtained according to Preparation XXXV are added. The reaction medium is stirred at room Temperature for 2 hours, then at the reflux temperature of the solvent for 16 hours and then cooled and filtered. The residual solid is washed with 5 ml of THF and the combined filtrates are concentrated under reduced pressure. The crude product is purified by reversed phase chromatography on RP18-grafted silica using a water/acetonitrile mixture (45/55; v/v) as the eluent to give 26 mg of the expected compound in the form of a white solid (yield=20%).
M.p.=90° C.

EXAMPLE 112

β-[[[(2S)-2,3-dihydro-1-[[3'-(trifluoromethyl)[1,1'-biphenyl]-4-yl]sulfonyl]-1H-indol-2-yl]carbonyl]amino]-(βS)-benzenebutanoic acid 1,1-dimethylethyl ester By following a procedure analogous to Example 98 starting from the t-butyl ester of (βS)-β-aminobenzenebutanoic acid, the expected product is obtained in the form of a white solid (yield=67%).
M.p.=50° C.

EXAMPLE 113

β-[[[(2S)-2,3-dihydro-1-[[3'-(trifluoromethyl)[1,1'-biphenyl]-4-yl]sulfonyl]-1H-indol-2-yl]carbonyl]amino]-(βS)-benzenebutanoic acid By following a procedure analogous to Example 25 starting from the compound obtained according to Example 112, the expected product is obtained in the form of a white solid (yield=98%).
M.p.=78-82° C.

Preparation XXXVIII 5-(4-Cyanophenoxy)pentanoic acid methyl ester

A solution of 408.6 mg (3.43 mmol) of 4-hydroxybenzonitrile in 15 ml of acetonitrile is prepared and 1.12 g (3.43 mmol) of cesium carbonate and then 803 mg (4.12 mmol) of the methyl ester of 5-bromopentanoic acid are added. The reaction mixture is stirred for 16 hours at room temperature and then concentrated under reduced pressure. The evaporation residue is taken up in ethyl acetate and the organic phase obtained is washed with water and then dried and concentrated. The crude product is purified by chromatography on silica gel using a dichloromethane/methylcyclohexane mixture (6/4; v/v) as the eluent to give the expected product in the form of a pasty solid (yield=71%).

$^1$H NMR (DMSO, 250 MHz) δ: 7.78-7.72 (m, 2H); 7.12-7.06 (m, 2H); 4.06 (t, 2H); 3.58 (s, 3H); 2.38 (t, 2H); 1.78-1.63 (m, 4H).

Preparation XXXIX

5-[4-(Aminomethyl)phenoxy]pentanoic acid methyl ester (hydrochloride)

By following a procedure analogous to Preparation XV (in the presence of hydrochloric acid) starting from the compound obtained according to Preparation XXXVIII, the expected product is obtained in the form of a white solid (yield=83%).
M.p.=198-200° C.

EXAMPLE 114

5-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]pentanoic acid methyl ester By following a procedure analogous to Example 98 starting from the compound obtained according to Preparation XXXIX, the expected product is obtained in the form of a white solid (yield=98%).
M.p.=50° C.

EXAMPLE 115

5-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]pentanoic acid By following a procedure analogous to Example 5 starting from the compound obtained according to Example 114, the expected acid is obtained in the form of a white solid (yield=98%).
M.p.=70° C.

Preparation XL

4-(3-Cyanophenoxy)butanoic acid methyl ester

By following a procedure analogous to Preparation XXXVIII starting from 3-hydroxybenzonitrile and the methyl ester of 4-bromobutanoic acid, the expected ester is obtained in the form of an orange liquid (yield=98%).
$^1$H NMR (DMSO, 250 MHz) δ: 7.49 (t, 1H); 7.40-7.37 (m, 2H); 7.29-7.22 (m, 1H); 4.05 (t, 2H); 3.60 (s, 3H); 2.51-2.45 (m, 2H); 2.05-1.93 (m, 2H).

Preparation XLI

4-[3-(Aminomethyl)phenoxy]butanoic acid methyl ester (hydrochloride)

By following a procedure analogous to Preparation XXXIX starting from the compound obtained according to Preparation XL, the expected ester is obtained in the form of a white solid (yield=87%).
M.p.=104° C.

EXAMPLE 116

4-[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]butanoic acid methyl ester By following a procedure analogous to Example 98 starting from the compound obtained according to Preparation XLI, the expected product is obtained in the form of a white solid (yield=96%).
M.p.=50° C.

EXAMPLE 117

4-[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]butanoic acid By following a procedure analogous to Example 5 starting from the compound obtained according to Example 116, the expected acid is obtained in the form of a white solid (yield=97%).
M.p.=70° C.

Preparation XLII

2-(2-Aminoethoxy)benzeneacetic acid 1-methylethyl ester (hydrochloride)

A solution of 865 mg (4.45 mmol) of the isopropyl ester of 2--hydroxybenzene-acetic acid in 5 ml of acetonitrile is prepared and 1.45 g (4.45 mmol) of cesium carbonate are added. The mixture is stirred for 10 min at room temperature and 500 mg (2.23 mmol) of t-butyl (2-bromoethyl)carbamate are then added. The reaction medium is stirred at room temperature for 16 hours and then concentrated under reduced pressure. The evaporation residue is subsequently treated with 4.7 ml of trifluoroacetic acid for 2 hours at room temperature and then diluted with water and ethyl acetate. The mixture is neutralized with sodium hydroxide solution and extracted with ethyl acetate. The organic phase obtained is dried over magnesium sulfate and partially concentrated under reduced pressure. The crude product is fixed to a sulfonic-grafted silica (Varian Megabond SCX) and released with a solution of ammonia in methanol. The expected product is obtained in the form of the base by concentration of the elution liquid, and then salified with a solution of hydrogen chloride in ethyl ether to give the expected salt in the form of a yellow oil (yield=61%).
$^1$H NMR (DMSO, 300 MHz) δ: 8.21 (s, 3H); 7.28-7.17 (m, 2H); 7.00-6.91 (m, 2H); 4.90 (hep, 1H); 4.17 (t, 2H); 3.60 (s, 2H); 3.15 (hex, 2H); 1.18 (d, 6H).

EXAMPLE 118

2-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzeneacetic acid 1-methylethyl ester By following a procedure analogous to Example 98 starting from the compound obtained according to Preparation XLII, the expected product is obtained in the form of a white solid (yield=92%).
$^1$H NMR (DMSO, 250 MHz) δ: 8.32 (t, 1H); 8.02-7.72 (m, 8H); 7.51 (d, 1H); 7.25-6.89 (m, 7H); 4.93-4.83 (m, 2H); 4.01 (t, 2H); 3.57-3.39 (m, 4H); 3.20-2.92 (m, 2H); 1.16 (d, 6H).

EXAMPLE 119

2-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzeneacetic acid By following a procedure analogous to Example 5 starting from the compound obtained according to Example 118, the expected product is obtained in the form of a white solid (yield=52%)
M.p.=131-134° C. .

EXAMPLE 120

N-[[4-[(dimethylamino)carbonyl]phenyl]methyl]-2,
3-dihydro-1-[[3'-(trifluoromethyl)[1,1'-biphenyl]-4-
yl]sulfonyl]-(2S)-1H-indole-2-carboxamide By following a procedure analogous to Example 98 starting from 4-(aminomethyl)-N,N-dimethylbenzenecarboxamide, the expected product is obtained in the form of a white solid (yield=54%).

M.p.=70° C.

Preparation XLIII 4-(3-Bromophenoxy)butanoic acid 1,1-dimethylethyl ester 1.3 g of 4-(3-bromophenoxy)butanoic acid, 8 ml of liquid isobutene and 2 drops of sulfuric acid are placed in a pressure-resistant reactor. The reactor is closed and stirred at room temperature for 16 hours. The residual pressure is released gently and the product is taken up with ethyl acetate and sodium bicarbonate solution. The organic phase is washed with water and then dried and concentrated under reduced pressure to give the expected ester in the form of a colorless liquid (yield=94%).

$^1$H NMR (DMSO, 250 MHz) δ: 7.26-7.21 (m, 1H); 7.13-7.09 (m, 2H); 6.96-6.92 (m, 1H); 3.98 (t, 2H); 2.34 (t, 2H); 1.95-1.86 (m, 2H); 1.41 (s, 9H).

Preparation XLIV

4-[3-[(E)-2-(1,3-dihydro-1,3-dioxo-2H-isoindol-2-
yl)ethenyl]phenoxy]butanoic acid 1,1-dimethylethyl ester A mixture of 342 mg (1.98 mmol) of N-(2-ethenyl)phthalimide, 620 mg (1.98 mmol) of the ester obtained according to Preparation XLIII, 13.3 mg (0.06 mmol) of palladium acetate, 450 μl (2.5 mmol) of diisopropylethylamine and 53 μl (0.22 mmol) of tri-t-butylphosphine in 8 ml of acetonitrile is prepared and heated by microwaves for 20 min at 150° C. After the solvent has been driven off, the crude product is purified by chromatography on silica gel using a toluene/ethyl acetate mixture (95/5; v/v) as the eluent to give 568 mg of the expected compound in the form of a yellow solid (yield=70%).

$^1$H NMR (DMSO, 300 MHz) δ: 7.96-7.87 (m, 4H); 7.47-7.06 (m, 5H); 6.85-6.82 (m, 1H); 4.02 (t, 2H); 2.38 (t, 2H); 1.98-1.92 (m, 2H); 1.42 (s, 9H).

Preparation XLV

4-[3-[2-(1,3-Dihydro-1,3-dioxo-2H-isoindol-2-yl)
ethyl]phenoxy]butanoic acid 1,1-dimethylethyl ester A solution of 565 mg (1.38 mmol) of the compound obtained according to Preparation XLIV in 8 ml of THF and 2 ml of ethanol is prepared and 209 mg of 10% palladium-on-charcoal are added. This mixture is hydrogenated under 3500 hPa at room temperature and then filtered and concentrated under reduced pressure to give 536 mg of the expected compound in the form of a beige solid (yield=94%).

$^1$H NMR (DMSO, 300 MHz) δ: 7.87-7.80 (m, 4H); 7.17-7.11 (m, 1H); 6.74-6.71 (m, 3H); 3.92-3.76 (m, 4H); 2.88 (t, 2H); 2.30 (t, 2H); 1.91-1.82 (m, 2H); 1.39 (s, 9H).

Preparation XLVI

4-[3-[2-(Amino)ethyl]phenoxy]butanoic acid 1,1-dimethylethyl ester

A solution of 250 mg (0.63 mmol) of the compound obtained according to Preparation XLV in 2.5 ml of ethanol is prepared and 230 mg (0.46 mmol) of hydrazine hydrate are added. This mixture is heated for 30 min at the reflux temperature of the solvent and then filtered and concentrated under pressure. The crude product is purified by chromatography on silica gel using a dichloromethane/methanol mixture (95/5; v/v) containing 1% of ammonia as the eluent to give 244 mg of the expected compound in the form of an oil (yield=67%).

$^1$H NMR (DMSO, 300 MHz) δ: 7.20-7.13 (m, 1H); 6.76-6.70 (m, 3H); 3.94 (t, 2H); 2.74 (m, 2H); 2.58 (t, 2H); 2.35 (t, 2H); 1.96-1.88 (m, 2H); 1.39 (s, 9H).

EXAMPLE 121

4-[3-[2-[[[(2S)-2,3-dihydro-1-[[3'-(trifluoromethyl)
[1,1'-biphenyl]-4-yl]sulfonyl]-1H-indol-2-yl]carbo-
nyl]amino]ethyl]phenoxy]butanoic acid 1,1-dimeth-
ylethyl ester By following a procedure analogous to Example 98 starting from the compound obtained according to Preparation XLVI, the expected product is obtained in the form of a beige solid (yield=88%).

$^1$H NMR (DMSO, 300 MHz) δ: 8.26 (t, 1H); 8.03-7.72 (m, 8H); 7.49 (d, 1H); 7.30-7.00 (m, 4H); 6.78-6.73 (m, 3H); 4.81 (dd, 1H); 3.94 (t, 2H); 3.42-3.30 (m, 2H); 3.06 (dd, 1H); 2.85 (dd, 1H); 2.71 (t, 2H); 2.35 (t, 2H); 1.93-1.88 (m, 2H); 1.37 (s, 9H).

EXAMPLE 122

4-[3-[2-[[[(2S)-2,3-dihydro-1-[[3'-(trifluoromethyl)
[1,1'-biphenyl]-4-yl]sulfonyl]-1H-indol-2-yl]carbo-
nyl]amino]ethyl]phenoxy]butanoic acid By following a procedure analogous to Example 25 starting from the compound obtained according to Example 121, the expected product is obtained in the form of a white solid (yield=89%).

M.p.=70° C.

By following a procedure analogous to Preparations XLIII to XLVI starting from 3-(3-bromophenoxy)propanoic acid, the compounds below are obtained in succession:

Preparation XLVII 3-(3-Bromophenoxy)propanoic acid
1,1-dimethylethyl ester

Colorless liquid (yield=98%).

$^1$H NMR (DMSO, 300 MHz) δ: 7.24 (t, 1H); 7.14-7.11 (m, 2H); 6.96-6.92 (m, 1H); 4.17 (t, 2H); 2.65 (t, 2H); 1.40 (s, 9H).

Preparation XLVIII

3-[3-[(E)-2-(1,3-dihydro-1,3-dioxo-2H-isoindol-2-yl)ethenyl]phenoxy]propanoic acid 1,1-dimethylethyl ester Yellow solid (yield=21%).
$^1$H NMR (DMSO, 300 MHz) δ: 7.96-7.87 (m, 4H); 7.47-7.07 (m, 5H); 6.86-6.81 (m, 1H); 4.21 (t, 2H); 2.67 (t, 2H); 1.42 (s, 9H).

Preparation IL

3-[3-[2-(1,3-Dihydro-1,3-dioxo-2H-isoindol-2-yl)ethyl]phenoxy]propanoic acid 1,1-dimethylethyl ester Colorless oil (yield=98%).
$^1$H NMR (DMSO, 250 MHz) δ: 7.84-7.81 (m, 4H); 7.15 (t, 1H); 6.76-6.71 (m, 3H); 4.07 (t, 2H); 3.81 (t, 2H); 2.89 (t, 2H); 2.61 (t, 2H); 1.39 (s, 9H).

Preparation L

3-[3-[2-(Amino)ethyl]phenoxy]propanoic acid 1,1-dimethylethyl ester

Colorless oil (yield=91%).
$^1$H NMR (DMSO, 300 MHz) δ: 7.20-7.14 (m, 1H); 6.78-6.71 (m, 3H); 4.13 (t, 2H); 2.74 (m, 2H); 2.66-2.56 (m, 4H); 1.39 (s, 9H).

EXAMPLE 123

3-[3-[2-[[[(2S)-2,3-dihydro-1-[[3'-(trifluoromethyl)[1,1'-biphenyl]-4-yl]sulfonyl]-1H-indol-2-yl]carbonyl]amino]ethyl]phenoxy]propanoic acid 1,1-dimethylethyl ester By following a procedure analogous to Example 98 starting from the compound obtained according to Preparation L, the expected product is obtained in the form of a beige solid (yield=81%).
$^1$H NMR (DMSO, 300 MHz) δ: 8.23 (t, 1H); 8.02-7.72 (m, 8H); 7.48 (d, 1H); 7.30-7.11 (m, 3H); 7.02 (t, 1H); 6.77-6.74 (m, 3H); 4.80 (dd, 1H); 4.13 (t, 2H); 3.39-3.31 (m, 2H); 3.08 (dd, 1H); 2.85 (dd, 1H); 2.73-2.62 (m, 4H); 1.39 (s, 9H).

EXAMPLE 124

3-[3-[2-[[[(2S)-2,3-dihydro-1-[[3'-(trifluoromethyl)[1,1'-biphenyl]-4-yl]sulfonyl]-1H-indol-2-yl]carbonyl]amino]ethyl]phenoxy]propanoic acid By following a procedure analogous to Example 25 starting from the compound obtained according to Example 123, the expected product is obtained in the form of a white solid (yield=45%).
M.p.=78° C.

Preparation LI

4-[4-[2-(Amino)ethyl]phenoxy]butanoic acid methyl ester (hydrochloride)

By following a procedure analogous to Preparation XV starting from the methyl ester of 4-[4-(cyanomethyl)phenoxy]butanoic acid, the expected product is obtained in the form of a white solid (yield=68%).
M.p.=168-172° C.

EXAMPLE 125

4-[4-[2-[[[(2S)-2,3-dihydro-1-[[3'-(trifluoromethyl)[1,1'-biphenyl]-4-sulfonyl]-1H-indol-2-yl]carbonyl]amino]ethyl]phenoxy]butanoic acid methyl ester By following a procedure analogous to Example 98 starting from the compound obtained according to Preparation LI, the expected product is obtained in the form of a white solid (yield=98%).
$^1$H NMR (DMSO, 250 MHz) δ: 8.18 (t, 1H); 8.03-7.72 (m, 8H); 7.49 (d, 1H); 7.26 (t, 1H); 7.13-7.01 (m, 4H); 6.80 (d, 2H); 4.80 (dd, 1H); 3.94 (t, 2H); 3.60 (s, 3H); 3.40-3.30 (m, 2H); 3.04 (dd, 1H); 2.85 (dd, 1H); 2.66 (t, 2H); 2.46 (t, 2H); 2.00-1.89 (m, 2H).

EXAMPLE 126

4-[4-[2-[[[(2S)-2,3-dihydro-1-[[3'-(trifluoromethyl)[1,1'-biphenyl]-4-yl]sulfonyl]-1H-indol-2-yl]carbonyl]amino]ethyl]phenoxy]butanoic acid By following a procedure analogous to Example 5 starting from the compound obtained according to Example 125, the expected product is obtained in the form of a white solid (yield=75%).
M.p.=70° C.

Preparation LII

3-[4-[2-(Amino)ethyl]phenoxy]propanoic acid (hydrochloride)

By following a procedure analogous to Preparation XV starting from 3-[4-(cyanomethyl)phenoxy]propanoic acid, the expected product is obtained in the form of a white solid (yield=23%).
M.p.=216° C.

EXAMPLE 127

3-[4-[2-[[[(2S)-2,3-dihydro-1-[[3'-(trifluoromethyl)[1,1'-biphenyl]-4-yl]sulfonyl]-1H-indol-2-yl]carbonyl]amino]ethyl]phenoxy]propanoic acid A solution of 115 mg (0.47 mmol) of the compound obtained according to Preparation LII in 1.3 ml of water is prepared and 777 µl of triethylamine and 4.7 ml of acetonitrile are added. Finally, a solution of 240.9 mg (0.51 mmol) of the acid chloride obtained according to Preparation XXXV in 2 ml of acetonitrile is added at room temperature, with stirring. The reaction medium is stirred for 30 min and then concentrated under reduced pressure. The evaporation residue is taken up with slightly acidified water and ethyl acetate. The organic phase is separated off, washed with water and then dried and concentrated under reduced pressure. The crude product is purified by chromatography on silica gel using a dichloromethane/ethyl acetate mixture (95/5; v/v) containing 1% of acetic acid as the eluent to give 144 mg of the expected compound in the form of a white solid (yield=48%).
M.p.=70° C.

Preparation LIII

5-[3-(Aminomethyl)phenoxy]pentanoic acid methyl ester (hydrochloride)

By following a procedure analogous to Preparation XV starting from the methyl ester of 5-(3-cyanophenoxy)pentanoic acid, the expected product is obtained in the form of a white solid (yield=94%).

M.p.=94-98° C.

EXAMPLE 128

5-[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]pentanoic acid methyl ester By following a procedure analogous to Example 98 starting from the compound obtained according to Preparation LIII, the expected product is obtained in the form of a white solid (yield=98%).

$^1$H NMR (DMSO, 250 MHz) δ: 8.74 (t, 1H); 8.03-7.72 (m, 8H); 7.51 (d, 1H); 7.24-7.03 (m, 4H); 6.86-6.80 (m, 3H); 4.92 (dd, 1H); 4.32 (d, 2H); 3.90 (t, 2H); 3.56 (s, 3H); 3.18 (dd, 1H); 2.97 (dd, 1H); 2.36 (t, 2H); 1.73-1.63 (m, 4H).

EXAMPLE 129

5-[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]pentanoic acid By following a procedure analogous to Example 5 starting from the compound obtained according to Example 128, the expected product is obtained in the form of a white solid (yield=75%).

M.p.=70° C.

Preparation LIV

4-[4-(Aminomethyl)phenoxy]butanoic acid methyl ester (hydrochloride)

By following a procedure analogous to Preparation XV starting from the methyl ester of 4-(4-cyanophenoxy)butanoic acid, the expected product is obtained in the form of a white solid (yield=63%).

M.p.=218° C.

EXAMPLE 130

4-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]butanoic acid methyl ester By following a procedure analogous to Example 127 starting from the compound obtained according to Preparation LIV, the expected product is obtained in the form of a white solid (yield=98%).

M.p.=50° C.

EXAMPLE 131

4-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]butanoic acid By following a procedure analogous to Example 5 starting from the compound obtained according to Example 130, the expected product is obtained in the form of a white solid (yield=84%).

M.p.=78-80° C.

Preparation LV

3-[3-(Aminomethyl)phenoxy]propanoic acid (hydrochloride)

By following a procedure analogous to Preparation XV starting from 3-(3-cyanophenoxy)propanoic acid, the expected product is obtained in the form of a white solid (yield=73%).

M.p.=134-138° C.

EXAMPLE 132

3-[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]propanoic acid By following a procedure analogous to Example 127 starting from the compound obtained according to Preparation LV, the expected product is obtained in the form of a white solid (yield=98%).

M.p.=70° C.

Preparation LVI

3-[4-(Aminomethyl)phenoxy]propanoic acid (hydrochloride)

By following a procedure analogous to Preparation XV starting from 3-(4-cyanophenoxy)propanoic acid, the expected product is obtained in the form of a white solid (yield=78%).

M.p.=163-165° C.

EXAMPLE 133

3-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]propanoic acid By following a procedure analogous to Example 127 starting from the compound obtained according to Preparation LVI, the expected product is obtained in the form of a white solid (yield=76%).

M.p.=72° C.

EXAMPLE 134

4-[2-[[[(2S)-2,3-dihydro-1-[[3'-(trifluoromethyl)[1,1'-biphenyl]-4-yl]sulfonyl]-1H-indol-2-yl]carbonyl]amino]ethyl]benzoic acid By following a procedure analogous to Example 127 starting from 4-(2-aminoethyl)benzoic acid, the expected product is obtained in the form of a white solid (yield=89%).
M.p.=106° C.

Preparation LVII 3-(4-Cyanophenoxy)-2,2-dimethylpropanoic acid methyl ester

A mixture of 2.65 g (10.1 mmol) of triphenylphosphine and 20 ml of toluene is prepared and 2 ml (10.2 mmol) of DIAD (diisopropyl azodicarboxylate) are added at 0° C. The solution obtained is added to a solution of 1 g (8.4 mmol) of 4-hydroxybenzonitrile and 1.30 ml (10.2 mmol) of methyl 2,2-dimethyl-3--hydroxy-propanoate in 10 ml of toluene at 0° C. The reaction mixture is subsequently stirred for 30 min at 80° C. and then concentrated under reduced pressure. The crude product is purified by chromatography on silica gel using toluene as the eluent to give the expected compound in the form of a colorless oil (yield=89%).
$^1$H NMR (DMSO, 250 MHz) δ: 7.75 (d, 2H); 7.10 (d, 2H); 4.08 (s, 2H); 3.61 (s, 3H); 1.24 (s, 6H).

Preparation LVIII

3-[4-(Aminomethyl)phenoxy]-2,2-dimethylpropanoic acid methyl ester (hydrochloride)

By following a procedure analogous to Preparation XV starting from the compound obtained according to Preparation LVII, the expected product is obtained in the form of a white solid (yield=96%).
M.p.=140-145° C.

EXAMPLE 135

3-[4-[[[[(2S)-2,3-dihydro-1-[[2'-(trifluoromethyl)[1,1'-biphenyl]-4-yl]sulfonyl]-1H-indol-2-yl]carbonyl]amino]methyl]phenoxy]-2,2-dimethylpropanoic acid methyl ester By following a procedure analogous to Example 21 starting from the amine obtained according to Preparation LVIII, the expected product is obtained in the form of a white solid (yield=75%).
M.p.=68-75° C.

EXAMPLE 136

3-[4-[[[[(2S)-2,3-dihydro-1-[[2'-(trifluoromethyl)[1,1'-biphenyl]-4-yl]sulfonyl]-1H-indol-2-yl]carbonyl]amino]methyl]phenoxy]-2,2-dimethylpropanoic acid By following a procedure analogous to Example 5 starting from the ester obtained according to Example 135, the expected product is obtained in the form of a white solid (yield=74%).
M.p.=98-105° C.

EXAMPLE 137

3-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]-2,2-dimethylpropanoic acid methyl ester By following a procedure analogous to Example 4 starting from the amine obtained according to Preparation LVIII, the expected product is obtained in the form of a colorless oil (yield=51%).
$^1$H NMR (DMSO, 300 MHz) δ: 8.66 (t, 1H); 8.03-7.70 (m, 8H); 7.50 (d, 1H); 7.24-7.12 (m, 4H); 7.03 (t, 1H); 6.86 (d, 2H); 4.88 (dd, 1H); 4.33-4.20 (m, 2H); 3.95 (s, 2H); 3.60 (s, 3H); 3.16 (dd, 1H); 2.94 (dd, 1H); 1.23 (s, 6H).

EXAMPLE 138

3-[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]-2,2-dimethylpropanoic acid By following a procedure analogous to Example 5 starting from the ester obtained according to Example 137, the expected product is obtained in the form of a white solid (yield=88%).
M.p.=95-105° C.

EXAMPLE 139

2,3-Dihydro-N-[[2-(methylamino)phenyl]methyl]-1-[[3'-(trifluoromethyl)[1,1'-biphenyl]-4-yl]sulfonyl]-(2S)-1H-indole-2-carboxamide 0.028 ml (0.19 mmol) of triethylamine and 0.018 ml (0.19 mmol) of methyl sulfate are added to a solution of 100 mg (0.18 mmol) of the compound obtained according to Example 61 in 3 ml of ethyl ether. The mixture is refluxed for 8 hours and then concentrated under reduced pressure. The crude product is purified by reversed phase chromatography on RP18-grafted silica using an acetonitrile/water mixture (6/4; v/v) as the eluent to give the expected product in the form of a white powder (yield=62%).
M.p.=86° C.

EXAMPLE 140

2,3-Dihydro-N-[[2-(dimethylamino)phenyl]methyl]-1-[[3'-(trifluoromethyl)[1,1'-biphenyl]-4-yl]sulfonyl]-(2S)-1H-indole-2-carboxamide A solution of 100 mg (0.18 mmol) of the compound obtained according to Example 61 in 2 ml of acetonitrile is prepared and 0.07 ml (0.9 mmol) of 36% aqueous formaldehyde solution is added at room temperature. The reaction mixture is stirred for 15 min at room temperature and 23 mg (0.36 mmol) of sodium cyanoborohydride are then added. The mixture is stirred again for 15 min, 0.05 ml of acetic acid is added and stirring is continued for 2 hours at room temperature. The solvent is then driven off under reduced pressure and the residue is taken up with dichloromethane. The organic phase is washed with N sodium hydroxide solution and then with water, dried over magnesium sulfate and concentrated under reduced pressure. The crude product is purified by chromatography on silica gel using a toluene/isopropanol mixture (95/5; v/v) as the eluent to give the expected product in the form of a white foam (yield=95%).
M.p.=66° C.

EXAMPLE 141

3-[4-[2-[[[(2S)-2,3-dihydro-1-[[3'-(trifluoromethyl)[1,1'-biphenyl]-4-yl]sulfonyl]-1H-indol-2-yl]carbonyl]amino]ethyl]phenyl]propanoic acid 1,1-dimethylethyl ester By following a procedure analogous to Example 4 starting from the t-butyl ester of 4-(2-aminoethyl)benzenepropanoic acid, the expected product is obtained in the form of an amorphous solid (yield=89%).

$^1$H NMR (DMSO, 250 MHz) δ: 8.21 (t, 1H); 8.03-7.72 (m, 8H); 7.49 (d, 1H); 7.30-7.03 (m, 7H); 4.81 (dd, 1H); 3.39-3.31 (m, 2H); 3.21 (dd, 1H); 2.88-2.66 (m, 5H); 2.50 (t, 2H); 1.35 (s, 9H).

EXAMPLE 142

3-[4-[2-[[[(2S)-2,3-dihydro-1-[[3'-(trifluoromethyl)[1,1'-biphenyl]-4-yl]sulfonyl]-1H-indol-2-yl]carbonyl]amino]ethyl]phenyl]propanoic acid By following a procedure analogous to Example 25 starting from the ester obtained according to Example 141, the expected product is obtained in the form of a beige solid (yield=94%).

M.p.=86° C.

Preparation LIX

4-[(2-Aminoethyl)thio]-3-chlorobenzeneacetic acid methyl ester (trifluoroacetate)

A solution of 957 mg (2.76 mmol) of the methyl ester of 3-chloro-4-[[2-[[(1,1-dimethylethoxy)carbonyl]amino]ethyl]thio]benzeneacetic acid in 7 ml of trifluoroacetic acid is prepared. The reaction mixture is stirred for 16 hours at room temperature and then concentrated under reduced pressure to give the expected compound in the form of a beige oil (yield=98%).

$^1$H NMR (DMSO, 250 MHz) δ: 7.91 (broad s, 3H); 7.44 (dd, 1H); 7.41 (s, 1H); 7.28 (dd, 1H); 3.71 (s, 2H); 3.62 (s, 3H); 3.22 (t, 2H); 3.04 (m, 2H).

EXAMPLE 143

3-Chloro-4-[[2-[[[(2S)-2,3-dihydro-1-[[2'-(trifluoromethyl)[1,1'-biphenyl]-4-yl]sulfonyl]-1H-indol-2-yl]carbonyl]amino]ethyl]thio]benzeneacetic acid methyl ester By following a procedure analogous to Example 21 starting from the amine obtained according to Preparation LIX, the expected product is obtained in the form of an oil (yield=88%).

$^1$H NMR (DMSO, 250 MHz) δ: 8.51 (t, 1H); 7.83-7.60 (m, 5H); 7.51-7.04 (m, 10H); 4.82 (dd, 1H); 3.68 (s, 2H); 3.61 (s, 3H); 3.41-2.99 (m, 6H).

EXAMPLE 144

3-Chloro-4-[[2-[[[(2S)-2,3-dihydro-1-[[2'-(trifluoromethyl)[1,1'-biphenyl]-4-yl]sulfonyl]-1H-indol-2-yl]carbonyl]amino]ethyl]thio]benzeneacetic acid By following a procedure analogous to Example 5 starting from the ester obtained according to Example 143, the expected product is obtained in the form of a white solid (yield=66%).

M.p.=86° C.

EXAMPLE 145

3-Chloro-4-[[2-[[[(2S)-2,3-dihydro-1-[[3'-(trifluoromethyl)[1,1'-biphenyl]-4-yl]sulfonyl]-1H-indol-2-yl]carbonyl]amino]ethyl]thio]benzeneacetic acid methyl ester By following a procedure analogous to Example 4 starting from the amine obtained according to Preparation LIX, the expected product is obtained in the form of an oil (yield=88%).

$^1$H NMR (DMSO, 300 MHz): δ=8.51 (t, 1H); 8.03-7.72 (m, 8H); 7.53-7.47 (m, 2H); 7.39 (d, 1H); 7.25-7.03 (m, 3H); 6.90 (td, 1H); 4.83 (dd, 1H); 3.66 (s, 2H); 3.61 (s, 3H); 3.42-2.95 (m, 6H).

EXAMPLE 146

3-Chloro-4-[[2-[[[(2S)-2,3-dihydro-1-[[3'-(trifluoromethyl)[1,1'-biphenyl]-4-yl]sulfonyl]-1H-indol-2-yl]carbonyl]amino]ethyl]thio]benzeneacetic acid By following a procedure analogous to Example 5 starting from the ester obtained according to Example 145, the expected product is obtained in the form of a white solid (yield=83%).

M.p.=70° C.

Preparation LX 2-(2-Aminoethoxy)benzoic acid 1-methylethyl ester (hydrochloride)

By following a procedure analogous to Preparation XLII starting from the isopropyl ester of 2-hydroxybenzoic acid, the expected product is obtained in the form of an amorphous solid (yield=37%).

$^1$H NMR (DMSO, 300 MHz) δ: 8.20 (broad s, 3H); 7.67 (dd, 1H); 7.55 (td, 1H); 7.20 (dd, 1H); 7.07 (td, 1H); 5.11 (hep, 1H); 4.27 (t, 2H); 3.19 (t, 2H); 1.30 (d, 6H).

EXAMPLE 147

2-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzoic acid 1-methylethyl ester By following a procedure analogous to Example 4 starting from the compound obtained according to Preparation LX, the expected product is obtained in the form of a white solid (yield=73%).

$^1$H NMR (DMSO, 250 MHz) δ: 8.31 (t, 1H); 8.03-7.78 (m, 8H); 7.60 (dd, 1H); 7.52-7.46 (m, 2H); 7.13 (t, 1H); 7.12-6.99 (m, 4H); 5.11 (hep, 1H); 4.86 (dd, 1H); 4.09 (t, 2H); 3.53 (m, 2H); 3.20-2.92 (m, 2H); 1.29 (d, 6H).

EXAMPLE 148

2-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]benzoic acid By following a procedure analogous to Example 5 starting from the compound obtained according to Example 147, the expected product is obtained in the form of a white solid (yield=11%).
M.p.=70° C.

EXAMPLE 149

N-[[4-[(dimethylamino)carbonyl]phenyl]methyl]-2,3-dihydro-1-[[2'-(trifluoromethyl)[1,1'-biphenyl]-4-yl]sulfonyl]-(2S)-1H-indole-2-carboxamide By following a procedure analogous to Example 21 starting from 4-(aminomethyl)-N,N-dimethylbenzenecarboxamide, the expected product is obtained in the form of a white solid (yield=80%).
M.p.=105-106° C.

EXAMPLE 150

N-[[4-[(dimethylamino)methyl]phenyl]methyl]-2,3-dihydro-1-[[2'-(trifluoromethyl)[1,1'-biphenyl]-4-yl]sulfonyl]-(2S)-1H-indole-2-carboxamide By following a procedure analogous to Example 21 starting from N,N-dimethyl-1,4-benzenedimethanamine, the expected product is obtained in the form of a white solid (yield=32%).
M.p.=53° C.

EXAMPLE 151

N-[[4-[(dimethylamino)methyl]phenyl]methyl]-2,3-dihydro-1-[[3'-(trifluoromethyl)[1,1'-biphenyl]-4-yl]sulfonyl]-(2S)-1H-indole-2-carboxamide By following a procedure analogous to Example 4 starting from N,N-dimethyl-1,4-benzenedimethanamine, the expected product is obtained in the form of a white solid (yield=25%).
M.p.=70° C.

Preparation LXI 4-(2-Aminoethoxy)-3-chlorobenzeneacetic acid methyl ester (trifluoroacetate)

By following a procedure analogous to Preparation XLII starting from the methyl ester of 3-chloro-4-hydroxybenzeneacetic acid, the expected product is obtained in the form of an amorphous solid (yield=88%).
$^1$H NMR (DMSO, 300 MHz) δ: 7.99 (broad s, 3H); 7.37 (d, 1H); 7.23-7.13 (m, 2H); 4.23 (t, 2H); 3.66 (s, 2H); 3.61 (s, 3H); 3.25 (m, 2H).

EXAMPLE 152

3-Chloro-4-[2-[[[(2S)-2,3-dihydro-1-[[3'-(trifluoromethyl)[1,1'-biphenyl]-4-yl]-sulfonyl]-1H-indol-2-yl]carbonyl]amino]ethoxy]benzeneacetic acid methyl ester By following a procedure analogous to Example 4 starting from the compound obtained according to Preparation LXI, the expected product is obtained in the form of a poorly crystalline solid (yield=49%).
$^1$H NMR (DMSO, 250 MHz) δ: 8.36 (t, 1H); 8.03-7.72 (m, 8H); 7.49 (d, 1H); 7.34 (s, 1H); 7.15-7.02 (m, 5H); 4.89 (dd, 1H); 4.12 (m, 2H); 3.63-3.44 (m, 7H); 3.20-2.92 (m, 2H).

EXAMPLE 153

3-Chloro-4-[2-[[[(2S)-2,3-dihydro-1-[[3'-(trifluoromethyl)[1,1'-biphenyl]-4-yl]-sulfonyl]-1H-indol-2-yl]carbonyl]amino]ethoxy]benzeneacetic acid By following a procedure analogous to Example 5 starting from the compound obtained according to Example 152, the expected product is obtained in the form of a white solid (yield=80%).
M.p.=96° C.

EXAMPLE 154

2,3-Dihydro-N-[2-(2-pyridinyloxy)ethyl]-1-[[3'-(trifluoromethyl)[1,1'-biphenyl]-4-yl]sulfonyl]-(2S)-1H-indole-2-carboxamide By following a procedure analogous to Example 4 starting from 2-(2-aminoethoxy)pyridine hydrochloride, the expected product is obtained in the form of a white foam (yield=84%).
M.p.=85° C.

EXAMPLE 155

2,3-Dihydro-N-[(3-nitrophenyl)methyl]-1-[[3'-(trifluoromethyl)[1,1'-biphenyl]-4-yl]sulfonyl]-(2S)-1H-indole-2-carboxamide By following a procedure analogous to Example 4 starting from 3-nitrobenzene-methanamine hydrochloride, the expected product is obtained in the form of a white foam (yield=97%).
$^1$H NMR (DMSO, 250 MHz) δ: 8.97 (t, 1H); 8.17-7.72 (m, 11H); 7.64 (t, 1H); 7.53 (d, 1H); 7.26 (t, 1H); 7.14 (d, 1H); 7.04 (td, 1H); 4.91 (dd, 1H); 4.48 (d, 2H); 3.20 (dd, 1H); 2.96 (dd, 1H).

EXAMPLE 156

N-[(3-aminophenyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 61 starting from the compound obtained according to Example 155, the expected product is obtained in the form of a white foam (yield=96%).
M.p.=82° C.

EXAMPLE 157

2,3-Dihydro-N-[(4-nitrophenyl)methyl]-1-[[3'-(trifluoromethyl)[1,1'-biphenyl]-4-yl]sulfonyl]-(2S)-1H-indole-2-carboxamide By following a procedure analogous to Example 4 starting from 4-nitrobenzene-methanamine hydrochloride, the expected product is obtained in the form of a white foam (yield=79%).
$^1$H NMR (DMSO, 250 MHz) δ: 8.96 (t, 1H); 8.19 (dd, 2H); 8.02-7.70 (m, 8H); 7.57-7.51 (m, 3H); 7.26-7.14 (m, 2H); 7.04 (td, 1H); 4.91 (dd, 1H); 4.55-4.40 (m, 2H); 3.21 (dd, 1H); 2.99 (dd, 1H).

EXAMPLE 158

N-[(4-aminophenyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 61 starting from the compound obtained according to Example 157, the expected product is obtained in the form of a white foam (yield=98%).
M.p.=84° C.

Preparation LXII 2,3-Dihydro-1-[(4'-fluoro[1,1'-biphenyl]-4-yl)sulfonyl]-(2S)-1H-indole-2-carboxylic acid methyl ester A mixture of 0.545 g (2.55 mmol) of the hydrochloride of the methyl ester of 2,3-dihydro-(2S)-1H-indole-2-carboxylic acid and 10 ml of acetonitrile is prepared and 0.9 g (3.32 mmol) of 4'-fluoro[1,1'-biphenyl]-4-sulfonyl chloride and 0.62 ml of N-methylmorpholine are added. The reaction mixture is stirred for 16 hours at room temperature and then concentrated under reduced pressure. The residue is taken up in 100 ml of ethyl acetate and washed with 3 times 75 ml of water. The organic phase is dried over magnesium sulfate and then concentrated under reduced pressure. The crude product is purified by chromatography on silica gel using a toluene/ethyl acetate mixture (98/2; v/v) as the eluent to give 0.83 g of the expected compound in the form of a white solid (yield=79%).
$^1$H NMR (DMSO, 300 MHz) δ: 7.93-7.74 (m, 6H); 7.42 (d, 1H); 7.34-7.14 (m, 4H); 7.01 (t, 1H); 5.10 (dd, 1H); 3.73 (s, 3H); 3.38 (dd, 1H); 3.09 (dd, 1H).

Preparation LXIII 2,3-Dihydro-1-[(4'-fluoro[1,1'-biphenyl]-4-yl)sulfonyl]-(2S)-1H-indole-2-carboxylic acid By following a procedure analogous to Example 5 starting from the compound obtained according to Preparation LXII, the expected product is obtained in the form of a white solid (yield=98%).
M.p.=145-150° C.

EXAMPLE 159

2,3-Dihydro-N-(phenylmethyl)-1-[(4'-fluoro[1,1'-biphenyl]-4-yl)sulfonyl]-(2S)-1H-indole-2-carboxamide A solution of 50 mg (0.126 mmol) of the acid obtained according to Preparation LXIII in 3 ml of dichloromethane is mixed with 140 mg of DCC-grafted resin (activated beforehand by washing with dichloromethane), and 5 mg (0.036 mmol) of HOAT and 18 mg (0.17 mmol) of benzylamine are added. The reaction mixture is stirred at room temperature for 16 hours. About 50 mg of IR 120 resin are added and the mixture is stirred again for 3 hours. The resins are then filtered off and the filtrate is concentrated under reduced pressure to give the expected compound in the form of a white solid (yield=85%).
M.p.=65° C.

EXAMPLE 160

N-[2-(4-chlorophenyl)ethyl]-2,3-dihydro-1-[(4'-fluoro[1,1'-biphenyl]-4-yl)sulfonyl]-(2S)-1H-indole-2-carboxamide By following a procedure analogous to Example 159 starting from 2-(4-chlorophenyl)ethanamine, the expected product is obtained in the form of a white solid (yield=91%).
M.p.=126° C.

EXAMPLE 161

4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid methyl ester By following a procedure analogous to Example 159 starting from the methyl ester of 4-(2-aminoethoxy)benzoic acid, the expected product is obtained in the form of a white solid (yield=94%).
M.p.=70-72° C.

EXAMPLE 162

4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid By following a procedure analogous to Example 5 starting from the ester obtained according to Example 161, the expected product is obtained in the form of a white solid (yield=94%).
M.p.=108° C.

EXAMPLE 162a

4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid sodium salt The salt is obtained by lyophilizing the solution obtained by mixing the acid with an equimolecular amount of sodium hydroxide in water.
M.p.=214-224° C.

EXAMPLE 163

2,3-Dihydro-N-(2-oxo-2-phenylethyl)-1-[(4'-fluoro[1,1'-biphenyl]-4-yl)sulfonyl]-(2S)-1H-indole-2-carboxamide By following a procedure analogous to Example 159 starting from 2-oxo-2-phenylethanamine, the expected product is obtained in the form of a yellow solid (yield=51%).
M.p.=80-82° C.

EXAMPLE 164

2,3-Dihydro-N-(2,2-diphenylethyl)-1-[(4'-fluoro[1,1'-biphenyl]-4-yl)sulfonyl]-(2S)-1H-indole-2-carboxamide By following a procedure analogous to Example 159 starting from 2,2-diphenylethanamine, the expected product is obtained in the form of a white solid (yield =86%).
M.p.=80-82° C.

EXAMPLE 165

1-[(4'-Fluoro[1,1'-biphenyl]-4-yl)sulfonyl]-2,3-dihydro-N-[(1S,2R)-2--phenyl-cyclopropyl]-(2S)-1H-indole-2-carboxamide By following a procedure analogous to Example 159 starting from (1S,2R)-2-phenylcyclopropylamine, the expected product is obtained in the form of a yellow solid (yield=75%).
M.p.=80° C.

EXAMPLE 166

4-[2-[[[(2S)-1-[(4'-fluoro[1,1'-biphenyl]-4-yl)sulfonyl]-2,3-dihydro-1H-indol-2-yl]carbonyl]amino] ethoxy]benzeneacetic acid A solution of 100 mg (0.252 mmol) of the acid obtained according to Preparation LXIII in 2 ml of dichloromethane is prepared and 40.5 µl of thionyl chloride and 77 µl of triethylamine are added at 0° C. The mixture is stirred for 15 min at 0° C. and then concentrated under reduced pressure. A suspension of 54 mg of 4-(2-aminoethoxy)benzeneacetic acid in 2 ml of dichloromethane and 77 µl of triethylamine is then added to the resulting acid chloride. The reaction medium is stirred at room temperature for 3 hours and then diluted with 10 ml of dichloromethane and washed with water. The organic phase is dried over magnesium sulfate and concentrated under reduced pressure. The crude product is purified by chromatography on silica gel using a dichloromethane/methanol mixture (95/5; v/v) as the eluent to give 29 mg of the expected compound in the form of a yellow solid (yield=20%).
M.p.=81° C.

EXAMPLE 167

β-[[[(2S)-1-[(4'-fluoro[1,1'-biphenyl]-4-yl)sulfonyl]-2,3-dihydro-1H-indol-2-yl]carbonyl]amino]-(βS)-benzenebutanoic acid 1,1-dimethylethyl ester By following a procedure analogous to Preparation I starting from the t-butyl ester of (βS)-β-aminobenzenebutanoic acid, the expected product is obtained in the form of a beige solid (yield=62%).
M.p.=67-73° C.

EXAMPLE 168

β[[[(2S)-1-[(4'-fluoro[1,1'-biphenyl]-4-yl)sulfonyl]-2,3-dihydro-1H-indol-2-yl]carbonyl]amino]-(βS)-benzenebutanoic acid By following a procedure analogous to Example 25 starting from the ester obtained according to Example 167, the expected product is obtained in the form of a white solid (yield=44%).
M.p.=87-90° C.

EXAMPLE 169

4-[[[[(2S)-2,3-dihydro-1-[[3'-(trifluoromethyl)[1,1'-biphenyl]-4-yl]sulfonyl]-1H-indol-2-yl]carbonyl] amino]methyl]benzeneacetic acid sodium salt A solution of 540 mg (0.91 mmol) of the acid obtained according to Example 85 in 5 ml of THF is prepared and 0.905 ml of 1 N aqueous sodium hydroxide solution is added at 0° C. The reaction mixture is stirred for 1.5 hours at 0° C. and then concentrated under reduced pressure to a residual volume of about 1.5 ml. The residue is taken up in solution in water at room temperature and the solution is filtered and then lyophilized to give the expected salt in the form of a white powder.
M.p.=138-140° C.

Preparation LXIV

4-Methoxy-2,3-dihydro-1H-indole-2-carboxylic acid methyl ester 119 mg (4.90 mmol) of magnesium turnings are added to a solution of 500 mg (2.44 mmol) of 4-methoxy-1H-indole-2-carboxylic acid in 10 ml of methanol. The mixture is stirred for 3 hours in a bath at 110° C. and then for 1 hour at room temperature. 20 ml of hydrochloric acid are added at 0° C. and the mixture is stirred for one hour. 3 N ammonia solution is then added to pH 10 and the mixture is extracted with 3 times 50 ml of ethyl acetate. The organic phases are dried over magnesium sulfate, filtered and concentrated under reduced pressure. The evaporation residue is purified by chromatography on a silica column using a dichloromethane/ethyl acetate mixture (98/5, then 95/5; v/v) as the eluent to give the expected product in the form of a brown oil with a yield of 64%.
$^1$H NMR (DMSO, 250 MHz) δ: 6.91 (t, 1H); 6.24-6.20 (m, 2H); 5.97 (d, 1H); 4.41-4.34 (m; 1H); 3.71 (s, 3H); 3.65 (s, 3H); 3.17 (dd, 1H); 2.97 (dd, 1H).

Preparation LXV

1-[(4-Iodophenyl)sulfonyl]-4-methoxy-2,3-dihydro-1H-indole-2-carboxylic acid methyl ester By following a procedure analogous to Preparation XI starting from the ester obtained according to Preparation LXIV and 4-iodobenzenesulfonyl chloride, the expected compound is obtained in the form of a white solid with a yield of 87%.
$^1$H NMR (DMSO, 300 MHz) δ: 7.95 (d, 2H); 7.59 (d, 2H); 7.20 (t, 1H); 6.97 (d, 1H); 6.68 (d, 1H); 5.07 (dd, 1H); 3.73 (s, 3H); 3.71 (s, 3H); 3.24 (dd, 1H); 2.93 (dd, 1H).

Preparation LXVI

4-Methoxy-2,3-dihydro-1-[[3'-(trifluoromethyl)[1,1'-biphenyl]-4-yl]sulfonyl]-1H-indole-2-carboxylic acid methyl ester By following a procedure analogous to Example 2 starting from the ester obtained according to Preparation LXV, the expected compound is obtained in the form of a white powder with a yield of 73%.
$^1$H NMR (DMSO, 300 MHz) δ: 8.04-8.02 (m, 2H); 7.95 (s; 4H); 7.81-7.69 (m, 2H); 7.21 (t, 1H); 7.05 (d, 1H); 6.68 (d, 1H); 5.13 (dd, 1H); 3.74 (s, 3H); 3.72 (s, 3H); 3.24 (dd, 1H); 2.95 (dd, 1H).

Preparation LXVII

4-Methoxy-2,3-dihydro-1-[[3'-(trifluoromethyl)[1,1'-biphenyl]-4-yl]sulfonyl]-1H-indole-2-carboxylic acid By following a procedure analogous to Example 5 starting from the ester obtained according to Preparation LXVI, the expected acid is obtained in the form of a white powder with a yield of 97%.

¹H NMR (DMSO, 300 MHz) δ: 13.27 (broad s, 1H); 8.04-8.02 (m, 2H); 7.94 (s, 4H); 7.81-7.69 (m, 2H); 7.21 (t, 1H); 7.04 (d, 1H); 6.67 (d, 1H); 4.98 (dd, 1H); 3.72 (s, 3H); 3.24 (dd, 1H); 2.89 (dd, 1H).

EXAMPLE 170

4-[[[[2,3-Dihydro-4-methoxy-1-[[3'-(trifluoromethyl)[1,1'-biphenyl]-4-yl]sulfonyl]-1H-indol-2-yl]carbonyl]amino]methyl]benzeneacetic acid methyl ester By following a procedure analogous to Example 21 starting from the acid obtained according to Preparation LXVII, the expected compound is obtained in the form of a white powder with a yield of 95%.
M.p.=80° C.

EXAMPLE 171

4-[[[[2,3-Dihydro-4-methoxy-1-[[3'-(trifluoromethyl)[1,1'-biphenyl]-4-yl]sulfonyl]-1H-indol-2-yl]carbonyl]amino]methyl]benzeneacetic acid By following a procedure analogous to Example 5 starting from the ester obtained according to Example 170, the expected acid is obtained in the form of a white powder with a yield of 97%.
M.p.=100° C.

Preparation LXVIII

2-Fluoro-4-[2-[[(phenylmethoxy)carbonyl]amino]ethoxy]benzoic acid methyl ester

By following a procedure analogous to Preparation XXXVIII starting from the benzyl ester of (2-bromoethyl)carbamic acid and the methyl ester of 2-fluoro-4-hydroxybenzoic acid, the expected compound is obtained in the form of an oil with a yield of 42%.
¹H NMR (DMSO, 300 MHz) δ: 7.82 (t, NH); 7.40-7.20 (m, 6H); 6.95-6.80 (m, 2H); 5.01 (s, 2H); 4.08 (t, 2H); 3.79 (s, 3H); 3.38 (t, 2H).

Preparation LXIX

2-Fluoro-4-(2-aminoethoxy)benzoic acid methyl ester hydrochloride

A solution of 1.93 g (5.55 mmol) of the compound obtained according to Preparation LXVIII in 10 ml of methanol is prepared and 10 ml of a saturated solution of hydrogen chloride in methanol are added, followed by 0.2 g of 10% palladium-on-charcoal. The mixture is stirred under hydrogen atmospheric pressure at room temperature for 14 hours and then filtered and concentrated under reduced pressure to give 1.38 g of the expected compound in the form of a white solid (yield=99%).
M.p.=231-234° C.

Preparation LXX 3,5-Dimethyl-4-[2-[[(phenylmethoxy)carbonyl]amino]ethoxy]benzoic acid methyl ester By following a procedure analogous to Preparation LXVIII starting from the methyl ester of 3,5-dimethyl-4-hydroxybenzoic acid, the expected compound is obtained in the form of an oil with a yield of 49%.
¹H NMR (DMSO, 300 MHz) δ: 7.70-7.60 (m, 2H); 7.57 (t, NH); 7.45-7.20 (m, 5H); 5.05 (s, 2H); 3.90-3.70 (m, 5H); 3.50-3.30 (m, 2H); 2.24 (s, 6H).

Preparation LXXI 3,5-Dimethyl-4-(2-aminoethoxy)benzoic acid methyl ester hydrochloride A solution of 0.802 g (2.24 mmol) of the compound obtained according to Preparation LXX in 14 ml of methanol is prepared and 2.7 ml of N hydrochloric acid and then 0.1 g of 10% palladium-on-charcoal are added. The mixture is stirred under hydrogen atmospheric pressure at room temperature for 17 hours and then filtered and concentrated under reduced pressure. The residual solid is triturated in ethyl ether to give 0.516 g of the expected compound in the form of a white solid (yield=88%).
¹H NMR (DMSO, 300 MHz) δ: 8.29 (broad s, 3H); 7.67 (s, 2H); 3.99 (t, 2H); 3.81 (s, 3H); 3.23 (t, 2H); 2.30 (s, 6H).

Preparation LXXII

3-Chloro-4-[2-[[(phenylmethoxy)carbonyl]amino]ethoxy]benzoic acid methyl ester

By following a procedure analogous to Preparation LXVIII starting from the methyl ester of 3-chloro-4-hydroxybenzoic acid, the expected compound is obtained in the form of a white solid with a yield of 68%.
M.p.=81° C.

Preparation LXXIII

3-Chloro-4-(2-aminoethoxy)benzoic acid methyl ester hydrochloride

By following a procedure analogous to Preparation LXXI starting from the compound obtained according to Preparation LXXII, the expected compound is obtained in the form of a white solid with a yield of 99%.
¹H NMR (DMSO, 300 MHz) δ: 8.26 (broad s, NH₂); 8.00-7.90 (m, 2H); 7.33 (d, 1H); 4.39 (t, 2H); 3.84 (s, 3H); 3.40-3.20 (m, 2H).

Preparation LXXIV

3-Fluoro-4-[2-[[(phenylmethoxy)carbonyl]amino]ethoxy]benzoic acid methyl ester

By following a procedure analogous to Preparation LXVIII starting from the methyl ester of 3-fluoro-4-hydroxybenzoic acid, the expected compound is obtained in the form of a white solid with a yield of 80%.
¹H NMR (CDCl₃, 300 MHz) δ: 7.85-7.70 (m, 2H); 7.40-7.30 (m, 5H); 6.95 (t, 1H); 5.29 (t, 1H); 5.12 (s, 2H); 4.16 (t, 2H); 3.89 (s, 3H); 3.66 (q, 2H).

Preparation LXXV

3-Fluoro-4-(2-aminoethoxy)benzoic acid methyl ester hydrochloride

By following a procedure analogous to Preparation LXIX starting from the compound obtained according to Prepara-

Preparation LXXVI

α-Methyl-4-[2-[[(phenylmethoxy)carbonyl]amino] ethoxy]benzeneacetic acid methyl ester By following a procedure analogous to Preparation LXVIII starting from the methyl ester of α-methyl-4-hydroxybenzeneacetic acid, the expected compound is obtained in the form of an oil with a yield of 53%.

$^1$H NMR (DMSO, 300 MHz) δ: 7.5 (t, NH); 7.40-7.05 (m, 7H); 6.87 (d, 2H); 5.03 (s, 2H); 3.96 (t, 2H); 3.72 (q, 1H); 3.56 (s, 3H); 3.40-3.30 (m, 2H); 1.34 (d, 3H).

Preparation LXXVII 4-(2-Aminoethoxy)-α-methylbenzeneacetic acid methyl ester hydrochloride By following a procedure analogous to Preparation LXXI starting from the compound obtained according to Preparation LXXVI, the expected compound is obtained in the form of a beige solid with a yield of 76%.

$^1$H NMR (DMSO, 300 MHz) δ: 8.19 (broad s, NH$_3$); 7.21 (d, 2H); 6.95 (d, 2H); 4.16 (t, 2H); 3.75 (q, 1H); 3.57 (s, 3H); 3.25-3.10 (m, 2H); 1.35 (d, 3H).

Preparation LXXVIII

3-Methoxy-4-[2-[[(phenylmethoxy)carbonyl]amino] ethoxy]benzeneacetic acid methyl ester By following a procedure analogous to Preparation LXVIII starting from the methyl ester of 4-hydroxy-3-methoxybenzeneacetic acid, the expected compound is obtained in the form of a yellow oil with a yield of 51%.

$^1$H NMR (CDCl$_3$, 300 MHz) δ: 7.50-7.30 (m, 5H); 6.95-6.65 (m, 3H); 5.11 (s, 2H); 4.20-4.0 (m, 2H); 3.84 (s, 3H); 3.69 (s, 3H); 3.65-3.50 (m, 4H).

Preparation LXXIX 4-(2-Aminoethoxy)-3-methoxybenzeneacetic acid methyl ester (hydrochloride)

By following a procedure analogous to Preparation LXXI starting from the compound obtained according to Preparation LXXVIII, the expected compound is obtained in the form of an off-white solid with a yield of 86%.

M.p.=77-80° C.

Preparation LXXX 2,6-Difluoro-4-[2-[[(phenylmethoxy)carbonyl] amino]ethoxy]benzoic acid methyl ester By following a procedure analogous to Preparation LXVIII starting from the methyl ester of 2,6-difluoro-4-hydroxybenzoic acid, the expected compound is obtained in the form of a white solid with a yield of 75%.

M.p.=95-97° C.

Preparation LXXXI 2,6-Difluoro-4-(2-aminoethoxy)benzoic acid methyl ester hydrochloride By following a procedure analogous to Preparation LXIX starting from the compound obtained according to Preparation LXXX, the expected compound is obtained in the form of a white solid with a yield of 70%.

M.p.=185° C.

Preparation LXXXII

4-[2-[[(Phenylmethoxy)carbonyl]amino]ethoxy]-3-(trifluoromethyl)benzoic acid methyl ester By following a procedure analogous to Preparation LXVIII starting from the methyl ester of 4-hydroxy-3-(trifluoromethyl)benzoic acid, the expected compound is obtained in the form of a colorless pasty solid with a yield of 51%.

$^1$H NMR (DMSO, 300 MHz) δ: 8.25-8.05 (m, 2H); 7.50-7.25 (m, 6H); 5.01 (s, 2H); 4.25 (t, 2H); 3.86 (s, 3H); 3.43 (t, 2H).

Preparation LXXXIII 4-(2-Aminoethoxy)-3-(trifluoromethyl)benzoic acid methyl ester hydrochloride By following a procedure analogous to Preparation LXIX starting from the compound obtained according to Preparation LXXXII, the expected compound is obtained in the form of a white solid with a yield of 99%.

M.p.=220-222° C.

Preparation LXXXIV

4-[2-[[(Phenylmethoxy)carbonyl]amino]ethoxy]-2-(trifluoromethyl)benzoic acid methyl ester By following a procedure analogous to Preparation LXVIII starting from the methyl ester of 4-hydroxy-2-(trifluoromethyl)benzoic acid, the expected compound is obtained in the form of a colorless oil with a yield of 64%.

$^1$H NMR (CDCl$_3$, 300 MHz) δ: 8.95-8.85 (m, 1H); 7.54 (t, NH); 7.45-7.25 (m, 7H); 5.03 (s, 2H); 4.16 (t, 2H); 3.83 (s, 3H); 3.42 (t, 2H).

Preparation LXXXV 4-(2-Aminoethoxy)-2-(trifluoromethyl)benzoic acid methyl ester hydrochloride By following a procedure analogous to Preparation LXIX starting from the compound obtained according to Preparation LXXXIV, the expected compound is obtained in the form of a white solid with a yield of 93%.

M.p.=172-175° C.

Preparation LXXXVI

3-Methyl-4-[2-[[(phenylmethoxy)carbonyl]amino] ethoxy]benzoic acid methyl ester

By following a procedure analogous to Preparation LXVIII starting from the methyl ester of 3-methyl-4-hydroxybenzoic acid, the expected compound is obtained in the form of a yellow oil with a yield of 79%.

--- tion LXXIV, the expected compound is obtained in the form of a white solid with a yield of 98%.

M.p.=240-247° C.

¹H NMR (DMSO, 300 MHz) δ: 7.85-7.70 (m, 2H); 7.50 (t, NH); 7.40-7.35 (m, 5H); 7.03 (d, 1H); 5.04 (s, 2H); 4.07 (t, 2H); 3.80 (s, 3H); 3.50-3.40 (m, 2H); 2.17 (s, 3H).

Preparation LXXXVII 4-(2-Aminoethoxy)-3-methylbenzoic acid methyl ester hydrochloride By following a procedure analogous to Preparation LXIX starting from the compound obtained according to Preparation LXXXVI, the expected compound is obtained in the form of a pink solid with a yield of 60%.
M.p.=200-201° C.

Preparation LXXXVIII

3-[(4-Cyanophenyl)thio]propanoic acid ethyl ester 1 g (3.46 mmol) of the ethyl ester of 3-[(4-bromophenyl)thio]propanoic acid and 0.62 g (7 mmol) of cuprous cyanide are mixed with 10 ml of DMF in a reactor. The reaction mixture is stirred under gentle reflux for 7 hours and then cooled, poured into 50 ml of water and extracted with ethyl acetate. The organic phase is separated off, washed with water and then dried over magnesium sulfate and concentrated under reduced pressure. The crude product obtained is purified by chromatography on silica gel using a toluene/ethyl acetate mixture (98/2; v/v) as the eluent to give the expected product with a yield of 98%.
¹H NMR (CDCl₃, 300 MHz) δ: 7.55 (d, 2H); 7.32 (d, 2H); 4.16 (q, 2H); 3.25 (t, 2H); 2.68 (t, 2H); 1.26 (t, 3H).

Preparation LXXXIX

3-[[4-(Aminomethyl)phenyl]thio]propanoic acid ethyl ester 0.83 g (3.5 mmol) of the compound obtained according to Preparation LXXXVIII, 15 ml of ethanol, 8 ml of ethanol saturated with ammonia and 0.4 g of Raney nickel are introduced into a reactor. The mixture is stirred under hydrogen atmospheric pressure for 2 h at room temperature and then filtered and concentrated under reduced pressure. The evaporation residue is taken up with ethyl ether and extracted with N hydrochloric acid solution. The acidic aqueous phase obtained is washed with 20 ml of ethyl ether and then brought to basic pH by adding concentrated sodium bicarbonate solution, and extracted with ethyl acetate. This organic phase is washed with water, dried over magnesium sulfate and concentrated under reduced pressure to give 360 mg of the expected product in the form of a beige oil (yield=42%).
¹H NMR (DMSO, 300 MHz) δ: 7.30 (m, 4H); 4.05 (q, 2H); 3.69 (s, 2H); 3.12 (t, 2H); 2.57 (t, 2H); 1.17 (t, 3H).

Preparation XC

3-[[2-(Hydroxymethyl)phenyl]thio]propanoic acid ethyl ester

A solution of 3 g (21.4 mmol) of 2-(hydroxymethyl)thiophenol in 30 ml of absolute ethanol is prepared and 1.46 g (21.4 mmol) of sodium ethylate are added in portions. The mixture is stirred for 10 min at room temperature and 2.74 ml (21.4 mmol) of the ethyl ester of 3-bromopropanoic acid are then added. The mixture is stirred for 30 min at room temperature and then concentrated under reduced pressure. The evaporation residue is taken up with 25 ml of 2 N hydrochloric acid and extracted with ethyl acetate. The organic phase is washed with water, dried over magnesium sulfate and concentrated under reduced pressure. The crude product obtained is purified by chromatography on silica gel using a cyclohexane/ethyl acetate mixture (80/20; v/v) as the eluent to give the expected product in the form of a yellow oil with a yield of 68%.
¹H NMR (CDCl₃, 300 MHz) δ: 7.50-7.40 (m, 2H); 7.40-7.20 (m, 2H); 4.77 (s, 2H); 4.11 (q, 2H); 3.16 (t, 2H); 2.60 (t, 2H); 1.24 (t, 3H).

Preparation XCI

3-[[2-(Chloromethyl)phenyl]thio]propanoic acid ethyl ester

A solution of 0.480 g (2 mmol) of the compound obtained according to Preparation XC in 10 ml of DCM is prepared and 0.174 ml (2.4 mmol) of thionyl chloride is added gradually at 0° C. The mixture is stirred for 30 min at this temperature and then poured into saturated sodium bicarbonate solution and extracted with 50 ml of DCM. The organic phase is washed with water, dried over magnesium sulfate and concentrated under reduced pressure to give the expected product in the form of a yellow oil with a yield of 98%.
¹H NMR (CDCl₃, 300 MHz) δ: 7.50-7.40 (m, 2H); 7.40-7.20 (m, 2H); 4.80 (s, 2H); 4.14 (q, 2H); 3.20 (t, 2H); 2.62 (t, 2H); 1.26 (t, 3H).

Preparation XCII

3-[[2-(Azidomethyl)phenyl]thio]propanoic acid ethyl ester

A solution of 0.260 g (1 mmol) of the compound obtained according to Preparation XCI in 1 ml of acetone is prepared and 68 mg (1.05 mmol) of sodium azide in 0.5 ml of water are added. The mixture is stirred for 1 hour at room temperature and then extracted with ethyl acetate. The organic phase is washed with aqueous sodium chloride solution, dried over magnesium sulfate and concentrated under reduced pressure to give the expected product in the form of a colorless oil with a yield of 90%.
¹H NMR (CDCl₃, 300 MHz) δ: 7.46 (dd, 1H); 7.40-7.20 (m, 3H); 4.54 (s, 2H); 4.14 (q, 2H); 3.18 (t, 2H); 2.62 (t, 2H); 1.26 (t, 3H).

Preparation XCIII

3-[[2-(Aminomethyl)phenyl]thio]propanoic acid ethyl ester

A solution of 0.1 g (0.38 mmol) of the compound obtained according to Preparation XCII in 2 ml of THF is prepared in a reactor adapted for hydrogenation under pressure, and 1 ml of methanol saturated with hydrogen chloride and 10 mg of 10% palladium-on-charcoal are added. The mixture is stirred for 48 hours at room temperature under a hydrogen pressure of 5000 hPa and then filtered and concentrated under reduced pressure to give the expected product in the form of a colorless oil with a yield of 98%, which is used in the next steps without further purification.

Preparation XCIV

3-[(2-Cyanophenyl)amino]propanoic acid methyl ester

A solution of 0.66 g (3.47 mmol) of 3-[(2-cyanophenyl)amino]propanoic acid in 10 ml of methanol is prepared and 0.3 ml of thionyl chloride is added. The mixture is stirred for 48 hours under gentle reflux of the methanol and then concentrated under reduced pressure. The residual solid is taken up in ethyl acetate and the organic phase obtained is washed with water to pH 7 and then dried over magnesium sulfate and concentrated under reduced pressure to give the expected product in the form of a beige oil with a yield of 90%.

$^1$H NMR (DMSO, 300 MHz) δ: 7.50-7.35 (m, 2H); 6.80 (d, 1H); 6.66, (t, 1H); 6.07 (t, NH); 3.61 (s, 3H); 3.50-3.35 (m, 2H); 2.63 (t, 2H).

Preparation XCV

3-[[2-(Aminomethyl)phenyl]amino]propanoic acid methyl ester

A solution of 0.64 g (3.13 mmol) of the compound obtained according to Preparation XCIV in 10 ml of methanol is prepared in a reactor adapted for hydrogenation under pressure, and 0.26 ml of concentrated hydrochloric acid and 128 mg of 10% palladium-on-charcoal are added. The mixture is stirred for 18 hours at room temperature under a hydrogen pressure of 10,000 hPa and then filtered and concentrated under reduced pressure. The crude product is taken up with ethyl acetate and extracted with N hydrochloric acid. The acidic aqueous phase is washed with ethyl acetate and then brought to basic pH with sodium bicarbonate solution and extracted with ethyl acetate. This organic phase is washed with water and then dried and concentrated under reduced pressure to give the expected product in the form of a light brown oil with a yield of 55%.

$^1$H NMR (CDCl$_3$, 300 MHz) δ: 7.18 (td, 1H); 7.03 (d, 1H); 6.75-6.60 (m, 2H); 3.87 (s, 2H); 3.70 (s, 3H); 3.49 (t, 2H); 2.68 (t, 2H).

Preparation XCVI

[2-(5-Methyl-2-nitrophenoxy)ethyl]carbamic acid 1,1-dimethylethyl ester

A solution of 1 g (6.53 mmol) of 5-methyl-2-nitrophenol in 40 ml of THF is prepared and 1.61 g (10 mmol) of the t-butyl ester of 2-hydroxyethylcarbamic acid and 2.62 g (10 mmol) of triphenylphosphine are added. The mixture is stirred for 10 min at room temperature and 1.98 g (9.8 mmol) of DIAD are then added at 0° C. The reaction medium is stirred for 4 hours at room temperature and then concentrated under reduced pressure. The yellow oil obtained is purified by chromatography on silica gel using a toluene/ethyl acetate mixture (98/2; v/v) as the eluent to give the expected product in the form of a yellow solid with a yield of 91%.

M.p.=68° C.

Preparation XCVII 2-(5-Methyl-2-nitrophenoxy)ethanamine hydrochloride

By following a procedure analogous to Preparation XXVIII starting from the compound obtained according to Preparation XCVI, the expected compound is obtained in the form of a beige solid with a yield of 93%.

M.p.=184° C.

Preparation XCVIII

[2-(5-Fluoro-2-nitrophenoxy)ethyl]carbamic acid 1,1-dimethylethyl ester

By following a procedure analogous to Preparation XCVI starting from 5-fluoro-2-nitrophenol, the expected compound is obtained in the form of a fine white solid with a yield of 96%.

$^1$H NMR (DMSO, 250 MHz) δ: 7.99 (dd, 1H); 7.33 (dd, 1H); 6.95 (ddd, 1H); 4.18 (t, 2H); 3.40-3.20 (m, 2H); 1.37 (s, 9H).

Preparation IC 2-(5-Fluoro-2-nitrophenoxy)ethanamine hydrochloride

By following a procedure analogous to Preparation XXVIII starting from the compound obtained according to Preparation XCVIII, the expected compound is obtained in the form of a white solid with a yield of 84%.

$^1$H NMR (DMSO, 250 MHz) δ: 8.40-8.10 (broad s, NH$_3$); 8.05 (dd, 1H); 7.42 (dd, 1H); 7.03 (ddd, 1H); 4.42 (t, 2H); 3.30-3.10 (m, 2H).

Preparation C

3-[[3-(Hydroxymethyl)phenyl]thio]propanoic acid ethyl ester

A solution of 1.27 g (9.07 mmol) of 3-mercaptobenzenemethanol in 20 ml of ethanol is prepared under an argon atmosphere and a solution of 0.93 g (13.7 mmol) of sodium ethylate in 6 ml of ethanol is added. The mixture is stirred for 5 min at room temperature and a solution of 1.81 g (10 mmol) of the ethyl ester of 3-bromopropanoic acid in 6 ml of ethanol is then added. The mixture is stirred for 72 hours at the reflux temperature of the solvent and then cooled, poured into water and extracted three times with ethyl ether. The combined organic phases are washed with water and then dried over magnesium sulfate and concentrated under reduced pressure. The orange oil obtained is purified by chromatography on silica gel using a DCM/methylcyclohexane mixture (98/2; v/v) as the eluent to give the expected product in the form of a yellow oil with a yield of 65%.

$^1$H NMR (DMSO, 300 MHz) δ: 7.35-7.10 (m, 4H); 5.21 (t, OH); 4.47 (d, 2H); 4.06 (q, 2H); 3.15 (t, 2H); 2.60 (t, 2H), 1.17 (t, 3H).

Preparation CI

3-[[3-(Chloromethyl)phenyl]thio]propanoic acid ethyl ester

A solution of 1.3 g (5.4 mmol) of the ester obtained according to Preparation C in 15 ml of DCM is prepared and 0.9 ml of thionyl chloride is added at 0° C. The mixture is stirred for 3 hours at room temperature and then concentrated under reduced pressure. The residual product is taken up with toluene and concentrated again under reduced pressure. The yellow oil obtained is purified by chromatography on silica gel using an ethyl acetate/methylcyclohexane mixture (1/9; v/v)

as the eluent to give the expected product in the form of a yellow oil with a yield of 93%.

$^1$H NMR (DMSO, 300 MHz) δ: 7.50-7.20 (m, 4H); 4.74 (..., 2H); 4.06 (q, 2H); 3.18 (t, 2H); 2.62 (t, 2H), 1.17 (t, 3H).

Preparation CII

3-[[3-[[Bis[(1,1-dimethylethoxy)carbonyl]amino]methyl]phenyl]thio]propanoic acid ethyl ester By following a procedure analogous to Preparation XXVII starting from the compound obtained according to Preparation CI, the expected compound is obtained in the form of a translucent oil with a yield of 68%.

$^1$H NMR (DMSO, 250 MHz) δ: 7.40-7.00 (m, 4H); 4.66 (s, 2H); 4.05 (q, 2H); 3.14 (t, 2H); 2.59 (t, 2H), 1.38 (s, 18H); 1.17 (t, 3H).

Preparation CIII

3-[[3-(Aminomethyl)phenyl]thio]propanoic acid ethyl ester hydrochloride

By following a procedure analogous to Preparation XXVIII starting from the compound obtained according to Preparation CII, the expected compound is obtained in the form of a colorless oil with a yield of 22%.

$^1$H NMR (DMSO, 300 MHz) δ: 7.40-7.10 (m, 4H); 4.05 (q, 2H); 3.68 (s, 2H); 3.15 (t, 2H); 2.60 (t, 2H), 1.88 (broad s, NH$_2$); 1.17 (t, 3H).

Preparation CIV 2,3-Dihydro-1-[[4'-fluoro-2'-methyl[1,1'-biphenyl]-4-yl]sulfonyl]-(2S)-1H-indole-2-carboxylic acid By following a procedure analogous to Preparation IV starting from 4-fluoro-2-methylphenylboronic acid, the expected compound is obtained in the form of a yellow solid with a yield of 95%.

M.p.=62-67° C.

Preparation CV 2,3-Dihydro-1-[[2',4'-difluoro[1,1'-biphenyl]-4-yl]sulfonyl]-(2S)-1H-indole-2-carboxylic acid By following a procedure analogous to Preparation IV starting from 2,4-difluorophenylboronic acid, the expected compound is obtained in the form of a yellow solid with a yield of 74%.

M.p.=88-92° C.

Preparation CVI 2,3-Dihydro-1-[[3'-methyl[1,1'-biphenyl]-4-yl]sulfonyl]-(2S)-1H-indole-2-carboxylic acid By following a procedure analogous to Preparation IV starting from 3-methylphenylboronic acid, the expected compound is obtained in the form of a white solid with a yield of 98%.

M.p.=123-128° C.

Preparation CVII 2,3-Dihydro-1-[[2'-chloro-4'-fluoro[1,1'-biphenyl]-4-yl]sulfonyl]-(2S)-1H-indole-2-carboxylic acid By following a procedure analogous to Preparation IV starting from 2-chloro-4-fluorophenylboronic acid, the expected compound is obtained in the form of a poorly crystalline solid with a yield of 97%.

$^1$H NMR (DMSO, 300 MHz) δ: 8.15 (d, 2H); 7.90-7.50 (m, 6H); 7.50-7.30 (m, 2H); 7.21 (t, 1H); 5.20 (dd, 1H); 3.58 (dd, 1H); 3.27 (dd, 1H).

Preparation CVIII 2,3-Dihydro-1-[[3'-chloro[1,1'-biphenyl]-4-yl]sulfonyl]-(2S)-1H-indole-2-carboxylic acid By following a procedure analogous to Preparation IV starting from 3-chlorophenylboronic acid, the expected compound is obtained in the form of a pale yellow solid with a yield of 73%.

M.p.=78° C.

Preparation CIX 2,3-Dihydro-1-[[3'-ethyl[1,1'-biphenyl]-4-yl]sulfonyl]-(2S)-1H-indole-2-carboxylic acid By following a procedure analogous to Preparation IV starting from 3-ethylphenylboronic acid, the expected compound is obtained in the form of a white solid with a yield of 78%.

M.p.=70-72° C.

Preparation CX

4-[2-[[[(2S)-2,3-dihydro-1-[[4-(4,4,5,5-tetramethyl-1,3,2-dioxaborolan-2-yl)phenyl]sulfonyl]-1H-indol-2-yl]carbonyl]amino]ethoxy]benzeneacetic acid methyl ester 792 mg (8.08 mmol) of potassium acetate, 66 mg (0.081 mmol) of PdCl$_2$dppf, 753 mg (2.96 mmol) of bis(pinacolato)diboron (or 4,4,4',4',5,5,5',5'-octamethyl-2,2'-bi-1,3,2-dioxaborolane) and 18 ml of previously degassed DMSO are introduced into a round-bottomed flask. 1.67 g (2.70 mmol) of the iodinated compound obtained according to Preparation VIIa are then added at room temperature, with stirring. The reaction mixture is subsequently stirred at 80° C. for 3 hours and then cooled and diluted in toluene. The organic phase is washed with water, dried over magnesium sulfate and concentrated under reduced pressure to give the expected product in the form of a light brown oil with a yield of 98%.

$^1$H NMR (DMSO, 300 MHz) δ: 8.37 (t, NH); 7.78 (s, 4H); 7.45 (d, 1H); 7.30-6.80 (m, 7H); 4.83 (dd, 1H); 4.00 (t, 2H); 3.60 (s, 3H); 3.60-3.35 (m, 2H); 3.07 (dd, 1H); 2.89 (dd, 1H); 2.30 (s, 2H); 1.28 (s, 12H).

Preparation CXI 2,3-Dihydro-1-[(4'-fluoro-2'-methoxy[1,1'-biphenyl]-4-yl)sulfonyl]-(2S)-1H-indole-2-carboxylic acid By following a procedure analogous to Preparation IV starting from 4-fluoro-2-methoxyphenylboronic acid, the expected compound is obtained in the form of a beige solid with a yield of 97%.

M.p.=93-100° C.

Preparation CXII 2,3-Dihydro-1-[[2'-chloro-5'-(trifluoromethyl)[1,1'-biphenyl]-4-yl]sulfonyl]-(2S)-1H-indole-2-carboxylic acid By following a procedure analogous to Preparation IV starting from 2-chloro-5-(trifluoromethyl)phenylboronic acid, the expected compound is obtained in the form of a beige solid with a yield of 93%.
M.p.=79-83° C.

EXAMPLE 172

4-[[[[(2S)-1-[(4'-fluoro[1,1'-biphenyl]-4-yl)sulfonyl]-2,3-dihydro-1H-indol-2-yl]carbonyl]amino]methyl]benzoic acid methyl ester A solution of 150 mg (0.38 mmol) of the acid obtained according to Preparation LXIII in 5 ml of DCM is prepared and 160 mg (0.84 mmol) of EDCI, 114 mg (0.84 mmol) of HOAT, 3.32 ml (2.26 mmol) of triethylamine and finally 76 mg (0.38 mmol) of the methyl ester of 4-(aminomethyl)benzoic acid (in the form of its hydrochloride) are added. The reaction mixture is subsequently stirred at room temperature for 20 hours and then diluted in 10 ml of DCM. The organic phase is washed with N hydrochloric acid solution and then with sodium bicarbonate solution, dried over magnesium sulfate and concentrated under reduced pressure. The crude product obtained is purified by chromatography on silica gel using a toluene/ethyl acetate/acetic acid mixture (8/2/0.1; v/v/v) as the eluent to give the expected product in the form of a beige powder with a yield of 57%.
M.p.=66-73° C.

EXAMPLE 173

β-[[[[(2S)-1-[(4'-fluoro[1,1'-biphenyl]-4-yl)sulfonyl]-2,3-dihydro-1H-indol-2-yl]carbonyl]amino]-(βS)-benzenebutanoic acid 1,1-dimethylethyl ester By following a procedure analogous to Example 172 starting from the t-butyl ester of (βS)-β-aminobenzenebutanoic acid, the expected product is obtained in the form of a beige powder (yield=62%).
M.p.=67-73° C.

EXAMPLE 174

N-[(2-chlorophenyl)methyl]-2,3-dihydro-1-[[3'-(trifluoromethyl)[1,1'--biphenyl]-4-yl]sulfonyl]-(2S)-1H-indole-2-carboxamide a) 2,3-Dihydro-1-[[3'-(trifluoromethyl)[1,1'-biphenyl]-4-yl]sulfonyl]-(2S)-1H-indole-2-carboxylic acid chloride The acid chloride is obtained from the corresponding acid by following a procedure analogous to Preparation VI.

b) N-[(2-chlorophenyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 17 starting from the above acid chloride and 2-chlorobenzylamine, the expected compound is obtained in the form of a fine white powder (yield=70%).

M.p.=142-144° C.

The compounds below are obtained by following a procedure analogous to Example 174:

EXAMPLE 175

N-[(2-fluorophenyl)methyl]-2,3-dihydro-1-[[3'-(trifluoromethyl)[1,1'-biphenyl]-4-yl]sulfonyl]-(2S)-1H-indole-2-carboxamide White solid (yield=83%).
M.p.=68-74° C.

EXAMPLE 176

N-[[2-(trifluoromethyl)phenyl]methyl]-2,3-dihydro-1-[[3'-(trifluoromethyl)[1,1'-biphenyl]-4-yl]sulfonyl]-(2S)-1H-indole-2-carboxamide White solid (yield=70%).
M.p.=127-129° C.

EXAMPLE 177

N-[(2-methylphenyl)methyl]-2,3-dihydro-1-[[3'-(trifluoromethyl)[1,1'-biphenyl]-4-yl]sulfonyl]-(2S)-1H-indole-2-carboxamide White solid (yield=85%).
M.p.=146-148° C.

EXAMPLE 178

N-[(2-methoxyphenyl)methyl]-2,3-dihydro-1-[[3'-(trifluoromethyl)[1,1'-biphenyl]-4-yl]sulfonyl]-(2S)-1H-indole-2-carboxamide White solid (yield=76%).
M.p.=153-155° C.

EXAMPLE 179

N-[(2-pyridinyl)methyl]-2,3-dihydro-1-[[3'-(trifluoromethyl)[1,1'-biphenyl]-4-yl sulfonyl]-(2S)-1H-indole-2-carboxamide White solid (yield=65%).
M.p.=77-79° C.

EXAMPLE 180

N-[(1-phenylcyclopropyl)methyl]-2,3-dihydro-1-[[3'-(trifluoromethyl)[1,1'-biphenyl]-4-yl]sulfonyl]-(2S)-1H-indole-2-carboxamide By following a procedure analogous to Preparation I starting from the acid obtained according to Preparation IV and 1-phenylcyclopropanemethanamine, the expected compound is obtained in the form of a beige oil (yield=56%).

$^1$H NMR (DMSO, 250 MHz) δ: 8.08 (t, NH); 8.05-7.95 (m, 2H); 7.94 (d, 2H); 7.88 (d, 2H); 7.85-7.65 (m, 2H); 7.45 (d, 1H); 7.30-7.05 (m, 7H); 7.02 (td, 1H); 4.87 (dd, 1H); 3.53 (dd, 1H); 3.27 (dd, 1H); 3.08 (dd, 1H); 2.75 (dd, 1H); 1.00-0.60 (m, 4H).

EXAMPLE 181

N-[(2-hydroxyphenyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 64 starting from the acid obtained according to Preparation IV and 2-hydroxybenzylamine, the expected compound is obtained in the form of a fine white solid (yield=99%).

$^1$H NMR (DMSO, 300 MHz) δ: 9.55 (s, OH); 8.54 (t, NH); 8.10-7.60 (m, 8H); 7.51 (d, 1H); 7.25 (t, 1H); 7.20-7.00 (m, 4H); 6.85-6.70 (m, 2H); 4.96 (dd, 1H); 4.40-4.15 (m, 2H); 3.15 (dd, 1H); 2.98 (dd, 1H).

EXAMPLE 182

4-[2-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]butanoic acid methyl ester 302 mg (0.55 mmol) of the compound obtained according to Example 181 and 5 ml of acetonitrile are mixed in a microwave reaction tube and 105 mg (0.55 mmol) of cesium carbonate and 198 mg (1.1 mmol) of the methyl ester of 4-bromobutanoic acid are added. The reaction medium is heated for 1 hour at 110° C. in a microwave oven and the acetonitrile is then driven off by evaporation under reduced pressure. The residue is taken up in water and ethyl acetate. The organic phase is separated off, dried over magnesium sulfate and concentrated under reduced pressure. The crude product is purified by chromatography on silica gel using a DCM/ethyl acetate mixture (99/1; v/v) as the eluent to give the product in the form of a white foam (yield=49%).

$^1$H NMR (DMSO, 300 MHz) δ: 8.50 (t, NH); 8.10-7.60 (m, 8H); 7.51 (d, 1H); 7.30-7.10 (m, 4H); 7.10-6.85 (m, 3H); 4.95 (dd, 1H); 4.40-4.15 (m, 2H); 4.2 (t, 2H); 3.60 (s, 3H); 3.18 (dd, 1H); 2.98 (dd, 1H); 2.52 (t, 2H); 2.10-1.90 (m, 2H).

EXAMPLE 183

4-[2-[[[[(2S)-2,3-dihydro-1-[[3'-(trifluoromethyl)[1,1'-biphenyl]-4-yl]sulfonyl]-1H-indol-2-yl]carbonyl]amino]methyl]phenoxy]butanoic acid By following a procedure analogous to Example 22 starting from the ester obtained according to Example 182, the expected compound is obtained in the form of a translucent oil (yield=93%).

$^1$H NMR (DMSO, 300 MHz) δ: 12.12 (broad s, COOH); 8.51 (t, NH); 8.10-7.60 (m, 8H); 7.52 (d, 1H); 7.30-7.10 (m, 4H); 7.10-6.85 (m, 3H); 4.95 (dd, 1H); 4.40-4.15 (m, 2H); 4.02 (t, 2H); 3.17 (dd, 1H); 2.99 (dd, 1H); 2.43 (t, 2H); 2.10-1.90 (m, 2H).

EXAMPLE 184

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzeneacetic acid methyl ester a) 2,3-Dihydro-1-[(4'-fluoro-2'-methyl[1,1'-biphenyl]-4-yl)sulfonyl]-(2S)-1H-indole-2-carboxylic acid chloride The acid chloride is obtained from the corresponding acid (Preparation CIV) by following a procedure analogous to Preparation VI.

b) 4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzeneacetic acid methyl ester By following a procedure analogous to Example 98 starting from the above acid chloride and the hydrochloride of the methyl ester of 4-(2-aminoethoxy)benzeneacetic acid, the expected compound is obtained in the form of a yellow solid (yield=25%).

M.p.=58-62° C.

EXAMPLE 185

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzeneacetic acid By following a procedure analogous to Example 22 starting from the ester obtained according to Example 184, the expected compound is obtained in the form of a beige solid (yield=89%).

M.p.=99-105° C.

EXAMPLE 186

4-[[[[(2S)-1-[(4'-fluoro-2'-methyl[1,1'-biphenyl]-4-yl)sulfonyl]-2,3-dihydro-1H-indol-2-yl]carbonyl]amino]methyl]benzeneacetic acid methyl ester By following a procedure analogous to Example 184 starting from one equivalent of the hydrochloride of the methyl ester of 4-(aminomethyl)benzeneacetic acid, the expected compound is obtained in the form of a yellow solid (yield=35%).

M.p.=71-75° C.

EXAMPLE 187

4-[[[[(2S)-1-[(4'-fluoro-2'-methyl[1,1'-biphenyl]-4-yl)sulfonyl]-2,3-dihydro-1H-indol-2-yl]carbonyl]amino]methyl]benzeneacetic acid By following a procedure analogous to Example 22 starting from the ester obtained according to Example 186, the expected compound is obtained in the form of a beige solid (yield=86%).

M.p.=95-100° C.

EXAMPLE 188

N-[2-[[[(2S)-1-[(4'-fluoro-2'-methyl[1,1'-biphenyl]-4-yl)sulfonyl]-2,3-dihydro-1H-indol-2-yl]carbonyl]amino]methyl]phenyl]-β-alanine methyl ester By following a procedure analogous to Example 186 starting from the compound obtained according to Preparation XCV, the expected compound is obtained in the form of a white solid (yield=30%).

M.p.=78-80° C.

EXAMPLE 189

N-[2-[[[[(2S)-1-[(4'-fluoro-2'-methyl[1,1'-biphenyl]-4-yl)sulfonyl]-2,3-dihydro-1H-indol-2-yl]carbonyl]amino]methyl]phenyl]-β-alanine By following a procedure analogous to Example 22 starting from the ester obtained according to Example 188, the expected compound is obtained in the form of a white solid (yield=94%).
M.p.=118-126° C.

EXAMPLE 190

N-[2-[[[[(2S)-1-[(4'-fluoro-2'-chloro[1,1'-biphenyl]-4-yl)sulfonyl]-2,3-dihydro-1H-indol-2-yl]carbonyl]amino]methyl]phenyl]-β-alanine methyl ester By following a procedure analogous to Example 21 starting from the compound obtained according to Preparation XCV and the acid obtained according to Preparation CVII, the expected compound is obtained in the form of a white solid (yield=46%).
M.p.=70-73° C.

EXAMPLE 191

N-[2-[[[[(2S)-1-[(4'-fluoro-2'-chloro[1,1'-biphenyl]-4-yl)sulfonyl]-2,3-dihydro-1H-indol-2-yl]carbonyl]amino]methyl]phenyl]-β-alanine By following a procedure analogous to Example 22 starting from the ester obtained according to Example 190, the expected compound is obtained in the form of a white solid (yield=87%).
M.p.=105-111° C.

EXAMPLE 192

N-[2-[[[[(2S)-1-[(4'-fluoro-2'-methoxy[1,1'-biphenyl]-4-yl)sulfonyl]-2,3-dihydro-1H-indol-2-yl]carbonyl]amino]methyl]phenyl]-β-alanine methyl ester By following a procedure analogous to Example 184 starting from the acid obtained according to Preparation CXI and the compound obtained according to Preparation XCV, the expected compound is obtained in the form of a white solid (yield=28%).
M.p.=78-80° C.

EXAMPLE 193

N-[2-[[[[(2S)-1-[(4'-fluoro-2'-methoxy[1,1'-biphenyl]-4-yl)sulfonyl]-2,3-dihydro-1H-indol-2-yl]carbonyl]amino]methyl]phenyl]-β-alanine By following a procedure analogous to Example 22 starting from the ester obtained according to Example 192, the expected compound is obtained in the form of a white solid (yield=49%).
M.p.=121-125° C.

EXAMPLE 194

N-[2-[[[[(2S)-1-[(2',4'-difluoro[1,1-b]phenyl]-4-yl)sulfonyl]-2,3-dihydro-1H-indol-2-yl]carbonyl]amino]methyl]phenyl]-β-alanine methyl ester By following a procedure analogous to Example 192 starting from the acid obtained according to Preparation CV, the expected compound is obtained in the form of a white solid (yield=51%).
M.p.=63-66° C.

EXAMPLE 195

N-[2-[[[[(2S)-1-[(2',4'-difluoro[1,1'-biphenyl]-4-yl)sulfonyl]-2,3-dihydro-1H-indol-2-yl]carbonyl]amino]methyl]phenyl]-β-alanine By following a procedure analogous to Example 22 starting from the ester obtained according to Example 194, the expected compound is obtained in the form of a white solid (yield=87%).
M.p.=106-110° C.

EXAMPLE 196

3-[[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]propanoic acid ethyl ester By following a procedure analogous to Example 98 starting from the amine obtained according to Preparation LXXXIX, the expected compound is obtained in the form of an oil (yield=30%).
$^1$H NMR (DMSO, 300 MHz) δ: 8.78 (t, NH); 8.10-8.00 (m, 2H); 8.00-7.85 (m, 4H); 7.85-7.65 (m, 2H); 7.51 (d, 1H); 7.35-7.20 (m, 5H); 7.15 (d, 1H); 7.04 (t, 1H); 4.90 (dd, 1H); 4.32 (t, 2H); 4.05 (q, 2H); 3.30-3.05 (m, 3H); 2.95 (dd, 1H); 2.58 (t, 2H); 1.17 (t, 3H).

EXAMPLE 197

3-[[4-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]propanoic acid By following a procedure analogous to Example 22 starting from the ester obtained according to Example 196, the expected compound is obtained in the form of a white solid (yield=53%).
M.p.=77-81° C.

EXAMPLE 198

3-[[2-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]propanoic acid ethyl ester By following a procedure analogous to Example 21 starting from the acid obtained according to Preparation IV and the compound obtained according to Preparation XCIII, the expected compound is obtained in the form of an oil (yield=53%).
$^1$H NMR (CDCl$_3$, 300 MHz) δ: 7.80-7.05 (m, 16H); 4.73 (dd, 1H); 4.75-4.50 (m, 2H); 4.14 (q, 2H); 3.32 (dd, 1H); 3.14 (t, 2H); 2.84 (dd, 1H); 2.60 (t, 2H); 1.25 (t, 3H).

EXAMPLE 199

3-[[2-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]propanoic acid By following a procedure analogous to Example 22 starting from the ester obtained according to Example 198, the expected compound is obtained in the form of a white solid (yield=51%).
M.p.=85-89° C.

EXAMPLE 200

3,5-Dimethyl-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid methyl ester By following a procedure analogous to Example 198 starting from the compound obtained according to Preparation LXXI, the expected product is obtained in the form of a white solid (yield=51%).
M.p.=81-83° C.

EXAMPLE 201

3,5-Dimethyl-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 200, the expected compound is obtained in the form of a white solid (yield=59%).
M.p.=120-126° C.

EXAMPLE 202

3,5-Dimethyl-4-[2-[[[(2S)-1-[[4'-fluoro[1,1'-biphenyl]-4-yl]sulfonyl]-2,3-dihydro-1H-indol-2-yl]carbonyl]amino]ethoxy]benzoic acid methyl ester By following a procedure analogous to Example 200 starting from the acid obtained according to Preparation LXIII, the expected product is obtained in the form of a white solid (yield=68%).
M.p.=91° C.

EXAMPLE 203

3,5-Dimethyl-4-[2-[[[(2S)-1-[[4'-fluoro[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 202, the expected compound is obtained in the form of a white solid (yield=59%).
M.p.=124-128° C.

EXAMPLE 204

3-Chloro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid methyl ester By following a procedure analogous to Example 172 starting from the acid obtained according to Preparation IV and the compound obtained according to Preparation LXXIII, the expected compound is obtained in the form of a white powder (yield=42%).
M.p.=84-88° C.

EXAMPLE 205

3-Chloro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 204, the expected compound is obtained in the form of a white solid (yield=46%).
M.p.=135-140° C.

EXAMPLE 206

3-Chloro-4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid methyl ester By following a procedure analogous to Example 204 starting from the acid obtained according to Preparation LXIII, the expected compound is obtained in the form of a white solid (yield=55%).
M.p.=84-90° C.

EXAMPLE 207

3-Chloro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 206, the expected compound is obtained in the form of a yellow solid (yield=56%).
M.p.=175-182° C.

EXAMPLE 208

3-Fluoro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid methyl ester By following a procedure analogous to Example 204 starting from the compound obtained according to Preparation LXXV, the expected compound is obtained in the form of a white solid (yield=50%).
M.p.=65-70° C.

EXAMPLE 209

3-Fluoro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 208, the expected compound is obtained in the form of a white solid (yield=64%).
M.p.=96-104° C.

EXAMPLE 210

3-Fluoro-4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid methyl ester By following a procedure analogous to Example 206 starting from the compound obtained according to Preparation LXXV, the expected compound is obtained in the form of a white solid (yield=56%).
M.p.=82-87° C.

EXAMPLE 211

3-Fluoro-4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid By following a procedure analogous to Example 22 starting from the ester obtained according to Example 210, the expected compound is obtained in the form of a white solid (yield=56%).

M.p.=118° C.

EXAMPLE 212

4-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]-α-methylbenzeneacetic acid methyl ester By following a procedure analogous to Example 204 starting from the compound obtained according to Preparation LXXVII, the expected compound is obtained in the form of a white solid (yield=49%).

M.p.=71-74° C.

EXAMPLE 213

4-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]-α-methylbenzeneacetic acid By following a procedure analogous to Example 22 starting from the ester obtained according to Example 212, the expected compound is obtained in the form of a white solid (yield=93%).

M.p.=92-96° C.

EXAMPLE 214

4-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]-3-methoxybenzeneacetic acid methyl ester By following a procedure analogous to Example 98 starting from one equivalent of the compound obtained according to Preparation LXXIX, the expected compound is obtained in the form of a white powder (yield=40%).

M.p.=52-60° C.

EXAMPLE 215

4-[2-[[[(2S)-2,3-dihydro-1-[[3'-(trifluoromethyl)[1,1'-biphenyl]-4-yl]sulfonyl]-1H-indol-2-yl]carbonyl]amino]ethoxy]-3-methoxybenzeneacetic acid By following a procedure analogous to Example 22 starting from the ester obtained according to Example 214, the expected compound is obtained in the form of a white solid (yield=86%).

M.p.=89-98° C.

EXAMPLE 216

N-[4-[[[[(2S)-2,3-dihydro-1-[[3'-(trifluoromethyl)[1,1'-biphenyl]-4-yl]-sulfonyl]-1H-indol-2-yl]carbonyl]amino]methyl]phenyl]glycine methyl ester By following a procedure analogous to Example 198 starting from the hydrochloride of the methyl ester of N-[4-(aminomethyl)phenyl]glycine, the expected compound is obtained in the form of a white powder (yield=32%).

M.p.=85° C.

EXAMPLE 217

N-[4-[[[[(2S)-2,3-dihydro-1-[[3'-(trifluoromethyl)[1,1'-biphenyl]-4-yl]-sulfonyl]-1H-indol-2-yl]carbonyl]amino]methyl]phenyl]glycine By following a procedure analogous to Example 22 starting from the ester obtained according to Example 216, the expected compound is obtained in the form of a yellow solid (yield=40%).

M.p.=139° C.

EXAMPLE 218

2,6-Difluoro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid methyl ester By following a procedure analogous to Example 198 starting from the compound obtained according to Preparation LXXXI, the expected compound is obtained in the form of a white solid (yield=65%).

M.p.=68-71° C.

EXAMPLE 219

2,6-Difluoro-4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid methyl ester By following a procedure analogous to Example 218 starting from the acid obtained according to Preparation LXIII, the expected compound is obtained in the form of a white solid (yield=55%).

M.p.=83° C.

EXAMPLE 220

4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]-3-(trifluoromethyl)benzoic acid methyl ester By following a procedure analogous to Example 198 starting from the compound obtained according to Preparation LXXXIII, the expected compound is obtained in the form of a white solid (yield=74%).

M.p.=92-98° C.

EXAMPLE 221

4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]-3-(trifluoromethyl)benzoic acid By following a procedure analogous to Example 22 starting from the ester obtained according to Example 220, the expected compound is obtained in the form of a white solid (yield=51%)

M.p.=111-116° C. .

EXAMPLE 222

4-[2-[[[(2S)-1-[(4'-fluoro[1,1'-biphenyl]-4-yl)sulfonyl]-2,3-dihydro-1H-indol-2-yl]carbonyl]amino]ethoxy]-3-(trifluoromethyl)benzoic acid methyl ester By following a procedure analogous to Example 220 starting from the acid obtained according to Preparation LXIII, the expected compound is obtained in the form of a white solid (yield=69%).
M.p.=90-95° C.

EXAMPLE 223

4-[2-[[[(2S)-1-[(4'-fluoro[1,1'-biphenyl]-4-yl)sulfonyl]-2,3-dihydro-1H-indol-2-yl]carbonyl]amino]ethoxy]-3-(trifluoromethyl)benzoic acid By following a procedure analogous to Example 22 starting from the ester obtained according to Example 222, the expected compound is obtained in the form of a white solid (yield=85%).
M.p.=139-142° C.

EXAMPLE 224

4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]-2-(trifluoromethyl)benzoic acid methyl ester By following a procedure analogous to Example 198 starting from the compound obtained according to Preparation LXXXV, the expected compound is obtained in the form of a white solid (yield=48%).
M.p.=75-79° C.

EXAMPLE 225

4-[2-[[[(2S)-1-[(4'-fluoro[1,1'-biphenyl]-4-yl)sulfonyl]-2,3-dihydro-1H-indol-2-yl]carbonyl]amino]ethoxy]-2-(trifluoromethyl)benzoic acid methyl ester By following a procedure analogous to Example 224 starting from the acid obtained according to Preparation LXIII, the expected compound is obtained in the form of a white solid (yield=83%).
M.p.=62-70° C.

EXAMPLE 226

3-Methyl-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid methyl ester By following a procedure analogous to Example 198 starting from the compound obtained according to Preparation LXXXVII, the expected compound is obtained in the form of a white solid (yield=21%).
M.p.=68-74° C.

EXAMPLE 227

3-Methyl-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 226, the expected compound is obtained in the form of a white solid (yield=83%).
M.p.=102-108° C.

EXAMPLE 228

4-[2-[[[(2S)-1-[(4'-fluoro[1,1'-biphenyl]-4-yl)sulfonyl]-2,3-dihydro-1H-indol-2-yl]carbonyl]amino]ethoxy]-3-methylbenzoic acid methyl ester By following a procedure analogous to Example 226 starting from the acid obtained according to Preparation LXIII, the expected compound is obtained in the form of a pink solid (yield=61%).
M.p.=81-85° C.

EXAMPLE 229

4-[2-[[[(2S)-1-[(4'-fluoro[1,1'-biphenyl]-4-yl)sulfonyl]-2,3-dihydro-1H-indol-2-yl]carbonyl]amino]ethoxy]-3-methylbenzoic acid By following a procedure analogous to Example 22 starting from the ester obtained according to Example 226, the expected compound is obtained in the form of a white solid (yield=48%).
M.p.=112-118° C.

EXAMPLE 230

2-Fluoro-4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid methyl ester By following a procedure analogous to Example 228 starting from the compound obtained according to Preparation LXIX, the expected compound is obtained in the form of a white solid (yield=58%).
M.p.=77-81° C.

EXAMPLE 231

2-Fluoro-4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid By following a procedure analogous to Example 22 starting from the ester obtained according to Example 230, the expected compound is obtained in the form of a beige solid (yield=52%).
M.p.=109-113° C.

EXAMPLE 232

2-Fluoro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid methyl ester By following a procedure analogous to Example 198 starting from the compound obtained according to Preparation LXIX, the expected compound is obtained in the form of a white solid (yield=22%).
M.p.=63-70° C.

EXAMPLE 233

2-Fluoro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 232, the expected compound is obtained in the form of a white solid (yield=90%).
M.p.=97-105° C.

EXAMPLE 234

2,3-Dihydro-N-[2-(5-methyl-2-nitrophenoxy)ethyl]-1-[[3'-(trifluoromethyl)[1,1'-biphenyl]-4-yl]sulfonyl]-(2S)-1H-indole-2-carboxamide A solution of 480 mg (1.07 mmol) of the acid obtained according to Preparation IV in 10 ml of dichloromethane is prepared and 226 mg (1.18 mmol) of EDCI and 30 mg (0.22 mmol) of HOAT are then added. After stirring for 10 minutes at room temperature, 250 mg (1.07 mmol) of the compound obtained according to Preparation XCVII and 0.315 ml (2.25 mmol) of triethylamine are added. The reaction medium is then stirred at room temperature for 20 hours. The mixture is then treated by adding dichloromethane and the organic phase is washed with water, then dried over magnesium sulfate and then concentrated under reduced pressure. The crude product obtained is then purified by chromatography on silica gel using a dichloromethane/ethyl acetate mixture (99/1; v/v) as the eluent to give the expected product in the form of a beige foam (yield=42%).
$^1$H NMR (DMSO, 250 MHz) δ: 8.37 (t, NH); 8.10-7.60 (m, 9H); 7.49 (d, 1H); 7.30-6.85 (m, 5H); 4.86 (dd, 1H); 4.30-4.10 (m, 2H); 3.70-3.40 (m, 2H); 3.12 (dd, 1H); 2.94 (dd, 1H); 2.37 (s, 3H).

EXAMPLE 235

2,3-Dihydro-N-[2-(2-amino-5-methylphenoxy)ethyl]-1-[[3'-(trifluoromethyl)[1,1'-biphenyl]-4-yl]sulfonyl]-(2S)-1H-indole-2-carboxamide By following a procedure analogous to Example 61 starting from the nitro derivative obtained according to Example 234, the expected compound is obtained in the form of a white solid (yield=86%).
$^1$H NMR (DMSO, 250 MHz) δ: 8.46 (t, NH); 8.10-7.60 (m, 8H); 7.49 (d, 1H); 7.24 (td, 1H); 7.13 (d, 1H); 7.02 (td, 1H); 6.70-6.40 (m, 3H); 4.86 (dd, 1H); 4.57 (broad s, NH$_2$); 3.95 (t, 2H); 3.70-3.40 (m, 2H); 3.18 (dd, 1H); 2.96 (dd, 1H); 2.14 (s, 3H).

EXAMPLE 236

2,3-Dihydro-N-[2-(5-fluoro-2-nitrophenoxy)ethyl]-1-[[3'-(trifluoromethyl)[1,1'-biphenyl]-4-yl]sulfonyl]-(2S)-1H-indole-2-carboxamide By following a procedure analogous to Example 234 starting from the compound obtained according to Preparation IC, the expected compound is obtained in the form of a bright yellow foam (yield=54%).
$^1$H NMR (DMSO, 250 MHz) δ: 8.37 (t, NH); 8.10-7.60 (m, 9H); 7.49 (d, 1H); 7.37 (dd, 1H); 7.24 (td, 1H); 7.20-6.90 (m, 3H); 4.85 (dd, 1H); 4.30-4.10 (m, 2H); 3.70-3.40 (m, 2H); 3.15 (dd, 1H); 2.94 (dd, 1H).

EXAMPLE 237

2,3-Dihydro-N-[2-(2-amino-5-fluorophenoxy)ethyl]-1-[[3'-(trifluoromethyl)[1,1'-biphenyl]-4-yl]sulfonyl]-(2S)-1H-indole-2-carboxamide By following a procedure analogous to Example 235 starting from the nitro derivative obtained according to Example 236, the expected compound is obtained in the form of a pale pink foam (yield=90%).
$^1$H NMR (DMSO, 250 MHz) δ: 8.49 (t, NH); 8.10-7.65 (m, 8H); 7.49 (d, 1H); 7.24 (td, 1H); 7.12 (d, 1H); 7.02 (td, 1H); 6.73 (dd, 1H); 6.65-6.40 (m, 2H); 4.85 (dd, 1H); 4.72 (broad s, NH$_2$); 3.98 (t, 2H); 3.70-3.40 (m, 2H); 3.18 (dd, 1H); 2.96 (dd, 1H).

EXAMPLE 238

2,3-Dihydro-N-[2-(2-nitrophenoxy)ethyl]-1-[[3'-(trifluoromethyl)[1,1'-biphenyl]-4-yl]sulfonyl]-(2S)-1H-indole-2-carboxamide By following a procedure analogous to Example 234 starting from 2-(2-nitrophenoxy)ethanamine, the expected compound is obtained in the form of a yellow foam (yield=51%).
$^1$H NMR (DMSO, 300 MHz) δ: 8.39 (t, NH); 8.10-7.65 (m, 9H); 7.63 (td, 1H); 7.49 (d, 1H); 7.39 (d, 1H); 7.25 (td, 1H); 7.20-7.10 (m, 2H); 7.02 (td, 1H); 4.86 (dd, 1H); 4.30-4.15 (m, 2H); 3.65-3.40 (m, 2H); 3.15 (dd, 1H); 2.94 (dd, 1H).

EXAMPLE 239

2,3-Dihydro-N-[2-(2-aminophenoxy)ethyl]-1-[[3'-(trifluoromethyl)[1,1'-biphenyl]-4-yl]sulfonyl]-(2S)-1H-indole-2-carboxamide By following a procedure analogous to Example 235 starting from the nitro derivative obtained according to Example 238, the expected compound is obtained in the form of a white foam (yield=59%).
$^1$H NMR (DMSO, 250 MHz) δ: 8.48 (t, NH); 8.10-7.65 (m, 8H); 7.49 (d, 1H); 7.23 (td, 1H); 7.12 (d, 1H); 7.02 (td, 1H); 6.78 (dd, 1H); 6.75-6.60 (m, 2H); 6.55-6.40 (m, 1H); 4.86 (dd, 1H); 4.76 (broad s, NH$_2$); 3.96 (t, 2H); 3.65-3.40 (m, 2H); 3.18 (dd, 1H); 2.96 (dd, 1H).

EXAMPLE 240

3-[[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]propanoic acid ethyl ester A solution of 129 mg (0.29 mmol) of the acid obtained according to Preparation IV in 3 ml of dichloromethane is prepared and 61 mg (0.32 mmol) of EDCI and 44 mg (0.32 mmol) of HOAT are then added. After stirring for 10 minutes at room temperature, 69 mg (0.29 mmol) of the hydrochloride of the ethyl ester of 3-[[3-(aminomethyl)phenyl]thio]propanoic acid (Preparation CIII) are added. The reaction medium is then stirred at room temperature for 6 hours. The mixture is then treated by adding dichloromethane and the organic phase is washed with water and then dried over magnesium sulfate and concentrated under reduced pressure. The crude product obtained is then purified by chromatography on silica gel using a dichloromethane/ethyl acetate mixture (98/2; v/v) as the eluent to give the expected product in the form of a translucent oil (yield=49%).

¹H NMR (DMSO, 300 MHz) δ: 8.79 (t, NH); 8.10-7.65 (m, 8H); 7.51 (d, 1H); 7.35-7.00 (m, 7H); 4.91 (dd, 1H); 4.34 (d, 2H); 4.05 (q, 2H); 3.30-3.10 (m, 3H); 2.97 (dd, 1H); 2.60 (t, 2H); 1.16 (t, 3H).

EXAMPLE 241

3-[[3-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]thio]propanoic acid By following a procedure analogous to Example 22 starting from the ester obtained according to Example 240, the expected compound is obtained in the form of a translucent oil (yield=22%).
¹H NMR (DMSO, 250 MHz) δ: 12.30 (broad s, COOH); 8.79 (t, NH); 8.10-7.65 (m, 8H); 7.51 (d, 1H); 7.35-7.00 (m, 7H); 4.90 (dd, 1H); 4.34 (dd, 2H); 3.30-3.05 (m, 3H); 2.97 (dd, 1H); 2.60-2.40 (m, 2H).

EXAMPLE 242

3-[[[(2S)-1-[(2'-chloro-4'-fluoro[1,1'-biphenyl]-4-yl)sulfonyl]-2,3-dihydro-1H-indol-2-yl]carbonyl]amino]-4,4,4-trifluorobutanoic acid ethyl ester By following a procedure analogous to Example 21 starting from the acid obtained according to Preparation CVII and the ethyl ester of 3-amino-4,4,4-trifluorobutanoic acid, the expected compound is obtained in the form of a white powder (yield=55%).
M.p.=57-60° C.

EXAMPLE 243

N-[(3-amino-4-pyridinyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 234 (with 3 equivalents of triethylamine) starting from the dihydrochloride of 3-amino-4-pyridinemethanamine, the expected compound is obtained in the form of a white powder (yield=85%).
M.p.=105-108° C.

EXAMPLE 244

4-[3-[[[(2S)-2,3-dihydro-1-[[3'-(trifluoromethyl)[1,1'-biphenyl]-4-yl]sulfonyl]-1H-indol-2-yl]carbonyl]amino]propyl]benzeneacetic acid methyl ester By following a procedure analogous to Example 234 starting from the hydrochloride of the methyl ester of 4-(3-aminopropyl)benzeneacetic acid, the expected compound is obtained in the form of a white oil (yield=98%).
¹H NMR (DMSO, 300 MHz) δ: 8.25 (t, NH); 8.10-7.65 (m, 8H); 7.49 (d, 1H); 7.24 (t, 1H); 7.20-7.10 (m, 5H); 7.02 (td, 1H); 4.81 (dd, 1H); 3.62 (s, 2H); 3.60 (s, 3H); 3.25-3.05 (m, 3H); 2.94 (dd, 1H); 2.57 (t, 2H); 1.80-1.60 (m, 2H).

EXAMPLE 245

4-[3-[[[(2S)-2,3-dihydro-1-[[3'-(trifluoromethyl)[1,1'-biphenyl]-4-yl]sulfonyl]-1H-indol-2-yl]carbonyl]amino]propyl]benzeneacetic acid By following a procedure analogous to Example 5 starting from the compound obtained according to Example 244, the expected compound is obtained in the form of a white foam (yield=99%).
¹H NMR (DMSO, 300 MHz) δ: 8.25 (t, NH); 8.10-7.65 (m, 8H); 7.49 (d, 1H); 7.24 (t, 1H); 7.20-7.10 (m, 5H); 7.02 (td, 1H); 4.81 (dd, 1H); 3.50 (s, 2H); 3.25-3.05 (m, 3H); 2.94 (dd, 1H); 2.57 (t, 2H); 1.80-1.60 (m, 2H).

EXAMPLE 246

1-[[2',4'-Difluoro[1,1'-biphenyl]-4-yl]sulfonyl]-2,3-dihydro-N-[(2-nitrophenyl)methyl]-(2S)-1H-indole-2-carboxamide By following a procedure analogous to Preparation XXXV starting from the acid obtained according to Preparation CV, the acid chloride is obtained, which is reacted with (2-nitrophenyl)methanamine according to the procedure described for Example 98 to give the expected product in the form of a white solid (yield=64%).
M.p.=99-102° C.

EXAMPLE 247

N-[(2-aminophenyl)methyl]-1-[[2',4'-difluoro[1,1'-biphenyl]-4-yl]sulfonyl]-2,3-dihydro-(2S)-1H-indole-2-carboxamide By following a procedure analogous to Preparation XCIII (but without adding hydrogen chloride) starting from the compound obtained according to Example 246, the expected compound is obtained in the form of a white solid (yield=49%).
M.p.=93-96° C.

EXAMPLE 248

2,3-Dihydro-1-[[4'-fluoro-2'-methyl[1,1'-biphenyl]-4-yl]sulfonyl]-N-[(2-nitrophenyl)methyl]-(2S)-1H-indole-2-carboxamide By following a procedure analogous to Example 246 starting from the acid obtained according to Preparation CIV, the expected product is obtained in the form of an orange solid (yield=87%).
M.p.=64-66° C.

EXAMPLE 249

N-[(2-aminophenyl)methyl]-2,3-dihydro-1-[[4'-fluoro-2'-methyl[1,1'-biphenyl]-4-yl]sulfonyl]-(2S)-1H-indole-2-carboxamide By following a procedure analogous to Example 247 starting from the compound obtained according to Example 248, the expected product is obtained in the form of a white solid (yield=58%).
M.p.=92-96° C.

EXAMPLE 250

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]benzeneacetic acid methyl ester By following a procedure analogous to Example 192 starting from the hydrochloride of the methyl ester of 4-(2-aminoethoxy)benzeneacetic acid, the expected product is obtained in the form of a white solid (yield=64%).
M.p.=70-75° C.

EXAMPLE 251

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 250, the expected product is obtained in the form of a white solid (yield=82%).
M.p.=102-110° C.

EXAMPLE 252

4-[[[[(2S)-1-[(4'-fluoro-2'-methoxy[1,1'-biphenyl]-4-yl)sulfonyl]-2,3-dihydro-1H-indol-2-yl]carbonyl]amino]methyl]benzeneacetic acid methyl ester By following a procedure analogous to Example 192 starting from the hydrochloride of the methyl ester of 4-(aminomethyl)benzeneacetic acid, the expected product is obtained in the form of a white solid (yield=62%).
M.p.=77-79° C.

EXAMPLE 253

4-[[[[(2S-1-[(4'-fluoro-2'-methoxy[1,1'-biphenyl]-4-yl)sulfonyl]-2,3-dihydro-1H-indol-2-yl]carbonyl]amino]methyl]benzeneacetic acid By following a procedure analogous to Example 22 starting from the compound obtained according to Example 252, the expected product is obtained in the form of a white solid (yield=95%).
M.p.=106-111° C.

EXAMPLE 254

N-[(2-aminophenyl)methyl]-1-[[4'-fluoro-2'-methoxy[1,1'-biphenyl]-4-yl]sulfonyl]-2,3-dihydro-(2S)-1H-indole-2-carboxamide By following a procedure analogous to Example 240 starting from the acid obtained according to Preparation CXI and (2-aminophenyl)methanamine, the expected product is obtained in the form of a white foam (yield=64%).
M.p.=92-97° C.

EXAMPLE 255

4-[[[[(2S)-1-[(2',4'-difluoro[1,1'-biphenyl]-4-yl)sulfonyl]-2,3-dihydro-1H-indol-2-yl]carbonyl]amino]methyl]benzeneacetic acid methyl ester By following a procedure analogous to Example 186 starting from the acid obtained according to Preparation CV, the expected compound is obtained in the form of a white solid (yield=59%).
M.p.=68-72° C.

EXAMPLE 256

4-[[[[(2S)-1-[(2',4'-difluoro[1,1'-biphenyl]-4-yl)sulfonyl]-2,3-dihydro-1H-indo-2-yl]carbonyl]amino]methyl]benzeneacetic acid By following a procedure analogous to Example 22 starting from the compound obtained according to Example 255, the expected product is obtained in the form of a white solid (yield=81%).
M.p.=117-121° C.

EXAMPLE 257

4-[2-[[[(2S)-1-[(2',4'-difluoro[1,1'-biphenyl]-4-yl)sulfonyl]-2,3-dihydro-1H-indol-2-yl]carbonyl]amino]ethoxy]benzeneacetic acid methyl ester By following a procedure analogous to Example 250 starting from the acid chloride obtained according to Preparation CV, the expected product is obtained in the form of a white solid (yield=49%).
M.p.=60-64° C.

EXAMPLE 258

4-[2-[[[(2S)-1-[(2',4'-difluoro[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 257, the expected product is obtained in the form of a white solid (yield=82%).
M.p.=92-99° C.

EXAMPLE 259

4-[[[[(2S)-1-[(3'-methyl[1,1'-biphenyl]-4-yl)sulfonyl]-2,3-dihydro-1H-indol-2-yl]carbonyl]amino]methyl]benzeneacetic acid methyl ester By following a procedure analogous to Example 186 starting from the acid chloride obtained according to Preparation CVI, the expected compound is obtained in the form of a white solid (yield=62%).
M.p.=66-68° C.

EXAMPLE 260

4-[[[[(2S)-1-[(3'-methyl[1,1'-biphenyl]-4-yl)sulfonyl]-2,3-dihydro-1H-indol-2-yl]carbonyl]amino]methyl]benzeneacetic acid By following a procedure analogous to Example 22 starting from the compound obtained according to Example 259, the expected product is obtained in the form of a white solid (yield=98%).
M.p.=118-120° C.

EXAMPLE 261

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]benzeneacetic acid methyl ester By following a procedure analogous to Example 184 starting from the acid obtained according to Preparation CVII, the expected compound is obtained in the form of a pink solid (yield=57%).
M.p.=68° C.

EXAMPLE 262

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 261, the expected product is obtained in the form of a white solid (yield=92%).
M.p.=90° C.

EXAMPLE 263

4-[[[[(2S)-1-[(2'-chloro-4'-fluoro[1,1'-biphenyl]-4-yl)sulfonyl]-2,3-dihydro-1H-indol-2-yl]carbonyl]amino]methyl]benzeneacetic acid methyl ester By following a procedure analogous to Example 186 starting from the acid obtained according to Preparation CVII, the expected compound is obtained in the form of a beige solid (yield=62%).
M.p.=70° C.

EXAMPLE 264

4-[[[[(2S)-1-[(2'-chloro-4'-fluoro[1,1'-biphenyl]-4-yl)sulfonyl]-2,3-dihydro-1H-indol-2-yl]carbonyl]amino]methyl]benzeneacetic acid By following a procedure analogous to Example 22 starting from the compound obtained according to Example 263, the expected product is obtained in the form of a white solid (yield=85%).
M.p.=119° C.

EXAMPLE 265

N-[(2-aminophenyl)methyl]-1-[[2'-chloro-4'-fluoro[1,1'-biphenyl]-4-yl]sulfonyl]-2,3-dihydro-(2S)-1H-indole-2-carboxamide By following a procedure analogous to Example 254 starting from the acid obtained according to Preparation CVII, the expected product is obtained in the form of a white solid (yield=53%).
M.p.=85-90° C.

EXAMPLE 266

4-[[[[(2S)-1-[(3'-chloro[1,1'-biphenyl]-4-yl)sulfonyl]-2,3-dihydro-1H-indol-2-yl]carbonyl]amino]methyl]benzeneacetic acid methyl ester By following a procedure analogous to Example 186 starting from the acid obtained according to Preparation CVIII, the expected compound is obtained in the form of an ecru solid (yield=64%).
M.p.=70° C.

EXAMPLE 267

4-[[[[(2S)-1-[(3'-chloro[1,1'-biphenyl]-4-yl)sulfonyl]-2,3-dihydro-1H-indol-2-yl]carbonyl]amino]methyl]benzeneacetic acid By following a procedure analogous to Example 22 starting from the compound obtained according to Example 266, the expected product is obtained in the form of a white solid (yield=85%).
M.p.=120° C.

EXAMPLE 268

4-[[[[(2S)-1-[(3'-ethyl[1,1'-biphenyl]-4-yl)sulfonyl]-2,3-dihydro-1H-indol-2-yl]-carbonyl]amino]methyl]benzeneacetic acid methyl ester By following a procedure analogous to Example 186 starting from the acid obtained according to Preparation CIX, the expected compound is obtained in the form of a beige powder (yield=60%).
M.p.=70-75° C.

EXAMPLE 269

4-[[[[(2S)-1-[(3'-ethyl[1,1'-biphenyl]-4-yl)sulfonyl]-2,3-dihydro-1H-indol-2-yl]carbonyl]amino]methyl]benzeneacetic acid By following a procedure analogous to Example 22 starting from the compound obtained according to Example 268, the expected product is obtained in the form of a white solid (yield=74%).
M.p.=98° C.

EXAMPLE 270

4-[2-[[[(2S)-1-[[4'-fluoro-2'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 1 starting from the compound obtained according to Preparation CX and 1-bromo-4-fluoro-2-(trifluoromethyl)-benzene, the expected product is obtained in the form of a colorless oil (yield=44%).
$^1$H NMR (DMSO, 300 MHz) δ: 8.41 (t, NH); 7.90-7.70 (m, 3H); 7.60 (td, 1H); 7.55-7.40 (m, 4H); 7.30-7.10 (m, 4H); 7.03 (t, 1H); 6.88 (d, 2H); 4.88 (dd, 1H); 4.10-3.95 (m, 2H); 3.60 (s, 2H); 3.59 (s, 3H); 3.60-3.30 (m, 2H); 3.03 (dd, 1H); 2.93 (dd, 1H).

EXAMPLE 271

4-[2-[[[(2S)-1-[[4'-fluoro-2'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 5 starting from the compound obtained according to Example 270, the expected product is obtained in the form of a white foam (yield=99%).
$^1$H NMR (DMSO, 300 MHz) δ: 8.41 (t, NH); 7.90-7.70 (m, 3H); 7.60 (td, 1H); 7.55-7.40 (m, 4H); 7.23 (td, 1H); 7.20-7.10 (m, 3H); 7.03 (td, 1H); 6.86 (dd, 2H); 4.88 (dd, 1H); 4.10-3.95 (m, 2H); 3.45 (s, 2H); 3.60-3.30 (m, 2H); 3.03 (dd, 1H); 2.93 (dd, 1H).

EXAMPLE 272

4-[2-[[[(2S)-1-[(2'-cyano-4'-fluoro[1,1'-biphenyl]-4-yl)sulfonyl]-2,3-dihydro-1H-indol-2-yl]carbonyl]amino]ethoxy]benzeneacetic acid methyl ester By following a procedure analogous to Example 270 starting from the compound obtained according to Preparation CX and 2-bromo-5-fluorobenzonitrile, the expected product is obtained in the form of a colorless oil (yield=73%).

$^1$H NMR (DMSO, 300 MHz) δ: 8.44 (t, NH); 8.10-7.85 (m, 3H); 7.80-7.65 (m, 4H); 7.48 (d, 1H); 7.24 (t, 1H); 7.20-7.10 (m, 3H); 7.03 (t, 1H); 6.89 (d, 2H); 4.90 (dd, 1H); 4.02 (t, 2H); 3.60 (s, 2H); 3.59 (s, 3H); 3.60-3.30 (m, 2H); 3.14 (dd, 1H); 2.94 (dd, 1H).

EXAMPLE 273

4-[2-[[[(2S)-1-[(2'-cyano-4'-fluoro[1,1'-biphenyl]-4-yl)sulfonyl]-2,3-dihydro-1H-indol-2-yl]carbonyl]amino]ethoxy]benzeneacetic acid By following a procedure analogous to Example 5 starting from the compound obtained according to Example 272, the expected product is obtained in the form of a white foam (yield=99%).

$^1$H NMR (DMSO, 300 MHz) δ: 12.24 (broad s, COOH); 8.44 (t, NH); 8.05-7.9 (m, 3H); 7.80-7.65 (m, 4H); 7.48 (d, 1H); 7.24 (td, 1H); 7.20-7.10 (m, 3H); 7.02 (t, 1H); 6.89 (d, 2H); 4.91 (dd, 1H); 4.10-3.90 (m, 2H); 3.48 (s, 2H); 3.60-3.30 (m, 2H); 3.14 (dd, 1H); 2.94 (dd, 1H).

EXAMPLE 274

4-[2-[[[(2S)-1-[(4'-chloro[1,1'-biphenyl]-4-yl)sulfonyl]-2,3-dihydro-1H-indol-2-yl]carbonyl]amino]ethoxy]benzeneacetic acid methyl ester By following a procedure analogous to Example 1 starting from the compound obtained according to Preparation VIIa and 4-chlorophenylboronic acid, the expected product is obtained in the form of a brown oil (yield=96%).

$^1$H NMR (DMSO, 300 MHz) δ: 8.41 (t, NH); 7.87 (d, 2H); 7.85 (d, 2H); 7.74 (dd, 2H); 7.60-7.40 (m, 3H); 7.30-7.10 (m, 4H); 7.02 (td, 1H); 6.89 (d, 2H); 4.87 (dd, 1H); 4.10-3.95 (m, 2H); 3.60 (s, 2H); 3.59 (s, 3H); 3.60-3.40 (m, 2H); 3.15 (dd, 1H); 2.94 (dd, 1H).

EXAMPLE 275

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 274 starting from 2-chloro-5-(trifluoromethyl)phenylboronic acid, the expected product is obtained in the form of a beige foam (yield=51%).

$^1$H NMR (DMSO, 300 MHz) δ: 8.44 (t, NH); 7.90 (d, 2H); 7.90-7.80 (m, 3H); 7.67 (d, 2H); 7.47 (d, 1H); 7.23 (td, 1H); 7.20-7.10 (m, 3H); 7.03 (td, 1H); 6.89 (dd, 2H); 4.89 (dd, 1H); 4.02 (t, 2H); 3.60 (s, 2H); 3.59 (s, 3H); 3.60-3.40 (m, 2H); 3.16 (dd, 1H); 2.94 (dd, 1H).

EXAMPLE 276

4-[2-[[[(2S)-1-[[2'-fluoro-5'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 274 starting from 2-fluoro-5-(trifluoromethyl)phenylboronic acid, the expected product is obtained in the form of a pink powder (yield=89%).

M.p.=52-55° C.

EXAMPLE 277

4-[2-[[[(2S)-1-[[2'-fluoro-5'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 5 starting from the compound obtained according to Example 276, the expected product is obtained in the form of a white powder (yield=94%).

M.p.=81-84° C.

EXAMPLE 278

4-[2-[[[(2S)-1-[(2'-fluoro-5'-methyl[1,1'-biphenyl]-4-yl)sulfonyl]-2,3-dihydro-1H-indol-2-yl]carbonyl]amino]ethoxy]benzeneacetic acid methyl ester By following a procedure analogous to Example 274 starting from 2-fluoro-5-methylphenylboronic acid, the expected product is obtained in the form of a pink powder (yield=90%).

M.p.=55-58° C.

EXAMPLE 279

4-[2-[[[(2S)-1-[(2'-fluoro-5'-methyl[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 278, the expected product is obtained in the form of a beige powder (yield=95%).

M.p.=82-85° C.

EXAMPLE 280

4-[2-[[[(2S)-1-[(2'-methoxy-5'-methyl[1,1'-biphenyl]-4-yl)sulfonyl]-2,3-dihydro-1H-indol-2-yl]carbonyl]amino]ethoxy]benzeneacetic acid methyl ester By following a procedure analogous to Example 274 starting from 2-methoxy-5-methylphenylboronic acid, the expected product is obtained in the form of a pink powder (yield=91%).

M.p.=57-60° C.

EXAMPLE 281

4-[2-[[[(2S)-1-[(2'-methoxy-5'-methyl[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 280, the expected product is obtained in the form of a yellow powder (yield=96%)

M.p.=85-88° C. .

EXAMPLE 282

4-[2-[[[(2S)-1-[(2',5'-dimethyl[1,1'-biphenyl]-4-yl)sulfonyl]-2,3-dihydro-1H-indol-2-yl]carbonyl]amino]ethoxy]benzeneacetic acid methyl ester By following a procedure analogous to Example 274 starting from 2,5-dimethylphenylboronic acid, the expected product is obtained in the form of a pink powder (yield=91%).
M.p.=56-59° C.

EXAMPLE 283

4-[2-[[[(2S)-1-[(2',5'-dimethyl[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 282, the expected product is obtained in the form of a beige powder (yield=96%).
M.p.=81-84° C.

EXAMPLE 284

4-[2-[[[(2S)-1-[[2'-methoxy-5'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 274 starting from 2-methoxy-5-(trifluoromethyl)phenylboronic acid, the expected product is obtained in the form of a pink powder (yield=85%).
M.p.=61-64° C.

EXAMPLE 285

4-[2-[[[(2S)-1-[[2'-methoxy-5'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the compound obtained according to Example 284, the expected product is obtained in the form of a white powder (yield=99%).
M.p.=85-88° C.

EXAMPLE 286

4-[2-[[[(2S)-1-[[2'-methyl-5'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 274 starting from 2-methyl-5-(trifluoromethyl)phenylboronic acid, the expected product is obtained in the form of a pink powder (yield=80%).
M.p.=46-49° C.

EXAMPLE 287

4-[2-[[[(2S)-1-[[2'-methyl-5'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the compound obtained according to Example 286, the expected product is obtained in the form of a white powder (yield=95%).
M.p.=80-84° C.

EXAMPLE 288

4-[2-[[[(2S)-1-[(2'-chloro-5'-methyl[1,1'-biphenyl]-4-yl)sulfonyl]-2,3-dihydro-1H-indol-2-yl]carbonyl]amino]ethoxy]benzeneacetic acid methyl ester By following a procedure analogous to Example 274 starting from 2-chloro-5-methylphenylboronic acid, the expected product is obtained in the form of a pink powder (yield=69%).
M.p.=50-53° C.

EXAMPLE 289

4-[2-[[[(2S)-1-[(2'-chloro-5'-methyl[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 288, the expected product is obtained in the form of a white powder (yield=96%).
M.p.=77-81° C.

EXAMPLE 290

4-[2-[[[(2S)-1-[(2',5'-dichloro[1,1'-biphenyl]-4-yl)sulfonyl]-2,3-dihydro-1H-indol-2-yl]carbonyl]amino]ethoxy]benzeneacetic acid methyl ester By following a procedure analogous to Example 274 starting from 2,5-dichlorophenylboronic acid, the expected product is obtained in the form of a yellow powder (yield=82%).
M.p.=61-65° C.

EXAMPLE 291

4-[2-[[[(2S)-1-[(2',5'-dichloro[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 290, the expected product is obtained in the form of a yellow powder (yield=82%).
M.p.=80-86° C.

EXAMPLE 292

4-[2-[[[(2S)-1-[(2'-chloro-5'-fluoro[1,1'-biphenyl]-4-yl)sulfonyl]-2,3-dihydro-1H-indol-2-yl]carbonyl]amino]ethoxy]benzeneacetic acid methyl ester By following a procedure analogous to Example 272 starting from 1-bromo-2-chloro-5-fluorobenzene, the expected product is obtained in the form of a white powder (yield=60%).
M.p.=52-56° C.

EXAMPLE 293

4-[2-[[[(2S)-1-[(2'-chloro-5'-fluoro[1,1'-biphenyl]-4-yl)sulfonyl]-2,3-dihydro-1H-indol-2-yl]carbonyl]amino]ethoxy]benzeneacetic acid By following a procedure analogous to Example 22 starting from the compound obtained according to Example 292, the expected product is obtained in the form of a white powder (yield=97%).
M.p.=78-84° C.

EXAMPLE 294

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]benzoic acid 1,1-dimethylethyl ester By following a procedure analogous to Example 21 starting from 1-[[2'-chloro-5'-(trifluoromethyl)[1,1'-biphenyl]-4-yl]sulfonyl]-2,3-dihydro-1H-(2S)-indole-2-carboxylic acid (Preparation CXII) and the t-butyl ester of 4-(2-aminoethoxy)benzoic acid, the expected product is obtained in the form of a white powder (yield=87%).
M.p.=75-80° C.

EXAMPLE 295

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 25 starting from the compound obtained according to Example 294, the expected product is obtained in the form of a white powder (yield=87%).
M.p.=117-121° C.

EXAMPLE 296

4-[[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethyl]amino]benzoic acid 1,1-dimethylethyl ester By following a procedure analogous to Example 21 (replacing the HOAT with HOBT) starting from the acid obtained according to Preparation CXII and the t-butyl ester of 4-[(2-aminoethyl)amino]benzoic acid, the expected product is obtained in the form of a yellow oil (yield=59%).
$^1$H NMR (DMSO, 300 MHz) δ: 8.40 (t, NH); 7.90 (d, 2H); 7.85-7.75 (m, 2H); 7.75-7.60 (m, 4H); 7.51 (d, 1H); 7.25 (t, 1H); 7.15-7.05 (m, 2H); 7.02 (t, 1H); 6.60 (d, 2H); 4.93 (dd, 1H); 3.50-3.00 (m, 5H); 2.96 (dd, 1H); 1.49 (s, 9H).

EXAMPLE 297

4-[[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethyl]amino]benzoic acid methyl ester By following a procedure analogous to Example 296 starting from the acid obtained according to Preparation CXII and the methyl ester of 4-[(2-aminoethyl)amino]benzoic acid (obtained by reacting the methyl ester of 4-aminobenzoic acid with 2-bromoethylamine at 120° C.), the expected product is obtained in the form of a white solid (yield=53%).
M.p.=96-98° C.

EXAMPLE 298

4-[[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethyl]amino]benzoic acid A solution of 220 mg (0.31 mmol) of the ester obtained according to Example 296 in 5 ml of ethyl acetate is prepared. 1.5 ml of a 4 M solution of hydrogen chloride in dioxane are added at 0° C. The reaction medium is stirred for 16 hours at room temperature. The mixture is then concentrated under reduced pressure and the crude product obtained is purified by chromatography on silica gel using a dichloromethane/methanol mixture (98/2; v/v) as the eluent to give the expected product in the form of a white foam (yield=23%).
M.p.=130° C.

EXAMPLE 299

4-[[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethyl]amino]benzeneacetic acid ethyl ester By following a procedure analogous to Example 296 starting from the ethyl ester of 4-[(2-aminoethyl)amino]benzeneacetic acid, the expected product is obtained in the form of a white solid (yield=72%).
M.p.=55-63° C.

EXAMPLE 300

4-[[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethyl]amino]benzeneacetic acid By following a procedure analogous to Example 22 starting from the ester obtained according to Example 299, the expected product is obtained in the form of a white solid (yield=41%).
M.p.=110-118° C.

EXAMPLE 301

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-3-methoxybenzeneacetic acid methyl ester By following a procedure analogous to Example 296 starting from the ester obtained according to Preparation LXXIX, the expected product is obtained in the form of a fine white solid (yield=62%).
M.p.=51-58° C.

EXAMPLE 302

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-3-methoxybenzeneacetic acid By following a procedure analogous to Example 22 starting from the ester obtained according to Example 301, the expected product is obtained in the form of a white solid (yield=96%).

M.p.=74-76° C.

Preparation CXIII

1-[4-[2-[[(Phenylmethoxy)carbonyl]amino]ethoxy]phenyl]cyclopropanecarboxylic acid methyl ester By following a procedure analogous to Preparation LXVIII starting from the methyl ester of 1-(4-hydroxyphenyl)cyclopropanecarboxylic acid, the expected product is obtained in the form of a yellow oil (yield=58%).

$^1$H NMR (CDCl$_3$, 300 MHz) δ: 7.40-7.30 (m, 7H); 6.82 (d, 2H); 5.22 (broad s, 1H); 5.22 (s, 2H); 4.03 (t, 2H); 3.65-3.55 (m, 5H); 1.65-1.55 (m, 2H); 1.20-1.10 (m, 2H).

Preparation CXIV

1-[4-(2-Aminoethoxy)phenyl]cyclopropanecarboxylic acid methyl ester (hydrochloride)

By following a procedure analogous to Preparation LXXI starting from the compound obtained according to Preparation CXIII, the expected product is obtained in the form of a white solid (yield=96%).

M.p.=119-122° C.

EXAMPLE 303

1-[4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]phenyl]cyclopropanecarboxylic acid methyl ester By following a procedure analogous to Example 296 starting from the compound obtained according to Preparation CXIV, the expected product is obtained in the form of a fine white solid (yield=78%).

M.p.=64-72° C.

EXAMPLE 304

1-[4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]phenyl]cyclopropanecarboxylic acid By following a procedure analogous to Example 22 starting from the ester obtained according to Example 303, the expected product is obtained in the form of a white solid (yield=22%).

M.p.=111° C.

EXAMPLE 305

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2-fluorobenzoic acid methyl ester By following a procedure analogous to Example 296 starting from the compound obtained according to Preparation LXIX, the expected product is obtained in the form of a fine white solid (yield=38%).

M.p.=84-85° C.

EXAMPLE 306

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2-methoxybenzoic acid By following a procedure analogous to Example 22 starting from the ester obtained according to Example 305, the expected product is obtained in the form of a white solid (yield=72%).

M.p.=98-104° C.

EXAMPLE 307

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2-(trifluoromethyl)benzoic acid methyl ester By following a procedure analogous to Example 296 starting from the compound obtained according to Preparation LXXXV, the expected product is obtained in the form of a fine white solid (yield=71%).

M.p.=79° C.

EXAMPLE 308

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2-(trifluoromethyl)benzoic acid By following a procedure analogous to Example 22 starting from the ester obtained according to Example 307, the expected product is obtained in the form of a white solid (yield=20%).

M.p.=102-109° C.

EXAMPLE 309

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2,6-difluorobenzoic acid methyl ester By following a procedure analogous to Example 296 starting from the compound obtained according to Preparation LXXXI, the expected product is obtained in the form of a fine white solid (yield=61%).

M.p.=78° C.

EXAMPLE 310

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2,6-difluorobenzoic acid By following a procedure analogous to Example 22 starting from the ester obtained according to Example 309, the expected product is obtained in the form of a white solid (yield=56%).

M.p.=103-114° C.

EXAMPLE 311

4-[[[[1-[(2',4'-Difluoro[1,1'-biphenyl]-4-yl)sulfonyl]-2,3-dihydro-1H-indol-2-yl]carbonyl]amino]methyl]benzoic acid The chloride of the acid obtained according to Preparation CV is prepared by the process described for Preparation VI and is reacted with 4-(aminomethyl)benzoic acid according to the procedure described in Example 17 to give the expected product in the form of a white solid (yield=69%).
M.p.=115° C.

EXAMPLE 312

4-[[[[1-[(2'-Chloro-4'-fluoro[1,1'-biphenyl]-4-yl)sulfonyl]-2,3-dihydro-1H-indol-2-yl]carbonyl]amino]methyl]benzoic acid By following a procedure analogous to Example 311 starting from the acid obtained according to Preparation CVII, the expected product is obtained in the form of a white solid (yield=61%).
M.p.=111-124° C.

EXAMPLE 313

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-α-methylbenzeneacetic acid methyl ester By following a procedure analogous to Example 296 starting from the ester obtained according to Preparation LXXVII, the expected product is obtained in the form of a fine white solid (yield=30%).
M.p.=55-63° C.

EXAMPLE 314

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-α-methylbenzeneacetic acid By following a procedure analogous to Example 22 starting from the ester obtained according to Example 313, the expected product is obtained in the form of a white solid (yield=98%).
M.p.=91-100° C.

Preparation CXV

3-Fluoro-4-[2-[[(phenylmethoxy)carbonyl]amino]ethoxy]benzeneacetic acid methyl ester By following a procedure analogous to Preparation LXVIII starting from the methyl ester of 3-fluoro-4-hydroxybenzeneacetic acid, the expected compound is obtained in the form of a white solid with a yield of 69%.
M.p.=44-45° C.

Preparation CXVI 4-(2-Aminoethoxy)-3-fluorobenzeneacetic acid methyl ester (hydrochloride)

By following a procedure analogous to Preparation LXXI starting from the compound obtained according to Preparation CXV, the expected compound is obtained in the form of a white solid with a yield of 94%.
M.p.=143-144° C.

EXAMPLE 315

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-3-fluorobenzeneacetic acid methyl ester By following a procedure analogous to Example 296 starting from the ester obtained according to Preparation CXVI, the expected product is obtained in the form of a fine white solid (yield=86%).
M.p.=56-62° C.

EXAMPLE 316

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-3-fluorobenzeneacetic acid By following a procedure analogous to Example 22 starting from the ester obtained according to Example 315, the expected product is obtained in the form of a white solid (yield=86%).
M.p.=100° C.

Preparation CXVII

2-Methyl-4-[2-[[(phenylmethoxy)carbonyl]amino]ethoxy]benzeneacetic acid methyl ester By following a procedure analogous to Preparation LXVIII starting from the methyl ester of 2-methyl-4-hydroxybenzeneacetic acid, the expected compound is obtained in the form of a colorless oil with a yield of 22%.
$^1$H NMR (DMSO, 300 MHz) δ: 7.47 (t, 1H); 7.45-7.25 (m, 5H); 7.07 (d, 1H); 6.80-6.60 (m, 2H); 5.03 (s, 2H); 3.95 (t, 2H); 3.70-3.50 (m, 5H); 3.45-3.25 (m, 2H); 2.18 (s, 3H).

Preparation CXVIII 4-(2-Aminoethoxy)-2-methylbenzeneacetic acid methyl ester (hydrochloride)

By following a procedure analogous to Preparation LXXI starting from the compound obtained according to Preparation CXVII, the expected compound is obtained in the form of a beige solid with a yield of 75%.
M.p.=168-171° C.

EXAMPLE 317

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2-methylbenzeneacetic acid methyl ester By following a procedure analogous to Example 296 starting from the ester obtained according to Preparation CXVIII, the expected product is obtained in the form of a colorless oil (yield=53%).
$^1$H NMR (DMSO, 300 MHz) δ: 7.80-7.20 (m, 9H); 7.15-7.05 (m, 3H); 6.75-6.65 (m, 2H); 4.68 (dd, 1H); 4.10-3.95 (m, 2H); 3.80-3.50 (m, 5H); 3.57 (s, 2H); 3.28 (dd, 1H); 2.82 (dd, 1H); 2.27 (s, 3H).

EXAMPLE 318

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-2-methylbenzeneacetic acid By following a procedure analogous to Example 22 starting from the ester obtained according to Example 317, the expected product is obtained in the form of a white solid (yield=46%).
M.p.=110-115° C.

EXAMPLE 319

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-3-chlorobenzeneacetic acid methyl ester By following a procedure analogous to Example 296 starting from the ester obtained according to Preparation LXI, the expected product is obtained in the form of a white powder (yield=63%).
M.p.=68-76° C.

EXAMPLE 320

4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]-3-chlorobenzeneacetic acid By following a procedure analogous to Example 22 starting from the ester obtained according to Example 319, the expected product is obtained in the form of a white solid (yield=89%).
M.p.=108-112° C.

EXAMPLE 321

3-Chloro-4-[2-[[[(2S)-1-[(4'-fluoro[1,1'-biphenyl]-4-yl)sulfonyl]-2,3-dihydro-1H-indol-2-yl]carbonyl]amino]ethoxy]benzeneacetic acid methyl ester By following a procedure analogous to Example 319 starting from the acid obtained according to Preparation LXIII, the expected product is obtained in the form of a white powder (yield=63%).
M.p.=68-76° C.

EXAMPLE 322

3-Chloro-4-[2-[[[(2S)-1-[(4'-fluoro[1,1'-biphenyl]-4-yl)sulfonyl]-2,3-dihydro-1H-indol-2-yl]carbonyl]amino]ethoxy]benzeneacetic acid By following a procedure analogous to Example 22 starting from the ester obtained according to Example 321, the expected product is obtained in the form of a white solid (yield=85%).
M.p.=102-110° C.

Preparation CXIX

α,α-Dimethyl-4-[2-[[(phenylmethoxy)carbonyl]amino]ethoxy]benzeneacetic acid methyl ester By following a procedure analogous to Preparation LXVIII starting from the methyl ester of α,α-dimethyl-4-hydroxybenzeneacetic acid, the expected compound is obtained in the form of a yellow oil with a yield of 62%.
$^1$H NMR (DMSO, 300 MHz) δ: 7.48 (t, 1H); 7.40-7.25 (m, 5H); 7.20 (d, 2H); 6.87 (d, 2H); 5.02 (s, 2H); 3.97 (t, 2H); 3.56 (s, 3H); 3.35 (q, 2H); 1.47 (s, 6H).

Preparation CXX

α,α-Dimethyl-4-(2-aminoethoxy)benzeneacetic acid methyl ester (hydrochloride)

By following a procedure analogous to Preparation LXXI starting from the compound obtained according to Preparation CXIX, the expected compound is obtained in the form of a yellow solid with a yield of 88%.
M.p.=108-112° C.

EXAMPLE 323

α,α-Dimethyl-4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 296 starting from the ester obtained according to Preparation CXX, the expected product is obtained in the form of a white powder (yield=61%).
M.p.=66-72° C.

EXAMPLE 324

α,α-Dimethyl-4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 323, the expected product is obtained in the form of a white solid (yield=23%).
M.p.=92-100° C.

Preparation CXXI

2-Chloro-4-[2-[[(phenylmethoxy)carbonyl]amino]ethoxy]benzoic acid methyl ester

By following a procedure analogous to Preparation LXVIII starting from the methyl ester of 2-chloro-4-hydroxybenzoic acid, the expected compound is obtained in the form of a white solid with a yield of 84%.
M.p.=88-90° C.

Preparation CXXII 4-(2-Aminoethoxy)-2-chlorobenzoic acid methyl ester (hydrobromide)

A solution of 500 mg (1.37 mmol) of the compound obtained according to Preparation CXXI in 5 ml of dichloromethane is prepared and 3.7 ml (20 mmol) of a 45% solution of hydrogen bromide in acetic acid are added at room temperature. The reaction mixture is stirred for 1 hour at room temperature and then diluted with ethyl ether. The precipitate obtained is filtered off, rinsed on the filter with ethyl ether and then dried at 40° C. under vacuum to give the expected product in the form of a white powder with a yield of 91%.

M.p.=195-197° C.

EXAMPLE 325

2-Chloro-4-[2-[[[(2S)-1-[[2'-chloro-5'-(trifluoromethyl)[1,1'-biphenyl]-4-yl]-sulfonyl]-2,3-dihydro-1H-indol-2-yl]carbonyl]amino]ethoxy]benzoic acid methyl ester By following a procedure analogous to Example 296 starting from the ester obtained according to Preparation CXXII, the expected product is obtained in the form of a white powder (yield=73%).

M.p.=70-76° C.

EXAMPLE 326

2-Chloro-4-[2-[[[(2S)-1-[[2'-chloro-5'-(trifluoromethyl)[1,1'-biphenyl]-4-yl]-sulfonyl]-2,3-dihydro-1H-indol-2-yl]carbonyl]amino]-ethoxy]benzoic acid By following a procedure analogous to Example 22 starting from the ester obtained according to Example 325, the expected product is obtained in the form of a white solid (yield=46%).

M.p.=106-112° C.

EXAMPLE 327

2-Chloro-4-[2-[[[(2S)-1-[(4'-fluoro[1,1'-biphenyl]-4-yl)sulfonyl]-2,3-dihydro-1H-indol-2-yl]carbonyl]amino]ethoxy]benzoic acid methyl ester By following a procedure analogous to Example 325 starting from the acid obtained according to Preparation LXIII, the expected product is obtained in the form of a pink powder (yield=70%).

M.p.=70-79° C.

EXAMPLE 328

2-Chloro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid methyl ester By following a procedure analogous to Example 325 starting from the acid obtained according to Preparation IV, the expected product is obtained in the form of a white powder (yield=83%).

M.p.=63-67° C.

EXAMPLE 329

2-Chloro-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzoic acid By following a procedure analogous to Example 22 starting from the ester obtained according to Example 328, the expected product is obtained in the form of a white solid (yield=39%).

M.p.=104-108° C.

Preparation CXXIII

α-(1-Methylethyl)-4-[2-[[(phenylmethoxy)carbonyl]amino]ethoxy]benzeneacetic acid methyl ester By following a procedure analogous to Preparation LXVIII starting from the methyl ester of α-(1-methylethyl)-4-hydroxybenzeneacetic acid, the expected compound is obtained in the form of a colorless oil with a yield of 79%.

$^1$H NMR (DMSO, 300 MHz) δ: 7.48 (t, 1H); 7.45-7.00 (m, 7H); 6.88 (d, 2H); 5.03 (s, 2H); 3.97 (t, 2H); 3.57 (s, 3H); 3.45-3.25 (m, 2H); 3.18 (d, 1H); 2.30-2.10 (m, 1H); 0.95 (d, 3H); 0.64 (d, 3H).

Preparation CXXIV

α-(1-Methylethyl)-4-(2-aminoethoxy)benzeneacetic acid methyl ester (hydrobromide)

By following a procedure analogous to Preparation CXXII starting from the compound obtained according to Preparation CXXIII, the expected compound is obtained in the form of an oil with a yield of 37%.

$^1$H NMR (DMSO, 300 MHz) δ: 7.94 (broad s, NH$_2$); 7.25 (d, 2H); 6.94 (d, 2H); 4.14 (t, 2H); 3.56 (s, 3H); 3.20 (q, 2H); 2.30-2.10 (m, 1H); 0.94 (d, 3H); 0.63 (d, 3H).

EXAMPLE 330

α-(1-Methylethyl)-4-[2-[[[(2S)-1-[[2'-chloro-5'-(trifluoromethyl)-[1,1'-biphenyl]-4-yl]sulfonyl]-2,3-dihydro-1H-indol-2-yl]carbonyl]amino]ethoxy]benzeneacetic acid methyl ester By following a procedure analogous to Example 296 starting from the ester obtained according to Preparation CXXIV, the expected product is obtained in the form of a white powder (yield=56%).

M.p.=68-75° C.

EXAMPLE 331

α-(1-Methylethyl)-4-[2-[[[(2S)-1-[[2'-chloro-5'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 330, the expected product is obtained in the form of a yellow solid (yield=18%).

M.p.=134-143° C.

EXAMPLE 332

α-(1-Methylethyl)-4-[2-[[[(2S)-1-[[3'-(trifluoromethyl)[1,1'-biphenyl]-4-yl]-sulfonyl]-2,3-dihydro-1H-indol-2-yl]carbonyl]amino]ethoxy]benzeneacetic acid methyl ester By following a procedure analogous to Example 330 starting from the acid obtained according to Preparation IV, the expected product is obtained in the form of a white powder (yield=63%).

M.p.=68-76° C.

EXAMPLE 333

α-(1-Methylethyl)-4-[2-[[[(2S)-1-[[2'-chloro-5'-(trifluoromethyl)-[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 332, the expected product is obtained in the form of a white solid (yield=14%).

M.p.=84-88° C.

EXAMPLE 334

2-[[[[(2S)-1-[[3'-(trifluoromethyl)[1,1'-biphenyl]-4-yl]sulfonyl]-2,3-dihydro-1H-indol-2-yl]carbonyl]amino]methyl]benzenepentanoic acid methyl ester By following a procedure analogous to Example 21 starting from the acid obtained according to Preparation IV and the hydrochloride of the methyl ester of 2-(aminomethyl)benzenepentanoic acid, the expected product is obtained in the form of a colorless oil (yield=80%).

$^1$H NMR (DMSO, 300 MHz) δ: 8.61 (t, NH); 8.10-8.00 (m, 2H); 8.00-7.85 (m, 4H); 7.85-7.70 (m, 2H); 7.50 (d, 1H); 7.30-7.10 (m, 6H); 7.03 (td, 1H); 4.93 (dd, 1H); 4.45-4.25 (m, 2H); 3.57 (s, 3H); 3.18 (dd, 1H); 2.96 (dd, 1H); 2.62 (t, 2H); 2.34 (t, 2H); 1.65-1.45 (m, 4H).

EXAMPLE 335

2-[[[[(2S)-1-[[3'-(trifluoromethyl)[1,1'-biphenyl]-4-yl]sulfonyl]-2,3-dihydro-1H-indol-2-yl]carbonyl]amino]methyl]benzenepentanoic acid By following a procedure analogous to Example 22 starting from the ester obtained according to Example 334, the expected product is obtained in the form of a white solid (yield=98%).

M.p.=98-99° C.

Preparation CXXV

[[2-[3-(Dimethylamino)propoxy]phenyl]methyl]carbamic acid phenylmethyl ester

By following a procedure analogous to Preparation XCVI starting from the benzyl ester of [(2-hydroxyphenyl)methyl]carbamic acid and 3-(dimethylamino)propanol, the expected product is obtained in the form of a colorless oil (yield=81%).

$^1$H NMR (DMSO, 300 MHz) δ: 7.63 (t, 1H); 7.40-7.15 (m, 7H); 6.95-6.80 (m, 2H); 5.04 (s, 2H); 4.19 (d, 2H); 4.00 (t, 2H); 2.39 (t, 2H); 2.14 (s, 6H); 1.85 (t, 2H).

Preparation CXXVI

2-[3-(Dimethylamino)propoxy]benzenemethanamine

By following a procedure analogous to Example 61 (but working in ethanol) starting from the compound obtained according to Preparation CXXV, the expected product is obtained in the form of a colorless oil (yield=97%).

$^1$H NMR (DMSO, 300 MHz) δ: 7.29 (d, 1H); 7.18 (td, 1H); 6.95-6.85 (m, 2H); 4.00 (t, 2H); 3.69 (s, 1H); 2.39 (t, 2H); 2.14 (s, 6H); 1.90-1.80 (m, 2H).

EXAMPLE 336

2,3-Dihydro-N-[[2-[3-(dimethylamino)propoxy]phenyl]methyl]-1-[[3'-(trifluoromethyl)[1,1'-biphenyl]-4-yl]sulfonyl]-(2S)-1H-indole-2-carboxamide (hydrochloride)

By following a procedure analogous to Preparation I starting from the acid obtained according to Preparation IV and the amine obtained according to Preparation CXXVI, an oil is obtained which is acidified with a solution of hydrogen chloride in ethyl acetate to give the hydrochloride in the form of a white solid (yield=86%).

M.p.=129-132° C.

Preparation CXXVII

4-[[2-[[[(Phenylmethoxy)carbonyl]amino]methyl]phenyl]amino]butanoic acid methyl ester A solution of 1 g (3.9 mmol) of the benzyl ester of [(2-aminophenyl)methyl]carbamic acid in 10 ml of acetonitrile is prepared in a reactor adapted for microwave reactions, and 1.06 g (5.85 mmol) of the methyl ester of 4-bromobutanoic acid and 0.81 g (5.85 mmol) of potassium carbonate are added. The reaction mixture is heated by microwaves for 1 hour at 150° C. and then cooled and taken up with ethyl acetate and water. The organic phase is separated off, washed with water, dried over magnesium sulfate and concentrated under reduced pressure. The yellow oil obtained is purified by chromatography on silica gel using a methylcyclohexane/ethyl acetate mixture (7/3; v/v) as the eluent to give the expected product in the form of a yellow oil with a yield of 35%.

$^1$H NMR (DMSO, 300 MHz) δ: 7.68 (t, NH); 7.40-7.25 (m, 5H); 7.06 (td, 1H); 6.99 (dd, 1H); 6.60-6.50 (m, 2H); 5.05 (broad s, NH+2H); 4.07 (d, 2H); 3.59 (s, 3H); 3.06 (q, 2H); 2.42 (t, 2H); 1.78 (quint, 2H).

Preparation CXXVIII

4-[[2-[[[(Phenylmethoxy)carbonyl]amino]methyl]phenyl]amino]butanoic acid

By following a procedure analogous to Example 22 starting from the ester obtained according to Preparation CXXVII, the expected product is obtained in the form of an oil (yield=93%).

$^1$H NMR (DMSO, 300 MHz) δ: 12.06 (s, COOH); 7.69 (t, NH); 7.40-7.25 (m, 5H); 7.04 (td, 1H); 6.97 (dd, 1H); 6.60-6.50 (m, 2H); 5.05 (broad s, NH+2H); 4.07 (d, 2H); 3.05 (t, 2H); 2.33 (t, 2H); 1.78 (quint, 2H).

Preparation CXXIX

4-[[2-(Aminomethyl)phenyl]amino]butanoic acid

By following a procedure analogous to Preparation XXXVII starting from the compound obtained according to Preparation CXXVIII, the expected product is obtained in the form of a white solid (yield=80%).

$^1$H NMR (DMSO, 300 MHz) δ: 7.10-7.00 (m, 2H); 6.50-6.54 (m, 2H); 3.72 (s, 2H); 3.08 (t, 2H); 2.24 (t, 2H); 1.81 (q, 2H).

Preparation CXXX 2,3-Dihydro-1-[[3'-(trifluoromethyl)[1,1'-biphenyl]-4-yl]sulfonyl]-(2S)-1H-indole-2-carboxylic acid chloride This compound is obtained by a procedure analogous to Preparation VI starting from the acid obtained according to Preparation IV, and is used directly in the next reaction.

EXAMPLE 337

4-[[2-[[[[(2S)-2,3-dihydro-1-[[3'-(trifluoromethyl)[1,1'-biphenyl]-4-yl]sulfonyl]-1H-indol-2-yl]carbonyl]amino]methyl]phenyl]amino]butanoic acid By following a procedure analogous to Example 17 starting from the compounds obtained according to Preparations CXXIX and CXXX, the expected compound is obtained in the form of a white solid (yield=17%).
M.p.=77-81° C.

EXAMPLE 338

N-[(2,3-dihydro-2-oxo-1H-indol-7-yl)methyl]-2,3-dihydro-1-[[3'-(trifluoromethyl)[1,1'-biphenyl]-4-yl]sulfonyl]-(2S)-1H-indole-2-carboxamide By following a procedure analogous to Preparation I starting from the acid obtained according to Preparation IV and 7-(aminomethyl)-1,3-dihydro-2H-indol-2-one, the expected product is obtained in the form of an orange solid (yield=12%).
M.p.=50° C.

EXAMPLE 339

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]-2-fluorobenzoic acid methyl ester By following a procedure analogous to Example 230 starting from the acid obtained according to Preparation CVII, the expected compound is obtained in the form of a white solid (yield=52%).
M.p.=71-76° C.

EXAMPLE 340

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]-2-fluorobenzoic acid By following a procedure analogous to Example 22 starting from the ester obtained according to Example 339, the expected compound is obtained in the form of a white solid (yield=71%).
M.p.=98-102° C.

EXAMPLE 341

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-2-fluorobenzoic acid methyl ester By following a procedure analogous to Example 230 starting from the acid obtained according to Preparation CXI, the expected compound is obtained in the form of a white solid (yield=66%).
M.p.=73-80° C.

EXAMPLE 342

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-2-fluorobenzoic acid By following a procedure analogous to Example 22 starting from the ester obtained according to Example 341, the expected compound is obtained in the form of a white solid (yield=62%).
M.p.=88-95° C.

EXAMPLE 343

4-[2-[[[(2S)-1-[(2',4'-difluoro[1,1'-biphenyl]-4-yl)sulfonyl]-2,3-dihydro-1H-indol-2-yl]carbonyl]amino]ethoxy]-2-fluorobenzoic acid methyl ester By following a procedure analogous to Example 230 starting from the acid obtained according to Preparation CV, the expected compound is obtained in the form of a white solid (yield=53%).
M.p.=65-68° C.

EXAMPLE 344

4-[2-[[[(2S)-1-[(2',4'-difluoro[1,1'-biphenyl]-4-yl)sulfonyl]-2,3-dihydro-1H-indol-2-yl]carbonyl]amino]ethoxy]-2-fluorobenzoic acid By following a procedure analogous to Example 22 starting from the ester obtained according to Example 343, the expected compound is obtained in the form of a white solid (yield=85%).
M.p.=91-94° C.

EXAMPLE 345

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]-2-fluorobenzoic acid methyl ester By following a procedure analogous to Example 230 starting from the acid obtained according to Preparation CIV, the expected compound is obtained in the form of a white solid (yield=83%).
M.p.=66-75° C.

EXAMPLE 346

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]-2-fluorobenzoic acid By following a procedure analogous to Example 22 starting from the ester obtained according to Example 345, the expected compound is obtained in the form of a white solid (yield=80%).
M.p.=109-118° C.

EXAMPLE 347

6-[[[(2S)-2,3-dihydro-1-[[3'-(trifluoromethyl)[1,1'-biphenyl]-4-yl]sulfonyl]-1H-indol-2-yl]carbonyl]amino]hexanoic acid methyl ester By following a procedure analogous to Example 98 starting from the methyl ester of 6-aminohexanoic acid, the expected compound is obtained in the form of a colorless paste (yield=52%).
$^1$H NMR (DMSO, 250 MHz) δ: 8.16 (t, NH); 8.10-8.00 (m, 2H); 8.00-7.85 (m, 4H); 7.85-7.72 (m, 2H); 7.49 (d, 1H); 7.24 (td, 1H); 7.13 (d, 1H); 7.02 (td, 1H); 4.80 (dd, 1H); 3.57 (s, 3H); 3.20-3.00 (m, 3H); 2.92 (dd, 1H); 2.28 (t, 2H); 1.60-1.35 (m, 4H); 1.35-1.20 (m, 2H).

EXAMPLE 348

6-[[[(2S)-2,3-dihydro-1-[[3'-(trifluoromethyl)[1,1'-biphenyl]-4-yl]sulfonyl]-1H-indol-2-yl]carbonyl]amino]hexanoic acid By following a procedure analogous to Example 22 starting from the ester obtained according to Example 347, the expected compound is obtained in the form of a yellow solid (yield=81%).
M.p.=50° C.
$^1$H NMR (DMSO, 300 MHz) δ: 11.97 (s, COOH), 8.17 (t, NH); 8.10-8.00 (m, 2H); 8.00-7.85 (m, 4H); 7.85-7.72 (m, 2H); 7.49 (d, 1H); 7.24 (td, 1H); 7.13 (d, 1H); 7.02 (td, 1H); 4.80 (dd, 1H); 3.20-3.00 (m, 3H); 2.92 (dd, 1H); 2.19 (t, 2H); 1.60-1.35 (m, 4H); 1.35-1.20 (m, 2H).

EXAMPLE 349

2-Methyl-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 21 starting from the acid obtained according to Preparation IV and the amine obtained according to Preparation CXVIII, the expected product is obtained in the form of a white solid (yield=61%).
M.p.=53-57° C.

EXAMPLE 350

2-Methyl-4-[2-[[[(2S)-1-[[3'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the compound obtained according to Example 349, the expected product is obtained in the form of a white powder (yield=51%).
M.p.=87-90° C.

EXAMPLE 351

2-Methyl-4-[2-[[[(2S)-1-[[2'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 349 starting from the acid obtained according to Preparation V, the expected product is obtained in the form of a white paste (yield=90%).
$^1$H NMR (DMSO, 300 MHz) δ: 8.40 (t, NH); 7.90-7.80 (m, 3H); 7.80-7.70 (m, 2H); 7.50-7.45 (m, 3H); 7.39 (d, 1H); 7.24 (t, 1H); 7.13 (d, 1H); 7.04 (t, 2H); 6.80-6.70 (m, 2H); 4.88 (dd, 1H); 3.99 (t, 2H); 3.58 (s, 5H); 3.58-3.40 (m, 2H); 3.10-2.90 (m, 2H); 2.17 (s, 3H).

EXAMPLE 352

2-Methyl-4-[2-[[[(2S)-1-[[2'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the compound obtained according to Example 351, the expected product is obtained in the form of a white powder (yield=68%).
M.p.=85-95° C.

Preparation CXXXI

2-Methyl-4-[[(trifluoromethyl)sulfonyl]oxy]benzeneacetic acid methyl ester 0.85 ml (6.11 mmol) of triethylamine is added to a solution of 0.55 g (3.06 mmol) of the methyl ester of 2-methyl-4-hydroxybenzeneacetic acid in 22 ml of DCM. The mixture is cooled to 0° C. and 0.62 ml (3.67 mmol) of trifluoromethanesulfonic anhydride is added. The reaction mixture is stirred at 0° C. for 1 hour and then diluted with 60 ml of DCM and washed with water. The organic phase is dried over magnesium sulfate and concentrated under reduced pressure. The crude product obtained is purified by chromatography on silica gel using a cyclohexane/ethyl acetate mixture (9/1; v/v) as the eluent to give 670 mg of the expected product in the form of a colorless oil (yield=70%).
$^1$H NMR (DMSO, 250 MHz) δ: 7.38 (d, 1H); 7.33 (d, 1H); 7.26 (dd, 1H); 3.77 (s, 2H); 3.63 (s, 3H); 2.27 (s, 3H).

Preparation CXXXII

4-Cyano-2-methylbenzeneacetic acid methyl ester 0.564 mg (1.8 mmol) of the compound obtained according to Preparation CXXXI, 5 ml of DMF, 208 mg of tetrakis(triphenylphosphine)palladium and 211 mg (1.8 mmol) of zinc cyanide are introduced into a microwave reactor. The reaction mixture is stirred at 150° C. for 5 min and then diluted with 25 ml of ethyl acetate and washed with water. The organic phase is dried over magnesium sulfate and concentrated under reduced pressure. The crude product obtained is purified by chromatography on silica gel using a cyclohexane/ethyl acetate mixture (8/2; v/v) as the eluent to give 150 mg of the expected product in the form of a white solid (yield=44%).
M.p.=52-54° C.

Preparation CXXXIII 4-(Aminomethyl)-2-methylbenzeneacetic acid methyl ester (hydrochloride)

By following a procedure analogous to Preparation LXIX starting from the ester obtained according to Preparation CXXXII, the expected product is obtained in the form of a white solid (yield=98%).
M.p.=218-220° C.

EXAMPLE 353

2-Methyl-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzeneacetic acid methyl ester By following a procedure analogous to Example 349 starting from the amine obtained according to Preparation CXXXIII, the expected product is obtained in the form of a white solid (yield=80%).
M.p.=60-67° C.

Preparation CXXXIV

4-[[[[(2S)-2,3-dihydro-1-[(4-iodophenyl)sulfonyl]-1H-indol-2-yl]carbonyl]-amino]methyl]benzoic acid methyl ester By following a procedure analogous to Preparation VIIa starting from the methyl ester of 4-(aminomethyl)benzoic acid, the expected compound is obtained in the form of a white solid (yield=92%).
M.p.=80-85° C.

Preparation CXXXV

4-[[[[(2S)-2,3-dihydro-1-[(4-iodophenyl)sulfonyl]-1H-indol-2-yl]carbonyl]amino]-methyl]benzoic acid By following a procedure analogous to Example 22 starting from the ester obtained according to Preparation CXXXIV, the expected compound is obtained in the form of a white powder (yield=98%).
M.p.=110-120° C.

EXAMPLE 354

4-[[[[(2S)-1-[(2'-methoxy-5'-methyl[1,1'-biphenyl]-4-yl)sulfonyl]-2,3-dihydro-1H-indol-2-yl]carbonyl]amino]methyl]benzoic acid By following a procedure analogous to Example 1 starting from the acid obtained according to Preparation CXXXV and 2-methoxy-5-methylphenylboronic acid, the expected product is obtained in the form of a white solid (yield=23%).
M.p.=153-165° C.

The products below are obtained by following a procedure analogous to Example 354 starting from different phenylboronic acids:

EXAMPLE 355

4-[[[[(2S)-1-[(2'-fluoro-5'-methyl[1,1'-biphenyl]-4-yl)sulfonyl]-2,3-dihydro-1H-indol-2-yl]carbonyl]amino]methyl]benzoic acid White solid (yield=62%).
M.p.=105-120° C.

EXAMPLE 356

4-[[[[(2S)-1-[[2'-fluoro-5'-(trifluoromethyl)[1,1'-biphenyl]-4-yl]sulfonyl]-2,3-dihydro-1H-indol-2-yl]carbonyl]amino]methyl]benzoic acid White solid (yield=84%)
M.p.=115-120° C. .

EXAMPLE 357

4-[[[[(2S)-1-[(2',5'-dimethyl[1,1'-biphenyl]-4-yl)sulfonyl]-2,3-dihydro-1H-indol-2-yl]carbonyl]amino]methyl]benzoic acid White solid (yield=81%).
M.p.=126-136° C.

EXAMPLE 358

4-[[[[(2S)-1-[[2'-chloro-5'-(trifluoromethyl)[1,1'-biphenyl]-4-yl]sulfonyl]-2,3-dihydro-1H-indol-2-yl]carbonyl]amino]methyl]benzoic acid Beige solid (yield=71%).
M.p.=120-130° C.

EXAMPLE 359

4-[[[[(2S)-1-[(3'-methyl[1,1'-biphenyl]-4-yl)sulfonyl]-2,3-dihydro-1H-indol-2-yl]carbonyl]amino]methyl]benzoic acid Beige solid (yield=51%).
M.p.=118-130° C.

EXAMPLE 360

4-[[[[(2S)-1-[[2'-methoxy-5'-(trifluoromethyl)[1,1'-biphenyl]-4-yl]sulfonyl]-2,3-dihydro-1H-indol-2-yl]carbonyl]amino]methyl]benzoic acid Yellow solid (yield=74%).
M.p.=122-130° C.

EXAMPLE 361

4-[[[[(2S)-1-[[2'-methyl-5'-(trifluoromethyl)[1,1'-biphenyl]-4-yl]sulfonyl]-2,3-dihydro-1H-indol-2-yl]carbonyl]amino]methyl]benzoic acid Beige solid (yield=76%).
M.p.=120-128° C.

EXAMPLE 362

4-[[[[(2S)-1-[(2'-chloro-5'-methyl[1,1'-biphenyl]-4-yl)sulfonyl]-2,3-dihydro-1H-indol-2-yl]carbonyl]amino]methyl]benzoic acid White solid (yield=37%).
M.p.=104-110° C.

The compounds below are obtained by following a procedure analogous to Preparations CXXXI to CXXXIII starting from the methyl ester of 4-hydroxy-3-methoxybenzeneacetic acid:

Preparation CXXXVI

3-Methoxy-4-[[(trifluoromethyl)sulfonyl]oxy]benzeneacetic acid methyl ester

White solid (yield=94%).
M.p.=57-59° C.

Preparation CXXXVII

4-Cyano-3-methoxybenzeneacetic acid methyl ester

White solid (yield=36%).
M.p.=57-60° C.

Preparation CXXXVIII 4-(Aminomethyl)-3-methoxybenzeneacetic acid methyl ester (hydrochloride)

Light yellow solid (yield=98%).
M.p.=180-184° C.

EXAMPLE 363

3-Methoxy-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzeneacetic acid methyl ester By following a procedure analogous to Example 353 starting from the amine obtained according to Preparation CXXXVIII, the expected product is obtained in the form of a white paste (yield=82%).
$^1$H NMR (DMSO, 250 MHz) δ: 8.48 (t, NH); 8.10-8.00 (m, 2H); 8.00-7.85 (m, 4H); 7.85-7.70 (m, 2H); 7.50 (d, 1H); 7.15 (td, 1H); 7.20-7.10 (m, 2H); 7.03 (td, 1H); 6.90 (d, 1H); 6.79 (dd, 1H); 4.95 (dd, 1H); 4.30-4.15 (m, 2H); 3.80 (s, 3H) ; 3.65 (s, 2H); 3.61 (s, 3H); 3.16 (dd, 1H); 2.97 (dd, 1H).

EXAMPLE 364

3-Methoxy-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzeneacetic acid By following a procedure analogous to Example 22 starting from the ester obtained according to Example 363, the expected compound is obtained in the form of a white powder (yield=95%).
M.p.=99-105° C.

EXAMPLE 365

3-Fluoro-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzeneacetic acid methyl ester By following a procedure analogous to Example 353 starting from the hydrochloride of the methyl ester of 4-(aminomethyl)-3-fluorobenzeneacetic acid, the expected product is obtained in the form of a white solid (yield=85%).
M.p.=50-57° C.

EXAMPLE 366

3-Fluoro-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzeneacetic acid By following a procedure analogous to Example 22 starting from the ester obtained according to Example 365, the expected compound is obtained in the form of a white powder (yield=95%).
M.p.=99-105° C.

EXAMPLE 367

3-Chloro-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzeneacetic acid methyl ester By following a procedure analogous to Example 353 starting from the hydrochloride of the methyl ester of 4-(aminomethyl)-3-chlorobenzeneacetic acid, the expected product is obtained in the form of a white solid (yield=59%).
M.p.=124-126° C.

EXAMPLE 368

3-Chloro-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzeneacetic acid By following a procedure analogous to Example 22 starting from the ester obtained according to Example 367, the expected compound is obtained in the form of a white powder (yield=85%).
M.p.=95-106° C.

EXAMPLE 369

3-Chloro-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzoic acid methyl ester By following a procedure analogous to Example 353 starting from the methyl ester of 4-(aminomethyl)-3-chlorobenzoic acid, the expected product is obtained in the form of a white solid (yield=89%).
M.p.=78-87° C.

EXAMPLE 370

3-Chloro-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzoic acid By following a procedure analogous to Example 22 starting from the ester obtained according to Example 369, the expected compound is obtained in the form of a white powder (yield=88%).
M.p.=110-120° C.

EXAMPLE 371

3-Methoxy-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzoic acid methyl ester By following a procedure analogous to Example 353 starting from the methyl ester of 4-(aminomethyl)-3-methoxybenzoic acid, the expected product is obtained in the form of a white solid (yield=76%).
M.p.=78-85° C.

EXAMPLE 372

3-Methoxy-4-[[[[(2S)-1-[[3'-(trifluoromethyl)[1,1'-biphenyl]-4-yl]sulfonyl]-2,3-dihydro-1H-indol-2-yl]carbonyl]amino]methyl]benzoic acid By following a procedure analogous to Example 22 starting from the ester obtained according to Example 371, the expected compound is obtained in the form of a white powder (yield=93%).
M.p.=108-120° C.

EXAMPLE 373

N-[2-(4-cyanophenoxy)ethyl]-2,3-dihydro-1-[[3'-(trifluoromethyl)[1,1'-biphenyl]-4-yl]sulfonyl]-(2S)-1H-indole-2-carboxamide By following a procedure analogous to Example 349 starting from 4-(2-aminoethoxy)benzonitrile, the expected compound is obtained in the form of a white powder (yield=71%).
M.p.=70-80° C.

EXAMPLE 374

2,6-Difluoro-4-[2-[[[(2S)-1-[(2',4'-difluoro[1,1'-biphenyl]-4-yl)sulfonyl]-2,3-dihydro-1H-indol-2-yl]carbonyl]amino]ethoxy]benzoic acid methyl ester By following a procedure analogous to Example 21 starting from the acid obtained according to Preparation CV and the amine obtained according to Preparation LXXXI, the expected product is obtained in the form of a white solid (yield=59%).
M.p.=69-77° C.

EXAMPLE 375

2,6-Difluoro-4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]benzoic acid methyl ester By following a procedure analogous to Example 374 starting from the acid obtained according to Preparation CXI, the expected product is obtained in the form of a white solid (yield=58%).
M.p.=65-76° C.

EXAMPLE 376

2,6-Difluoro-4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]benzoic acid methyl ester By following a procedure analogous to Example 374 starting from the acid obtained according to Preparation CVII, the expected product is obtained in the form of a white solid (yield=60%).
M.p.=68-74° C.

EXAMPLE 377

2,6-Difluoro-4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]benzoic acid By following a procedure analogous to Example 22 starting from the ester obtained according to Example 376, the expected compound is obtained in the form of a white powder (yield=55%).
M.p.=75-80° C.

EXAMPLE 378

4-[2-[[[(2S)-1-[[4'-methyl-2-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 1 starting from the compound obtained according to Preparation XI and 4-methylphenylboronic acid, the expected product is obtained in the form of a fine white solid (yield=81%).
M.p.=60° C.

EXAMPLE 379

4-[2-[[[(2S)-1-[[4'-methyl-2-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 378, the expected compound is obtained in the form of a white powder (yield=95%).
M.p.=92° C.

EXAMPLE 380

4-[2-[[[(2S)-1-[[4'-chloro-2-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 378 starting from 4-chlorophenylboronic acid, the expected product is obtained in the form of a fine white solid (yield=80%).
M.p.=60° C.

EXAMPLE 381

4-[2-[[[(2S)-1-[[4'-chloro-2-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 380, the expected compound is obtained in the form of a white powder (yield=92%).
M.p.=92° C.

EXAMPLE 382

4-[2-[[[(2S)-1-[[4'-fluoro-2-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 378 starting from 4-fluorophenylboronic acid, the expected product is obtained in the form of a fine white solid (yield=80%).
M.p.=60° C.

EXAMPLE 383

4-[2-[[[(2S)-1-[[4'-fluoro-2-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 382, the expected compound is obtained in the form of a white powder (yield=97%).
M.p.=92° C.

Preparation CXXXIX

4-[2-[[[(2S)-1-[(4-bromo-3-fluorophenyl)sulfonyl]-2,3-dihydro-1H-indol-2-yl]-carbonyl]amino]ethoxy]benzeneacetic acid methyl ester By following a procedure analogous to Preparation XI starting from 4-bromo-3-fluorobenzenesulfonyl chloride, the expected compound is obtained in the form of a white paste (yield=67%).
$^1$H NMR (DMSO, 250 MHz) δ: 8.42 (t, NH); 7.95-7.81 (m, 2H); 7.55 (dd, 1H); 7.43 (d, 1H); 7.35-7.10 (m, 4H); 7.03 (td, 1H); 6.95-6.80 (m, 2H); 4.89 (dd, 1H); 4.10-3.90 (m, 2H); 3.59 (s, 5H); 3.59-3.40 (m, 2H); 3.20 (dd, 1H); 2.93 (dd, 1H).

EXAMPLE 384

4-[2-[[[(2S)-1-[[2-fluoro-3'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 378 starting from 3-(trifluoromethyl)phenylboronic acid and the compound obtained according to Preparation CXXXIX, the expected product is obtained in the form of a pink foam (yield=69%).
$^1$H NMR (DMSO, 250 MHz) δ: 8.46 (t, NH); 7.92-7.70 (m, 7H); 7.48 (d, 1H); 7.30-7.10 (m, 4H); 7.03 (td, 1H); 6.95-6.85 (m, 2H); 4.95 (dd, 1H); 4.02 (t, 2H); 3.59 (s, 5H); 3.59-3.40 (m, 2H); 3.25 (dd, 1H); 2.96 (dd, 1H).

EXAMPLE 385

4-[2-[[[(2S)-1-[[2-fluoro-3'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 384, the expected compound is obtained in the form of a yellow powder (yield=93%).
M.p.=82° C.

Preparation CXL

4-[2-[[[(2S)-1-[(4-bromo-3-chlorophenyl)sulfonyl]-2,3-dihydro-1H-indol-2-yl]-carbonyl]amino]ethoxy]benzeneacetic acid methyl ester By following a procedure analogous to Preparation XI starting from 4-bromo-3-chlorobenzenesulfonyl chloride, the expected compound is obtained in the form of a white foam (yield=87%).
$^1$H NMR (DMSO, 250 MHz) δ: 8.44 (t, NH); 8.01 (d, 1H); 7.97 (d, 1H); 7.63 (dd, 1H); 7.42 (d, 1H); 7.30-7.10 (m, 4H); 7.04 (td, 1H); 6.95-6.85 (m, 2H); 4.91 (dd, 1H); 4.00 (t, 2H); 3.59 (s, 5H); 3.59-3.40 (m, 2H); 3.20 (dd, 1H); 2.92 (dd, 1H).

EXAMPLE 386

4-[2-[[[(2S)-1-[[2-chloro-3'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 384 starting from the compound obtained according to Preparation CXL, the expected product is obtained in the form of a yellow foam (yield=84%).
M.p.=60° C.

EXAMPLE 387

4-[2-[[[(2S)-1-[[2-fluoro-3'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 386, the expected compound is obtained in the form of a white foam (yield=98%).
M.p.=92° C.

Preparation CXLI

4-[2-[[[(2S)-1-[(4-bromo-3-methylphenyl)sulfonyl]-2,3-dihydro-1H-indol-2-yl]-carbonyl]amino]ethoxy]benzeneacetic acid methyl ester By following a procedure analogous to Preparation XI starting from 4-bromo-3-methylbenzenesulfonyl chloride, the expected compound is obtained in the form of a white foam (yield=87%).
$^1$H NMR (DMSO, 250 MHz) δ: 8.36 (t, NH); 7.80 (d, 1H); 7.74 (d, 1H); 7.50-7.40 (m, 2H); 7.35-7.10 (m, 4H); 7.02 (td, 1H); 6.95-6.85 (m, 2H); 4.86 (dd, 1H); 4.00 (t, 2H); 3.60 (s, 5H); 3.60-3.35 (m, 2H); 3.13 (dd, 1H); 2.91 (dd, 1H).

EXAMPLE 388

4-[2-[[[(2S)-1-[[2-methyl-3'-(trifluoromethyl)[1,1'-biphenyl]-4-yl]sulfonyl]-2,3-dihydro-1H-indol-2-yl]carbonyl]amino]ethoxy]benzeneacetic acid methyl ester By following a procedure analogous to Example 384 starting from the compound obtained according to Preparation CXLI, the expected product is obtained in the form of a white powder (yield=84%).
M.p.=60° C.

EXAMPLE 389

4-[2-[[[(2S)-1-[[2-methyl-3'-(trifluoromethyl)[1,1'-biphenyl]-4-yl]sulfonyl]-2,3-dihydro-1H-indol-2-yl]carbonyl]amino]ethoxy]benzeneacetic acid By following a procedure analogous to Example 22 starting from the ester obtained according to Example 388, the expected compound is obtained in the form of a white foam (yield=94%)
M.p.=92° C. .

Preparation CXLII

5-Cyano-2-pyridineacetic acid 1,1-dimethylethyl ester 0.715 g (10 mmol) of zinc, a few flakes of iodine and 0.845 ml (5.4 mmol) of t-butyl bromoacetate in 10 ml of THF are introduced into a microwave reactor. The mixture is heated by microwaves for 5 min at 110° C. and then filtered and added to a solution of 0.5 g (2.7 mmol) of 6-bromo-3-pyridinecarbonitrile in 15 ml of THF. 316 mg of tetrakis(triphenylphosphine)palladium are added and the reaction mixture is heated by microwaves at 120° C. for 5 min, with stirring, and then cooled, diluted with ammonium chloride solution and extracted with ethyl acetate. The organic phase is washed with water and then dried over magnesium sulfate and concentrated under reduced pressure. The crude product obtained is purified by chromatography on silica gel using a methylcyclohexane/ethyl acetate mixture (9/1; v/v) as the eluent to give 254 mg of the expected product in the form of a yellow solid (yield=43%).

$^1$H NMR (DMSO, 250 MHz) δ: 8.95 (d, 1H); 8.27 (dd, 1H); 7.57 (d, 1H); 3.87 (s, 2H); 1.39 (s, 9H).

Preparation CXLIII

5-(Aminomethyl)-2-pyridineacetic acid 1,1-dimethylethyl ester

A solution of 90 mg (0.41 mmol) of the compound obtained according to Preparation CXLII in 5 ml of methanol is prepared and 1520 mg of Raney nickel are added. The mixture is stirred under hydrogen atmospheric pressure at room temperature for 3 hours and then filtered and concentrated under reduced pressure to give the expected product in the form of a yellow oil (yield=90%).

$^1$H NMR (DMSO, 250 MHz) δ: 8.41 (d, 1H); 7.68 (dd, 1H); 7.24 (d, 1H); 3.70 (s, 2H); 3.68 (s, 2H); 1.39 (s, 9H).

EXAMPLE 390

5-[[[[(2S)-2,3-dihydro-1-[[3'-(trifluoromethyl)[1,1'-biphenyl]-4-yl]sulfonyl]-1H-indol-2-yl]carbonyl]amino]methyl]-2-pyridineacetic acid 1,1-dimethylethyl ester By following a procedure analogous to Example 349 starting from the compound obtained according to Preparation CXLIII, the expected product is obtained in the form of a yellow foam (yield=75%).

M.p.=70° C.

EXAMPLE 391

N-[(3-cyanophenyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 349 starting from 3-(aminomethyl)benzonitrile, the expected compound is obtained in the form of a white foam (yield=96%).

$^1$H NMR (DMSO, 300 MHz) δ: 8.88 (t, NH); 8.10-8.00 (m, 2H); 8.00-7.90 (m, 4H); 7.80 (d, 1H); 7.75-7.70 (m, 3H); 7.70-7.60 (m, 1H); 7.60-7.50 (m, 2H); 7.26 (td, 1H); 7.15 (d, 1H); 7.04 (td, 1H); 4.91 (dd, 1H); 4.41 (d, 2H); 3.20 (dd, 1H); 2.99 (dd, 1H).

EXAMPLE 392

N-[[3-(aminomethyl)phenyl]methyl]-2,3-dihydro-1-[[3'-(trifluoromethyl)[1,1'-biphenyl]-4-yl]sulfonyl]-(2S)-1H-indole-2-carboxamide (hydrochloride)

By following a procedure analogous to Preparation XV starting from the compound obtained according to Example 391, the expected compound is obtained in the form of a white foam (yield=96%).

M.p.=116° C.

EXAMPLE 393

N-[(2-amino-3-pyridinyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 349 starting from 2-amino-3-pyridinemethanamine, the expected compound is obtained in the form of a white solid (yield=32%).

M.p.=94° C.

Preparation CXLIV

4-[2-[[(Phenylmethoxy)carbonyl]amino]ethoxy]benzoic acid 1,1-dimethylethyl ester A solution of 33 g (0.17 mol) of the t-butyl ester of 4-hydroxybenzoic acid in 550 ml of acetonitrile is prepared and 43.8 g (0.17 mol) of the benzyl ester of 2-bromoethylcarbamic acid and 55.3 g (0.17 mol) of cesium carbonate are added. The mixture is stirred for 1 hour at 50° C. and then for 16 hours at room temperature. This reaction medium is then filtered and concentrated under reduced pressure. The evaporation residue is taken up in ethyl acetate, washed with 2 N sodium hydroxide solution and then with water and dried over magnesium sulfate. After concentration of this organic phase under reduced pressure, the crude product is purified by chromatography on silica gel using a dichloromethane/ethyl acetate mixture (98/2; v/v) as the eluent to give 37 g of the expected compound in the form of a colorless oil (yield=58%).

$^1$H NMR (DMSO, 300 MHz) δ: 7.83 (d, 2H); 7.50 (t, NH); 7.40-7.35 (m, 5H); 7.01 (d, 2H); 5.03 (s, 2H); 4.06 (t, 2H); 2.39 (q, 2H); 1.52 (s, 9H).

Preparation CXLV

4-[2-(Amino)ethoxy]benzoic acid 1,1-dimethylethyl ester

By following a procedure analogous to Example 61 starting from the compound obtained according to Preparation CXLIV, the expected compound is obtained in the form of a pink solid (yield=96%).

$^1$H NMR (DMSO, 300 MHz) δ: 7.84 (d, 2H); 7.01 (d, 2H); 4.00 (t, 2H); 2.91 (t, 2H); 2.80 (broad s, NH$_2$); 1.52 (s, 9H).

Preparation CXLVI

4-[2-[[[(2S)-2,3-dihydro-1-[(4-iodophenyl)sulfonyl]-1H-indol-2-yl]carbonyl]-amino]ethoxy]benzoic acid 1,1-dimethylethyl ester By following a procedure analogous to Preparation I starting from the compounds obtained according to Preparations IVa and CXLV, the expected compound is obtained in the form of a white foam (yield=96%).

$^1$H NMR (DMSO, 300 MHz) δ: 8.42 (t, NH); 7.93 (d, 2H); 7.84 (d, 2H); 7.53 (d, 2H); 7.42 (d, 1H); 7.22 (td, 1H); 7.13 (d 1H); 7.05-6.95 (m, 3H); 4.81 (dd, 1H); 4.10 (t, 2H); 3.60-3.40 (m, 2H); 3.13 (dd, 1H); 2.90 (dd, 1H); 1.53 (s, 9H).

EXAMPLE 394

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzoic acid 1,1-dimethylethyl ester By following a procedure analogous to Example 1 starting from the ester obtained according to Preparation CXLVI and 4-fluoro-2-methylphenylboronic acid, the expected product is obtained in the form of a white powder (yield=91%).

M.p.=84° C.

EXAMPLE 395

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzoic acid By following a procedure analogous to Example 298 starting from the ester obtained according to Example 394, the expected product is obtained in the form of a white powder (yield=98%).

M.p.=96° C.

EXAMPLE 396

4-[2-[[[(2S)-1-[(2',4'-difluoro[1,1'-biphenyl]-4-yl)sulfonyl]-2,3-dihydro-1H-indol-2-yl]carbonyl]amino]ethoxy]benzoic acid 1,1-dimethylethyl ester By following a procedure analogous to Example 394 starting from 2,4-difluorophenylboronic acid, the expected product is obtained in the form of a beige powder (yield=88%).

M.p.=80° C.

EXAMPLE 397

4-[2-[[[(2S)-1-[(2',4'-difluoro[1,1'-biphenyl]-4-yl)sulfonyl]-2,3-dihydro-1H-indol-2-yl]carbonyl]amino]ethoxy]benzoic acid By following a procedure analogous to Example 298 starting from the ester obtained according to Example 396, the expected product is obtained in the form of a yellow powder (yield=99%).

M.p.=92° C.

EXAMPLE 398

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]benzoic acid 1,1-dimethylethyl ester By following a procedure analogous to Example 394 starting from 2-chloro-4-fluorophenylboronic acid, the expected product is obtained in the form of a white powder (yield=95%).

M.p.=78° C.

EXAMPLE 399

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]benzoic acid By following a procedure analogous to Example 298 starting from the ester obtained according to Example 398, the expected product is obtained in the form of a yellow powder (yield=98%).

M.p.=90° C.

EXAMPLE 400

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]benzoic acid 1,1-dimethylethyl ester By following a procedure analogous to Example 394 starting from 4-fluoro-2-methoxyphenylboronic acid, the expected product is obtained in the form of a white powder (yield=94%).

M.p.=86° C.

EXAMPLE 401

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]benzoic acid By following a procedure analogous to Example 298 starting from the ester obtained according to Example 400, the expected product is obtained in the form of a white powder (yield=94%).

M.p.=102° C.

Preparation CXLVII 2,3-Dihydro-1-[[3'-(trifluoromethyl)[1,1'-biphenyl]-4-yl]sulfonyl]-1H-indole-2-carboxylic acid By following a procedure analogous to Preparation IV starting from 1,2-dihydroindole-2-carboxylic acid, the expected product is obtained in the form of a pink powder (yield=73% for the iodinated intermediate derivative and 60% for the expected compound).

M.p.=166-170° C.

EXAMPLE 402

4-[[[[2,3-Dihydro-1-[[3'-(trifluoromethyl)[1,1'-biphenyl]-4-yl]sulfonyl]-1H-indol-2-yl]carbonyl]amino]methyl]benzeneacetic acid methyl ester By following a procedure analogous to Example 84 starting from the racemic acid obtained according to Preparation CXLVII, the expected product is obtained in the form of a white powder (yield=90%).

M.p.=74° C.

EXAMPLE 403

4-[[[[2,3-Dihydro-1-[[3'-(trifluoromethyl)[1,1'-biphenyl]-4-yl]sulfonyl]-1H-indol-2-yl]carbonyl]amino]methyl]benzeneacetic acid By following a procedure analogous to Example 22 starting from the compound obtained according to Example 402, the expected product is obtained in the form of a white powder (yield=84%).
M.p.=96° C.

EXAMPLE 404

4-[2-[[[2,3-Dihydro-1-[[3'-(trifluoromethyl)[1,1'-biphenyl]-4-yl]sulfonyl]-1H-indol-2-yl]carbonyl]amino]ethoxy]benzeneacetic acid methyl ester By following a procedure analogous to Example 21 starting from the racemic acid obtained according to Preparation CXLVII and the hydrochloride of the methyl ester of 4-(2-aminoethoxy)benzeneacetic acid, the expected product is obtained in the form of a light yellow powder (yield=62%).
M.p.=85° C.

EXAMPLE 405

4-[2-[[[2,3-Dihydro-1-[[3'-(trifluoromethyl)[1,1'-biphenyl]-4-yl]sulfonyl]-1H-indol-2-yl]carbonyl]amino]ethoxy]benzeneacetic acid By following a procedure analogous to Example 22 starting from the compound obtained according to Example 404, the expected product is obtained in the form of a white powder (yield=75%).
M.p.=92° C.

EXAMPLE 406

4-[2-[[[2,3-Dihydro-4-methoxy-1-[[3'-(trifluoromethyl)[1,1'-biphenyl]-4-yl]-sulfonyl]-1H-indol-2-yl]carbonyl]amino]ethoxy]benzeneacetic acid methyl ester By following a procedure analogous to Example 170 starting from the hydrochloride of the methyl ester of 4-(2-aminoethoxy)benzeneacetic acid, the expected product is obtained in the form of a light yellow powder (yield=81%).
M.p.=64° C.

EXAMPLE 407

4-[2-[[[2,3-Dihydro-4-methoxy-1-[[3'-(trifluoromethyl)[1,1'-biphenyl]-4-yl]-sulfonyl]-1H-indol-2-yl]carbonyl]amino]ethoxy]benzeneacetic acid By following a procedure analogous to Example 22 starting from the compound obtained according to Example 406, the expected product is obtained in the form of a white powder (yield=78%).
M.p.=96° C.

Preparation CXLVIII 2,3-Dihydro-1-[[2'-chloro-5'-(trifluoromethyl)[1,1'-biphenyl]-4-yl]sulfonyl]-1H-indole-2-carboxylic acid By following a procedure analogous to Preparation CXLVII starting from 2-chloro-5-(trifluoromethyl)phenylboronic acid, the expected product is obtained in the form of a white powder (yield=95% for the second part of the process).
M.p.=90° C.

EXAMPLE 408

4-[2-[[[2,3-Dihydro-1-[[2'-chloro-5'-(trifluoromethyl)[1,1'-biphenyl]-4-yl]sulfonyl]-1H-indol-2-yl]carbonyl]amino]ethoxy]benzeneacetic acid methyl ester By following a procedure analogous to Example 404 starting from the racemic acid obtained according to Preparation CXLVIII, the expected product is obtained in the form of a white powder (yield=76%).
M.p.=60° C.

EXAMPLE 409

4-[2-[[[2,3-Dihydro-1-[[2'-chloro-5'-(trifluoromethyl)[1,1'-biphenyl]-4-yl]sulfonyl]-1H-indol-2-yl]carbonyl]amino]ethoxy]benzeneacetic acid By following a procedure analogous to Example 22 starting from the compound obtained according to Example 408, the expected product is obtained in the form of a white powder (yield=75%).
M.p.=84° C.

Preparation CIL 2,3-Dihydro-N-[2-[4-[(hydroxyamino)iminomethyl]phenoxy]ethyl]-1-[[3'-(trifluoromethyl)[1,1'-biphenyl]-4-yl]sulfonyl]-(2S)-1H-indole-2-carboxamide A mixture of 208 mg (0.35 mmol) of the compound obtained according to Example 373 and 4 ml of ethanol is prepared and 100 mg (1.54 mmol) of hydroxylamine and 0.23 ml (1.6 mmol) of triethylamine are added. The mixture is stirred for 7 hours at the reflux temperature of the solvent. This reaction medium is then filtered and concentrated under reduced pressure. The crude product is purified by chromatography on silica gel using a dichloromethane/ethanol mixture (97/3; v/v) as the eluent to give the expected compound in the form of a gray solid (yield=84%).

EXAMPLE 410

N-[2-[4-(4,5-dihydro-5-oxo-1,2,4-oxadiazol-3-yl)phenoxy]ethyl]-2,3-dihydro-1-[[3'-(trifluoromethyl)[1,1'-biphenyl]-4-yl]sulfonyl]-(2S)-1H-indole-2-carboxamide A solution of 182 mg (0.29 mmol) of the compound obtained according to Preparation CIL in 8 ml of pyridine is prepared and 0.07 ml (0.73 mmol) of ethyl chloroformate is added. The mixture is stirred for 24 hours at 100° C. and then cooled and diluted in 50 ml of ethyl acetate, washed with N hydrochloric acid solution and then with water and dried over magnesium sulfate. After concentration of this organic phase under reduced pressure, the crude product is purified by reversed phase gradient HPLC on a C18-grafted silica column using an acetonitrile/water/0.1% TFA mixture as the eluent to give the expected compound in the form of a white solid (yield=30%).
M.p.=123-130° C.

EXAMPLE 411

N-[(4-cyanophenyl)methyl]-2,3-dihydro-1-[[3'-(trifluoromethyl)[1,1'-biphenyl]-4-yl]sulfonyl]-(2S)-1H-indole-2-carboxamide By following a procedure analogous to Example 373 starting from 4-(aminomethyl)benzonitrile, the expected compound is obtained in the form of a white powder (yield=39%).
M.p.=80-89° C.

Preparation CL 2,3-Dihydro-N-[[4-[(hydroxyamino)iminomethyl]phenyl]methyl]-1-[[3'-(trifluoromethyl)[1,1'-biphenyl]-4-yl]sulfonyl]-(2S)-1H-indole-2-carboxamide By following a procedure analogous to Preparation CIL starting from the compound obtained according to Example 411, the expected compound is obtained in the form of a white powder (yield=88%).
M.p.=110-115° C.

EXAMPLE 412

N-[[4-(4,5-dihydro-5-oxo-1,2,4-oxadiazol-3-yl)phenyl]methyl]-2,3-dihydro-1-[[3'-(trifluoromethyl)[1,1'-biphenyl]-4-yl]sulfonyl]-(2S)-1H-indole-2-carboxamide By following a procedure analogous to Example 410 starting from the compound obtained according to Preparation CL, the expected compound is obtained in the form of a white powder (yield=58%).
M.p.=171-173° C.

Preparation CLI 4-(Aminomethyl)benzeneacetonitrile a) 4-(Azidomethyl)benzeneacetonitrile A solution of 3.10 g (14.8 mmol) of 4-(bromomethyl)benzeneacetonitrile in 15 ml of ethanol is prepared and 20 mg of lithium iodide, 25 mg of tetrabutylammonium sulfate and 1.06 g (16.3 mmol) of sodium azide are added. The mixture is stirred for 1 hour under reflux and then concentrated under reduced pressure and taken up in 50 ml of MTBE. The white precipitate formed is filtered off on a bed of silica and the filtrate is concentrated under reduced pressure to give the expected compound in the form of an orange oil (yield=96%).

b) 4-(Aminomethyl)benzeneacetonitrile 2.45 g (14.2 mmol) of the compound obtained above and 33 ml of THF are mixed and 5.58 g (21.3 mmol) of triphenylphosphine are added. The reaction medium is stirred for 15 min at room temperature, 1.3 ml of water are then added and the mixture is stirred for 12 hours. It is concentrated at room temperature under reduced pressure and taken up in 150 ml of N hydrochloric acid. This aqueous phase is washed twice with 50 ml of DCM and then brought to basic pH by adding dilute sodium hydroxide solution, and extracted with 100 ml of DCM. The organic phase is washed once with water, dried over magnesium sulfate and concentrated under reduced pressure to give the expected compound in the form of a yellow oil (yield=80%).

$^1$H NMR (DMSO, 300 MHz) δ: 7.35 (d, 2H); 7.27 (d, 2H); 3.98 (s, 2H); 3.47 (s, 2H); 2.70 (broad s, 2H).

EXAMPLE 413

N-[[4-(cyanomethyl)phenyl]methyl]-2,3-dihydro-1-[[3'-(trifluoromethyl)[1,1'-biphenyl]-4-yl]sulfonyl]-(2S)-1H-indole-2-carboxamide By following a procedure analogous to Example 198 starting from the compound obtained according to Preparation CLI, the expected compound is obtained in the form of a white powder (yield=76%).
M.p.=75-80° C.

EXAMPLE 414

2,3-Dihydro-N-[2-(3-pyridazinyloxy)ethyl]-1-[[3'-(trifluoromethyl)[1,1'-biphenyl]-4-yl]sulfonyl]-(2S)-1H-indole-2-carboxamide By following a procedure analogous to Example 198 starting from 2-(3-pyridazinyloxy)ethanamine, the expected compound is obtained in the form of a white powder (yield=37%).
M.p.=65-71° C.

EXAMPLE 415

2,6-Difluoro-4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzoic acid methyl ester By following a procedure analogous to Example 21 starting from the compounds obtained according to Preparations CIV and LXXXI, the expected compound is obtained in the form of a white powder (yield=42%).
M.p.=65-72° C.

EXAMPLE 416

2,6-Difluoro-4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzoic acid By following a procedure analogous to Example 22 starting from the ester obtained according to Example 415, the expected compound is obtained in the form of a white powder (yield=58%).
M.p.=97-111° C.

Preparation CLII

2-Fluoro-4-[2-[[(phenylmethoxy)carbonyl]amino]ethoxy]benzeneacetic acid methyl ester By following a procedure analogous to Preparation CXLIV starting from the methyl ester of 2-fluoro-4-hydroxybenzeneacetic acid, the expected compound is obtained in the form of a colorless oil (yield=51%).

$^1$H NMR (DMSO, 300 MHz) δ: 7.50 (t, NH); 7.45-7.30 (m, 5H); 7.23 (t, 1H); 6.85-6.70 (m, 2H); 5.03 (s, 2H); 3.99 (t, 2H); 3.64 (s, 2H); 3.61 (s, 3H); 3.45-3.30 (m, 2H).

Preparation CLIII

4-(2-Aminoethoxy)-2-fluorobenzeneacetic acid methyl ester (hydrochloride)

By following a procedure analogous to Example 61 (in the presence of N hydrochloric acid in the hydrogenation medium) starting from the compound obtained according to Preparation CLII, the expected compound is obtained in the form of a light yellow solid (yield=98%).

M.p.=199° C.

EXAMPLE 417

2-Fluoro-4-[2-[[[(2S)-1-[[2'-chloro-5'-(trifluoromethyl)[1,1'-biphenyl]-4-yl]-sulfonyl]-2,3-dihydro-1H-indol-2-yl]carbonyl]amino]ethoxy]benzeneacetic acid methyl ester By following a procedure analogous to Example 21 starting from the compounds obtained according to Preparations CXII and CLIII, the expected compound is obtained in the form of a colorless oil (yield=22%).

$^1$H NMR (CDCl$_3$, 300 MHz) δ: 7.85-7.35 (m, 6H); 7.35-20 (m, 3H); 7.20-7.05 (m, 3H); 6.70-6.50 (m, 2H); 4.66 (dd, 1H); 4.10-3.95 (m, 2H); 3.80-3.55 (m, 7H); 3.32 (dd, 1H); 2.83 (dd, 1H).

EXAMPLE 418

2-Fluoro-4-[2-[[[(2S)-1-[[2'-chloro-5'-(trifluoromethyl)[1,1'-biphenyl]-4-yl]-sulfonyl]-2,3-dihydro-1H-indol-2-yl]carbonyl]amino]ethoxy]benzeneacetic acid By following a procedure analogous to Example 22 starting from the ester obtained according to Example 417, the expected compound is obtained in the form of a white powder (yield=80%).

M.p.=105° C.

The compounds below are obtained by following a procedure analogous to Example 21 (but replacing the HOAT with HOBT) for the coupling, and a procedure analogous to Example 22 for obtaining the Examples in acid form, starting from acids and amines described above:

EXAMPLE 419

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-3-methylbenzoic acid methyl ester White powder (yield=60%).
M.p.=82-84° C.

EXAMPLE 420

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-3-methylbenzoic acid White powder (yield=50%).
M.p.=114° C.

EXAMPLE 421

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-3-(trifluoromethyl)benzoic acid methyl ester White powder (yield=47%).
M.p.=81° C.

EXAMPLE 422

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-3-(trifluoromethyl)benzoic acid White powder (yield=67%).
M.p.=123° C.

EXAMPLE 423

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-3,5-dimethylbenzoic acid methyl ester Beige powder (yield=70%).
M.p.=90-93° C.

EXAMPLE 424

4-[2-[[[(2S)-1-[(4'-fluoro-2'-methoxy[1,1'-biphenyl]-4-yl)sulfonyl]-2,3-dihydro-1H-indol-2-yl]carbonyl]amino]ethoxy]-3,5-dimethylbenzoic acid White powder (yield=63%).
M.p.=129° C.

EXAMPLE 425

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]-3-(trifluoromethyl)benzoic acid methyl ester White powder (yield=53%).
M.p.=65° C.

EXAMPLE 426

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]-3-(trifluoromethyl)benzoic acid White powder (yield=88%).
M.p.=113-118° C.

EXAMPLE 427

4-[2-[[[(2S)-1-[(2',4'-difluoro[1,1'-biphenyl]-4-yl)sulfonyl]-2,3-dihydro-1H-indol-2-yl]carbonyl]amino]ethoxy]-3,5-dimethylbenzoic acid methyl ester White powder (yield=68%).
M.p.=85-89° C.

EXAMPLE 428

4-[2-[[[(2S)-1-[(2',4'-difluoro[1,1'-biphenyl]-4-yl)
sulfonyl]-2,3-dihydro-1H-indol-2-yl]carbonyl]
amino]ethoxy]-3,5-dimethylbenzoic acid White powder (yield=67%).
M.p.=122° C.

EXAMPLE 429

3-Fluoro-4-[2-[[[(2S)-1-[(4'-fluoro-2'-methoxy[1,1'-
biphenyl]-4-yl)sulfonyl]-2,3-dihydro-1H-indol-2-yl]
carbonyl]amino]ethoxy]benzoic acid methyl ester White powder (yield=65%).
M.p.=87° C.

EXAMPLE 430

3-Fluoro-4-[2-[[[(2S)-1-[(4'-fluoro-2'-methoxy[1,1'-
biphenyl]-4-yl)sulfonyl]-2,3-dihydro-1H-indol-2-yl]
carbonyl]amino]ethoxy]benzoic acid White powder (yield=73%).
M.p.=106-108° C.

EXAMPLE 431

4-[2-[[[(2S)-1-[(2'-chloro-4'-fluoro[1,1'-biphenyl]-4-
yl)sulfonyl]-2,3-dihydro-1H-indol-2-yl]carbonyl]
amino]ethoxy]-3-fluorobenzoic acid methyl ester White powder (yield=69%).
M.p.=84° C.

EXAMPLE 432

4-[2-[[[(2S)-1-[(2'-chloro-4'-fluoro[1,1'-biphenyl]-4-
yl)sulfonyl]-2,3-dihydro-1H-indol-2-yl]carbonyl]
amino]ethoxy]-3-fluorobenzoic acid White powder (yield=64%).
M.p.=118° C.

EXAMPLE 433

4-[2-[[[(2S)-1-[(2',4'-difluoro[1,1'-biphenyl]-4-yl)
sulfonyl]-2,3-dihydro-1H-indol-2-yl]carbonyl]
amino]ethoxy]-3-fluorobenzoic acid methyl ester White powder (yield=51%).
M.p.=58-61° C.

EXAMPLE 434

4-[2-[[[(2S)-1-[(2',4'-difluoro[1,1'-biphenyl]-4-yl)
sulfonyl]-2,3-dihydro-1H-indol-2-yl]carbonyl]
amino]ethoxy]-3-fluorobenzoic acid White powder (yield=76%).
M.p.=105-110° C. (decomposition).

EXAMPLE 435

3-Fluoro-4-[2-[[[(2S)-1-[(4'-fluoro-2'-methyl[1,1'-
biphenyl]-4-yl)sulfonyl]-2,3-dihydro-1H-indol-2-yl]
carbonyl]amino]ethoxy]benzoic acid methyl ester White powder (yield=67%).
M.p.=74-79° C.

EXAMPLE 436

3-Fluoro-4-[2-[[[(2S)-1-[(4'-fluoro-2'-methyl[1,1'-
biphenyl]-4-yl)sulfonyl]-2,3-dihydro-1H-indol-2-yl]
carbonyl]amino]ethoxy]benzoic acid White powder (yield=76%).
M.p.=118° C.

EXAMPLE 437

4-[2-[[[(2S)-1-[(2',4'-difluoro[1,1'-biphenyl]-4-yl)
sulfonyl]-2,3-dihydro-1H-indol-2-yl]carbonyl]
amino]ethoxy]-3-(trifluoromethyl)benzoic acid
methyl ester White powder (yield=51%).
M.p.=97° C.

EXAMPLE 438

4-[2-[[[(2S)-1-[(2',4'-difluoro[1,1'-biphenyl]-4-yl)
sulfonyl]-2,3-dihydro-1H-indol-2-yl]carbonyl]
amino]ethoxy]-3-(trifluoromethyl)benzoic acid White powder (yield=72%).
M.p.=202-205° C.

EXAMPLE 439

4-[2-[[[(2S)-1-[(2'-chloro-4'-fluoro[1,1'-biphenyl]-4-
yl)sulfonyl]-2,3-dihydro-1H-indol-2-yl]carbonyl]
amino]ethoxy]-3-(trifluoromethyl)benzoic acid
methyl ester White powder (yield=56%).
M.p.=65-70° C.

EXAMPLE 440

4-[2-[[[(2S)-1-[(2'-chloro-4'-fluoro[1,1'-biphenyl]-4-
yl)sulfonyl]-2,3-dihydro-1H-indol-2-yl]carbonyl]
amino]ethoxy]-3-(trifluoromethyl)benzoic acid White powder (yield=69%).
M.p.=218-222° C.

EXAMPLE 441

4-[2-[[[(2S)-1-[(2'-chloro-4'-fluoro[1,1'-biphenyl]-4-
yl)sulfonyl]-2,3-dihydro-1H-indol-2-yl]carbonyl]
amino]ethoxy]-3,5-dimethylbenzoic acid methyl
ester White powder (yield=50%).
M.p.=87° C.

EXAMPLE 442

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]-3,5-dimethylbenzoic acid White powder (yield=46%).
M.p.=124° C.

EXAMPLE 443

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]-3-methylbenzoic acid methyl ester White powder (yield=51%).
M.p.=88° C.

EXAMPLE 444

4-[2-[[[(2S)-1-[(2'-chloro-4'-fluoro[1,1'-biphenyl]-4-yl)sulfonyl]-2,3-dihydro-1H-indol-2-yl]carbonyl]amino]ethoxy]-3-methylbenzoic acid White powder (yield=47%).
M.p.=116° C.

EXAMPLE 445

3,5-Dimethyl-4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzoic acid methyl ester White powder (yield=67%).
M.p.=74° C.

EXAMPLE 446

3,5-Dimethyl-4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]benzoic acid White powder (yield=49%).
M.p.=119° C.

EXAMPLE 447

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]-3-methylbenzoic acid methyl ester Colorless oil (yield=34%).

EXAMPLE 448

4-[2-[[[(2S)-1-[(4'-fluoro-2'-methyl[1,1'-biphenyl]-4-yl)sulfonyl]-2,3-dihydro-1H-indol-2-yl]carbonyl]amino]ethoxy]-3-methylbenzoic acid This acid is obtained by saponifying the above ester with sodium hydroxide. White powder (yield=40%).
M.p.=108-112° C.

EXAMPLE 449

1-[[2'-Chloro-4'-fluoro[1,1'-biphenyl]-4-yl]sulfonyl]-2,3-dihydro-N-[3-(4-methyl-1-piperazinyl)propyl]-(2S)-1H-indole-2-carboxamide White solid (yield=45%).
M.p.=67° C.

EXAMPLE 450

1-[[2'-Chloro-4'-fluoro[1,1'-biphenyl]-4-yl]sulfonyl]-2,3-dihydro-N-[3-(1-pyrrolidinyl)propyl]-(2S)-1H-indole-2-carboxamide Amorphous white solid (yield=32%).
M.p.=70° C.

EXAMPLE 451

1-[[2'-Chloro-4'-fluoro[1,1'-biphenyl]-4-yl]sulfonyl]-2,3-dihydro-N-[4-(1-pyrrolidinyl)butyl]-(2S)-1H-indole-2-carboxamide Yellow solid (yield=59%).
M.p.=60° C.

EXAMPLE 452

1-[[2'-Chloro-4'-fluoro[1,1'-biphenyl]-4-yl]sulfonyl]-2,3-dihydro-N-[2-(1-piperidinyl)ethyl]-(2S)-1H-indole-2-carboxamide Amorphous white solid (yield=57%).
M.p.=84° C.

EXAMPLE 453

1-[[2'-Chloro-4'-fluoro[1,1'-biphenyl]-4-yl]sulfonyl]-2,3-dihydro-N-[4-(dimethylamino)butyl]-(2S)-1H-indole-2-carboxamide Amorphous white solid (yield=52%).
M.p.=59-63° C.

EXAMPLE 454

4-[2-[[[(2S)-2,3-dihydro-1-[(4'-fluoro-2'-methoxy[1,1'-biphenyl]-4-yl)sulfonyl]-1H-indol-2-yl]carbonyl]amino]ethoxy]-3-methylbenzoic acid methyl ester White powder (yield=60%).
M.p.=82-84° C.

EXAMPLE 455

4-[2-[[[(2S)-1-[(2',4'-difluoro[1,1'-biphenyl]-4-yl)sulfonyl]-2,3-dihydro-1H-indol-2-yl]carbonyl]amino]ethoxy]-3-methylbenzoic acid 1,1-dimethylethyl ester White powder (yield=47%).
M.p.=68-72° C.

EXAMPLE 456

4-[2-[[[(2S)-1-[(2',4'-difluoro[1,1'-biphenyl]-4-yl)
sulfonyl]-2,3-dihydro-1H-indol-2-yl]carbonyl]
amino]ethoxy]-3-methylbenzoic acid This acid is obtained by the process described in Example 298 starting from the above ester.
White powder (yield=80%).
M.p.=106-111° C.

EXAMPLE 457

1-[[2'-Chloro-4'-fluoro[1,1'-biphenyl]-4-yl]sulfonyl]-
2,3-dihydro-N-[(2-amino-3-pyridinyl)methyl]-(2S)-
1H-indole-2-carboxamide White solid (yield=48%).
M.p.=88-100° C.

EXAMPLE 458

1-[[2'-Chloro-4'-fluoro[1,1'-biphenyl]-4-yl]sulfonyl]-
2,3-dihydro-N-[(2-amino-N-oxide-3-pyridinyl)methyl]-(2S)-1H-indole-2-carboxamide A solution of 80 mg (0.14 mmol) of the compound obtained according to Example 457 in 2 ml of chloroform is prepared and 51 mg (0.28 mmol) of 3-chloroperbenzoic acid are added. The mixture is stirred at room temperature for 16 hours and then diluted with sodium bicarbonate solution and extracted with ethyl acetate. The organic phase is washed with water, dried over magnesium sulfate and concentrated under reduced pressure. The crude product is purified by chromatography on silica gel using a DCM/methanol mixture (95/5; v/v) as the eluent to give the expected product in the form of a white solid (yield=43%).
M.p.=135-147° C.

Preparation CLIV

6-[2-[(1,1-Dimethylethoxy)carbonyl]amino]ethoxy]-
3-pyridinecarboxylic acid methyl ester By following a procedure analogous to Preparation LVII (replacing the DIAD with DBAD) starting from the methyl ester of 6-hydroxy-3-pyridinecarboxylic acid and t-butyl (2-hydroxyethyl)carbamate, the expected compound is obtained in the form of an oil which crystallizes (yield=45%).

Preparation CLV 6-(2-Aminoethoxy)-3-pyridinecarboxylic acid
methyl ester (trifluoroacetate)

By following a procedure analogous to Preparation II starting from the compound obtained according to Preparation CLIV, the expected compound is obtained in the form of a yellow oil (yield=99%).

EXAMPLE 459

6-[2-[[[(2S)-1-[(2'-chloro-4'-fluoro[1,1'-biphenyl]-4-
yl)sulfonyl]-2,3-dihydro-1H-indol-2-yl]carbonyl]
amino]ethoxy]-3-pyridinecarboxylic acid methyl
ester By following a procedure analogous to Example 296 starting from the compounds obtained according to Preparations CVII and CLV, the expected compound is obtained in the form of a white powder (yield=89%).
M.p.=78-85° C.

EXAMPLE 460

6-[2-[[[(2S)-1-[(2'-chloro-4'-fluoro[1,1'-biphenyl]-4-
yl)sulfonyl]-2,3-dihydro-1H-indol-2-yl]carbonyl]
amino]ethoxy]-3-pyridinecarboxylic acid By following a procedure analogous to Example 22 starting from the ester obtained according to Example 459, the expected compound is obtained in the form of a white powder (yield=81%).
M.p.=88-98° C.

Preparation CLVI

N-[2-[[[[(2S)-2,3-dihydro-1-[(4-iodophenyl)sulfo-
nyl]-1H-indol-2-yl]carbonyl]-amino]methyl]phenyl]-
β-alanine methyl ester By following a procedure analogous to Example 66 starting from the compounds obtained according to Preparations IVa and XXIII, the expected product is obtained in the form of a white solid (yield=93%).
M.p.=67-75° C.

Preparation CLVII

N-[2-[[[[(2S)-2,3-dihydro-1-[(4-iodophenyl)sulfo-
nyl]-1H-indol-2-yl]carbonyl]-amino]methyl]phenyl]-
N-methyl-β-alanine methyl ester A solution of 300 mg (0.48 mmol) of the compound obtained according to Preparation CLVI in 4 ml of acetonitrile is prepared and 0.18 ml (2.4 mmol) of paraformaldehyde is added, followed, after stirring for 15 min at room temperature, by 60 mg (0.96 mmol) of sodium borohydride. The mixture is stirred at room temperature for 15 min and 0.15 ml of acetic acid is then added. The reaction medium is stirred for 5 hours at room temperature and concentrated under reduced pressure. The residue is diluted in DCM and washed with N sodium hydroxide solution and then with water to give the product in the form of a colorless oil (yield=98%).

EXAMPLE 461

N-[2-[[[[(2S)-1-[(2'-chloro-4'-fluoro[1,1'-biphenyl]-
4-yl)sulfonyl]-2,3-dihydro-1H-indol-2-yl]carbonyl]
amino]methyl]phenyl]-N-methyl-f-alanine methyl
ester By following a procedure analogous to Example 1 starting from the compound obtained according to Preparation CLVII and 2-chloro-4-fluorophenylboronic acid, the expected product is obtained in the form of a white solid (yield=96%).
M.p.=88° C.

EXAMPLE 462

N-[2-[[[[(2S)-1-[(2'-chloro-4'-fluoro[1,1'-biphenyl]-
4-yl)sulfonyl]-2,3-dihydro-1H-indol-2-yl]carbonyl]
amino]methyl]phenyl]-N-methyl-β-alanine By following a procedure analogous to Example 22 starting from the compound obtained according to Example 461, the expected product is obtained in the form of a white solid (yield=96%)
M.p.=75-83° C. .

EXAMPLE 463

1-[[2'-Chloro-4'-fluoro[1,1'-biphenyl]-4-yl]sulfonyl]-
2,3-dihydro-N-[(3-amino-4-pyridinyl)methyl]-(2S)-
1H-indole-2-carboxamide By following a procedure analogous to Example 21 starting from the compound obtained according to Preparation CVII and (3-amino-4-pyridinyl)methanamine dihydrochloride, the expected compound is obtained in the form of a white paste (yield=80%).

$^1$H NMR (DMSO, 250 MHz) δ: 8.75 (t, NH); 7.94 (s, 1H); 7.89 (d, 2H); 7.72 (d, 1H); 7.65-7.55 (m, 3H); 7.55-7.40 (m, 2H); 7.40-7.10 (m, 3H); 7.05 (t, 1H); 6.96 (d, 1H); 5.22 (s, NH$_2$); 4.93 (dd, 1H); 4.17 (t, 2H); 3.19 (dd, 1H); 2.99 (dd, 1H).

EXAMPLE 464

1-[[2'-Chloro-4'-fluoro[1,1'-biphenyl]-4-yl]sulfonyl]-
2,3-dihydro-N-[(3-amino-N-oxide-4-pyridinyl)me-
thyl]-(2S)-1H-indole-2-carboxamide By following a procedure analogous to Example 458 starting from the compound obtained according to Example 463, the expected product is obtained in the form of a yellow powder (yield=58%).

M.p.=142-148° C.

Preparation CLVIII

1-[(4-Iodophenyl)sulfonyl]-2,3-dihydro-5-methoxy-
1H-indole-2-carboxylic acid methyl ester By following a procedure analogous to Preparation LXV starting from the methyl ester of 2,3-dihydro-5-methoxy-1H-indole-2-carboxylic acid, the expected product is obtained in the form of a beige solid (yield=81%).

M.p.=154° C.

Preparation CLIX 2,3-Dihydro-1-[[2',4'-difluoro[1,1'-biphenyl]-4-yl]
sulfonyl]-5-methoxy-1H-indole-2-carboxylic acid
methyl ester By following a procedure analogous to Example 1 starting from the ester obtained according to Preparation CLVIII and 2,4-difluorophenylboronic acid, the expected product is obtained in the form of a foam (yield=77%).

$^1$H NMR (DMSO, 300 MHz) δ: 7.87 (d, 2H); 7.71 (d, 2H); 7.70-7.55 (m, 1H); 7.45-7.30 (m, 2H); 7.22 (td, 1H); 6.85-6.70 (m, 2H); 5.08 (dd, 1H); 3.72 (s, 3H); 3.68 (s, 3H); 3.23 (dd, 1H); 3.04 (dd, 1H).

Preparation CLX 2,3-Dihydro-1-[[2',4'-difluoro[1,1'-biphenyl]-4-yl]
sulfonyl]-5-methoxy-1H-indole-2-carboxylic acid By following a procedure analogous to Example 5 starting from the ester obtained according to Preparation CLIX, the expected product is obtained in the form of a yellow foam (yield=83%).

$^1$H NMR (DMSO, 250 MHz) δ: 7.87 (d, 2H); 7.70 (d, 2H); 7.70-7.55 (m, 1H); 7.45-7.30 (m, 2H); 7.22 (td, 1H); 6.85-6.70 (m, 2H); 4.92 (dd, 1H); 3.67 (s, 3H); 3.17 (dd, 1H); 2.98 (dd, 1H).

Preparation CLXI 2,3-Dihydro-1-[[2',4'-difluoro[1,1'-biphenyl]-4-yl]
sulfonyl]-5-methoxy-1H-indole-2-carboxylic acid
chloride By following a procedure analogous to Preparation VI starting from the acid obtained according to Preparation CLX, the expected product is obtained in the form of a yellow foam (used without further purification for the next coupling).

EXAMPLE 465

4-[[[[1-[(2',4'-Difluoro[1,1'-biphenyl]-4-yl)sulfonyl]-
2,3-dihydro-5-methoxy-1H-indol-2-yl]carbonyl]
amino]methyl]benzoic acid By following a procedure analogous to Example 17 starting from the compound obtained according to Preparation CLXI and 4-(aminomethyl)benzoic acid, the expected product is obtained in the form of a white solid (yield=36%).

M.p.=143° C.

This racemic compound was resolved by preparative HPLC on a 250×20 mm column packed with a Chiralpack AD-H 5 μm chiral phase (Daicel). The eluent used is a mixture consisting of 20% of hexane and 80% of 2-propanol with 0.05% of formic acid and the flow rate is 18.9 ml/min. Detection is effected by UV at 205 nm and the operating temperature is set at 40° C. The separated compounds are analyzed by chromatography on a 250×4.6 mm Chiralpack AD-H 5 μm chiral column. The eluent is a mixture consisting of 50% of hexane and 50% of 2-propanol with 0.05% of formic acid and the flow rate is 1 ml/min. Detection is effected by UV at 205 nm and the operating temperature is 40° C. Under these conditions the retention times are 10.70 min and 12.42 min respectively. The enantiomeric excess is greater than 95.5% for each of the enantiomers.

EXAMPLE 466

4-[2-[[[1-[(2',4'-Difluoro[1,1'-biphenyl]-4-yl)sulfo-
nyl]-2,3-dihydro-5-methoxy-1H-indol-2-yl]carbonyl]
amino]ethoxy]benzoic acid 1,1-dimethylethyl ester By following a procedure analogous to Example 294 starting from the acid obtained according to Preparation CLX, the expected product is obtained in the form of a white foam (yield=73%).

$^1$H NMR (DMSO, 300 MHz) δ: 8.38 (t, NH); 7.90-7.75 (m, 4H); 7.69 (dd, 2H); 7.62 (td, 1H); 7.42 (d, 2H); 7.20 (td, 1H); 7.01 (d, 2H); 6.81 (dd, 1H); 6.72 (d, 1H); 4.83 (dd, 1H); 4.09 (t, 2H); 3.67 (s, 3H); 3.60-3.35 (m, 2H); 3.05-2.80 (m, 2H); 1.52 (s, 9H).

EXAMPLE 467

4-[2-[[[1-[(2',4'-Difluoro[1,1'-biphenyl]-4-yl)sulfo-
nyl]-2,3-dihydro-5-methoxy-1H-indol-2-yl]carbonyl]
amino]ethoxy]benzoic acid By following a procedure analogous to Example 298 starting from the ester obtained according to Example 466, the expected product is obtained in the form of a beige solid (yield=76%).
M.p.=91° C.

Preparation CLXII 2,3-Dihydro-1-[[4'-fluoro[1,1'-biphenyl]-4-yl]sulfonyl]-4-methoxy-1H-indole-2-carboxylic acid methyl ester By following a procedure analogous to Preparation LXVI starting from the ester obtained according to Preparation LXV and 4-fluorophenylboronic acid, the expected compound is obtained in the form of an orange foam (yield=64%).
$^1$H NMR (DMSO, 250 MHz) δ: 7.91 (d, 2H); 7.84 (d, 2H); 7.80-7.65 (m, 2H); 7.32 (t, 2H); 7.22 (t, 1H); 7.04 (d, 1H); 6.68 (d, 1H); 5.11 (dd, 1H); 3.74 (s, 3H); 3.72 (s, 3H); 3.26 (dd, 1H); 2.94 (dd, 1H).

Preparation CLXIII 2,3-Dihydro-1-[[4'-fluoro[1,1'-biphenyl]-4-yl]sulfonyl]-4-methoxy-1H-indole-2-carboxylic acid By following a procedure analogous to Example 5 starting from the ester obtained according to Preparation CLXII, the expected product is obtained in the form of a white foam (yield=94%).
$^1$H NMR (DMSO, 250 MHz) δ: 7.92 (d, 2H); 7.89 (d, 2H); 7.80-7.65 (m, 2H); 7.32 (t, 2H); 7.20 (t, 1H); 7.03 (d, 1H); 6.67 (d, 1H); 4.97 (dd, 1H); 3.72 (s, 3H); 3.24 (dd, 1H); 2.89 (dd, 1H).

EXAMPLE 468

4-[2-[[[1-[(4'-Fluoro[1,1'-biphenyl]-4-yl)sulfonyl]-2,3-dihydro-4-methoxy-1H-indol-2-yl]carbonyl]amino]ethoxy]benzoic acid 1,1-dimethylethyl ester By following a procedure analogous to Example 294 starting from the acid obtained according to Preparation CLXIII, the expected product is obtained in the form of a white foam (yield=70%).
$^1$H NMR (DMSO, 250 MHz) δ: 8.42 (t, NH); 7.90-7.70 (m, 8H); 7.40-7.15 (m, 3H); 7.10 (d, 1H); 7.02 (d, 2H); 6.68 (d, 1H); 4.88 (dd, 1H); 4.11 (t, 2H); 3.70 (s, 3H); 3.65-3.40 (m, 2H); 3.02 (dd, 1H); 2.78 (dd, 1H); 1.53 (s, 9H).

EXAMPLE 469

4-[2-[[[1-[(4'-Fluoro[1,1'-biphenyl]-4-yl)sulfonyl]-2,3-dihydro-4-methoxy-1H-indol-2-yl]carbonyl]amino]ethoxy]benzoic acid By following a procedure analogous to Example 298 starting from the ester obtained according to Example 468, the expected product is obtained in the form of a white solid (yield=80%).
M.p.=113° C.

Preparation CLXIV 2,3-Dihydro-1-[[2',4'-difluoro[1,1'-biphenyl]-4-yl]sulfonyl]-4-methoxy-1H-indole-2-carboxylic acid methyl ester By following a procedure analogous to Preparation CLXII starting from 2,4-difluorophenylboronic acid, the expected product is obtained in the form of a brown solid (yield=98%).
M.p.=162° C.

Preparation CLXV 2,3-Dihydro-1-[[2',4'-difluoro[1,1'-biphenyl]-4-yl]sulfonyl]-4-methoxy-1H-indole-2-carboxylic acid By following a procedure analogous to Example 5 starting from the ester obtained according to Preparation CLXIV, the expected product is obtained in the form of an oil (yield=95%).
$^1$H NMR (DMSO, 300 MHz) δ: 7.94 (d, 2H); 7.71 (d, 2H); 7.75-7.55 (m, 1H); 7.50-7.35 (m, 1H); 7.30-7.15 (m, 2H); 7.02 (d, 1H); 6.67 (d, 1H); 4.97 (dd, 1H); 3.73 (s, 3H); 3.25 (dd, 1H); 2.90 (dd, 1H).

EXAMPLE 470

4-[2-[[[1-[(2',4'-Difluoro[1,1'-biphenyl]-4-yl)sulfonyl]-2,3-dihydro-4-methoxy-1H-indol-2-yl]carbonyl]amino]ethoxy]benzoic acid 1,1-dimethylethyl ester By following a procedure analogous to Example 294 starting from the acid obtained according to Preparation CLXV, the expected product is obtained in the form of a white solid (yield=66%).
M.p.=135° C.

EXAMPLE 471

4-[2-[[[1-[(2',4'-Difluoro[1,1'-biphenyl]-4-yl)sulfonyl]-2,3-dihydro-4-methoxy-1H-indol-2-yl]carbonyl]amino]ethoxy]benzoic acid By following a procedure analogous to Example 298 starting from the ester obtained according to Example 470, the expected product is obtained in the form of a beige solid (yield=84%).
M.p.=206° C.

Preparation CLXVI 2,3-Dihydro-1-[[2',4'-difluoro[1,1'-biphenyl]-4-yl]sulfonyl]-4-methoxy-1H-indole-2-carboxylic acid chloride By following a procedure analogous to Preparation VI starting from the acid obtained according to Preparation CLXV, the expected product is obtained in the form of a beige paste (used without further purification for the next coupling).

EXAMPLE 472

4-[[[[1-[(2',4'-Difluoro[1,1'-biphenyl]-4-yl)sulfonyl]-2,3-dihydro-4-methoxy-1H-indol-2-yl]carbonyl]amino]methyl]benzoic acid By following a procedure analogous to Example 17 starting from the compound obtained according to Preparation CLXVI and 4-(aminomethyl)benzoic acid, the expected product is obtained in the form of a white solid (yield=10%).
M.p.=139° C.

EXAMPLE 473

4-[[[[1-[(2',4'-Difluoro[1,1'-biphenyl]-4-yl)sulfonyl]-2,3-dihydro-4-methoxy-1H-indol-2-yl]carbonyl]amino]methyl]benzeneacetic acid methyl ester By following a procedure analogous to Example 472 starting from the hydrochloride of the methyl ester of 4-(aminomethyl)benzeneacetic acid, the expected product is obtained in the form of an oil (yield=77%).

$^1$H NMR (DMSO, 300 MHz) δ: 8.72 (t, NH); 7.91 (dd, 2H); 7.71 (dd, 2H); 7.70-7.55 (m, 1H); 7.45-7.30 (m, 1H); 7.30-7.15 (m, 6H); 7.12 (d, 1H); 6.70 (d, 1H); 4.91 (dd, 1H); 4.32 (t, 2H); 3.72 (s, 3H); 3.65 (s, 2H); 3.60 (s, 3H); 3.07 (dd, 1H); 2.82 (dd, 1H).

EXAMPLE 474

4-[[[[1-[(2',4'-Difluoro[1,1'-biphenyl]-4-yl)sulfonyl]-2,3-dihydro-4-methoxy-1H-indol-2-yl]carbonyl]amino]methyl]benzeneacetic acid By following a procedure analogous to Example 5 starting from the ester obtained according to Example 473, the expected product is obtained in the form of a white foam (yield=98%).

$^1$H NMR (DMSO, 250 MHz) δ: 8.70 (t, NH); 7.90 (dd, 2H); 7.71 (dd, 2H); 7.70-7.55 (m, 1H); 7.50-7.35 (m, 1H); 7.30-7.15 (m, 6H); 7.12 (d, 1H); 6.70 (d, 1H); 4.91 (dd, 1H); 4.32 (t, 2H); 3.72 (s, 3H); 3.54 (s, 2H); 3.07 (dd, 1H); 2.82 (dd, 1H).

Preparation CLXVII

7-Methoxy-2,3-dihydro-1H-indole-2-carboxylic acid methyl ester

By following a procedure analogous to Preparation LXIV starting from the methyl ester of 7-methoxy-2-indolecarboxylic acid, the expected product is obtained in the form of a beige oil (yield=98%).

$^1$H NMR (DMSO, 250 MHz) δ: 6.75-6.50 (m, 3H); 5.33 (d, NH); 4.37 (ddd, 1H); 3.74 (s, 3H); 3.65 (s, 3H); 3.32 (dd, 1H); 3.08 (dd, 1H).

Preparation CLXVIII

1-[(4-Iodophenyl)sulfonyl]-2,3-dihydro-7-methoxy-1H-indole-2-carboxylic acid methyl ester By following a procedure analogous to Preparation CLVIII starting from the methyl ester of 2,3-dihydro-7-methoxy-1H-indole-2-carboxylic acid, the expected product is obtained in the form of a white solid (yield=62%).

M.p.=161° C.

Preparation CLXIX 2,3-Dihydro-1-[[2',4'-difluoro[1,1'-biphenyl]-4-yl]sulfonyl]-7-methoxy-1H-indole-2-carboxylic acid methyl ester By following a procedure analogous to Preparation CLXIV starting from the ester obtained according to Preparation CLXVIII, the expected product is obtained in the form of a beige oil (yield=57%).

$^1$H NMR (DMSO, 300 MHz) δ: 8.01 (d, 2H); 7.76 (d, 2H); 7.75-7.65 (m, 1H); 7.50-7.35 (m, 1H); 7.30-7.15 (m, 1H); 7.05 (t, 1H); 6.84 (d, 2H); 5.50 (dd, 1H); 3.72 (s, 3H); 3.50 (s, 3H); 3.45 (dd, 1H); 3.15 (dd, 1H).

Preparation CLXX 2,3-Dihydro-1-[[2',4'-difluoro[1,1'-biphenyl]-4-yl]sulfonyl]-7-methoxy-1H-indole-2-carboxylic acid By following a procedure analogous to Example 5 starting from the ester obtained according to Preparation CLXIX, the expected product is obtained in the form of a beige foam (yield=98%).

$^1$H NMR (DMSO, 300 MHz) δ: 8.05 (d, 2H); 7.80-7.60 (m, 3H); 7.50-7.35 (m, 1H); 7.30-7.15 (m, 1H); 7.04 (t, 1H); 6.83 (d, 2H); 5.35 (dd, 1H); 3.49 (s, 3H); 3.33 (dd, 1H); 3.11 (dd, 1H).

EXAMPLE 475

4-[2-[[[1-[(2',4'-Difluoro[1,1'-biphenyl]-4-yl)sulfonyl]-2,3-dihydro-7-methoxy-1H-indol-2-yl]carbonyl]amino]ethoxy]benzoic acid 1,1-dimethylethyl ester By following a procedure analogous to Example 470 starting from the acid obtained according to Preparation CLXX, the expected product is obtained in the form of a colorless oil (yield=81%).

$^1$H NMR (DMSO, 250 MHz) δ: 8.25 (t, NH); 7.91 (dd, 2H); 7.80 (dd, 2H); 7.70-7.50 (m, 3H); 7.45-7.30 (m, 1H); 7.28-7.10 (m, 1H); 7.10-6.90 (m, 3H); 6.90-6.75 (m, 2H); 5.26 (dd, 1H); 4.08 (t, 2H); 3.53 (s, 3H); 3.60-3.40 (m, 2H); 3.19 (dd, 1H); 2.92 (dd, 1H); 1.52 (s, 9H).

EXAMPLE 476

4-[2-[[[1-[(2',4'-Difluoro[1,1'-biphenyl]-4-yl)sulfonyl]-2,3-dihydro-7-methoxy-1H-indol-2-yl]carbonyl]amino]ethoxy]benzoic acid By following a procedure analogous to Example 298 starting from the ester obtained according to Example 475, the expected product is obtained in the form of a white solid (yield=83%).

M.p.=234° C.

EXAMPLE 477

4-[[[[1-[(2',4'-Difluoro[1,1'-biphenyl]-4-yl)sulfonyl]-2,3-dihydro-7-methoxy-1H-indol-2-yl]carbonyl]amino]methyl]benzoic acid By following a procedure analogous to Preparation CLXVI and Example 472 starting from the compound obtained according to Preparation CLXX, the expected product is obtained in the form of a white solid (yield=24%).

M.p.=218° C.

Preparation CLXXI 2,3-Dihydro-1-[[2'-chloro-4'-fluoro[1,1'-biphenyl]-4-yl]sulfonyl]-4-methoxy-1H-indole-2-carboxylic acid methyl ester By following a procedure analogous to Example 2 starting from the ester obtained according to Preparation LXV and 2-chloro-4-fluorophenylboronic acid, the expected product is obtained in the form of a white powder (yield=78%).
M.p.=80° C.

Preparation CLXXII 2,3-Dihydro-1-[[2'-chloro-4'-fluoro[1,1'-biphenyl]-4-yl]sulfonyl]-4-methoxy-1H-indole-2-carboxylic acid By following a procedure analogous to Example 5 starting from the ester obtained according to Preparation CLXXI, the expected product is obtained in the form of a white powder (yield=82%).
M.p.=137-138° C.

EXAMPLE 478

4-[[[[1-[(2'-Chloro-4'-fluoro[1,1'-biphenyl]-4-yl)sulfonyl]-2,3-dihydro-4-methoxy-1H-indol-2-yl]carbonyl]amino]methyl]benzoic acid By following a procedure analogous to Preparation CLXVI and Example 472 starting from the compound obtained according to Preparation CLXXII, the expected product is obtained in the form of a white solid (yield=36%).
M.p.=225-234° C.

EXAMPLE 479

4-[2-[[[1-[(2'-Chloro-4'-fluoro[1,1'-biphenyl]-4-yl)sulfonyl]-2,3-dihydro-4-methoxy-1H-indol-2-yl]carbonyl]amino]ethoxy]benzoic acid 1,1-dimethylethyl ester By following a procedure analogous to Example 470 starting from the acid obtained according to Preparation CLXXII, the expected product is obtained in the form of a white solid (yield=94%).
M.p.=79-85° C.

EXAMPLE 480

4-[2-[[[1-[(2'-Chloro-4'-fluoro[1,1'-biphenyl]-4-yl)sulfonyl]-2,3-dihydro-4-methoxy-1H-indol-2-yl]carbonyl]amino]ethoxy]benzoic acid By following a procedure analogous to Example 298 starting from the ester obtained according to Example 479, the expected product is obtained in the form of a pale orange solid (yield=65%).
M.p.=190-204° C.

Preparation CLXXIII 2-(Difluoromethoxy)-4-fluorobromobenzene

This compound is obtained in the form of an oil (unpurified) by refluxing a mixture of 2-bromo-5-fluorophenol and ethyl bromodifluoroacetate in acetone overnight in the presence of potassium carbonate.

Preparation CLXXIV (2S)-2,3-dihydro-1-[[2'-(difluoromethoxy)-4'-fluoro[1,1'-biphenyl]-4-yl]sulfonyl]-1H-indole-2-carboxylic acid By following a procedure analogous to Preparation CX starting from the compound obtained according to Preparation IVa, (2S)-2,3-dihydro-1-[[4-(4,4,5,5-tetramethyl-1,3,2-dioxaborolan-2-yl)phenyl]sulfonyl]-1H-indole-2-carboxylic acid is obtained; this is then reacted according to Example 1 with the compound obtained according to Preparation CLXXIII to give the expected product in the form of a beige solid (yield=52%).

EXAMPLE 481

4-[2-[[[(2S)-1-[[2'-(difluoromethoxy)-4'-fluoro[1,1'-biphenyl]-4-yl]sulfonyl]-2,3-dihydro-1H-indol-2-yl]carbonyl]amino]ethoxy]benzoic acid 1,1-dimethylethyl ester By following a procedure analogous to Example 470 starting from the acid obtained according to Preparation CLXXIV, the expected product is obtained in the form of a white solid (yield=61%).
M.p.=60-70° C.

EXAMPLE 482

4-[2-[[[(2S)-1-[[2'-(difluoromethoxy)-4'-fluoro[1,1'-biphenyl]-4-yl]sulfonyl]-2,3-dihydro-1H-indol-2-yl]carbonyl]amino]ethoxy]benzoic acid By following a procedure analogous to Example 298 starting from the ester obtained according to Example 481, the expected product is obtained in the form of a white solid (yield=78%).
M.p.=70° C.

EXAMPLE 483

4-[[[[(2S)-1-[[2'-(difluoromethoxy)-4'-fluoro[1,1'-biphenyl]-4-yl]sulfonyl]-2,3-dihydro-1H-indol-2-yl]carbonyl]amino]methyl]benzoic acid By following a procedure analogous to Preparation CLXVI and Example 472 starting from the compound obtained according to Preparation CLXXIV, the expected product is obtained in the form of a white solid (yield=26%).
M.p.=92-97° C.

The compounds below are obtained by following a procedure analogous to Preparation CLXXIV and Examples 481 to 483:

EXAMPLE 484

4-[2-[[[1-[[2'-(Difluoromethoxy)-4'-fluoro[1,1'-biphenyl]-4-yl]sulfonyl]-2,3-dihydro-4-methoxy-1H-indol-2-yl]carbonyl]amino]ethoxy]benzoic acid 1,1-dimethylethyl ester White solid (yield=71%).
M.p.=60-76° C.

EXAMPLE 485

4-[2-[[[1-[[2'-(Difluoromethoxy)-4'-fluoro[1,1'-biphenyl]-4-yl]sulfonyl]-2,3-dihydro-4-methoxy-1H-indol-2-yl]carbonyl]amino]ethoxy]benzoic acid White solid (yield=98%).
M.p.=69-73° C.

EXAMPLE 486

4-[[[[1-[[2'-(Difluoromethoxy)-4'-fluoro[1,1'-biphenyl]-4-yl]sulfonyl]-2,3-dihydro-4-methoxy-1H-indol-2-yl]carbonyl]amino]methyl]benzoic acid White solid (yield=60%).
M.p.=230-240° C.
The chemical structures of the compounds described above are listed in the following Table:

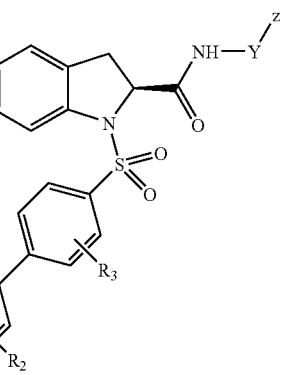

| Ex. | R₁ | R₂ | R₃ | Y | Z |
|-----|------|----|----|--------|---|
| 1 | 4'-CF₃ | H | H | (CH₂)₂ | 2-fluorophenyl |
| 2 | 3'-CF₃ | H | H | (CH₂)₂ | 2-fluorophenyl |
| 3 | 2'-CF₃ | H | H | (CH₂)₂ | 2-fluorophenyl |
| 4 | 3'-CF₃ | H | H | (CH₂)₂ | methyl 3-methylbenzoate |
| 5 | 3'-CF₃ | H | H | (CH₂)₂ | 3-methylbenzoic acid |
| 6 | 3'-CF₃ | H | H | 1-methylcyclohexyl-ethyl | phenyl |

-continued
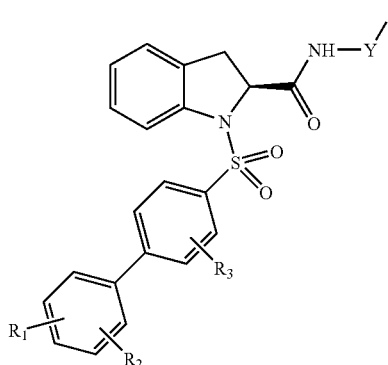
| Ex. | R₁ | R₂ | R₃ | Y | Z |
|---|---|---|---|---|---|
| 7 | 2'-CF₃ | H | H | (CH₂)₂ | N-piperidinyl |
| 8 | 2'-CF₃ | H | H | (CH₂)₃ | N-pyrrolidinyl |
| 9 | 2'-CF₃ | H | H | (CH₂)₃ | 2-methyl-N-piperidinyl |
| 10 | 2'-CF₃ | H | H | (CH₂)₄ | N-pyrrolidinyl |
| 11 | 2'-CF₃ | H | H | (CH₂)₂ | N-morpholinyl |
| 12 | 2'-CF₃ | H | H | (CH₂)₃ | 4-methyl-N-piperazinyl |
| 13 | 2'-CF₃ | H | H | (CH₂)₃—O— | —CH₃ |
| 14 | 2'-CF₃ | H | H | (CH₂)₃ | 2-oxo-N-pyrrolidinyl |
| 15 | 2'-CF₃ | H | H | CH₂ | CF₃ |
| 16 | 2'-CF₃ | H | H | (CH₂)₃ | N-imidazolyl |

-continued

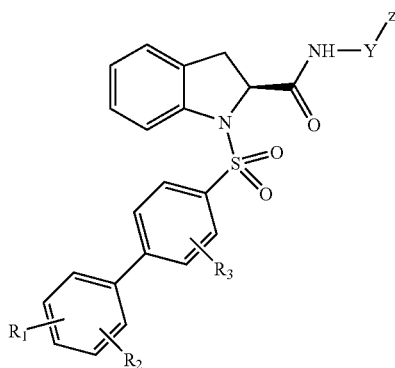

| Ex. | R₁ | R₂ | R₃ | Y | Z |
|---|---|---|---|---|---|
| 17 | 2'-CF₃ | H | H | CH₂ | 4-carboxyphenyl (methyl-substituted) |
| 18 | 2'-CF₃ | H | H | (CH₂)₂—O— | 4-carboxyphenyl (methyl-substituted) |
| 19 | 2'-CF₃ | H | H | (CH₂)₄ | —COOH |
| 20 | 2'-CF₃ | H | H | (CH₂)₃ | CF₃ |
| 21 | 2'-CF₃ | H | H | CH₂ | methyl 4-methylphenylacetate |
| 22 | 2'-CF₃ | H | H | CH₂ | 4-methylphenylacetic acid |
| 23 | 2'-CF₃ | H | H | (CH₂)₂ | CF₃ |
| 24 | 2'-CF₃ | H | H | (CH₂)₂ | tert-butyl 4-methylphenylacetate |
| 25 | 2'-CF₃ | H | H | (CH₂)₂ | 4-methylphenylacetic acid |
| 26 | 2'-CF₃ | H | H | (CH₂)₂ | tert-butyl 3-methylphenylacetate |

-continued
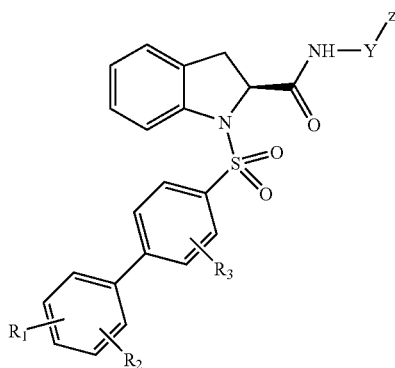
| Ex. | R₁ | R₂ | R₃ | Y | Z |
|---|---|---|---|---|---|
| 27 | 2'-CF₃ | H | H | (CH₂)₂ | 3-methylphenylacetic acid |
| 28 | 2'-CF₃ | H | H | (CH₂)₅ | methyl acetate |
| 29 | 2'-CF₃ | H | H | (CH₂)₅ | acetic acid |
| 30 | 2'-CF₃ | H | H | (CH₂)₄ | N(CH₃)₂ |
| 31 | 2'-CF₃ | H | H | (CH₂)₃ | methyl acetate |
| 32 | 2'-CF₃ | H | H | (CH₂)₃ | acetic acid |
| 33 | 2'-CF₃ | H | H | (CH₂)₂—O— | 4-methylphenylacetic acid |
| 34 | 3'-CF₃ | 4'-Cl | H | (CH₂)₂—O— | 4-methylphenylacetic acid |
| 35 | 5'-CF₃ | 2'-Cl | H | (CH₂)₂—O— | 4-methylphenylacetic acid |
| 36 | 4'-CF₃ | 3'-Cl | H | (CH₂)₂—O— | 4-methylphenylacetic acid |

-continued
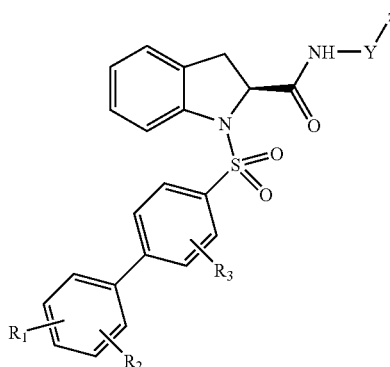
| Ex. | R₁ | R₂ | R₃ | Y | Z |
|---|---|---|---|---|---|
| 37 | 2'-O—CF₃ | H | H | (CH₂)₂—O— | 4-CH₂COOH-phenyl |
| 38 | 3'-O—CF₃ | H | H | (CH₂)₂—O— | 4-CH₂COOH-phenyl |
| 39 | 3'-O—CH₃ | H | H | (CH₂)₂—O— | 4-CH₂COOH-phenyl |
| 40 | 2'-F | H | H | (CH₂)₂—O— | 4-CH₂COOH-phenyl |
| 41 | 2'-CH₃ | H | H | (CH₂)₂—O— | 4-CH₂COOH-phenyl |
| 42 | 3'-iPr | H | H | (CH₂)₂—O— | 4-CH₂COOH-phenyl |
| 43 | 2'-O—CH₃ | H | H | (CH₂)₂—O— | 4-CH₂COOH-phenyl |
| 44 | 3'-Cl | H | H | (CH₂)₂—O— | 4-CH₂COOH-phenyl |
| 45 | 4'-Cl | H | H | (CH₂)₂—O— | 4-CH₂COOH-phenyl |
| 46 | 2'-Cl | H | H | (CH₂)₂—O— | 4-CH₂COOH-phenyl |

-continued

| Ex. | R₁ | R₂ | R₃ | Y | Z |
|---|---|---|---|---|---|
| 47 | 3'-F | H | H | (CH₂)₂—O— | 4-(carboxymethyl)phenyl |
| 48 | 2'-CF₃ | H | H | (CH₂)₂—O— | 4-(carboxymethyl)phenyl |
| 49 | 3'-CH₃ | H | H | (CH₂)₂—O— | 4-(carboxymethyl)phenyl |
| 50 | 3'-CF₃ | H | H | (CH₂)₂ | 4-pyridyl |
| 51 | 3'-CF₃ | H | H | (CH₂)₂ | 3-pyridyl |
| 52 | 3'-CF₃ | H | H | CH₂ | 4-pyridyl |
| 53 | 3'-CF₃ | H | H | CH₂ | 3-pyridyl |
| 54 | 3'-CF₃ | H | H | (CH₂)₂—O— | 3-(methoxycarbonyl)phenyl |
| 55 | 3'-CF₃ | H | H | (CH₂)₂—O— | 3-carboxyphenyl |
| 56 | H | H | 2-CF₃ | (CH₂)₂—O— | 4-(methoxycarbonylmethyl)phenyl |

-continued
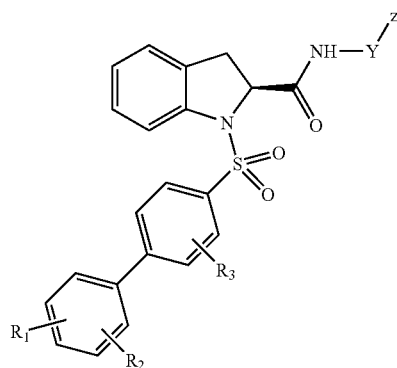
| Ex. | R₁ | R₂ | R₃ | Y | Z |
|---|---|---|---|---|---|
| 57 | H | H | 2-CF₃ | (CH₂)₂—O— | 4-methylphenylacetic acid |
| 58 | 3'-CF₃ | H | H | (CH₂)₂—O— | methyl 3-methylphenylacetate |
| 59 | 3'-CF₃ | H | H | (CH₂)₂—O— | 3-methylphenylacetic acid |
| 60 | 3'-CF₃ | H | H | CH₂ | 2-methyl-nitrobenzene |
| 61 | 3'-CF₃ | H | H | CH₂ | 2-methylaniline |
| 62 | 3'-CF₃ | H | H | CH₂ | methyl 4-(2-methylphenyl)butanoate |
| 63 | 3'-CF₃ | H | H | CH₂ | 4-(2-methylphenyl)butanoic acid |
| 64 | 3'-CF₃ | H | H | CH₂ | 2-methylphenol |

-continued
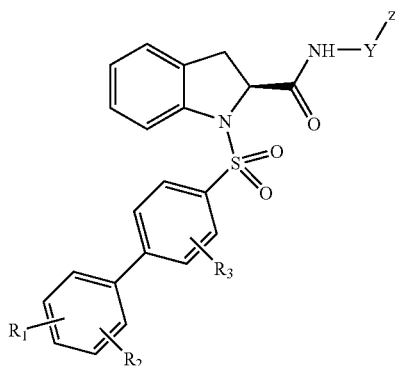
| Ex. | R₁ | R₂ | R₃ | Y | Z |
|---|---|---|---|---|---|
| 65 | 3'-CF₃ | H | H | CH₂ | 2-methyl-benzonitrile |
| 66 | 3'-CF₃ | H | H | CH₂ | methyl 2-(3-methylphenoxy)acetate |
| 67 | 3'-CF₃ | H | H | CH₂ | methyl 2-(4-methylphenoxy)acetate |
| 68 | 3'-CF₃ | H | H | CH₂ | methyl 3-(4-methylphenylamino)propanoate |
| 69 | 3'-CF₃ | H | H | CH₂ | 3-(4-methylphenylamino)propanoic acid |
| 70 | 3'-CF₃ | H | H | CH₂ | methyl 3-(3-methylphenylamino)propanoate |
| 71 | 3'-CF₃ | H | H | CH₂ | 3-(3-methylphenylamino)propanoic acid |

-continued
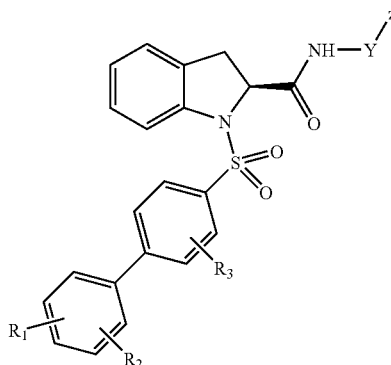
| Ex. | R₁ | R₂ | R₃ | Y | Z |
|---|---|---|---|---|---|
| 72 | 3'-CF₃ | H | H | CH₂ | 2-methylphenyl-NH-CH₂CH₂-C(O)OMe |
| 73 | 3'-CF₃ | H | H | CH₂ | 2-methylphenyl-NH-CH₂CH₂-C(O)OH |
| 74 | 3'-CF₃ | H | H | CH₂ | 2-methylphenyl-O-CH₂CH₂-C(O)OMe |
| 75 | 3'-CF₃ | H | H | CH₂ | 2-methylphenyl-O-CH₂CH₂-C(O)OH |
| 76 | 3'-CF₃ | H | H | CH₂ | 3-methylphenyl-S-CH₂-C(O)OMe |
| 77 | 3'-CF₃ | H | H | CH₂ | 3-methylphenyl-S-CH₂-C(O)OH |
| 78 | 3'-CF₃ | H | H | CH₂ | 4-methylphenyl-C(O)OMe |
| 79 | 3'-CF₃ | H | H | CH₂ | 4-methylphenyl-C(O)OH |

-continued
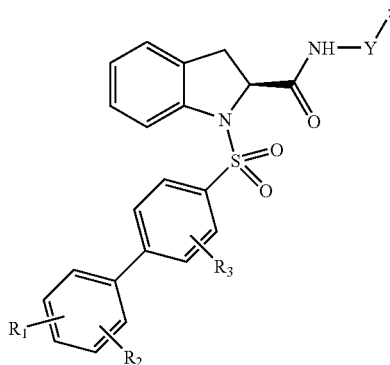
| Ex. | R₁ | R₂ | R₃ | Y | Z |
|---|---|---|---|---|---|
| 80 | 3'-CF₃ | H | H | CH₂ | 3-methylbenzoic acid methyl ester |
| 81 | 3'-CF₃ | H | H | CH₂ | 3-methylbenzoic acid |
| 82 | 3'-CF₃ | H | H | CH₂ | 2-methylbenzoic acid tert-butyl ester |
| 83 | 3'-CF₃ | H | H | CH₂ | 2-methylbenzoic acid |
| 84 | 3'-CF₃ | H | H | CH₂ | 4-methylphenylacetic acid methyl ester |
| 85 | 3'-CF₃ | H | H | CH₂ | 4-methylphenylacetic acid |
| 86 | 3'-CF₃ | H | H | CH₂ | 3-methylphenylacetic acid methyl ester |
| 87 | 3'-CF₃ | H | H | CH₂ | 3-methylphenylacetic acid |

-continued
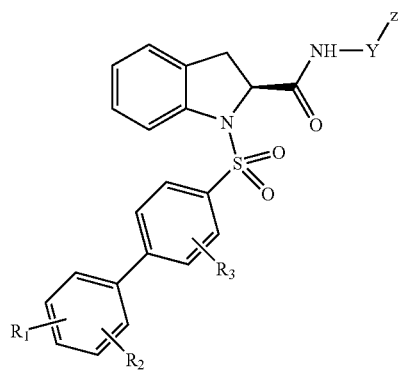
| Ex. | R₁ | R₂ | R₃ | Y | Z |
|---|---|---|---|---|---|
| 88 | 3'-CF₃ | H | H | CH₂ | 4-(methyl propanoate)phenyl |
| 89 | 3'-CF₃ | H | H | CH₂ | 4-(propanoic acid)phenyl |
| 90 | 3'-CF₃ | H | H | CH₂ | 3-(ethyl propanoate)phenyl |
| 91 | 3'-CF₃ | H | H | CH₂ | 3-(propanoic acid)phenyl |
| 92 | 3'-CF₃ | H | H | CH₂ | 2-(ethyl propanoate)phenyl |
| 93 | 3'-CF₃ | H | H | CH₂ | 2-(propanoic acid)phenyl |
| 94 | 3'-CF₃ | H | H | CH₂ | 4-(methyl butanoate)phenyl |
| 95 | 3'-CF₃ | H | H | CH₂ | 4-(butanoic acid)phenyl |

-continued

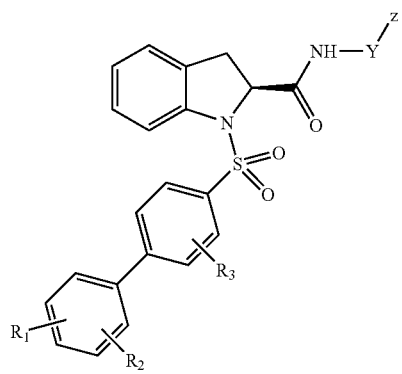

| Ex. | R₁ | R₂ | R₃ | Y | Z |
|---|---|---|---|---|---|
| 96 | 3'-CF₃ | H | H | CH₂ | 3-methylphenyl-(CH₂)₃-C(=O)-OMe |
| 97 | 3'-CF₃ | H | H | CH₂ | 3-methylphenyl-(CH₂)₃-C(=O)-OH |
| 98 | 3'-CF₃ | H | H | (CH₂)₂—O— | 4-methylphenyl-CH₂-C(=O)-O-C(CH₃)₃ |
| 99 | 3'-CF₃ | H | H | (CH₂)₂—O— | 4-methylphenyl-CH₂-C(=O)-OH |
| 100 | 3'-CF₃ | H | H | (CH₂)₂—O— | 4-methylphenyl-C(=O)-OH |
| 101 | 3'-CF₃ | H | H | (CH₂)₂ | 4-methylphenyl-CH₂-C(=O)-O-C(CH₃)₃ |
| 102 | 3'-CF₃ | H | H | (CH₂)₂ | 4-methylphenyl-CH₂-C(=O)-OH |
| 103 | 3'-CF₃ | H | H | (CH₂)₂ | 3-methylphenyl-CH₂-C(=O)-O-C(CH₃)₃ |
| 104 | 3'-CF₃ | H | H | (CH₂)₂ | 3-methylphenyl-CH₂-C(=O)-OH |

-continued
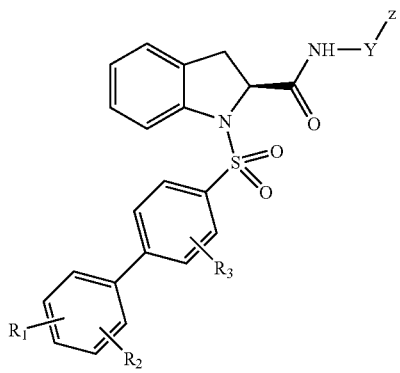
| Ex. | R₁ | R₂ | R₃ | Y | Z |
|---|---|---|---|---|---|
| 105 | 3'-CF₃ | H | H | (CH₂)₂—O— | 4-pyridyl |
| 106 | 3'-CF₃ | H | H | (CH₂)₂—O— | 3-pyridyl |
| 107 | 3'-CF₃ | H | H | (S)-2-methylpentyl-benzyl | —COOH |
| 108 | 3'-CF₃ | H | H | 2-methylbutyl-benzyl | —COOH |
| 109 | 3'-CF₃ | H | H | (CH₂)₆ | —COOH |
| 110 | 3'-CF₃ | H | H | (CH₂)₈ | —COOH |
| 111 | 3'-CF₃ | H | H | 1-ethylpropyl-phenyl | —COOH |
| 112 | 3'-CF₃ | H | H | (S)-2-methylbutyl-benzyl | —COOC(CH₃)₃ |

-continued
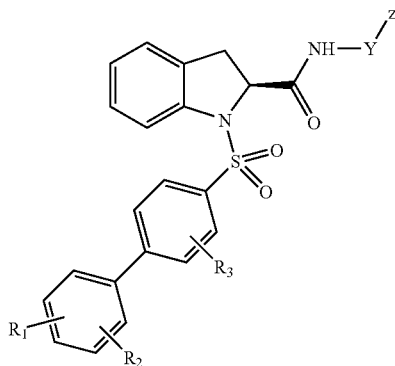
| Ex. | R₁ | R₂ | R₃ | Y | Z |
|---|---|---|---|---|---|
| 113 | 3'-CF₃ | H | H | (S)-CH(CH₂Ph)(CH₂CH₃) | —COOH |
| 114 | 3'-CF₃ | H | H | CH₂ | 4-CH₃-C₆H₄-O-(CH₂)₄-COOCH₃ |
| 115 | 3'-CF₃ | H | H | CH₂ | 4-CH₃-C₆H₄-O-(CH₂)₄-COOH |
| 116 | 3'-CF₃ | H | H | CH₂ | 3-CH₃-C₆H₄-O-(CH₂)₃-COOCH₃ |
| 117 | 3'-CF₃ | H | H | CH₂ | 3-CH₃-C₆H₄-O-(CH₂)₃-COOH |
| 118 | 3'-CF₃ | H | H | (CH₂)₂—O— | 2-CH₃-C₆H₄-CH₂-C(O)-OCH(CH₃)₂ |
| 119 | 3'-CF₃ | H | H | (CH₂)₂—O— | 2-CH₃-C₆H₄-CH₂-C(O)-OH |
| 120 | 3'-CF₃ | H | H | CH₂ | 4-CH₃-C₆H₄-C(O)-N(CH₃)₂ |

-continued
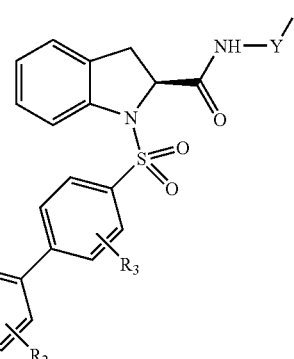
| Ex. | R₁ | R₂ | R₃ | Y | Z |
|---|---|---|---|---|---|
| 121 | 3'-CF₃ | H | H | (CH₂)₂ | 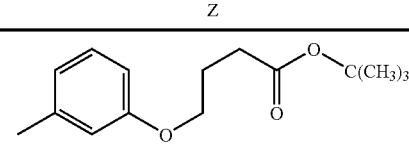 |
| 122 | 3'-CF₃ | H | H | (CH₂)₂ | 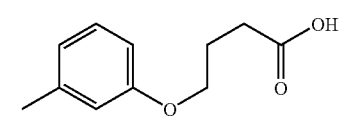 |
| 123 | 3'-CF₃ | H | H | (CH₂)₂ | 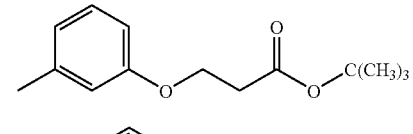 |
| 124 | 3'-CF₃ | H | H | (CH₂)₂ | 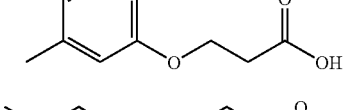 |
| 125 | 3'-CF₃ | H | H | (CH₂)₂ | 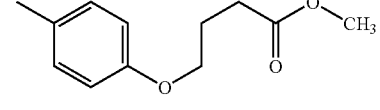 |
| 126 | 3'-CF₃ | H | H | (CH₂)₂ | 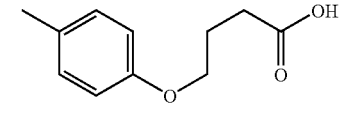 |
| 127 | 3'-CF₃ | H | H | (CH₂)₂ | 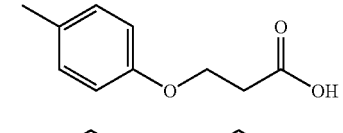 |
| 128 | 3'-CF₃ | H | H | CH₂ | 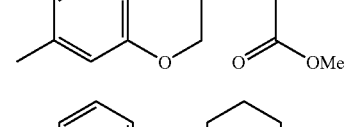 |
| 129 | 3'-CF₃ | H | H | CH₂ | 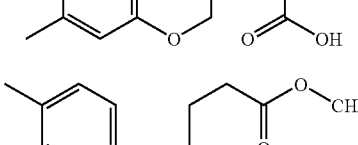 |
| 130 | 3'-CF₃ | H | H | CH₂ | 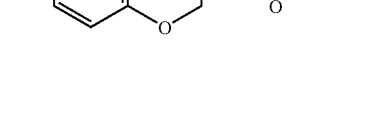 |

-continued

| Ex. | R₁ | R₂ | R₃ | Y | Z |
|---|---|---|---|---|---|
| 131 | 3'-CF₃ | H | H | CH₂ | 4-(carboxypropoxy)phenyl |
| 132 | 3'-CF₃ | H | H | CH₂ | 3-(carboxyethoxy)phenyl |
| 133 | 3'-CF₃ | H | H | CH₂ | 4-(carboxyethoxy)phenyl |
| 134 | 3'-CF₃ | H | H | (CH₂)₂ | 4-carboxyphenyl |
| 135 | 2'-CF₃ | H | H | CH₂ | 4-(2,2-dimethyl-3-methoxy-3-oxopropoxy)phenyl |
| 136 | 2'-CF₃ | H | H | CH₂ | 4-(2,2-dimethyl-2-carboxyethoxy)phenyl |
| 137 | 3'-CF₃ | H | H | CH₂ | 4-(2,2-dimethyl-3-methoxy-3-oxopropoxy)phenyl |
| 138 | 3'-CF₃ | H | H | CH₂ | 4-(2,2-dimethyl-2-carboxyethoxy)phenyl |
| 139 | 3'-CF₃ | H | H | CH₂ | N-methyl-2-methylaniline |

-continued

| Ex. | R₁ | R₂ | R₃ | Y | Z |
|---|---|---|---|---|---|
| 140 | 3'-CF₃ | H | H | CH₂ | 2-((CH₃)₂N)-phenyl, methyl |
| 141 | 3'-CF₃ | H | H | (CH₂)₂ | 4-methylphenyl-CH₂CH₂C(O)O-C(CH₃)₃ |
| 142 | 3'-CF₃ | H | H | (CH₂)₂ | 4-methylphenyl-CH₂CH₂C(O)OH |
| 143 | 2'-CF₃ | H | H | —(CH₂)₂—S— | 3-Cl-4-methylphenyl-CH₂C(O)OMe |
| 144 | 2'-CF₃ | H | H | —(CH₂)₂—S— | 3-Cl-4-methylphenyl-CH₂C(O)OH |
| 145 | 3'-CF₃ | H | H | (CH₂)₂—S— | 3-Cl-4-methylphenyl-CH₂C(O)OMe |
| 146 | 3'-CF₃ | H | H | (CH₂)₂—S— | 3-Cl-4-methylphenyl-CH₂C(O)OH |
| 147 | 3'-CF₃ | H | H | (CH₂)₂—O— | (CH₃)₂HCO-C(O)-2-methylphenyl |
| 148 | 3'-CF₃ | H | H | (CH₂)₂—O— | HO-C(O)-2-methylphenyl |

-continued
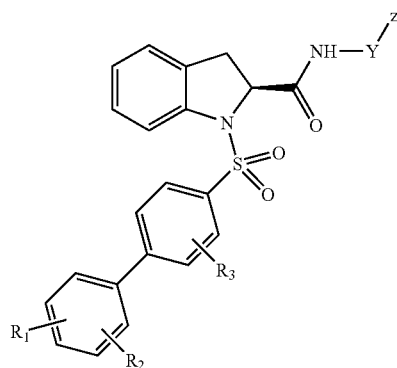
| Ex. | R₁ | R₂ | R₃ | Y | Z |
|---|---|---|---|---|---|
| 149 | 2'-CF₃ | H | H | CH₂ | 4-(N(CH₃)₂C(O))-phenyl |
| 150 | 2'-CF₃ | H | H | CH₂ | 4-(CH₂N(CH₃)₂)-phenyl |
| 151 | 3'-CF₃ | H | H | CH₂ | 4-(CH₂N(CH₃)₂)-phenyl |
| 152 | 3'-CF₃ | H | H | (CH₂)₂—O— | 3-Cl-4-Me-phenyl-CH₂C(O)OMe |
| 153 | 3'-CF₃ | H | H | (CH₂)₂—O— | 3-Cl-4-Me-phenyl-CH₂C(O)OH |
| 154 | 3'-CF₃ | H | H | (CH₂)₂—O— | pyridin-2-yl |
| 155 | 3'-CF₃ | H | H | CH₂ | 3-NO₂-phenyl |
| 156 | 3'-CF₃ | H | H | CH₂ | 3-NH₂-phenyl |
| 157 | 3'-CF₃ | H | H | CH₂ | 4-NO₂-phenyl |
| 158 | 3'-CF₃ | H | H | CH₂ | 4-NH₂-phenyl |

-continued
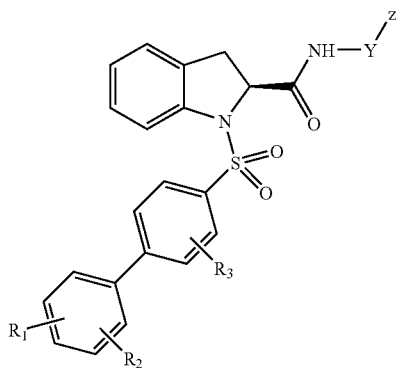
| Ex. | R₁ | R₂ | R₃ | Y | Z |
|---|---|---|---|---|---|
| 159 | 4'-F | H | H | CH₂ | phenyl |
| 160 | 4'-F | H | H | (CH₂)₂ | 4-Cl-phenyl |
| 161 | 4'-F | H | H | (CH₂)₂—O— | 4-(COOMe)-phenyl |
| 162 | 4'-F | H | H | (CH₂)₂—O— | 4-(COOH)-phenyl |
| 163 | 4'-F | H | H | CH₂ | C(O)-phenyl |
| 164 | 4'-F | H | H | CH(Et)(CH-phenyl) | phenyl |
| 165 | 4'-F | H | H | trans-cyclopropyl | phenyl |
| 166 | 4'-F | H | H | (CH₂)₂—O— | 4-(CH₂COOH)-phenyl |
| 167 | 4'-F | H | H | CH(Et)(phenyl) | —COOC(CH₃)₃ |

-continued
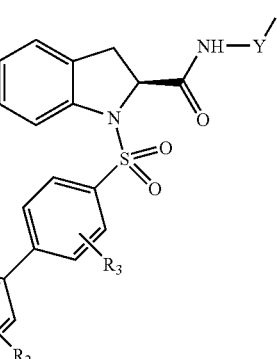
| Ex. | R₁ | R₂ | R₃ | Y | Z |
|---|---|---|---|---|---|
| 168 | 4'-F | H | H | 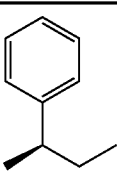 | —COOH |
| 169 | 3'-CF₃ | H | H | CH₂ | 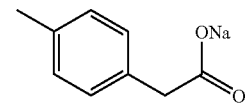 |
| 170* | 3'-CF₃ | H | H | CH₂ | 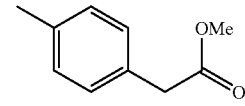 |
| 171* | 3'-CF₃ | H | H | CH₂ | 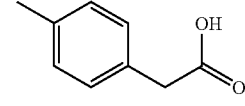 |
| 172 | 4'-F | H | H | CH₂ | 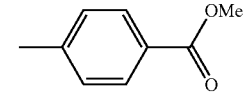 |
| 173 | 4'-F | H | H | 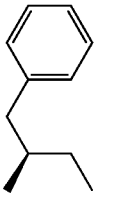 | —COOC(CH₃)₃ |
| 174 | 3'-CF₃ | H | H | CH₂ | 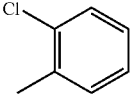 |
| 175 | 3'-CF₃ | H | H | CH₂ | 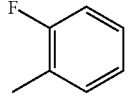 |
| 176 | 3'-CF₃ | H | H | CH₂ | 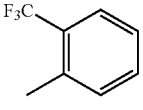 |

-continued

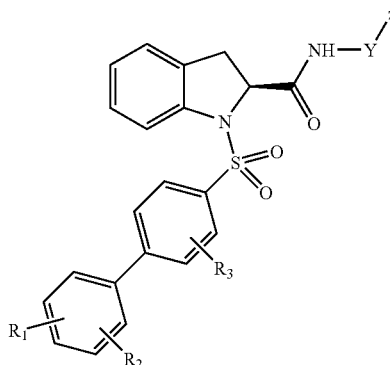

| Ex. | R₁ | R₂ | R₃ | Y | Z |
|---|---|---|---|---|---|
| 177 | 3'-CF₃ | H | H | CH₂ | 2-methylphenyl (o-tolyl with CH₃) |
| 178 | 3'-CF₃ | H | H | CH₂ | 2-methoxyphenyl |
| 179 | 3'-CF₃ | H | H | CH₂ | 2-pyridyl |
| 180 | 3'-CF₃ | H | H | 1-ethyl-1-methylcyclopropyl | phenyl |
| 181 | 3'-CF₃ | H | H | CH₂ | 2-hydroxyphenyl |
| 182 | 3'-CF₃ | H | H | CH₂ | 2-(3-methoxycarbonylpropoxy)phenyl |
| 183 | 3'-CF₃ | H | H | CH₂ | 2-(3-carboxypropoxy)phenyl |
| 184 | 2'-CH₃ | 4'-F | H | (CH₂)₂—O— | 4-(methoxycarbonylmethyl)phenyl |
| 185 | 2'-CH₃ | 4'-F | H | (CH₂)₂—O— | 4-(carboxymethyl)phenyl |
| 186 | 2'-CH₃ | 4'-F | H | CH₂ | 4-(methoxycarbonylmethyl)phenyl |

-continued

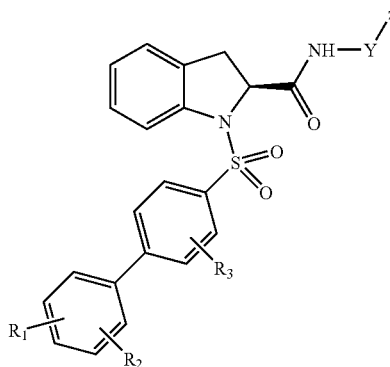

| Ex. | R₁ | R₂ | R₃ | Y | Z |
|---|---|---|---|---|---|
| 187 | 2'-CH₃ | 4'-F | H | CH₂ | 4-methylphenyl-CH₂-COOH |
| 188 | 2'-CH₃ | 4'-F | H | CH₂ | 2-methylphenyl-N(-)-CH₂CH₂-C(O)OMe |
| 189 | 2'-CH₃ | 4'-F | H | CH₂ | 2-methylphenyl-N(-)-CH₂CH₂-COOH |
| 190 | 2'-Cl | 4'-F | H | CH₂ | 2-methylphenyl-N(-)-CH₂CH₂-C(O)OMe |
| 191 | 2'-Cl | 4'-F | H | CH₂ | 2-methylphenyl-N(-)-CH₂CH₂-COOH |
| 192 | 2'-OCH₃ | 4'-F | H | CH₂ | 2-methylphenyl-N(-)-CH₂CH₂-C(O)OMe |
| 193 | 2'-OCH₃ | 4'-F | H | CH₂ | 2-methylphenyl-N(-)-CH₂CH₂-COOH |
| 194 | 2'-F | 4'-F | H | CH₂ | 2-methylphenyl-N(-)-CH₂CH₂-C(O)OMe |
| 195 | 2'-F | 4'-F | H | CH₂ | 2-methylphenyl-N(-)-CH₂CH₂-COOH |
| 196 | 3'-CF₃ | H | H | CH₂ | 4-methylphenyl-S-CH₂CH₂-C(O)O-CH₂CH₃ |

-continued
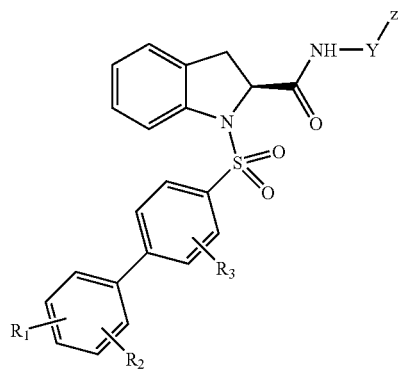
| Ex. | R₁ | R₂ | R₃ | Y | Z |
|---|---|---|---|---|---|
| 197 | 3'-CF₃ | H | H | CH₂ | 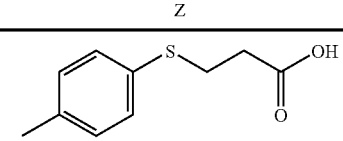 |
| 198 | 3'-CF₃ | H | H | CH₂ | 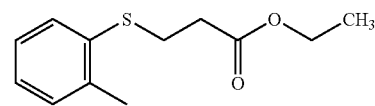 |
| 199 | 3'-CF₃ | H | H | CH₂ | 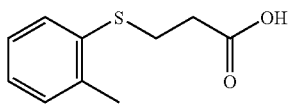 |
| 200 | 3'-CF₃ | H | H | (CH₂)₂—O— | 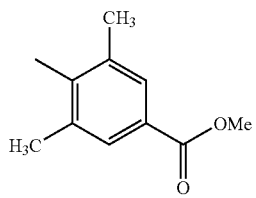 |
| 201 | 3'-CF₃ | H | H | (CH₂)₂—O— | 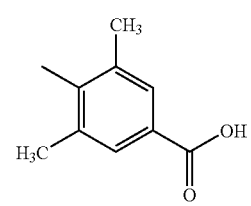 |
| 202 | 4'-F | H | H | (CH₂)₂—O— | 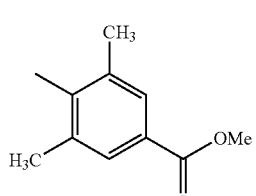 |
| 203 | 4'-F | H | H | (CH₂)₂—O— | 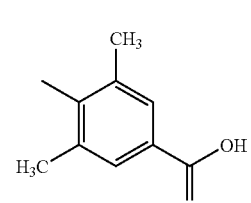 |

-continued
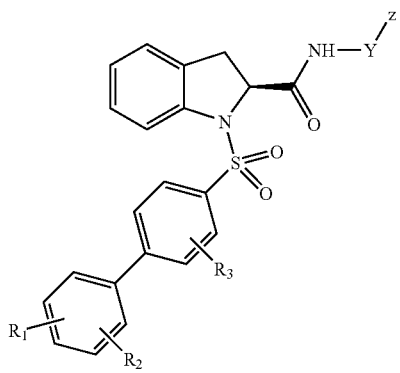
| Ex. | R₁ | R₂ | R₃ | Y | Z |
|---|---|---|---|---|---|
| 204 | 3'-CF₃ | H | H | (CH₂)₂—O— | 3-Cl, 4-Me, methyl benzoate |
| 205 | 3'-CF₃ | H | H | (CH₂)₂—O— | 3-Cl, 4-Me, benzoic acid |
| 206 | 4'-F | H | H | (CH₂)₂—O— | 3-Cl, 4-Me, methyl benzoate |
| 207 | 4'-F | H | H | (CH₂)₂—O— | 3-Cl, 4-Me, benzoic acid |
| 208 | 3'-CF₃ | H | H | (CH₂)₂—O— | 3-F, 4-Me, methyl benzoate |

-continued
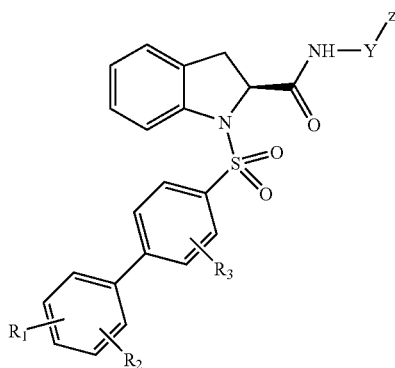
| Ex. | R₁ | R₂ | R₃ | Y | Z |
|---|---|---|---|---|---|
| 209 | 3'-CF₃ | H | H | (CH₂)₂—O— | 3-fluoro-4-methylbenzoic acid |
| 210 | 4'-F | H | H | (CH₂)₂—O— | methyl 3-fluoro-4-methylbenzoate |
| 211 | 4'-F | H | H | (CH₂)₂—O— | 3-fluoro-4-methylbenzoic acid |
| 212 | 3'-CF₃ | H | H | (CH₂)₂—O— | methyl 2-(4-methylphenyl)propanoate |
| 213 | 3'-CF₃ | H | H | (CH₂)₂—O— | 2-(4-methylphenyl)propanoic acid |
| 214 | 3'-CF₃ | H | H | (CH₂)₂—O— | methyl 2-(3-methoxy-4-methylphenyl)acetate |
| 215 | 3'-CF₃ | H | H | (CH₂)₂—O— | 2-(3-methoxy-4-methylphenyl)acetic acid |

-continued

| Ex. | R₁ | R₂ | R₃ | Y | Z |
|---|---|---|---|---|---|
| 216 | 3'-CF₃ | H | H | CH₂ | *N-(p-tolyl)glycine methyl ester* |
| 217 | 3'-CF₃ | H | H | CH₂ | *N-(p-tolyl)glycine* |
| 218 | 3'-CF₃ | H | H | (CH₂)₂—O— | *methyl 2,6-difluoro-4-methylbenzoate* |
| 219 | 4'-F | H | H | (CH₂)₂—O— | *methyl 2,6-difluoro-4-methylbenzoate* |
| 220 | 3'-CF₃ | H | H | (CH₂)₂—O— | *methyl 3-(trifluoromethyl)-4-methylbenzoate* |
| 221 | 3'-CF₃ | H | H | (CH₂)₂—O— | *3-(trifluoromethyl)-4-methylbenzoic acid* |
| 222 | 4'-F | H | H | (CH₂)₂—O— | *methyl 3-(trifluoromethyl)-4-methylbenzoate* |
| 223 | 4'-F | H | H | (CH₂)₂—O— | *3-(trifluoromethyl)-4-methylbenzoic acid* |

-continued
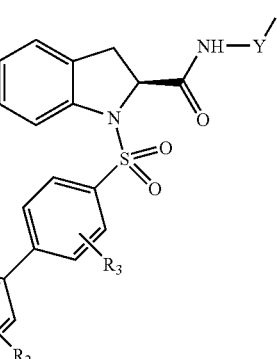
| Ex. | R₁ | R₂ | R₃ | Y | Z |
|---|---|---|---|---|---|
| 224 | 3'-CF₃ | H | H | (CH₂)₂—O— | 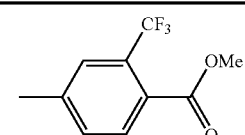 |
| 225 | 4'-F | H | H | (CH₂)₂—O— | 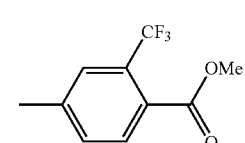 |
| 226 | 3'-CF₃ | H | H | (CH₂)₂—O— | 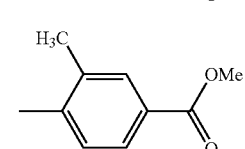 |
| 227 | 3'-CF₃ | H | H | (CH₂)₂—O— | 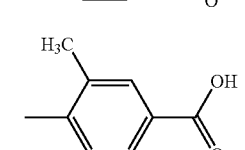 |
| 228 | 4'-F | H | H | (CH₂)₂—O— | 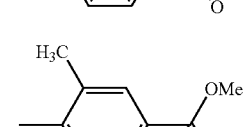 |
| 229 | 4'-F | H | H | (CH₂)₂—O— | 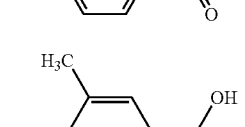 |
| 230 | 4'-F | H | H | (CH₂)₂—O— | 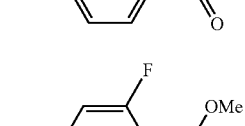 |
| 231 | 4'-F | H | H | (CH₂)₂—O— | 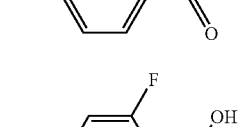 |

-continued
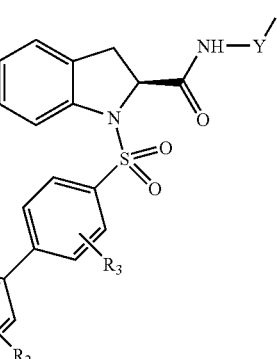
| Ex. | R₁ | R₂ | R₃ | Y | Z |
|---|---|---|---|---|---|
| 232 | 3'-CF₃ | H | H | (CH₂)₂—O— | 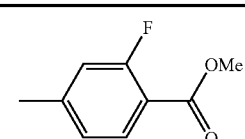 |
| 233 | 3'-CF₃ | H | H | (CH₂)₂—O— | 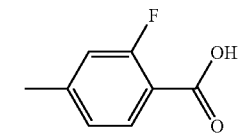 |
| 234 | 3'-CF₃ | H | H | (CH₂)₂—O— | 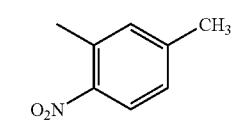 |
| 235 | 3'-CF₃ | H | H | (CH₂)₂—O— | 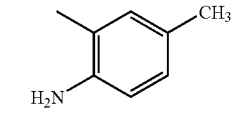 |
| 236 | 3'-CF₃ | H | H | (CH₂)₂—O— | 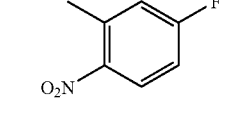 |
| 237 | 3'-CF₃ | H | H | (CH₂)₂—O— | 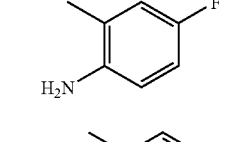 |
| 238 | 3'-CF₃ | H | H | (CH₂)₂—O— | 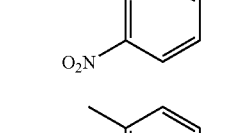 |
| 239 | 3'-CF₃ | H | H | (CH₂)₂—O— | 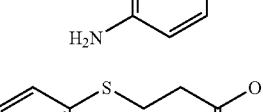 |
| 240 | 3'-CF₃ | H | H | CH₂ |  |

-continued
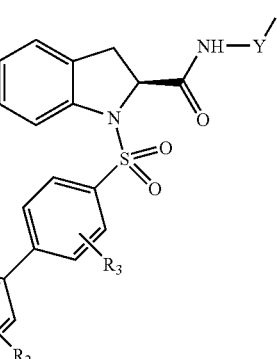
| Ex. | R₁ | R₂ | R₃ | Y | Z |
|---|---|---|---|---|---|
| 241 | 3'-CF₃ | H | H | CH₂ | 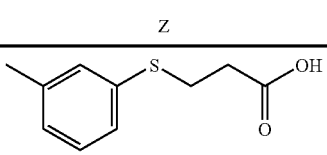 |
| 242 | 2'-Cl | 4'-F | H | 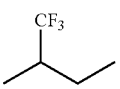 | —COOH |
| 243 | 3'-CF₃ | H | H | CH₂ | 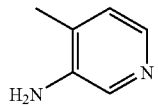 |
| 244 | 3'-CF₃ | H | H | (CH₂)₃ | 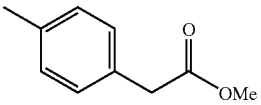 |
| 245 | 3'-CF₃ | H | H | (CH₂)₃ | 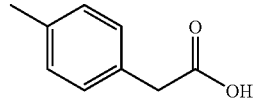 |
| 246 | 2'-F | 4'-F | H | CH₂ | 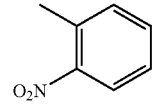 |
| 247 | 2'-F | 4'-F | H | CH₂ | 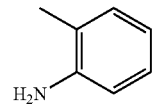 |
| 248 | 2'-CH₃ | 4'-F | H | CH₂ | 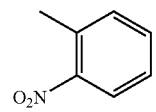 |
| 249 | 2'-CH₃ | 4'-F | H | CH₂ | 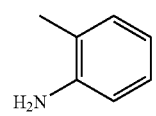 |
| 250 | 2'-OCH₃ | 4'-F | H | (CH₂)₂—O— | 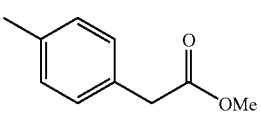 |

-continued

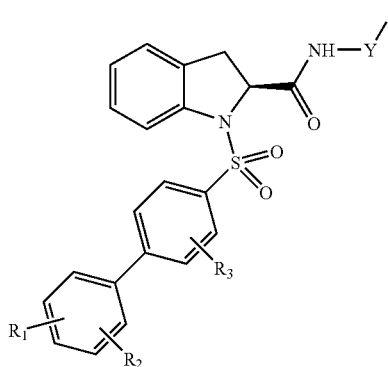

| Ex. | R₁ | R₂ | R₃ | Y | Z |
|---|---|---|---|---|---|
| 251 | 2'-OCH₃ | 4'-F | H | (CH₂)₂—O— | 4-methylphenylacetic acid |
| 252 | 2'-OCH₃ | 4'-F | H | CH₂ | methyl 4-methylphenylacetate |
| 253 | 2'-OCH₃ | 4'-F | H | CH₂ | 4-methylphenylacetic acid |
| 254 | 2'-OCH₃ | 4'-F | H | CH₂ | 2-methylaniline |
| 255 | 2'-F | 4'-F | H | CH₂ | methyl 4-methylphenylacetate |
| 256 | 2'-F | 4'-F | H | CH₂ | 4-methylphenylacetic acid |
| 257 | 2'-F | 4'-F | H | (CH₂)₂—O— | methyl 4-methylphenylacetate |
| 258 | 2'-F | 4'-F | H | (CH₂)₂—O— | 4-methylphenylacetic acid |
| 259 | 3'-CH₃ | H | H | CH₂ | methyl 4-methylphenylacetate |
| 260 | 3'-CH₃ | H | H | CH₂ | 4-methylphenylacetic acid |

-continued

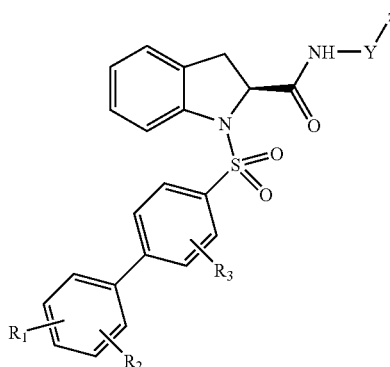

| Ex. | R₁ | R₂ | R₃ | Y | Z |
|---|---|---|---|---|---|
| 261 | 2'-Cl | 4'-F | H | (CH₂)₂—O— | 4-methylphenyl-CH₂-C(O)OMe |
| 262 | 2'-Cl | 4'-F | H | (CH₂)₂—O— | 4-methylphenyl-CH₂-C(O)OH |
| 263 | 2'-Cl | 4'-F | H | CH₂ | 4-methylphenyl-CH₂-C(O)OMe |
| 264 | 2'-Cl | 4'-F | H | CH₂ | 4-methylphenyl-CH₂-C(O)OH |
| 265 | 2'-Cl | 4'-F | H | CH₂ | 2-methyl-aniline (H₂N) |
| 266 | 3'-Cl | H | H | CH₂ | 4-methylphenyl-CH₂-C(O)OMe |
| 267 | 3'-Cl | H | H | CH₂ | 4-methylphenyl-CH₂-C(O)OH |
| 268 | 3'-C₂H₅ | H | H | CH₂ | 4-methylphenyl-CH₂-C(O)OMe |
| 269 | 3'-C₂H₅ | H | H | CH₂ | 4-methylphenyl-CH₂-C(O)OH |
| 270 | 2'-CF₃ | 4'-F | H | (CH₂)₂—O— | 4-methylphenyl-CH₂-C(O)OMe |

-continued

| Ex. | R₁ | R₂ | R₃ | Y | Z |
|---|---|---|---|---|---|
| 271 | 2'-CF₃ | 4'-F | H | (CH₂)₂—O— | 4-methylphenylacetic acid |
| 272 | 2'-CN | 4'-F | H | (CH₂)₂—O— | methyl 4-methylphenylacetate |
| 273 | 2'-CN | 4'-F | H | (CH₂)₂—O— | 4-methylphenylacetic acid |
| 274 | 4'-Cl | H | H | (CH₂)₂—O— | methyl 4-methylphenylacetate |
| 275 | 2'-Cl | 5'-CF₃ | H | (CH₂)₂—O— | methyl 4-methylphenylacetate |
| 276 | 2'-F | 5'-CF₃ | H | (CH₂)₂—O— | methyl 4-methylphenylacetate |
| 277 | 2'-F | 5'-CF₃ | H | (CH₂)₂—O— | 4-methylphenylacetic acid |
| 278 | 2'-F | 5'-CH₃ | H | (CH₂)₂—O— | methyl 4-methylphenylacetate |
| 279 | 2'-F | 5'-CH₃ | H | (CH₂)₂—O— | 4-methylphenylacetic acid |
| 280 | 2'-OCH₃ | 5'-CH₃ | H | (CH₂)₂—O— | methyl 4-methylphenylacetate |

-continued

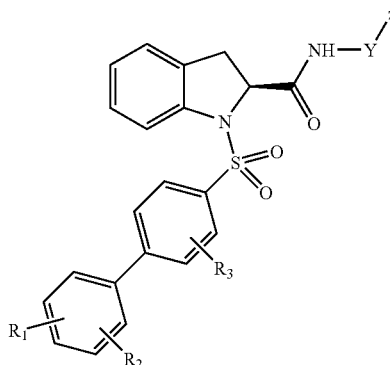

| Ex. | R₁ | R₂ | R₃ | Y | Z |
|---|---|---|---|---|---|
| 281 | 2'-OCH₃ | 5'-CH₃ | H | (CH₂)₂—O— | 4-methylphenylacetic acid |
| 282 | 2'-CH₃ | 5'-CH₃ | H | (CH₂)₂—O— | methyl 4-methylphenylacetate |
| 283 | 2'-CH₃ | 5'-CH₃ | H | (CH₂)₂—O— | 4-methylphenylacetic acid |
| 284 | 2'-OCH₃ | 5'-CF₃ | H | (CH₂)₂—O— | methyl 4-methylphenylacetate |
| 285 | 2'-OCH₃ | 5'-CF₃ | H | (CH₂)₂—O— | 4-methylphenylacetic acid |
| 286 | 2'-CH₃ | 5'-CF₃ | H | (CH₂)₂—O— | methyl 4-methylphenylacetate |
| 287 | 2'-CH₃ | 5'-CF₃ | H | (CH₂)₂—O— | 4-methylphenylacetic acid |
| 288 | 2'-Cl | 5'-CH₃ | H | (CH₂)₂—O— | methyl 4-methylphenylacetate |
| 289 | 2'-Cl | 5'-CH₃ | H | (CH₂)₂—O— | 4-methylphenylacetic acid |
| 290 | 2'-Cl | 5'-Cl | H | (CH₂)₂—O— | methyl 4-methylphenylacetate |

-continued
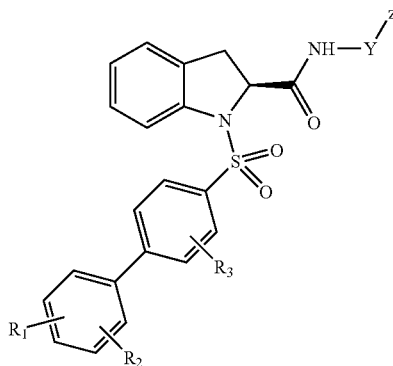
| Ex. | R₁ | R₂ | R₃ | Y | Z |
|---|---|---|---|---|---|
| 291 | 2'-Cl | 5'-Cl | H | $(CH_2)_2$—O— | 4-methylphenylacetic acid |
| 292 | 2'-Cl | 5'-F | H | $(CH_2)_2$—O— | methyl 4-methylphenylacetate |
| 293 | 2'-Cl | 5'-F | H | $(CH_2)_2$—O— | 4-methylphenylacetic acid |
| 294 | 2'-Cl | 5'-CF₃ | H | $(CH_2)_2$—O— | tert-butyl 4-methylbenzoate |
| 295 | 2'-Cl | 5'-CF₃ | H | $(CH_2)_2$—O— | 4-methylbenzoic acid |
| 296 | 2'-Cl | 5'-CF₃ | H | $(CH_2)_2$—NH— | tert-butyl 4-methylbenzoate |
| 297 | 2'-Cl | 5'-CF₃ | H | $(CH_2)_2$—NH— | methyl 4-methylbenzoate |
| 298 | 2'-Cl | 5'-CF₃ | H | $(CH_2)_2$—NH— | 4-methylbenzoic acid |

-continued

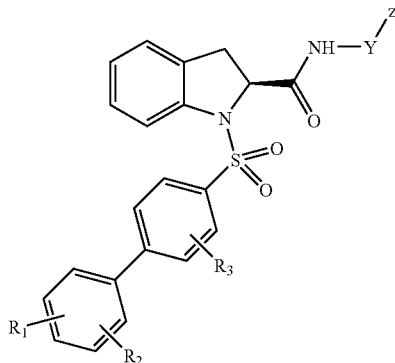

| Ex. | R₁ | R₂ | R₃ | Y | Z |
|---|---|---|---|---|---|
| 299 | 2'-Cl | 5'-CF₃ | H | (CH₂)₂—NH— | 4-methylphenyl-CH₂-C(O)-O-CH₂CH₃ |
| 300 | 2'-Cl | 5'-CF₃ | H | (CH₂)₂—NH— | 4-methylphenyl-CH₂-C(O)-OH |
| 301 | 2'-Cl | 5'-CF₃ | H | (CH₂)₂—O— | 4-methyl-3-methoxyphenyl-CH₂-C(O)-OMe |
| 302 | 2'-Cl | 5'-CF₃ | H | (CH₂)₂—O— | 4-methyl-3-methoxyphenyl-CH₂-C(O)-OH |
| 303 | 2'-Cl | 5'-CF₃ | H | (CH₂)₂—O— | 4-methylphenyl-cyclopropyl-C(O)-OMe |
| 304 | 2'-Cl | 5'-CF₃ | H | (CH₂)₂—O— | 4-methylphenyl-cyclopropyl-C(O)-OH |
| 305 | 2'-Cl | 5'-CF₃ | H | (CH₂)₂—O— | 4-methyl-2-fluorophenyl-C(O)-O-CH₃ |
| 306 | 2'-Cl | 5'-CF₃ | H | (CH₂)₂—O— | 4-methyl-2-fluorophenyl-C(O)-OH |

-continued
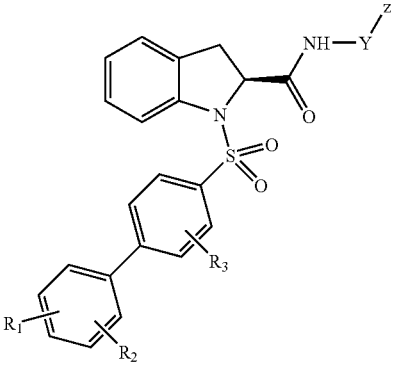
| Ex. | R₁ | R₂ | R₃ | Y | Z |
|---|---|---|---|---|---|
| 307 | 2'-Cl | 5'-CF₃ | H | (CH₂)₂—O— | 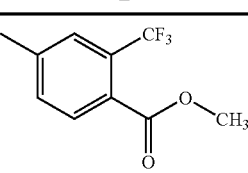 |
| 308 | 2'-Cl | 5'-CF₃ | H | (CH₂)₂—O— | 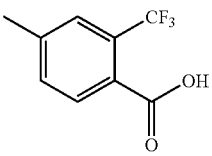 |
| 309 | 2'-Cl | 5'-CF₃ | H | (CH₂)₂—O— | 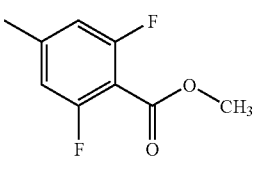 |
| 310 | 2'-Cl | 5'-CF₃ | H | (CH₂)₂—O— | 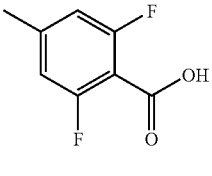 |
| 311 | 4'-F | 2'-F | H | —CH— | 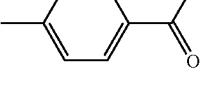 |
| 312 | 4'-F | 2'-Cl | H | —CH₂— | 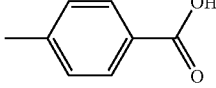 |
| 313 | 2'-Cl | 5'-CF₃ | H | (CH₂)₂—O— | 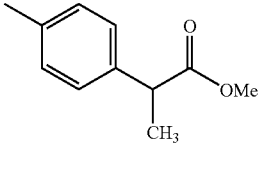 |
| 314 | 2'-Cl | 5'-CF₃ | H | (CH₂)₂—O— | 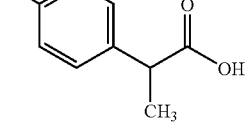 |

-continued

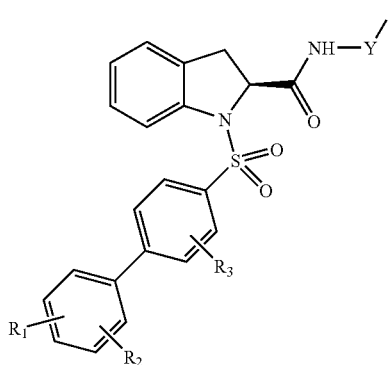

| Ex. | R₁ | R₂ | R₃ | Y | Z |
|---|---|---|---|---|---|
| 315 | 2'-Cl | 5'-CF₃ | H | (CH₂)₂—O— | 4-methyl-3-fluorophenyl acetic acid methyl ester |
| 316 | 2'-Cl | 5'-CF₃ | H | (CH₂)₂—O— | 4-methyl-3-fluorophenyl acetic acid |
| 317 | 2'-Cl | 5'-CF₃ | H | (CH₂)₂—O— | 2,4-dimethylphenyl acetic acid methyl ester |
| 318 | 2'-Cl | 5'-CF₃ | H | (CH₂)₂—O— | 2,4-dimethylphenyl acetic acid |
| 319 | 2'-Cl | 5'-CF₃ | H | (CH₂)₂—O— | 4-methyl-3-chlorophenyl acetic acid methyl ester |
| 320 | 2'-Cl | 5'-CF₃ | H | (CH₂)₂—O— | 4-methyl-3-chlorophenyl acetic acid |
| 321 | 4'-F | H | H | (CH₂)₂—O— | 4-methyl-3-chlorophenyl acetic acid methyl ester |
| 322 | 4'-F | H | H | (CH₂)₂—O— | 4-methyl-3-chlorophenyl acetic acid |
| 323 | 2'-Cl | 5'-CF₃ | H | (CH₂)₂—O— | 2-(4-methylphenyl)-2-methylpropanoic acid methyl ester |

-continued

| Ex. | R₁ | R₂ | R₃ | Y | Z |
|---|---|---|---|---|---|
| 324 | 2'-Cl | 5'-CF₃ | H | (CH₂)₂—O— | 2-(4-methylphenyl)-2-methylpropanoic acid |
| 325 | 2'-Cl | 5'-CF₃ | H | (CH₂)₂—O— | methyl 2-chloro-4-methylbenzoate |
| 326 | 2'-Cl | 5'-CF₃ | H | (CH₂)₂—O— | 2-chloro-4-methylbenzoic acid |
| 327 | 4'-F | H | H | (CH₂)₂—O— | methyl 2-chloro-4-methylbenzoate |
| 328 | 3'-CF₃ | H | H | (CH₂)₂—O— | methyl 2-chloro-4-methylbenzoate |
| 329 | 3'-CF₃ | H | H | (CH₂)₂—O— | 2-chloro-4-methylbenzoic acid |
| 330 | 2'-Cl | 5'-CF₃ | H | (CH₂)₂—O— | methyl 2-(4-methylphenyl)-3-methylbutanoate |

-continued
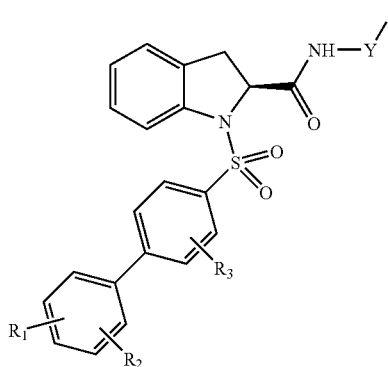
| Ex. | R₁ | R₂ | R₃ | Y | Z |
|---|---|---|---|---|---|
| 331 | 2'-Cl | 5'-CF₃ | H | (CH₂)₂—O— | 2-(p-tolyl)-3-methylbutanoic acid |
| 332 | 3'-CF₃ | H | H | (CH₂)₂—O— | methyl 2-(p-tolyl)-3-methylbutanoate |
| 333 | 3'-CF₃ | H | H | (CH₂)₂—O— | 2-(p-tolyl)-3-methylbutanoic acid |
| 334 | 3'-CF₃ | H | H | —CH₂— | methyl 5-(o-tolyl)pentanoate |
| 335 | 3'-CF₃ | H | H | —CH₂— | 5-(o-tolyl)pentanoic acid |
| 336 | 3'-CF₃ | H | H | —CH₂— | 3-(2-methylphenoxy)-N,N-dimethylpropan-1-amine |
| 337 | 3'-CF₃ | H | H | —CH₂— | 4-((2-methylphenyl)amino)butanoic acid |
| 338 | 3'-CF₃ | H | H | —CH₂— | 7-methylindolin-2-one |

-continued
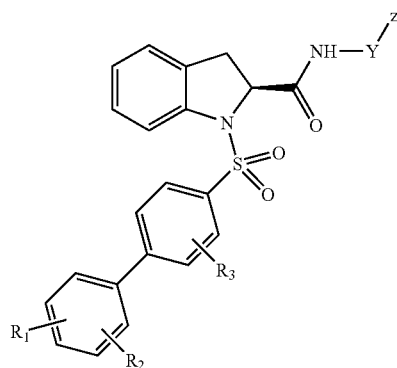
| Ex. | R₁ | R₂ | R₃ | Y | Z |
|---|---|---|---|---|---|
| 339 | 2'-Cl | 4'-F | H | (CH₂)₂—O— | 2-fluoro-4-methyl methyl benzoate |
| 340 | 2'-Cl | 4'-F | H | (CH₂)₂—O— | 2-fluoro-4-methyl benzoic acid |
| 341 | 2'-OCH₃ | 4'-F | H | (CH₂)₂—O— | 2-fluoro-4-methyl methyl benzoate |
| 342 | 2'-OCH₃ | 4'-F | H | (CH₂)₂—O— | 2-fluoro-4-methyl benzoic acid |
| 343 | 2'-F | 4'-F | H | (CH₂)₂—O— | 2-fluoro-4-methyl methyl benzoate |
| 344 | 2'-F | 4'-F | H | (CH₂)₂—O— | 2-fluoro-4-methyl benzoic acid |
| 345 | 2'-CH₃ | 4'-F | H | (CH₂)₂—O— | 2-fluoro-4-methyl methyl benzoate |

-continued
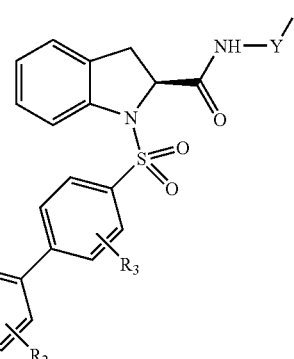
| Ex. | R₁ | R₂ | R₃ | Y | Z |
|---|---|---|---|---|---|
| 346 | 2'-CH₃ | 4'-F | H | (CH₂)₂—O— | 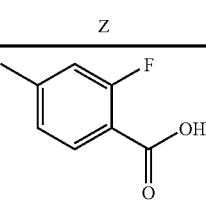 |
| 347 | 3'-CF₃ | H | H | —(CH₂)₅— | 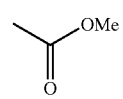 |
| 348 | 3'-CF₃ | H | H | —(CH₂)₅— | 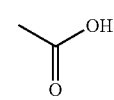 |
| 349 | 3'-CF₃ | H | H | (CH₂)₂—O— | 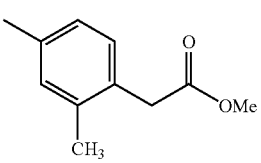 |
| 350 | 3'-CF₃ | H | H | (CH₂)₂—O— | 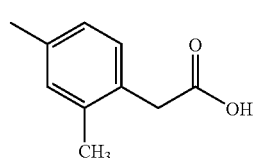 |
| 351 | 2'-CF₃ | H | H | (CH₂)₂—O— | 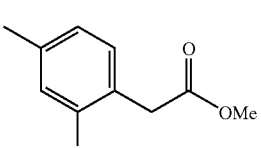 |
| 352 | 2'-CF₃ | H | H | (CH₂)₂—O— | 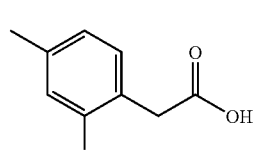 |
| 353 | 3'-CF₃ | H | H | —CH₂— | 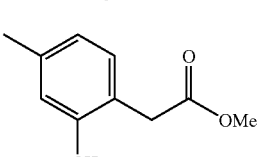 |

-continued
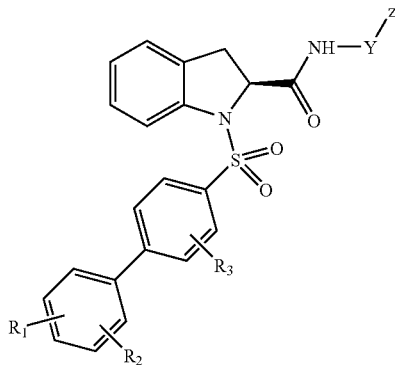
| Ex. | R₁ | R₂ | R₃ | Y | Z |
|---|---|---|---|---|---|
| 354 | 2'-OCH₃ | 5'-CH₃ | H | —CH₂— | 4-carboxyphenyl |
| 355 | 2'-F | 5'-CH₃ | H | —CH₂— | 4-carboxyphenyl |
| 356 | 2'-F | 5'-CF₃ | H | —CH₂— | 4-carboxyphenyl |
| 357 | 2'-CH₃ | 5'-CH₃ | H | —CH₂— | 4-carboxyphenyl |
| 358 | 2'-Cl | 5'-CF₃ | H | —CH₂— | 4-carboxyphenyl |
| 359 | 3'-CH₃ | H | H | —CH₂— | 4-carboxyphenyl |
| 360 | 2'-OCH₃ | 5'-CF₃ | H | —CH₂— | 4-carboxyphenyl |

-continued
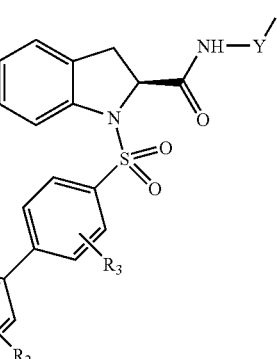
| Ex. | R₁ | R₂ | R₃ | Y | Z |
|---|---|---|---|---|---|
| 361 | 2'-CH₃ | 5'-CF₃ | H | —CH₂— | 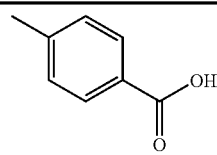 |
| 362 | 2'-Cl | 5'-CH₃ | H | —CH₂— | 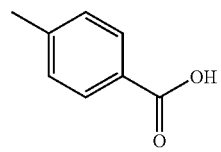 |
| 363 | 3'-CF₃ | H | H | —CH₂— | 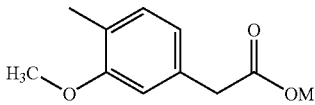 |
| 364 | 3'-CF₃ | H | H | —CH₂— | 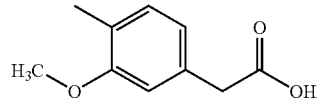 |
| 365 | 3'-CF₃ | H | H | —CH₂— | 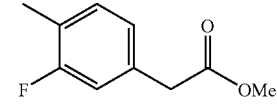 |
| 366 | 3'-CF₃ | H | H | —CH₂— | 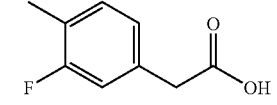 |
| 367 | 3'-CF₃ | H | H | —CH₂— | 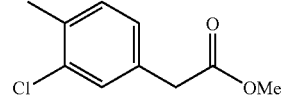 |
| 368 | 3'-CF₃ | H | H | —CH₂— | 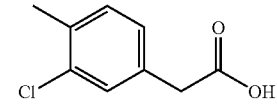 |
| 369 | 3'-CF₃ | H | H | —CH₂— | 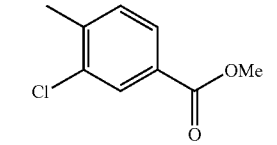 |

-continued
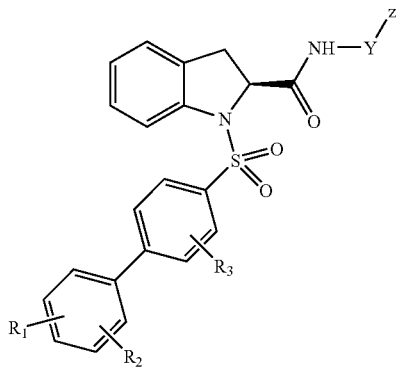
| Ex. | R₁ | R₂ | R₃ | Y | Z |
|---|---|---|---|---|---|
| 370 | 3'-CF₃ | H | H | —CH₂— | 3-chloro-4-methylbenzoic acid |
| 371 | 3'-CF₃ | H | H | —CH₂— | methyl 3-methoxy-4-methylbenzoate |
| 372 | 3'-CF₃ | H | H | —CH₂— | 3-methoxy-4-methylbenzoic acid |
| 373 | 3'-CF₃ | H | H | —(CH₂)₂—O— | 4-methylbenzonitrile |
| 374 | 2'-F | 4'-F | H | —(CH₂)₂—O— | methyl 2,6-difluoro-4-methylbenzoate |
| 375 | 2'-OCH₃ | 4'-F | H | —(CH₂)₂—O— | methyl 2,6-difluoro-4-methylbenzoate |
| 376 | 2'-Cl | 4'-F | H | —(CH₂)₂—O— | methyl 2,6-difluoro-4-methylbenzoate |

-continued

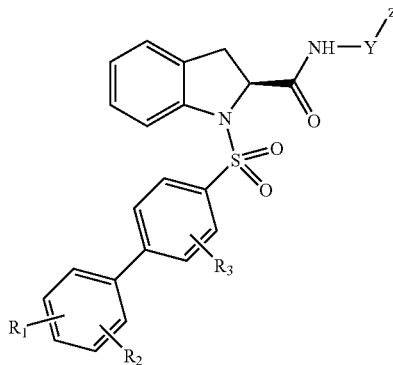

| Ex. | R₁ | R₂ | R₃ | Y | Z |
|---|---|---|---|---|---|
| 377 | 2'-Cl | 4'-F | H | —(CH₂)₂—O— | 4-methyl-2,6-difluorobenzoic acid |
| 378 | 4'-CH₃ | H | 2-CF₃ | —(CH₂)₂—O— | methyl (4-methylphenyl)acetate |
| 379 | 4'-CH₃ | H | 2-CF₃ | —(CH₂)₂—O— | (4-methylphenyl)acetic acid |
| 380 | 4'-Cl | H | 2-CF₃ | —(CH₂)₂—O— | methyl (4-methylphenyl)acetate |
| 381 | 4'-Cl | H | 2-CF₃ | —(CH₂)₂—O— | (4-methylphenyl)acetic acid |
| 382 | 4'F | H | 2-CF₃ | —(CH₂)₂—O— | methyl (4-methylphenyl)acetate |
| 383 | 4'-F | H | 2-CF₃ | —(CH₂)₂—O— | (4-methylphenyl)acetic acid |
| 384 | 3'-CF₃ | H | 2-F | —(CH₂)₂—O— | methyl (4-methylphenyl)acetate |
| 385 | 3'-CF₃ | H | 2-F | —(CH₂)₂—O— | (4-methylphenyl)acetic acid |

-continued
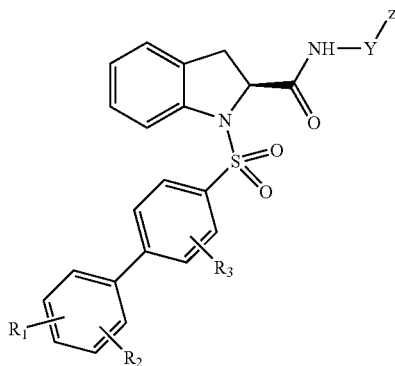
| Ex. | R₁ | R₂ | R₃ | Y | Z |
|---|---|---|---|---|---|
| 386 | 3'-CF₃ | H | 2-Cl | —(CH₂)₂—O— | 4-methylphenyl-CH₂-C(O)-OMe |
| 387 | 3'-CF₃ | H | 2-Cl | —(CH₂)₂—O— | 4-methylphenyl-CH₂-C(O)-OH |
| 388 | 3'-CF₃ | H | 2-CH₃ | —(CH₂)₂—O— | 4-methylphenyl-CH₂-C(O)-OMe |
| 389 | 3'-CF₃ | H | 2-CH₃ | —(CH₂)₂—O— | 4-methylphenyl-CH₂-C(O)-OH |
| 390 | 3'-CF₃ | H | H | —(CH₂)— | 5-methylpyridin-2-yl-CH₂-C(O)-O-C(CH₃)₃ |
| 391 | 3'-CF₃ | H | H | —(CH₂)— | 3-methylphenyl-CN |
| 392 | 3'-CF₃ | H | H | —(CH₂)— | 3-methylphenyl-CH₂-NH₂ |
| 393 | 3'-CF₃ | H | H | —(CH₂)— | 3-methyl-2-aminopyridinyl |
| 394 | 4'-F | 2'-CH₃ | H | —(CH₂)₂—O— | 4-methylphenyl-C(O)-O-C(CH₃)₃ |

-continued
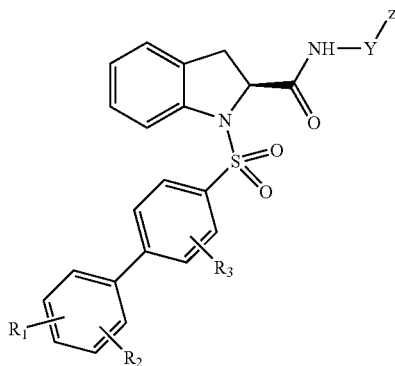
| Ex. | R₁ | R₂ | R₃ | Y | Z |
|---|---|---|---|---|---|
| 395 | 4'-F | 2'-CH₃ | H | —(CH₂)₂—O— | 4-methylbenzoic acid |
| 396 | 2'-F | 4'-F | H | —(CH₂)₂—O— | tert-butyl 4-methylbenzoate |
| 397 | 2'-F | 4'-F | H | —(CH₂)₂—O— | 4-methylbenzoic acid |
| 398 | 2'-Cl | 4'-F | H | —(CH₂)₂—O— | tert-butyl 4-methylbenzoate |
| 399 | 2'-Cl | 4'-F | H | —(CH₂)₂—O— | 4-methylbenzoic acid |
| 400 | 2'-OCH₃ | 4'-F | H | —(CH₂)₂—O— | tert-butyl 4-methylbenzoate |
| 401 | 2'-OCH₃ | 4'-F | H | —(CH₂)₂—O— | 4-methylbenzoic acid |

-continued
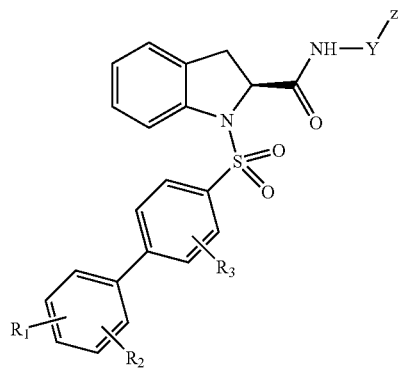
| Ex. | R₁ | R₂ | R₃ | Y | Z |
|---|---|---|---|---|---|
| 402 | 3'-CF₃ | H | H | —CH₂— | 4-MeC₆H₄CH₂C(O)OMe |
| 403 | 3'-CF₃ | H | H | —CH₂— | 4-MeC₆H₄CH₂C(O)OH |
| 404 | 3'-CF₃ | H | H | —(CH₂)₂—O— | 4-MeC₆H₄CH₂C(O)OMe |
| 405 | 3'-CF₃ | H | H | —(CH₂)₂—O— | 4-MeC₆H₄CH₂C(O)OH |
| 406* | 3'-CF₃ | H | H | —(CH₂)₂—O— | 4-MeC₆H₄CH₂C(O)OMe |
| 407* | 3'-CF₃ | H | H | —(CH₂)₂—O— | 4-MeC₆H₄CH₂C(O)OH |
| 408 | 2'-Cl | 5'-CF₃ | H | —(CH₂)₂—O— | 4-MeC₆H₄CH₂C(O)OMe |
| 409 | 2'-Cl | 5'-CF₃ | H | —(CH₂)₂—O— | 4-MeC₆H₄CH₂C(O)OH |
| 410 | 3'-CF₃ | H | H | —(CH₂)₂—O— | 4-Me-C₆H₄-(1,2,4-oxadiazol-5(4H)-one-3-yl) |

-continued
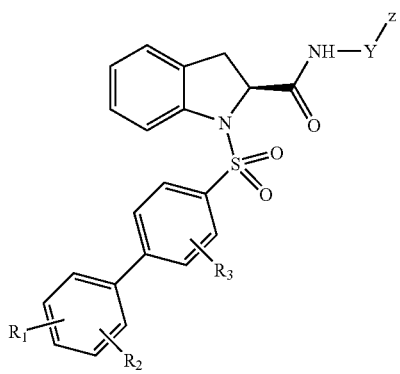
| Ex. | R₁ | R₂ | R₃ | Y | Z |
|---|---|---|---|---|---|
| 411 | 3'-CF₃ | H | H | —CH₂— | 4-cyanophenyl |
| 412 | 3'-CF₃ | H | H | —CH₂— | 3-(4-methylphenyl)-1,2,4-oxadiazol-5(4H)-one |
| 413 | 3'-CF₃ | H | H | —CH₂— | 4-methylphenyl-CH₂CN |
| 414 | 3'-CF₃ | H | H | —(CH₂)₂—O— | 3-methylpyridazine |
| 415 | 2'-CH₃ | 4'-F | H | —(CH₂)₂—O— | methyl 2,6-difluoro-4-methylbenzoate |
| 416 | 2'-CH₃ | 4'-F | H | —(CH₂)₂—O— | 2,6-difluoro-4-methylbenzoic acid |
| 417 | 2'-Cl | 5'-CF₃ | H | —(CH₂)₂—O— | methyl 2-fluoro-4-methylphenylacetate |
| 418 | 2'-Cl | 5'-CF₃ | H | —(CH₂)₂—O— | 2-fluoro-4-methylphenylacetic acid |

-continued
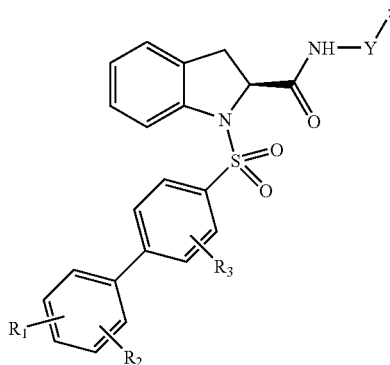
| Ex. | R₁ | R₂ | R₃ | Y | Z |
|---|---|---|---|---|---|
| 419 | 2'-OCH₃ | 4'-F | H | —(CH₂)₂—O— | 3-methyl-4-methyl benzoate methyl ester |
| 420 | 2'-OCH₃ | 4'-F | H | —(CH₂)₂—O— | 3-methyl-4-methyl benzoic acid |
| 421 | 2'-OCH₃ | 4'-F | H | —(CH₂)₂—O— | 3-CF₃-4-methyl benzoate methyl ester |
| 422 | 2'-OCH₃ | 4'-F | H | —(CH₂)₂—O— | 3-CF₃-4-methyl benzoic acid |
| 423 | 2'-OCH₃ | 4'-F | H | —(CH₂)₂—O— | 3,4,5-trimethyl benzoate methyl ester |
| 424 | 2'-OCH₃ | 4'-F | H | —(CH₂)₂—O— | 3,4,5-trimethyl benzoic acid |
| 425 | 2'-CH₃ | 4'-F | H | —(CH₂)₂—O— | 3-CF₃-4-methyl benzoate methyl ester |

-continued
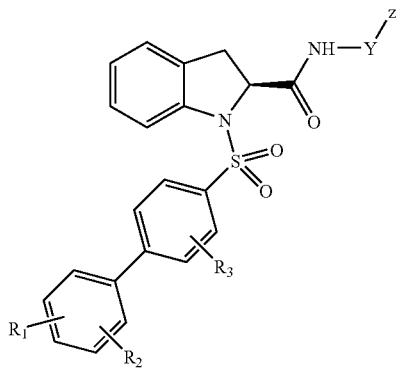
| Ex. | R₁ | R₂ | R₃ | Y | Z |
|---|---|---|---|---|---|
| 426 | 2'-CH₃ | 4'-F | H | —(CH₂)₂—O— | 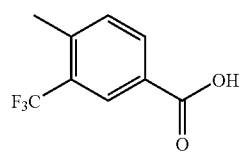 |
| 427 | 2'-F | 4'-F | H | —(CH₂)₂—O— | 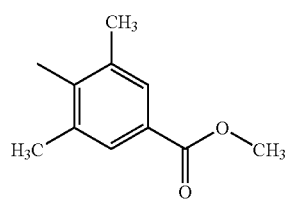 |
| 428 | 2'-F | 4'-F | H | —(CH₂)₂—O— | 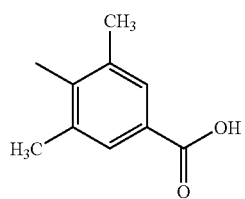 |
| 429 | 2'-OCH₃ | 4'-F | H | —(CH₂)₂—O— | 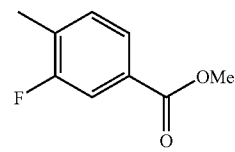 |
| 430 | 2'-OCH₃ | 4'-F | H | —(CH₂)₂—O— | 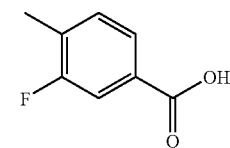 |
| 431 | 2'-Cl | 4'-F | H | —(CH₂)₂—O— | 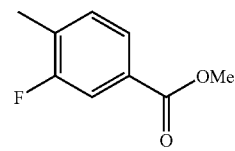 |

-continued
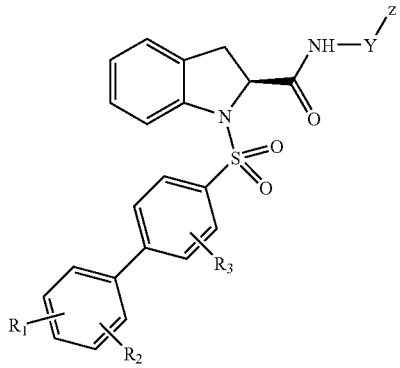
| Ex. | R₁ | R₂ | R₃ | Y | Z |
|---|---|---|---|---|---|
| 432 | 2'-Cl | 4'-F | H | —(CH₂)₂—O— | 3-F, 4-Me-benzoic acid |
| 433 | 2'-F | 4'-F | H | —(CH₂)₂—O— | methyl 3-F, 4-Me-benzoate |
| 434 | 2'-F | 4'-F | H | —(CH₂)₂—O— | 3-F, 4-Me-benzoic acid |
| 435 | 2'-CH₃ | 4'-F | H | —(CH₂)₂—O— | methyl 3-F, 4-Me-benzoate |
| 436 | 2'-CH₃ | 4'-F | H | —(CH₂)₂—O— | 3-F, 4-Me-benzoic acid |
| 437 | 2'-F | 4'-F | H | —(CH₂)₂—O— | methyl 3-CF₃, 4-Me-benzoate |
| 438 | 2'-F | 4'-F | H | —(CH₂)₂—O— | 3-CF₃, 4-Me-benzoic acid |

-continued
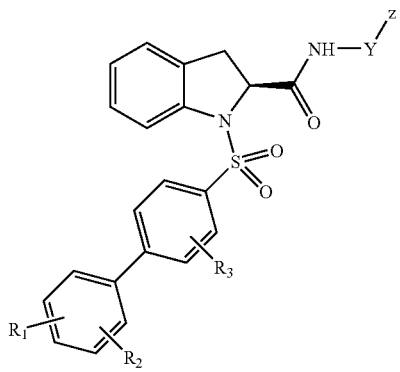
| Ex. | R₁ | R₂ | R₃ | Y | Z |
|---|---|---|---|---|---|
| 439 | 2'-Cl | 4'-F | H | —(CH₂)₂—O— | 4-methyl-3-(trifluoromethyl)benzoic acid methyl ester |
| 440 | 2'-Cl | 4'-F | H | —(CH₂)₂—O— | 4-methyl-3-(trifluoromethyl)benzoic acid |
| 441 | 2'-Cl | 4'-F | H | —(CH₂)₂—O— | 3,4,5-trimethylbenzoic acid methyl ester |
| 442 | 2'-Cl | 4'-F | H | —(CH₂)₂—O— | 3,4,5-trimethylbenzoic acid |
| 443 | 2'-Cl | 4'-F | H | —(CH₂)₂—O— | 3,4-dimethylbenzoic acid methyl ester |
| 444 | 2'-Cl | 4'-F | H | —(CH₂)₂—O— | 3,4-dimethylbenzoic acid |

-continued
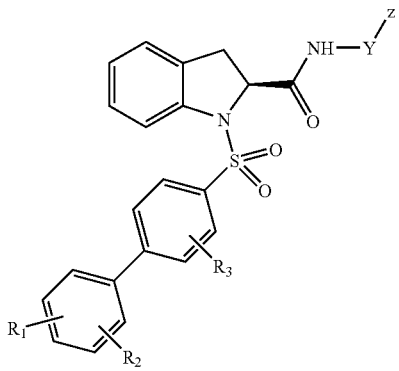
| Ex. | R₁ | R₂ | R₃ | Y | Z |
|---|---|---|---|---|---|
| 445 | 2'-CH₃ | 4'-F | H | —(CH₂)₂—O— | 3,4,5-trimethylphenyl methyl ester |
| 446 | 2'-CH₃ | 4'-F | H | —(CH₂)₂—O— | 3,4,5-trimethylbenzoic acid |
| 447 | 2'-CH₃ | 4'-F | H | —(CH₂)₂—O— | 3,4-dimethylphenyl methyl ester |
| 448 | 2'-CH₃ | 4'-F | H | —(CH₂)₂—O— | 3,4-dimethylbenzoic acid |
| 449 | 2'-Cl | 4'-F | H | —(CH₂)₃— | 4-methylpiperazin-1-yl |
| 450 | 2'-Cl | 4'-F | H | —(CH₂)₃— | pyrrolidin-1-yl |
| 451 | 2'-Cl | 4'-F | H | —(CH₂)₄— | pyrrolidin-1-yl |
| 452 | 2'-Cl | 4'-F | H | —(CH₂)₂— | piperidin-1-yl |

-continued
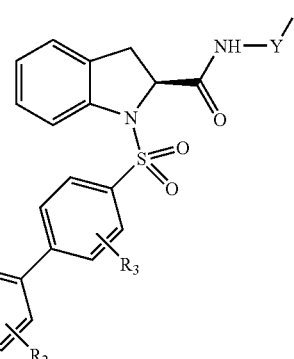
| Ex. | R₁ | R₂ | R₃ | Y | Z |
|---|---|---|---|---|---|
| 453 | 2'-Cl | 4'-F | H | —(CH₂)₄— | 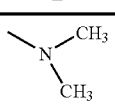 |
| 454 | 2'-OCH₃ | 4'-F | H | —(CH₂)₂—O— | 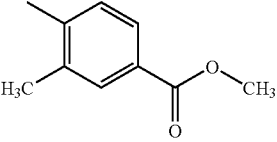 |
| 455 | 2'-F | 4'-F | H | —(CH₂)₂—O— | 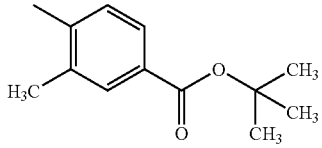 |
| 456 | 2'-F | 4'-F | H | —(CH₂)₂—O— | 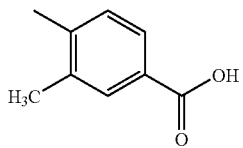 |
| 457 | 2'-Cl | 4'-F | H | —CH₂— | 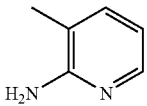 |
| 458 | 2'-Cl | 4'-F | H | —CH₂— | 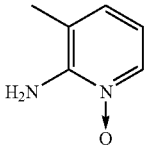 |
| 459 | 2'-Cl | 4'-F | H | —(CH₂)₂—O— | 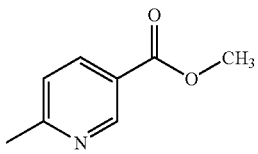 |
| 460 | 2'-Cl | 4'-F | H | —(CH₂)₂—O— | 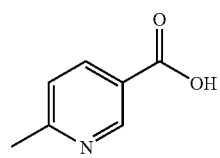 |

-continued
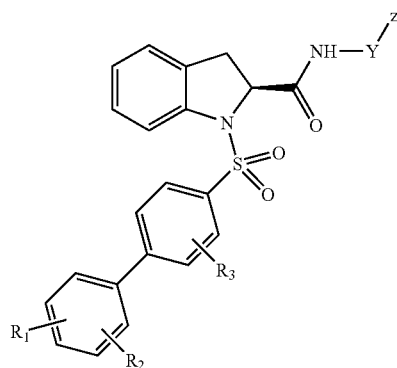
| Ex. | R₁ | R₂ | R₃ | Y | Z |
|---|---|---|---|---|---|
| 461 | 2'-Cl | 4'-F | H | —CH₂— | (methyl 3-(N-methyl-N-(2-methylphenyl)amino)propanoate) |
| 462 | 2'-Cl | 4'-F | H | —CH₂— | (3-(N-methyl-N-(2-methylphenyl)amino)propanoic acid) |
| 463 | 2'-Cl | 4'-F | H | —CH₂— | (3-amino-4-methylpyridine) |
| 464 | 2'-Cl | 4'-F | H | —CH₂— | (3-amino-4-methylpyridine N-oxide) |
| 465¤ | 2'-F | 4'-F | H | —CH₂— | (4-methylbenzoic acid) |
| 466¤ | 2'-F | 4'-F | H | —(CH₂)₂—O— | (tert-butyl 4-methylbenzoate) |
| 467¤ | 2'-F | 4'-F | H | —(CH₂)₂—O— | (4-methylbenzoic acid) |
| 468* | 4'-F | H | H | —(CH₂)₂—O— | (tert-butyl 4-methylbenzoate) |

-continued
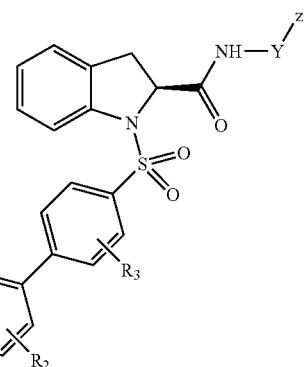
| Ex. | R₁ | R₂ | R₃ | Y | Z |
|---|---|---|---|---|---|
| 469* | 4'-F | H | H | —(CH₂)₂—O— | 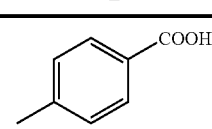 |
| 470* | 2'-F | 4'-F | H | —(CH₂)₂—O— | 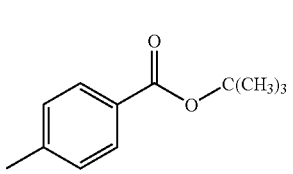 |
| 471* | 2'-F | 4'-F | H | —(CH₂)₂—O— | 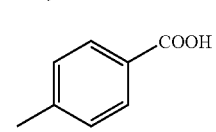 |
| 472* | 2'-F | 4'-F | H | —CH₂— | 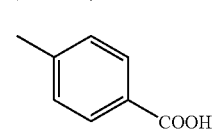 |
| 473* | 2'-F | 4'-F | H | —CH₂— | 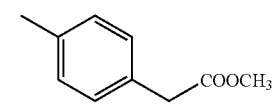 |
| 474* | 2'-F | 4'-F | H | —CH₂— | 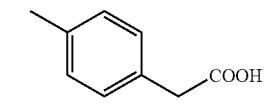 |
| 475# | 2'-F | 4'-F | H | —(CH₂)₂—O— | 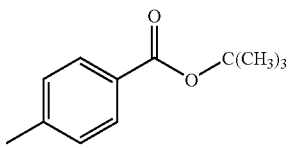 |
| 476# | 2'-F | 4'-F | H | —(CH₂)₂—O— | 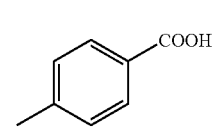 |
| 477# | 2'-F | 4'-F | H | —CH₂— | 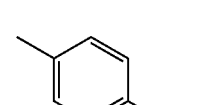 |

-continued
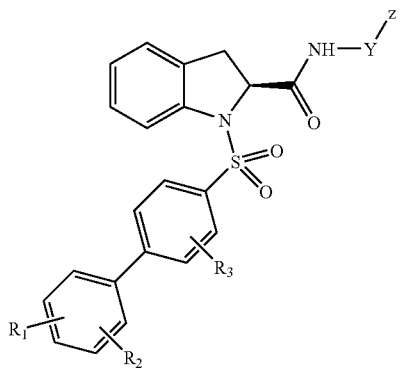
| Ex. | R₁ | R₂ | R₃ | Y | Z |
|---|---|---|---|---|---|
| 478* | 2'-Cl | 4'-F | H | —CH₂— | 4-carboxyphenyl |
| 479* | 2'-Cl | 4'-F | H | —(CH₂)₂—O— | 4-(tert-butoxycarbonyl)phenyl |
| 480* | 2'-Cl | 4'-F | H | —(CH₂)₂—O— | 4-carboxyphenyl |
| 481 | 2'-O—CHF₂ | 4'-F | H | —(CH₂)₂—O— | 4-(tert-butoxycarbonyl)phenyl |
| 482 | 2'-O—CHF₂ | 4'-F | H | —(CH₂)₂—O— | 4-carboxyphenyl |
| 483 | 2'-O—CHF₂ | 4'-F | H | —CH₂— | 4-carboxyphenyl |
| 484* | 2'-O—CHF₂ | 4'-F | H | —(CH₂)₂—O— | 4-(tert-butoxycarbonyl)phenyl |
| 485* | 2'-O—CHF₂ | 4'-F | H | —(CH₂)₂—O— | 4-carboxyphenyl |

-continued

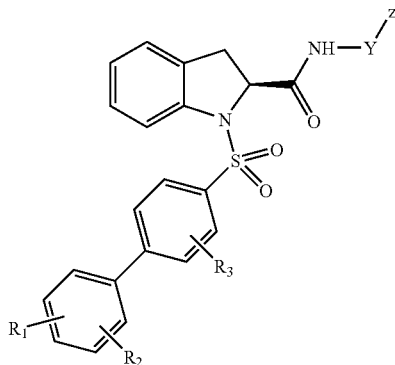

| Ex. | R$_1$ | R$_2$ | R$_3$ | Y | Z |
|---|---|---|---|---|---|
| 486* | 2'-O—CHF$_2$ | 4'-F | H | —CH$_2$— | 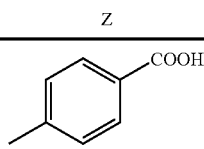 | iPr = 1-methylethyl (or isopropyl)
*Compounds 170, 171, 406, 407, 468, 469, 470, 471, 472, 473, 474, 478, 479, 480, 484, 485 and 486 are derivatives of racemic 4-methoxyindoline-2-carboxylic acid.
¤Compounds 465, 466 and 467 are derivatives of racemic 5-methoxyindoline-2-carboxylic acid.
Compounds 475, 476 and 477 are derivatives of racemic 7-methoxyindoline-2-carboxylic acid.

Biological Activity

Test for Transactivation of GAL4-LXR Chimeras Following Transient Transfection into COS-7 Cells The transactivation tests are based on the capacity of the nuclear receptors to:

(1) bind to a specific DNA sequence (RE=Response Element) located in front of a promoter, via their DNA binding domain (DBD);

(2) and increase the transcription of a gene under the control of this promoter in the presence of an agonistic ligand, via their ligand binding domain (LBD).

The aim of the COS-7 cell transactivation test developed here is to evaluate the effect of compounds on the activity of human LXRs: it makes it possible to validate the interaction of the compounds with the LXRs and determine the EC$_{50}$ of the interaction. This test is based on the use of "Gal4-LXR" chimeric proteins containing the LBD of the LXR (human LXRα or human LXRβ) fused with the DBD of Gal4. The COS-7 cells are thus transiently cotransfected with:

an expression vector coding for the chimeric protein "Gal4 (DBD)-LXRα(LBD)" or an expression vector coding for the chimera "Gal4(DBD)-LXRα(LBD)"; and a reporter vector containing Gal4-RE (Gal4-Response Element) recognizing the DBD of Gal4, and located in front of the minimal promoter P$_{TK}$ which controls the luciferase gene.

The activity of the luciferase thus produced generates luminescence in the presence of an excess of substrate, this being a quantifiable parameter which reflects the interaction of the compound with the LBD of the LXR.

The compounds according to the invention are evaluated relative to a reference compound (T-0901317, CAS RN: 293754-55-9).

In this test the compounds according to the invention have an EC$_{50}$ below 1 μM, some compounds having a value of 3 to 4 nM.

The biological properties of the compounds according to the invention demonstrate their potential value and their usefulness for application as active substances of drugs intended for the treatment or prevention of diseases dependent on a deregulation of the functions of the LXRα and LXRβ receptors, especially hypercholesterolemia and dyslipidemia, as well as obesity, diabetes, cardiovascular disease, certain types of neurodegeneration and inflammatory disease.

The invention further relates to the pharmaceutical compositions intended for the prevention or treatment of the aforesaid diseases when they contain at least one of the compounds of formula I according to the invention as the active principle.

These pharmaceutical compositions can be formulated in conventional manner and comprise at least one pharmaceutically acceptable excipient chosen according to the desired pharmaceutical form and desired mode of administration.

The compounds according to the invention can be administered by the oral, parenteral or any other desirable route in the form of unit doses containing from 5 to 250 mg of active principle, it being possible for these doses to be administered once to three times a day.

In particular, the compounds according to the invention can be administered orally in the form of tablets or capsules comprising conventional excipients such as stabilizers, surfactants, binders, lubricants and disintegrants, examples being lactose, starch, mannitol, cellulose derivatives, pyrrolidone derivatives, sodium laurylsulfate and magnesium stearate.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A sulfonylindoline compound, selected from the group consisting of:
   i) compounds corresponding to formula (I)

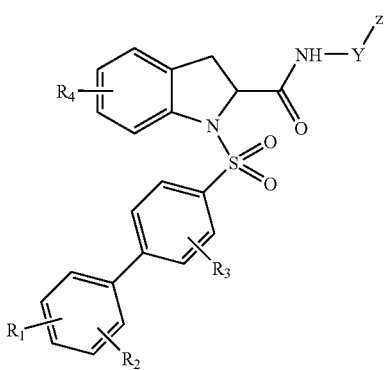

in which:
R$_1$ is a hydrogen atom, a halogen, a C$_1$-C$_4$ alkyl group, a C$_1$-C$_4$ alkoxy group, a trifluoromethyl group or a totally or partially halogenated methoxy group,
R$_2$ is a hydrogen atom, a halogen, a C$_1$-C$_4$ alkyl group or a trifluoromethyl group,
R$_3$ is a hydrogen atom, a halogen, a C$_1$-C$_4$ alkyl group or a trifluoromethyl group, with the proviso that R$_1$, R$_2$ and R$_3$ are not simultaneously a hydrogen atom,
R$_4$ is a hydrogen atom or a C$_1$-C$_4$ alkoxy group,
Y is a linear or branched C$_1$-C$_8$ alkylene group optionally substituted by a trifluoromethyl group or by a phenyl ring, or containing a cyclized part having 3 to 6 carbon atoms, or is a group —(CH$_2$)$_n$—W—,
W is an oxygen atom, a group —NH— or a sulfur atom,
n is 2, 3 or 4,
Z is an optionally partially halogenated C$_1$-C$_4$ alkyl group, trifluoromethyl, —COR$_a$, —CH$_2$—N(R)$_2$, or an aromatic, heteroaromatic or heterocyclic ring selected from phenyl, pyrrolidinyl, pyrrolidinylone, imidazolyl, pyridinyl, pyridinyl oxide, piperidinyl, piperazinyl, pyridazinyl, morpholinyl and indolinylone groups, and optionally substituted by one, two or three identical or different substituents selected from a halogen, a C$_1$-C$_4$ alkyl group, C$_1$-C$_4$ alkoxy, trifluoromethyl, nitro, N(R)$_2$, —CH$_2$—N(R)$_2$, —O—(CH$_2$)$_n$—N(R)$_2$, hydroxyl, cyano, C$_2$-C$_3$ cyanoalkyl, 5-oxo-1,2,4-oxadiazolidinyl and a group of the formula —X—[C(R)$_2$]$_p$—COR$_a$,
X is a single bond, an oxygen atom, —O—CH$_2$—, a sulfur atom, a group —NR— or a 1,1-cyclopropylene group,
R$_a$ is OR or N(R)$_2$,
R is a hydrogen atom or a C$_1$-C$_4$ alkyl group, and
p is equal to 0, 1, 2, 3 or 4; and
   ii) the pharmaceutically acceptable salts of said compounds of formula (I).

2. A compound according to claim 1, wherein the asymmetric carbon of the indoline group is of S configuration.

3. A compound according to claim 1, wherein R$_1$ is a fluorine atom or a trifluoromethyl group.

4. A compound according to claim 1, wherein
Y is a group —CH$_2$— or a group —(CH$_2$)$_2$—O— and Z is an aromatic ring substituted by a group containing a carboxylic acid group, said aromatic ring optionally containing one or two other substituents selected from a halogen, a C$_1$-C$_4$ alkyl group, preferably methyl, a C$_1$-C$_4$ alkoxy group, preferably methoxy, and a trifluoromethyl group.

5. A pharmaceutical composition comprising a compound according to claim 1 and at least one pharmaceutically acceptable carrier or adjuvant.

6. A method of treating a disorder or disease state selected from the group consisting of atherosclerosis, hypercholesterolemia, dyslipidemia, obesity and diabetes in a subject in need thereof, said method comprising administering to said subject a pharmacologically effective amount of a compound according to claim 1.

7. A method according to claim 6, wherein said disorder or disease state is atherosclerosis, hypercholesterolemia, dyslipidemia or obesity.

8. A method according to claim 6, wherein said disorder or disease state is diabetes.

9. A process for preparing a compound according to claim 1, said process comprising:
   reacting a benzenesulfonyl chloride corresponding to the formula IX

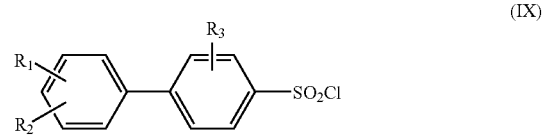

in which:
R$_1$ is a hydrogen atom, a halogen, a C$_1$-C$_4$ alkyl group, a C$_1$-C$_4$ alkoxy group, a trifluoromethyl group or a totally or partially halogenated methoxy group,
R$_2$ is a hydrogen atom, a halogen, a C$_1$-C$_4$ alkyl group or a trifluoromethyl group, and
R$_3$ is a hydrogen atom, a halogen, a C$_1$-C$_4$ alkyl group or a trifluoromethyl group, with the proviso that R$_1$, R$_2$ and R$_3$ are not simultaneously a hydrogen atom,
with an indoline compound corresponding to formula V

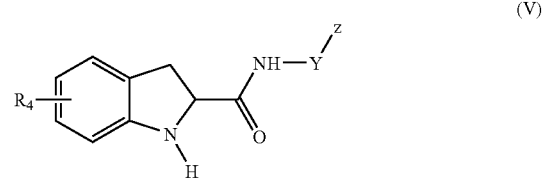

in which:
R$_4$ is a hydrogen atom or a C$_1$-C$_4$ alkoxy group,
Y is a linear or branched C$_1$-C$_8$ alkylene group optionally substituted by a trifluoromethyl group or by a phenyl ring, or containing a cyclized part having 3 to 6 carbon atoms, or is a group —$(CH_2)_n$—W—, W is an oxygen atom, a group —NH— or a sulfur atom, n is 2, 3 or 4, Z is an optionally partially halogenated $C_1$-$C_4$ alkyl group, trifluoromethyl, $COR_a$, $CH_2$—$N(R)_2$, or an aromatic, heteroaromatic or heterocyclic ring selected from phenyl, 1-pyrrolidinyl, pyrrolidinylone, 1-imidazolyl, pyridinyl, 1-piperidinyl, 4-alkyl-1-piperazinyl, pyridazinyl, 4-morpholinyl and indolinylone groups, and optionally substituted by one, two or three identical or different substituents selected from a halogen, a $C_1$-$C_4$ alkyl group, $C_1$-$C_4$ alkoxy, trifluoromethyl, nitro, $N(R)_2$, —$CH_2$—$N(R)_2$, —O—$(CH_2)_n$—$N(R)_2$, hydroxyl, cyano, $C_2$-$C_3$ cyanoalkyl and a group of the formula —X—$[C(R)_2]_p$—$COR_a$, X is a single bond, an oxygen atom, a sulfur atom, an NH group or a 1,1-cyclopropylene group, $R_a$ is OR or $N(R)_2$, R is a $C_1$-$C_4$ alkyl group, and p is equal to 0, 1, 2, 3 or 4, in an anhydrous solvent at room temperature, for 2 to 10 hours, to give a compound corresponding to the formula I

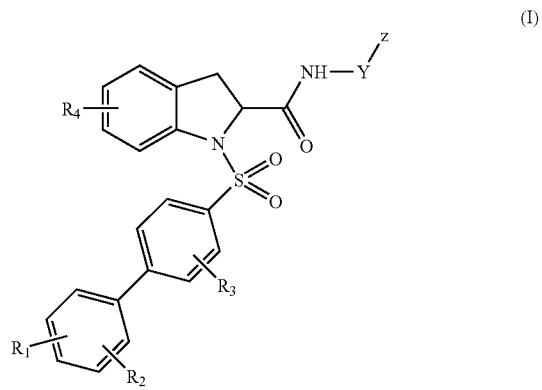

in which $R_1$, $R_2$, $R_3$, $R_4$, Y and Z are as defined above.

* * * * *